US012697379B2

(12) United States Patent (10) Patent No.: US 12,697,379 B2
McLean et al. (45) Date of Patent: Aug. 4, 2026

(54) PEGYLATED TETANUS NEUROTOXINS AND TREATMENT OF HYPOTONIA

(71) Applicant: Snoretox Pty Ltd, Kew (AU)

(72) Inventors: Thomas McLean, Melbourne (AU);
Peter Smooker, Melbourne (AU); **Luke
Norbury, Melbourne (AU); Peter
Coloe, Melbourne (AU); Russell
Conduit, Melbourne (AU); Anthony
Sasse**, Kew (AU)

(73) Assignee: Snoretox Pty Ltd, Victoria (AU)

( * ) Notice: Subject to any disclaimer, the term of this
patent is extended or adjusted under 35
U.S.C. 154(b) by 1142 days.

(21) Appl. No.: 17/261,975

(22) PCT Filed: Jul. 30, 2019

(86) PCT No.: PCT/AU2019/050793
§ 371 (c)(1),
(2) Date: Jan. 21, 2021

(87) PCT Pub. No.: WO2020/024002
PCT Pub. Date: Feb. 6, 2020

(65) Prior Publication Data
US 2021/0353724 A1 Nov. 18, 2021

(30) Foreign Application Priority Data
Jul. 31, 2018 (AU) ................................. 2018902779

(51) Int. Cl.
| | |
|---|---|
| *A61K 39/08* | (2006.01) |
| *A61K 38/00* | (2006.01) |
| *A61K 39/00* | (2006.01) |
| *A61K 47/60* | (2017.01) |
| *A61P 21/00* | (2006.01) |
| *C07K 14/33* | (2006.01) |

(52) U.S. Cl.
CPC .............. *A61K 39/08* (2013.01); *A61K 47/60*
(2017.08); *C07K 14/33* (2013.01); *A61K
2039/6037* (2013.01); *C12Y 304/24068*
(2013.01)

(58) Field of Classification Search
None
See application file for complete search history.

(56) References Cited

U.S. PATENT DOCUMENTS

| | | | | | |
|---|---|---|---|---|---|
| 7,494,661 | B2 * | 2/2009 | Sanders | .................. | A61P 17/06 |
| | | | | | 424/234.1 |
| 2002/0197278 | A1 | 12/2002 | Allison | | |
| 2009/0053248 | A1 | 2/2009 | Simpson et al. | | |
| 2023/0057367 | A1 * | 2/2023 | McLean | ............. | A61K 38/4886 |

FOREIGN PATENT DOCUMENTS

| | | |
|---|---|---|
| AU | 2003200441 B2 | 7/2006 |
| CN | 102414564 A | 4/2012 |
| CN | 106692963 A | 5/2017 |
| CN | 108350039 A | 7/2018 |
| EP | 1365800 | 3/2013 |
| IN | 201617001877 A | 8/2016 |
| JP | 2003-503059 A | 1/2003 |
| JP | 2004-521067 A | 7/2004 |
| WO | WO 2004/024909 | 3/2004 |
| WO | WO 2008/024879 | 2/2008 |
| WO | WO 2011/115483 | 9/2011 |
| WO | WO 2016/001762 | 1/2016 |
| WO | WO 2017/035507 A1 | 3/2017 |
| WO | WO 2019/118974 | 6/2019 |

OTHER PUBLICATIONS

Sasse et al. SLEEP 28: 1015-1016, 2005.*
KR Office Action in Korean Appln. No. 10-2021-7006098, mailed
on Dec. 6, 2024, 22 pages (with English translation).
NCBI Accession No. WP_011100836.1, "tetanus neurotoxin
[Clostridium tetani]," dated Feb. 5, 2018, 2 pages.
Da Silva Antunes et al., "Definition of human epitopes recognized
in tetanus toxoid and development of an assay strategy to detect ex
vivo tetanus CD4+ T cell responses," PloS one, Jan. 12, 2017,
12(1):e0169086, 12 pages.
Palermo et al., "Identification of a tetanus toxin specific epitope in
single amino acid resolution," Biotechnology Journal, Oct. 2017,
12(10):1700197.
PCT International Preliminary Report on Patentability in Interna-
tional Appln. No. PCT/AU2019/050793, dated Nov. 18, 2020, 8
pages.
PCT International Search Report and Written Opinion in Interna-
tional Appln. No. PCT/AU2019/050793, dated Oct. 3, 2019, 14
pages.
Wan et al., "Effect of protein immunogenicity and PEG size and
branching on the anti-PEG immune response to PEGylated pro-
teins," Process Biochemistry, Jan. 1, 2017, 52:183-91.
AU Search Report in Australian Application No. 2018902779, dated
Mar. 14, 2019, 8 pages.
Andreu et al., "Clostridium neurotoxin fragments as potential
targeting moieties for liposomal gene delivery to the CNS,"
Chembiochem, Jan. 25, 2008, 9(2):219-31.
Blum et al., "Entry of a recombinant, full-length, atoxic tetanus
neurotoxin into Neuro-2a cells," Infection and Immunity, Feb. 2014,
82(2):873-81.
CA Office Action in Canadian Appln. No. 3,108,079, dated Jan. 21,
2022, 4 pages.
EP Extended Search Report in European Appln. No. 19843147.0,
dated Jan. 28, 2022, 13 pages.

(Continued)

*Primary Examiner* — S. Devi
(74) *Attorney, Agent, or Firm* — Fish & Richardson P.C.

(57) ABSTRACT

The invention relates to a composition comprising a first
PEGylated tetanus neurotoxin (PEG-TeNT) comprising teta-
nus neurotoxin (TeNT) conjugated to polyethylene glycol
(PEG) and a second TeNT. The invention also relates to
various PEG-TeNTs. The invention also relates to a method
of treating hypotonia using the composition or various
PEG-TeNTs, and a kit comprising the composition or vari-
ous PEG-TeNTs. In one embodiment, the hypotonia is
obstructive sleep apnoea.

8 Claims, 25 Drawing Sheets

Specification includes a Sequence Listing.

(56) References Cited

OTHER PUBLICATIONS

EP Office Action by European Appln. No. 19843147.0, dated Oct. 27, 2021, 5 pages.

McLean et al., "Inactivated tetanus as an immunological smoke-screen: A major step towards harnessing tetanus-based therapeutics," Molecular Immunology, Nov. 1, 2020, 127:164-74.

Qazi et al., "Reduction of the ganglioside binding activity of the tetanus toxin HC fragment destroys immunogenicity: implications for development of novel tetanus vaccines," Infection and Immunity, Aug. 2006, 74(8):4884-91.

Rossetto et al., "Active-site mutagenesis of tetanus neurotoxin implicates TYR-375 and GLU-271 in metalloproteolytic activity," Toxicon, Aug. 1, 2001, 39(8):1151-9.

Conduit et al., "A neurotoxinological approach to the treatment of obstructive sleep apnoea," Sleep Medicine Reviews, Oct. 1, 2007, 11(5):361-75.

EP Extended Search Report in European Appln. No. 22183027.6, dated Dec. 21, 2022, 11 pages.

Zhang et al., "Moderate PEGylation of the carrier protein improves the polysaccharide-specific immunogenicity of meningococcal group A polysaccharide conjugate vaccine," Vaccine, Jun. 22, 2015, 33(28):3208-14.

CN Office Action in Chinese Appln. No. 201980057158.3, mailed on Jun. 20, 2024, 12 pages (with English translation).

CN Office Action in Chinese Appln. No. 201980057158.3, mailed on Nov. 25, 2024, 10 pages (with English translation).

EP Office Action in European Appln. No. 19843147.0, mailed on Jul. 19, 2023, 6 pages.

EP Office Action in European Appln. No. 22183027.6, mailed on Oct. 23, 2024, 5 pages.

JP Office Action in Japanese Appln. No. 2021-529491, mailed on Jan. 30, 2024, 2 pages (with English translation).

JP Office Action in Japanese Appln. No. 2021-529491, mailed on Jun. 20, 2024, 10 pages (with English translation).

JP Office Action in Japanese Appln. No. 2023-196375, mailed on Jan. 7, 2025, 13 pages (with English translation).

KR Office Action in Korean Appln. No. 10-2021-7006098, mailed on Feb. 4, 2025, 26 pages (with English translation).

MX Office Action in Mexican Appln. No. MX/a/2021/001181, mailed on Aug. 18, 2025, 18 pages (with English translation).

Spicer et al., "Selective chemical protein modification," Nature Communications, Sep. 2014, 5(1):4740.

EP Office Action in European Appln. No. 19843147.0, mailed on Jul. 17, 2025, 4 pages.

JP Office Action in Japanese Appln. No. 2021-529491, mailed on Apr. 7, 2025, 10 pages (with English translation).

* cited by examiner

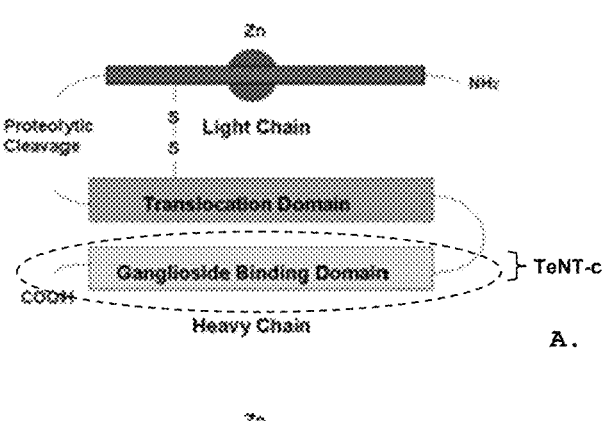
A.
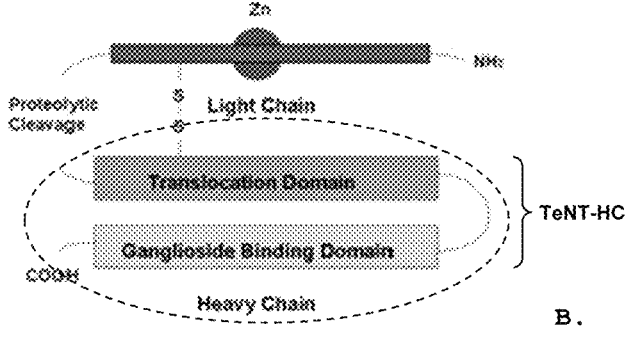
B.
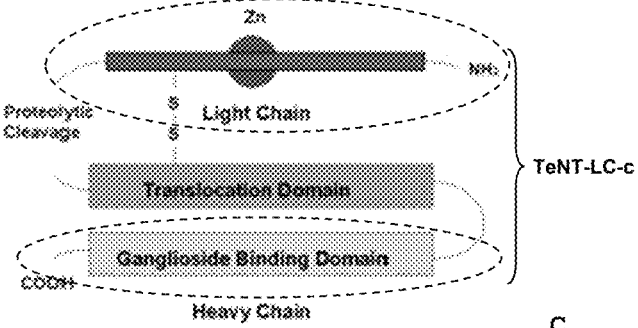
C.
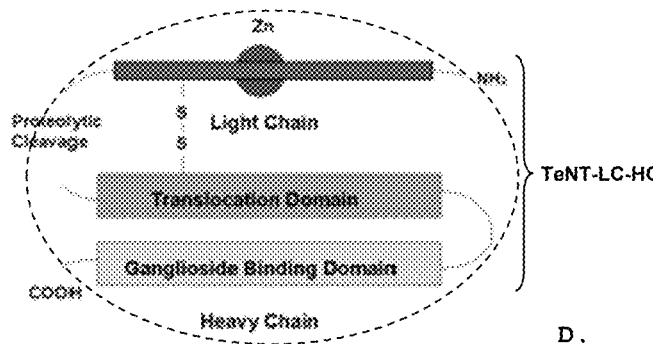
D.
Figure 1.

```
PITINNFRYS   DPVNNDTIIM   MEPPYCKGLD   IYYKAFKITD   RIWIVPERYE   FGTKPEDFNP
PSSLIEGASE   YYDPNYLRTD   SDKDRFLQTM   VKLFNRIKNN   VAGEALLDKI   INAIPYLGNS
YSLLDKFDTN   SNSVSFNLLE   QDPSGATTKS   AMLTNLIIFG   PGPVLNKNEV   RGIVLRVDNK
NYFPCRDGFG   SIMQMAFCPE   YVPTFDNVIE   NITSLTIGKS   KYFQDPALLL   MHELIHVLHG
LYGMQVSSHE   IIPSKQEIYM   QHTYPISAEE   LFTFGGQDAN   LISIDIKNDL   YEKTLNDYKA
IANKLSQVTS   CNDPNIDIDS   YKQIYQQKYQ   FDKDSNGQYI   VNEDKFQILY   NSIMYGFTEI
ELGKKFNIKT   RLSYFSMNHD   PVKIPNLLDD   TIYNDTEGFN   IESKDLKSEY   KGQNMRVNTN
AFRNVDGSGL   VSKLIGLCKK   IIPPTNIREN   LYNRTASLTD   LGGELCIKIK   NEDLTFIAEK
NSFSEEPFQD   EIVSYNTKNK   PLNFNYSLDK   IIVDYNLQSK   ITLPNDRTTP   VTKGIPYAPE
YKSNAASTIE   IHNIDDNTIY   QYLYAQKSPT   TLQRITMTNS   VDDALINSTK   IYSYFPSVIS
KVNQGAQGIL   FLQWVRDIID   DFTNESSQKT   TIDKISDVST   IVPYIGPALN   IVKQGYEGNF
IGALETTGVV   LLLEYIPEIT   LPVIAALSIA   ESSTQKEKII   KTIDNFLEKR   YEKWIEVYKL
VKAKWLGTVN   TQFQKRSYQM   YRSLEYQVDA   IKKIIDYEYK   IYSGPDKEQI   ADEINNLKNK
LEEKANKAMI   NINIFMRESS   RSFLVNQMIN   EAKKQLLEFD   TQSKNILMQY   IKANSKFIGI
TELKKLESKI   NKVFSTPIPF   SYSKNLDCWV   DNEEDIDVIL   KKSTILNLDI   NNDIISDISG
FNSSVITYPD   AQLVPGINGK   AIHLVNNESS   EVIVHKAMDI   EYNDMFNNFT   VSFWLRVPKV
SASHLEQYGT   NEYSIISSMK   KHSLSIGSGW   SVSLKGNNLI   WTLKDSAGEV   RQITFRDLPD
KFNAYLANKW   VFITITNDRL   SSANLYINGV   LMGSAEITGL   GAIREDNNIT   LKLDRCNNNN
QYVSIDKFRI   FCKALNPKEI   EKLYTSYLSI   TFLRDFWGNP   LRYDTEYYLI   PVASSSKDVQ
LKNITDYMYL   TNAPSYTNGK   LNIYYRRLYN   GLKFIIKRYT   PNNEIDSFVK   SGDFIKLYVS
YNNNEHIVGY   PKDGNAFNNL   DRILRVGYNA   PGIPLYKKME   AVKLRDLKTY   SVQLKLYDDK
NASLGLVGTH   NGQIGNDPNR   DILIASNWYF   NHLKDKILGC   DWYFVPTDEG   WTND
```
Figure 2 SEQ ID NO: 1.

```
GATCTCGATCCCGCGAAATTAATACGACTCACTATAGGGAGACCACAACGGTTTCCCTCTAGAAATAATTTTGTT
TAACTTTAAGAAGGAGATATACATATGCGGGGTTCTCATCATCATCATCATGGTATGGCTAGCATGACTGGT
GGACAGCAAATGGGTCGGGATCTGTACGACGATGACGATAAGGATCGATGGGGATCCGAGCTCGAGCCGATTACC
ATCAATAATTTTCGTTATTCAGATCCGGTGAATAATGATACCATCATCATGATGGAACCACCGTACTGTAAAGGG
CTGGATATTTATTATAAAGCGTTCAAAATCACCGACCGCATCTGGATCGTGCCGGAACGCTACGAATTCGGCACC
AAACCGGAAGATTTTAATCCGCCGAGTAGTCTGATCGAAGGTGCATCGGAATACTACGATCCGAATTATCTGCGT
ACTGACTCTGATAAAGATCGCTTTCTGCAAACGATGGTAAAACTGTTCAATCGTATCAAAAACAATGTAGCAGGC
GAAGCCCTGCTGGATAAAATCATCAACGCCATTCCGTATCTGGGAAACAGTTATTCTCTGCTGGATAAATTCGAT
ACAAACTCGAACTCTGTGTCATTCAACCTGCTGGAACAGGACCCGAGCGGCGCGACCACTAAGAGTGCGATGCTG
ACTAACCTGATTATTTTCGGTCCGGGACCGGTACTGAATAAAAATGAAGTTCGCGGCATTGTACTGCGTGTCGAT
AATAAAAACTATTTCCCATGTCGTGATGGCTTCGGCAGCATCATGCAGATGGCCTTTTGTCCGGAATATGTGCCA
ACTTTCGATAATGTGATTGAGAACATCACCTCTCTGACGATTGGTAAAAGTAAATATTTCCAGGATCCGGCTCTG
CTGCTGATGCATGAACTGATCCATGTTCTGCATGGCCTGTATGGCATGCAGGTTTCATCCCACGAAATTATCCCA
TCCAAACAGGAAATTTACATGCAGCATACATATCCGATTAGTGCCGAAGAACTGTTCACTTTTGGCGGCCAGGAT
GCGAACCTGATTTCGATTGACATTAAAAACGATCTGTATGAAAAAACTCTGAACGATTATAAAGCGATTGCCAAC
AAACTGTCTCAGGTAACCTCCTGTAACGATCCGAATATTGATATTGACAGTTATAAACAAATTTATCAGCAGAAG
TATCAGTTCGATAAAGACTCTAATGGCCAGTATATTGTTAACGAAGATAAATTCCAGATTCTGTACAATAGCATT
ATGTATGGCTTTACTGAGATCGAACTGGGTAAAAAATTTAACATCAAGACTCGTCTGAGCTATTTTAGCATGAAT
CATGATCCAGTGAAAATCCCGAATCTGCTGGATGATACGATTTATAATGATACCGAAGGATTTAACATCGAAAGC
AAGGATCTGAAATCCGAATATAAAGGGCAGAACATGCGCGTTAATACCAATGCATTTCGCAATGTTGATGGTTCA
GGCCTGGTGTCGAAACTGATTGGGCTGTGTAAGAAAATCATTCCACCGACAAATATTCGCGAAAATCTGTACAAC
CGTACGGCGAGCCTGACCGATCTGGGGGGAGAACTGTGTATTAAAATCAAAAATGAAGATCTGACCTTCATTGCT
GAGAAGAATAGCTTTTCCGAAGAGCCATTCCAGGACGAAATCGTGTCTTATAACACCAAGAATAAACCGCTGAAT
TTCAACTACTCCCTGGACAAAATCATTGTGGATTACAACCTGCAGAGTAAAATTACCCTGCCGAATGATCGTACC
ACCCCCGGTGACGAAAGGCATCCCTTACGCACCAGAATATAAATCAAATGCAGCCTCGACTATCGAGATCCATAAT
ATTGATGACAACACTATTTACCAGTACCTGTATGCTCAGAAATCTCCGACGACGCTGCAGCGCATCACCATGACT
AACAGCGTGGACGATGCCCTGATTAATAGCACCAAAATCTACTCTTACTTTCCGTCGGTGATCTCTAAGGTTAAT
CAGGGCGCGCAAGGTATCCTGTTTCTGCAATGGGTGCGTGATATTATTGATGATTTCACTAATGAATCTAGCCAG
AAAACGACAATTGATAAAATTTCGGATGTTTCCACCATCGTGCCTTACATCGGCCCAGCGCTGAACATCGTGAAG
CAGGGTTATGAGGGTAACTTTATCGGAGCACTGGAAACGACCGGCGTGGTTCTGCTGCTGGAATATATTCCGGAG
ATTACTCTGCCAGTTATTGCGGCTCTGTCGATTGCAGAGAGCTCAACGCAGAAAGAAAAAATTATTAAGACGATC
GACAATTTCCTGGAAAAGCGCTACGAAAAATGGATCGAAGTGTATAAGCTGGTGAAAGCGAAATGGCTGGGGACC
GTGAACACCCAGTTCCAAAAACGTTCCTATCAAATGTATCGTAGCCTGGAATATCAGGTGGACGCCATTAAAAAG
ATCATCGATTACGAATATAAGATCTACTCCGGTCCGGACAAAGAACAGATTGCGGACGAAATTAACAATCTGAAA
```
Figure 3-1 SEQ ID NO: 2

```
AATAAACTGGAGGAAAAAGCCAACAAAGCGATGATTAATATCAATATTTTCATGCGTGAAAGCAGCCGTAGCTTC
CTGGTCAATCAGATGATTAATGAAGCGAAGAAACAACTGCTGGAATTTGATACGCAATCTAAAAATATTCTGATG
CAATACATCAAAGCCAATTCTAAATTTATTGGGATCACGGAACTGAAAAAGCTGGAATCGAAAATCAATAAAGTC
TTTAGCACCCCGATTCCGTTCTCCTACTCGAAAAATCTGGATTGTTGGGTTGACAATGAAGAAGATATTGATGTT
ATTCTGAAAAAGAGCACGATCCTGAACCTGGATATTAATAACGATATTATCTCTGATATCAGTGGTTTTAATTCA
TCAGTTATTACTTACCCAGACGCTCAACTGGTGCCGGGAATCAATGGGAAAGCCATTCATCTGGTGAATAATGAA
TCAAGTGAAGTGATCGTGCATAAAGCGATGGATATCGAGTACAACGATATGTTTAATAATTTCACGGTGTCGTTC
TGGCTGCGTGTTCCGAAAGTGAGTGCCTCCCACCTGGAACAATATGGAACCAACGAATACTCAATCATTAGCAGC
ATGAAGAAACATTCGCTGAGTATTGGTTCAGGTTGGAGCGTTTCCCTGAAAGGGAACAATCTGATCTGGACACTG
AAGGACTCAGCGGGCGAAGTGCGTCAGATTACGTTTCGTGATCTGCCGGATAAATTTAATGCATACCTGGCTAAC
AAATGGGTGTTCATCACAATCACCAATGACCGTCTGTCGTCTGCAAACCTGTATATTAATGGGGTACTGATGGGC
TCGGCAGAAATTACAGGGCTGGGCGCCATTCGTGAAGATAACAATATTACGCTGAAACTGGATCGTTGTAATAAC
AATAATCAGTATGTGAGCATTGATAAATTTCGTATTTTCTGCAAAGCGCTGAACCCGAAAGAAATTGAAAAACTG
TATACCTCGTATCTGTCAATTACGTTTCTGCGCGATTTCTGGGGAAACCCGCTGCGTTACGATACGGAATACTAC
CTGATCCCGGGTAGCCAGTTCTAGTAAAGACGTTCAACTGAAAAATATTACCGACTACATGTATCTGACAAACGCT
CCATCATACACAAACGGCAAACTGAACATCTATTACCGTCGCCTGTACAATGGGCTGAAATTCATCATTAAACGT
TATACCCCGAATAACGAAATTGATTCCTTTGTGAAGTCCGGTGACTTCATTAAGCTGTATGTATCCTATAACAAT
AATGAACACATCGTTGGCTATCCGAAGGATGGCAATGCCTTTAACAACCTGGATCGTATTCTGCGTGTAGGTTAC
AACGCCCCGGGTATTCCGCTGTATAAGAAAATGGAAGCAGTGAAACTGCGTGATCTGAAAACATATTCCGTGCAA
CTGAAGCTGTATGATGACAAAAATGCTAGCCTGGGTCTGGTAGGCACGCATAACGGTCAGATTGGAAACGATCCT
AATCGTGACATCCTGATCGCCTCTAACTGGTATTTTAACCACCTGAAAGATAAAATTCTGGGCTGCGATTGGTAT
TTTGTCCCTACCGATGAAGGCTGGACGAACGATTAAAAGCTTGATCCGGCTGCTAACAAAGCCCGAAAGGAAGCT
GAGTTGGCTGCTGCCACCGCTGAGCAATAACTAGCATAACCCCTTGGGGCCTCTAAACGGGTCTTGAGGGGTTTT
TTGCTGAAAGGAGGAACTATATCCGGATCTGGCGTAATAGCGAAGAGGCCCGCACCGATCGCCCTTCCCAACAGT
TGCGCAGCCTGAATGGCGAATGGGACGCGCCCTGTAGCGGCGCATTAAGCGCGGCGGGTGTGGTGGTTACGCGCA
GCGTGACCGCTACACTTGCCAGCGCCCTAGCGCCCGCTCCTTTCGCTTTCTTCCCTTCCTTTCTCGCCACGTTCG
CCGGCTTTCCCCGTCAAGCTCTAAATCGGGGGCTCCCTTTAGGGTTCCGATTTAGTGCTTTACGGCACCTCGACC
CCAAAAAACTTGATTAGGGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCTATCTCGGTCTATTCTT
TTGATTTATAAGGGATTTTGCCGATTTCGGCCTATTGGTTAAAAAATGAGCTGATTTAACAAAAATTTAACGCGA
ATTTTAACAAAATATTAACGCTTACAATTTAGGTGGCACTTTTCGGGGAAATGTGCGCGGAACCCCTATTTGTTT
ATTTTTCTAAATACATTCAAATATGTATCCGCTCATGAGACAATAACCCTGATAAATGCTTCAATAATATTGAAA
AAGGAAGAGTATGAGTATTCAACATTTCCGTGTCGCCCTTATTCCCTTTTTTGCGGCATTTTGCCTTCCTGTTTTT
TGCTCACCCAGAAACGCTGGTGAAAGTAAAAGATGCTGAAGATCAGTTGGGTGCACGAGTGGGTTACATCGAACT
GGATCTCAACAGCGGTAAGATCCTTGAGAGTTTTCGCCCCGAAGAACGTTTTCCAATGATGAGCACTTTTAAAGT
TCTGCTATGTGGCGCGGTATTATCCCGTATTGACGCCGGGCAAGAGCAACTCGGTCGCCGCATACACTATTCTCA
GAATGACTTGGTTGAGTACTCACCAGTCACAGAAAAGCATCTTACGGATGGCATGACAGTAAGAGAATTATGCAG
TGCTGCCATAACCATGAGTGATAACACTGCGGCCAACTTACTTCTGACAACGATCGGAGGACCGAAGGAGCTAAC
CGCTTTTTTGCACAACATGGGGGATCATGTAACTCGCCTTGATCGTTGGGAACCGGAGCTGAATGAAGCCATACC
AAACGACGAGCGTGACACCACGATGCCTGTAGCAATGGCAACAACGTTGCGCAAACTATTAACTGGCGAACTACT
TACTCTAGCTTCCCGGCAACAATTAATAGACTGGATGGAGGCGGATAAAGTTGCAGGACCACTTCTGCGCTCGGC
CCTTCCGGCTGGCTGGTTTATTGCTGATAAATCTGGAGCCGGTGAGCGTGGGTCTCGCGGTATCATTGCAGCACT
GGGGCCAGATGGTAAGCCCTCCCGTATCGTAGTTATCTACACGACGGGGAGTCAGGCAACTATGGATGAACGAAA
TAGACAGATCGCTGAGATAGGTGCCTCACTGATTAAGCATTGGTAACTGTCAGACCAAGTTTACTCATATATACT
TTAGATTGATTTAAAACTTCATTTTTAATTTAAAAGGATCTAGGTGAAGATCCTTTTTGATAATCTCATGACCAA
AATCCCTTAACGTGAGTTTTCGTTCCACTGAGCGTCAGACCCCGTAGAAAAGATCAAAGGATCTTCTTGAGATCC
TTTTTTTCTGCGCGTAATCTGCTGCTTGCAAACAAAAAAACCACCGCTACCAGCGGTGGTTTGTTTGCCGGATCA
AGAGCTACCAACTCTTTTTCCGAAGGTAACTGGCTTCAGCAGAGCGCAGATACCAAATACTGTTCTTCTAGTGTA
GCCGTAGTTAGGCCACCACTTCAAGAACTCTGTAGCACCGCCTACATACCTCGCTCTGCTAATCCTGTTACCAGT
GGCTGCTGCCAGTGGCGATAAGTCGTGTCTTACCGGGTTGGACTCAAGACGATAGTTACCGGATAAGGCGCAGCG
GTCGGGCTGAACGGGGGGTTCGTGCACACAGCCCAGCTTGGAGCGAACGACCTACACCGAACTGAGATACCTACA
GCGTGAGCTATGAGAAAGCGCCACGCTTCCCGAAGGGAGAAAGGCGGACAGGTATCCGGTAAGCGGCAGGGTCGG
AACAGGAGAGCGCACGAGGGAGCTTCCAGGGGGAAACGCCTGGTATCTTTATAGTCCTGTCGGGTTTCGCCACCT
CTGACTTGAGCGTCGATTTTTGTGATGCTCGTCAGGGGGGCGGAGCCTATGGAAAAACGCCAGCAACGCGGCCTT
TTTACGGTTCCTGGCCTTTTGCTGGCCTTTTGCTCACATGTTCTTTCCTGCGTTATCCCCTGATTCTGTGGATAA
CCGTATTACCGCCTTTGAGTGAGCTGATACCGCTCGCCGCAGCCGAACGACCGAGCGCAGCGAGTCAGTGAGCGA
GGAAGCGGAAGAGCGCCCAATACGCAAACCGCCTCTCCCCGCGCGTTGGCCGATTCATTAATGCAG
```
Figure 3-2 SEQ ID NO: 2.

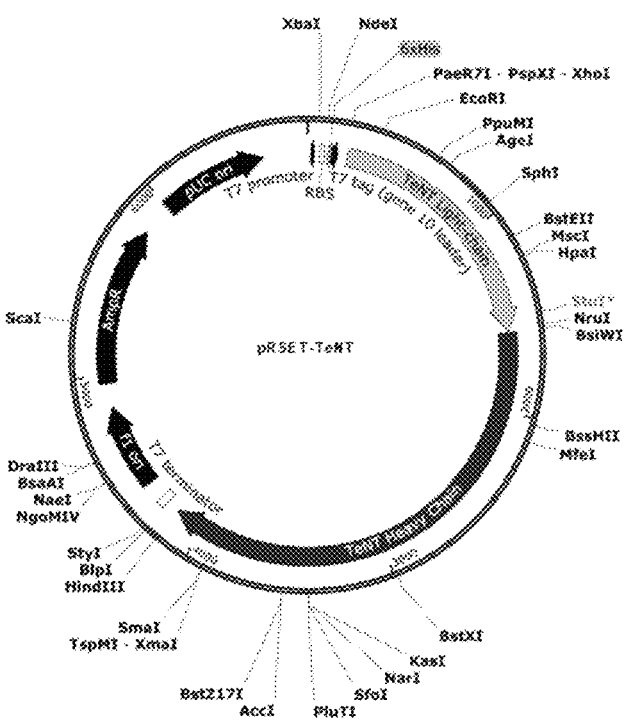

Figure 4.

```
SLTDLG
GELCIKIKNE  DLTFIAEKNS  FSEEPFQDEI  VSYNTKNKPL  NFNYSLDKII  VDYNLQSKIT
LPNDRTTPVT  KGIPYAPEYK  SNAASTIEIH  NIDDNTIYQY  LYAQKSPTTL  QRITMTNSVD
DALINSTKIY  SYFPSVISKV  NQGAQGILFL  QWVRDIIDDF  TNESSQKTTI  DKISDVSTIV
PYIGPALNIV  KQGYEGNFIG  ALETTGVVLL  LEYIPEITLP  VIAALSIAES  STQKEKIIKT
IDNFLEKRYE  KWIEVYKLVK  AKWLGTVNTQ  FQKRSYQMYR  SLEYQVDAIK  KIIDYEYKIY
SGPDKEQIAD  EINNLKNKLE  EKANKAMINI  NIFMRESSRS  FLVNQMINEA  KKQLLEFDTQ
SKNILMQYIK  ANSKFIGITE  LKKLESKINK  VFSTPIPFSY  SKNLDCWVDN  EEDIDVILKK
STILNLDINN  DIISDISGFN  SSVITYPDAQ  LVPGINGKAI  HLVNNESSEV  IVHKAMDIEY
NDMFNNFTVS  FWLRVPKVSA  SHLEQYGTNE  YSIISSMKKH  SLSIGSGWSV  SLKGNNLIWT
LKDSAGEVRQ  ITFRDLPDKF  NAYLANKWVF  ITITNDRLSS  ANLYINGVLM  GSAEITGLGA
IREDNNITLK  LDRCNNNNQY  VSIDKFRIFC  KALNPKEIEK  LYTSYLSITF  LRDFWGNPLR
YDTEYYLIPV  ASSSKDVQLK  NITDYMYLTN  APSYTNGKLN  IYYRRLYNGL  KFIIKRYTPN
NEIDSFVKSG  DFIKLYVSYN  NNEHIVGYPK  DGNAFNNLDR  ILRVGYNAPG  IPLYKKMEAV
KLRDLKTYSV  QLKLYDDKNA  SLGLVGTHNG  QIGNDPNRDI  LIASNWYFNH  LKDKILGCDW
YFVPTDEGWT  ND
```
Figure 5 SEQ ID NO: 3.

```
KNLDCWVDN  EEDIDVILKK  STILNLDINN  DIISDISGFN  SSVITYPDAQ  LVPGINGKAI
HLVNNESSEV  IVHKAMDIEY  NDMFNNFTVS  FWLRVPKVSA  SHLEQYGTNE  YSIISSMKKH
SLSIGSGWSV  SLKGNNLIWT  LKDSAGEVRQ  ITFRDLPDKF  NAYLANKWVF  ITITNDRLSS
ANLYINGVLM  GSAEITGLGA  IREDNNITLK  LDRCNNNNQY  VSIDKFRIFC  KALNPKEIEK
LYTSYLSITF  LRDFWGNPLR  YDTEYYLIPV  ASSSKDVQLK  NITDYMYLTN  APSYTNGKLN
IYYRRLYNGL  KFIIKRYTPN  NEIDSFVKSG  DFIKLYVSYN  NNEHIVGYPK  DGNAFNNLDR
ILRVGYNAPG  IPLYKKMEAV  KLRDLKTYSV  QLKLYDDKNA  SLGLVGTHNG  QIGNDPNRDI
LIASNWYFNH  LKDKILGCDW  YFVPTDEGWT  ND
```
Figure 6 SEQ ID NO: 4.

```
GATCTCGATCCCGCGAAATTAATACGACTCACTATAGGGAGACCACAACGGTTTCCCTCTAGAAATAATTTTGTT
TAACTTTAAGAAGGAGATATACATATGCGGGGTTCTCATCATCATCATCATGGTATGGCTAGCATGACTGGT
GGACAGCAAATGGGTCGGGATCTGTACGACGATGACGATAAGGATCGATGGGGATCCGAGCTCGAGAAAAATCTG
GATTGTTGGGTTGACAATGAAGAAGATATTGATGTTATTCTGAAAAAGAGCACGATCCTGAACCTGGATATTAAT
AACGATATTATCTCTGATATCAGTGGTTTTAATTCATCAGTTATTACTTACCCAGACGCTCAACTGGTGCCGGGA
ATCAATGGGAAAGCCATTCATCTGGTGAATAATGAATCAAGTGAAGTGATCGTGCATAAAGCGATGGATATCGAG
TACAACGATATGTTTAATAATTTCACGGTGTCGTTCTGGCTGCGTGTTCCGAAAGTGAGTGCCTCCCACCTGGAA
CAATATGGAACCAACGAATACTCAATCATTAGCAGCATGAAGAAACATTCGCTGAGTATTGGTTCAGGTTGGAGC
GTTTCCCTGAAAGGGAACAATCTGATCTGGACACTGAAGGACTCAGCGGGCGAAGTGCGTCAGATTACGTTTCGT
GATCTGCCGGATAAATTTAATGCATACCTGGCTAACAAATGGGTGTTCATCACAATCACCAATGACCGTCTGTCG
TCTGCAAACCTGTATATTAATGGGGTACTGATGGGCTCGGCAGAAATTACAGGGCTGGGCGCCATTCGTGAAGAT
AACAATATTACGCTGAAACTGGATCGTTGTAATAACAATAATCAGTATGTGAGCATTGATAAATTTCGTATTTTC
TGCAAAGCGCTGAACCCGAAAGAAATTGAAAAACTGTATACCTCGTATCTGTCAATTACGTTTCTGCGCGATTTC
TGGGGAAACCCGCTGCGTTACGATACGGAATACTACCTGATCCCGGTAGCCAGTTCTAGTAAAGACGTTCAACTG
AAAAATATTACCGACTACATGTATCTGACAAACGCTCCATCATACACAAACGGCAAACTGAACATCTATTACCGT
CGCCTGTACAATGGGCTGAAATTCATCATTAAACGTTATACCCCGAATAACGAAATTGATTCCTTTGTGAAGTCC
GGTGACTTCATTAAGCTGTATGTATCCTATAACAATAATGAACACATCGTTGGCTATCCGAAGGATGGCAATGCC
TTTAACAACCTGGATCGTATTCTGCGTGTAGGTTACAACGCCCCGGGTATTCCGCTGTATAAGAAAATGGAAGCA
GTGAAACTGCGTGATCTGAAAACATATTCCGTGCAACTGAAGCTGTATGATGACAAAAATGCTAGCCTGGGTCTG
GTAGGCACGCATAACGGTCAGATTGGAAACGATCCTAATCGTGACATCCTGATCGCCTCTAACTGGTATTTTAAC
CACCTGAAAGATAAAATTCTGGGCTGCGATTGGTATTTTGTCCCTACCGATGAAGGCTGGACGAACGATTAAGAA
TTCGAAGCTTGATCCGGCTGCTAACAAAGCCCGAAAGGAAGCTGAGTTGGCTGCTGCCACCGCTGAGCAATAACT
AGCATAACCCCTTGGGGCCTCTAAACGGGTCTTGAGGGGTTTTTTGCTGAAAGGAGGAACTATATCCGGATCTGG
CGTAATAGCGAAGAGGCCCGCACCGATCGCCCTTCCCAACAGTTGCGCAGCCTGAATGGCGAATGGGACGCGCCC
TGTAGCGGCGCATTAAGCGCGGCGGGTGTGGTGGTTACGCGCAGCGTGACCGCTACACTTGCCAGCGCCCTAGCG
CCCGCTCCTTTCGCTTTCTTCCCTTCCTTTCTCGCCACGTTCGCCGGCTTTCCCCGTCAAGCTCTAAATCGGGGG
CTCCCTTTAGGGTTCCGATTTAGTGCTTTACGGCACCTCGACCCCAAAAAACTTGATTAGGGTGATGGTTCACGT
AGTGGGCCATCGCCCTGATAGACGGTTTTTCGCCCTTTGACGTTGGAGTCCACGTTCTTTAATAGTGGACTCTTG
TTCCAAACTGGAACAACACTCAACCCTATCTCGGTCTATTCTTTTGATTTATAAGGGATTTTGCCGATTTCGGCC
TATTGGTTAAAAAATGAGCTGATTTAACAAAAATTTAACGCGAATTTTAACAAAATATTAACGCTTACAATTTAG
GTGGCACTTTTCGGGGAAATGTGCGCGGAACCCCTATTTGTTTATTTTTCTAAATACATTCAAATATGTATCCGC
TCATGAGACAATAACCCTGATAAATGCTTCAATAATATTGAAAAAGGAAGAGTATGAGTATTCAACATTTCCGTG
TCGCCCTTATTCCCTTTTTTGCGGCATTTTGCCTTCCTGTTTTTGCTCACCCAGAAACGCTGGTGAAAGTAAAAG
ATGCTGAAGATCAGTTGGGTGCACGAGTGGGTTACATCGAACTGGATCTCAACAGCGGTAAGATCCTTGAGAGTT
TTCGCCCCGAAGAACGTTTTCCAATGATGAGCACTTTTAAAGTTCTGCTATGTGGCGCGGTATTATCCCGTATTG
ACGCCGGGCAAGAGCAACTCGGTCGCCGCATACACTATTCTCAGAATGACTTGGTTGAGTACTCACCAGTCACAG
AAAAGCATCTTACGGATGGCATGACAGTAAGAGAATTATGCAGTGCTGCCATAACCATGAGTGATAACACTGCGG
CCAACTTACTTCTGACAACGATCGGAGGACCGAAGGAGCTAACCGCTTTTTTGCACAACATGGGGGATCATGTAA
CTCGCCTTGATCGTTGGGAACCGGAGCTGAATGAAGCCATACCAAACGACGAGCGTGACACCACGATGCCTGTAG
CAATGGCAACAACGTTGCGCAAACTATTAACTGGCGAACTACTTACTCTAGCTTCCCGGCAACAATTAATAGACT
GGATGGAGGCGGATAAAGTTGCAGGACCACTTCTGCGCTCGGCCCTTCCGGCTGGCTGGTTTATTGCTGATAAAT
CTGGAGCCGGTGAGCGTGGGTCTCGCGGTATCATTGCAGCACTGGGGCCAGATGGTAAGCCCTCCCGTATCGTAG
TTATCTACACGACGGGGAGTCAGGCAACTATGGATGAACGAAATAGACAGATCGCTGAGATAGGTGCCTCACTGA
TTAAGCATTGGTAACTGTCAGACCAAGTTTACTCATATATACTTTAGATTGATTTAAAACTTCATTTTTAATTTA
AAAGGATCTAGGTGAAGATCCTTTTTGATAATCTCATGACCAAAATCCCTTAACGTGAGTTTTCGTTCCACTGAG
CGTCAGACCCCGTAGAAAAGATCAAAGGATCTTCTTGAGATCCTTTTTTTCTGCGCGTAATCTGCTGCTTGCAAA
CAAAAAAACCACCGCTACCAGCGGTGGTTTGTTTGCCGGATCAAGAGCTACCAACTCTTTTTCCGAAGGTAACTG
GCTTCAGCAGAGCGCAGATACCAAATACTGTTCTTCTAGTGTAGCCGTAGTTAGGCCACCACTTCAAGAACTCTG
TAGCACCGCCTACATACCTCGCTCTGCTAATCCTGTTACCAGTGGCTGCTGCCAGTGGCGATAAGTCGTGTCTTA
CCGGGTTGGACTCAAGACGATAGTTACCGGATAAGGCGCAGCGGTCGGGCTGAACGGGGGGTTCGTGCACACAGC
CCAGCTTGGAGCGAACGACCTACACCGAACTGAGATACCTACAGCGTGAGCTATGAGAAAGCGCCACGCTTCCCG
AAGGGAGAAAGGCGGACAGGTATCCGGTAAGCGGCAGGGTCGGAACAGGAGAGCGCACGAGGGAGCTTCCAGGGG
GAAACGCCTGGTATCTTTATAGTCCTGTCGGGTTTCGCCACCTCTGACTTGAGCGTCGATTTTTGTGATGCTCGT
CAGGGGGGCGGAGCCTATGGAAAAACGCCAGCAACGCGGCCTTTTTACGGTTCCTGGCCTTTTGCTGGCCTTTTG
CTCACATGTTCTTTCCTGCGTTATCCCCTGATTCTGTGGATAACCGTATTACCGCCTTTGAGTGAGCTGATACCG
CTCGCCGCAGCCGAACGACCGAGCGCAGCGAGTCAGTGAGCGAGGAAGCGGAAGAGCGCCCAATACGCAAACCGC
CTCTCCCCGCGCGTTGGCCGATTCATTAATGCAG
```
Figure 7 SEQ ID NO: 5.

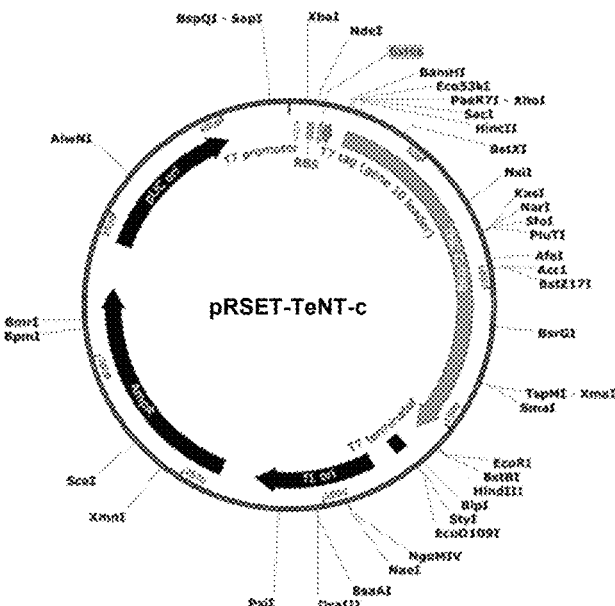

Figure 8.

PITINNFRYSDPVNNDTIIMMEPPYCKGLDIYYKAFKITDRIWIVPERYEFGTKPEDFNPPSSLIEGASEYYDPN
YLRTDSDKDRFLQTMVKLFNRIKNNVAGEALLDKIINAIPYLGNSYSLLDKFDTNSNSVSFNLLEQDPSGATTKS
AMLTNLIIFGPGPVLNKNEVRGIVLRVDNKNYFPCRDGFGSIMQMAFCPEYVPTFDNVIENITSLTIGKSKYFQD
PALLLMHELIHVLHGLYGMQVSSHEIIPSKQEIYMQHTYPISAEELFTFGGQDANLISIDIKNDLYEKTLNDYKA
IANKLSQVTSCNDPNIDIDSYKQIYQQKYQFDKDSNGQYIVNEDKFQILYNSIMYGFTEIELGKKFNIKTRLSYF
SMNHDPVKIPNLLDDTIYNDTEGFNIESKDLKSEYKGQNMRVNTNAFRNVDGSGLVSKLIGLCKKIIPPTNIREN
LYNRTASLTDLGGELCIKIKNEDLTFIAEKNSFSEEPFQDEIVSYNTKNKPLNFNYSLDKIIVDYNLQSKITLPN
DRTTPVTKGIPYAPEYKSNAASTIEIHNIDDNTIYQYLYAQKSPTTLQRITMTNSVDDALINSTKIYSYFPSVIS
KVNQGAQGILFLQWVRDIIDDFTNESSQKTTIDKISDVSTIVPYIGPALNIVKQGYEGNFIGALETTGVVLLLEY
IPEITLPVIAALSIAESSTQKEKIIKTIDNFLEKRYEKWIEVYKLVKAKWLGTVNTQFQKRSYQMYRSLEYQVDA
IKKIIDYEYKIYSGPDKEQIADEINNLKNKLEEKANKAMININIFMRESSRSFLVNQMINEAKKQLLEFDTQSKN
ILMQYIKANSKFIGITELKKLESKINKVFSTPIPFSYS
Figure 9 SEQ ID NO: 6.

GATCTCGATCCCGCGAAATTAATACGACTCACTATAGGGAGACCACAACGGTTTCCCTCTAGAAATAATTTTGTT
TAACTTTAAGAAGGAGATATACATATGCGGGGTTCTCATCATCATCATCATCATGGTATGGCTAGCATGACTGGT
GGACAGCAAATGGGTCGGGATCTGTACGACGATGACGATAAGGATCGATGGGGATCCGAGCTCGAGCCGATTACC
ATCAATAATTTTCGTTATTCAGATCCGGTGAATAATGATACCATCATCATGATGGAACCACCGTACTGTAAAGGG
CTGGATATTTATTATAAAGCGTTCAAAATCACCGACCGCATCTGGATCGTGCCGGAACGCTACGAATTCGGCACC
AAACCGGAAGATTTTAATCCGCCGAGTAGTCTGATCGAAGGTGCATCGGAATACTACGATCCGAATTATCTGCGT
ACTGACTCTGATAAAGATCGCTTTCTGCAAACGATGGTAAAACTGTTCAATCGTATCAAAAACAATGTAGCAGGC
GAAGCCCTGCTGGATAAAATCATCAACGCCATTCCGTATCTGGGAAACAGTTATTCTCTGCTGGATAAATTCGAT
ACAAACTCGAACTCTGTGTCATTCAACCTGCTGGAACAGGACCCGAGCGGCGCGACCACTAAGAGTGCGATGCTG
ACTAACCTGATTATTTTCGGTCCGGGACCGGTACTGAATAAAAATGAAGTTCGCGGCATTGTACTGCGTGTCGAT
AATAAAAACTATTTCCCATGTCGTGATGGCTTCGGCAGCATCATGCAGATGGCCTTTTGTCCGGAATATGTGCCA
ACTTTCGATAATGTGATTGAGAACATCACCTCTCTGACGATTGGTAAAAGTAAATATTTCCAGGATCCGGCTCTG
CTGCTGATGCATGAACTGATCCATGTTCTGCATGGCCTGTATGGCATGCAGGTTTCATCCCACGAAATTATCCCA
TCCAAACAGGAAATTTACATGCAGCATACATATCCGATTAGTGCCGAAGAACTGTTCACTTTTGGCGGCCAGGAT
GCGAACCTGATTTCGATTGACATTAAAAACGATCTGTATGAAAAAACTCTGAACGATTATAAAGCGATTGCCAAC
AAACTGTCTCAGGTAACCTCCTGTAACGATCCGAATATTGATATTGACAGTTATAAACAAATTTATCAGCAGAAG
TATCAGTTCGATAAAGACTCTAATGGCCAGTATATTGTTAACGAAGATAAATTCCAGATTCTGTACAATAGCATT
ATGTATGGCTTTACTGAGATCGAACTGGGTAAAAAATTTAACATCAAGACTCGTCTGAGCTATTTTAGCATGAAT
CATGATCCAGTGAAAATCCCGAATCTGCTGGATGATACGATTTATAATGATACCGAAGGATTTAACATCGAAAGC
Figure 10-1 SEQ ID NO: 7

```
AAGGATCTGAAATCCGAATATAAAGGGCAGAACATGCGCGTTAATACCAATGCATTTCGCAATGTTGATGGTTCA
GGCCTGGTGTCGAAACTGATTGGGCTGTGTAAGAAAATCATTCCACCGACAAATATTCGCGAAAATCTGTACAAC
CGTACGGCGAGCCTGACCGATCTGGGGGGGAGAACTGTGTATTAAAATCAAAAATGAAGATCTGACCTTCATTGCT
GAGAAGAATAGCTTTTCCGAAGAGCCATTCCAGGACGAAATCGTGTCTTATAACACCAAGAATAAACCGCTGAAT
TTCAACTACTCCCTGGACAAAATCATTGTGGATTACAACCTGCAGAGTAAAATTACCCTGCCGAATGATCGTACC
ACCCCGGTGACGAAAGGCATCCCTTACGCACCAGAATATAAATCAAATGCAGCCTCGACTATCGAGATCCATAAT
ATTGATGACAACACTATTTACCAGTACCTGTATGCTCAGAAATCTCCGACGACGCTGCAGCGCATCACCATGACT
AACAGCGTGGACGATGCCCTGATTAATAGCACCAAAATCTACTCTTACTTTCCGTCGGTGATCTCTAAGGTTAAT
CAGGGCGCGCAAGGTATCCTGTTTCTGCAATGGGTGCGTGATATTATTGATGATTTCACTAATGAATCTAGCCAG
AAAACGACAATTGATAAAATTTCGGATGTTTCCACCATCGTGCCTTACATCGGCCCAGCGCTGAACATCGTGAAG
CAGGGTTATGAGGGTAACTTTATCGGAGCACTGGAAACGACCGGCGTGGTTCTGCTGCTGGAATATATTCCGGAG
ATTACTCTGCCAGTTATTGCGGCTCTGTCGATTGCAGAGAGCTCAACGCAGAAAGAAAAAATTATTAAGACGATC
GACAATTTCCTGGAAAAGCGCTACGAAAAATGGATCGAAGTGTATAAGCTGGTGAAAGCGAAATGGCTGGGGACC
GTGAACACCCAGTTCCAAAAACGTTCCTATCAAATGTATCGTAGCCTGGAATATCAGGTGGACGCCATTAAAAAG
ATCATCGATTACGAATATAAGATCTACTCCGGTCCGGACAAAGAACAGATTGCGGACGAAATTAACAATCTGAAA
AATAAACTGGAGGAAAAAGCCAACAAAGCGATGATTAATATCAATATTTTCATGCGTGAAAGCAGCCGTAGCTTC
CTGGTCAATCAGATGATTAATGAAGCGAAGAAACAACTGCTGGAATTTGATACGCAATCTAAAAATATTCTGATG
CAATACATCAAAGCCAATTCTAAATTTATTGGGATCACGGAACTGAAAAAGCTGGAATCGAAAATCAATAAAGTC
TTTAGCACCCCGATTCCGTTCTCCTACTCGTAAGGTACCATGGAATTCGAAGCTTGATCCGGCTGCTAACAAAGC
CCGAAAGGAAGCTGAGTTGGCTGCTGCCACCGCTGAGCAATAACTAGCATAACCCCTTGGGGCCTCTAAACGGGT
CTTGAGGGGTTTTTTGCTGAAAGGAGGAACTATATCCGGATCTGGCGTAATAGCGAAGAGGCCCGCACCGATCGC
CCTTCCCAACAGTTGCGCAGCCTGAATGGCGAATGGGACGCGCCCTGTAGCGGCGCATTAAGCGCGGCGGGTGTG
GTGGTTACGCGCAGCGTGACCGCTACACTTGCCAGCGCCCTAGCGCCCGCTCCTTTCGCTTTCTTCCCTTCCTTT
CTCGCCACGTTCGCCGGCTTTCCCCGTCAAGCTCTAAATCGGGGGCTCCCTTTAGGGTTCCGATTTAGTGCTTTA
CGGCACCTCGACCCCAAAAAACTTGATTAGGGTGATGGTTCACGTAGTGGGCCATCGCCCTGATAGACGGTTTTT
CGCCCTTTGACGTTGGAGTCCACGTTCTTTAATAGTGGACTCTTGTTCCAAACTGGAACAACACTCAACCCTATC
TCGGTCTATTCTTTTGATTTATAAGGGATTTTGCCGATTTCGGCCTATTGGTTAAAAAATGAGCTGATTTAACAA
AAATTTAACGCGAATTTTAACAAAATATTAACGCTTACAATTTAGGTGGCACTTTTCGGGGAAATGTGCGCGGAA
CCCCTATTTGTTTATTTTTCTAAATACATTCAAATATGTATCCGCTCATGAGACAATAACCCTGATAAATGCTTC
AATAATATTGAAAAAGGAAGAGTATGAGTATTCAACATTTCCGTGTCGCCCTTATTCCCTTTTTTGCGGCATTTT
GCCTTCCTGTTTTTGCTCACCCAGAAACGCTGGTGAAAGTAAAAGATGCTGAAGATCAGTTGGGTGCACGAGTGG
GTTACATCGAACTGGATCTCAACAGCGGTAAGATCCTTGAGAGTTTTCGCCCCGAAGAACGTTTTCCAATGATGA
GCACTTTTAAAGTTCTGCTATGTGGCGCGGTATTATCCCGTATTGACGCCGGGCAAGAGCAACTCGGTCGCCGCA
TACACTATTCTCAGAATGACTTGGTTGAGTACTCACCAGTCACAGAAAAGCATCTTACGGATGGCATGACAGTAA
GAGAATTATGCAGTGCTGCCATAACCATGAGTGATAACACTGCGGCCAACTTACTTCTGACAACGATCGGAGGAC
CGAAGGAGCTAACCGCTTTTTTGCACAACATGGGGGATCATGTAACTCGCCTTGATCGTTGGGAACCGGAGCTGA
ATGAAGCCATACCAAACGACGAGCGTGACACCACGATGCCTGTAGCAATGGCAACAACGTTGCGCAAACTATTAA
CTGGCGAACTACTTACTCTAGCTTCCCGGCAACAATTAATAGACTGGATGGAGGCGGATAAAGTTGCAGGACCAC
TTCTGCGCTCGGCCCTTCCGGCTGGCTGGTTTATTGCTGATAAATCTGGAGCCGGTGAGCGTGGGTCTCGCGGTA
TCATTGCAGCACTGGGGCCAGATGGTAAGCCCTCCCGTATCGTAGTTATCTACACGACGGGGAGTCAGGCAACTA
TGGATGAACGAAATAGACAGATCGCTGAGATAGGTGCCTCACTGATTAAGCATTGGTAACTGTCAGACCAAGTTT
ACTCATATATACTTTAGATTGATTTAAAACTTCATTTTTAATTTAAAAGGATCTAGGTGAAGATCCTTTTTGATA
ATCTCATGACCAAAATCCCTTAACGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAACCACCGCTACCAGCGGTGGTTT
GTTTGCCGGATCAAGAGCTACCAACTCTTTTTCCGAAGGTAACTGGCTTCAGCAGAGCGCAGATACCAAATACTG
TTCTTCTAGTGTAGCCGTAGTTAGGCCACCACTTCAAGAACTCTGTAGCACCGCCTACATACCTCGCTCTGCTAA
TCCTGTTACCAGTGGCTGCTGCCAGTGGCGATAAGTCGTGTCTTACCGGGTTGGACTCAAGACGATAGTTACCGG
ATAAGGCGCAGCGGTCGGGCTGAACGGGGGGTTCGTGCACACAGCCCAGCTTGGAGCGAACGACCTACACCGAAC
TGAGATACCTACAGCGTGAGCTATGAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACGCCTGGTATCTTTATAGTCCTGTCG
GGTTTCGCCACCTCTGACTTGAGCGTCGATTTTTGTGATGCTCGTCAGGGGGGCGGAGCCTATGGAAAAACGCCA
GCAACGCGGCCTTTTTACGGTTCCTGGCCTTTTGCTGGCCTTTTGCTCACATGTTCTTTCCTGCGTTATCCCCTG
ATTCTGTGGATAACCGTATTACCGCCTTTGAGTGAGCTGATACCGCTCGCCGCAGCCGAACGACCGAGCGCAGCG
AGTCAGTGAGCGAGGAAGCGGAAGAGCGCCCAATACGCAAACCGCCTCTCCCCGCGCGTTGGCCGATTCATTAAT
GCAG
```

Figure 10-2 SEQ ID NO: 7.

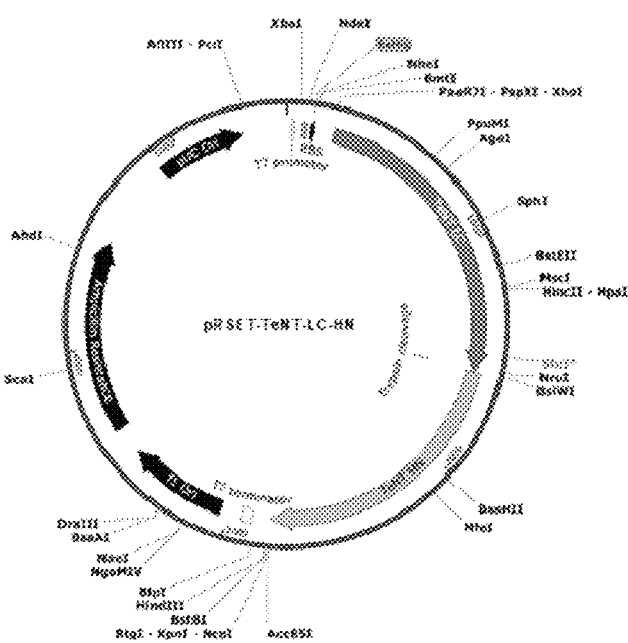

Figure 11.

KNLDCWVDNEEDIDVILKKSTILNLDINNDIISDISGFNSSVITYPDAQLVPGINGKAIHLVNNESSEVIVHKAM
DIEYNDMFNNFTVSFWLRVPKVSASHLEQYGTNEYSIISSMKKHSLSIGSGWSVSLKGNNLIWTLKDSAGEVRQI
TFRDLPDKFNAYLANKWVFITITNDRLSSANLYINGVLMGSAEITGLGAIREDNNITLKLDRCNNNNQYVSIDKF
RIFCKALNPKEIEKLYTSYLSITFLRDFWGNPLRYDTEYYLIPVASSSKDVQLKNITDYMYLTNAPSYTNGKLNI
YYRRLYNGLKFIIKRYTPNNEIDSFVKSGDFIKLYVSYNNNEHIVGYPKDGNAFNNLDRILEVGYNAPGIPLYKK
MEAVKLRDLKTYSVQLKLYDDKNASLGLVGTHNGQIGNDPNRDILIASNAYFNHLKDKILGCDWYFVPTDEGWTN
D
Figure 12 SEQ ID NO: 8.

GATCTCGATCCCGCGAAATTAATACGACTCACTATAGGGAGACCACAACGGTTTCCCTCTAGAAATAATTTTGTT
TAACTTTAAGAAGGAGATATACATATGCGGGGTTCTCATCATCATCATCATCATGGTATGGCTAGCATGACTGGT
GGACAGCAAATGGGTCGGGATCTGTACGACGATGACGATAAGGATCGATGGGGATCCGAGCTCGAGAAAAATTTG
GATTGCTGGGTCGACAATGAGGAGGACATTGATGTGATATTAAAGAAATCCACTATCTTAAATCTTGATATAAAC
AATGACATCATCTCGGATATATCTGGGTTCAATTCTTCCGTCATAACTTACCCTGATGCTCAACTGGTACCGGGA
ATTAATGGGAAGGCCATACACTTAGTCAACAACGAATCTTCCGAGGTGATTGTACATAAGGCAATGGACATAGAG
TACAATGACATGTTTAATAACTTTACTGTCTCGTTCTGGTTACGCGTGCCCAAAGTATCTGCCTCACACCTGGAA
CAGTATGGCACAAATGAATATTCTATTATCAGTAGTATGAAGAAACACTCGCTTTCTATAGGATCCGGCTGGAGT
GTTTCGCTGAAGGGCAATAACTTGATCTGGACCCTTAAAGATTCAGCGGGAGAAGTAAGACAAATAACTTTCCGG
GATTTGCCTGATAAGTTCAACGCATACCTGGCCAATAAGTGGGTTTTCATAACTATAACAAATGACCGCTTGTCT
AGCGCCAACTTATACATCAATGGAGTATTGATGGGTTCCGCTGAGATTACAGGCTTGGGTGCCATAAGAGAGGAC
AATAATATCACCCTGAAACTGGACCGCTGCAATAATAACAATCAGTACGTGAGCATAGATAAATTCCGTATTTTT
TGCAAAGCCCTGAACCCGAAAGAAATCGAAAAACTGTATACTTCATATCTGAGCATAACATTTCTGCGTGATTTT
TGGGGTAACCCGCTGCGTTATGATACCGAATACTACCTGATTCCGGTTGCCAGCAGCAGCAAAGATGTTCAGCTG
AAAAATATTACCGACTATATGTATCTGACAAATGCGCCGTCTTATACCAATGGCAAACTGAATATTTATTATCGC
CGGTTGTACAACGGGCTGAAGTTCATTATTAAACGGTACACCCCGAACAACGAAATCGATTCATTTGTTAAATCC
GGGGATTTCATAAAGTTATACGTGAGCTATAATAACAACGAGCATATTGTAGGTTATCCGAAAGACGGTAATGCT
TTCAACAACTTGGATCGGATACTGGAAGTTGGTTACAACGCCCCAGGTATTCCACTGTATAAGAAAATGGAAGCC
GTCAAGTTGCGTGATTTAAAGACGTACTCAGTACAGCTTAAATTATACGACGATAAGAATGCAAGCCTTGGATTG
GTTGGGACCCACAATGGTCAGATTGGAAATGACCCCAATCGGGACATTCTGATAGCATCCAACGCGTACTTCAAC
CATTTGAAAGATAAAATCCTGGGCTGTGATTGGTACTTTGTACCGACTGATGAAGGATGGACGAATGACTAAGAA
TTCGAAGCTTGATCCGGCTGCTAACAAAGCCCGAAAGGAAGCTGAGTTGGCTGCTGCCACCGCTGAGCAATAACT
AGCATAACCCCTTGGGGCCTCTAAACGGGTCTTGAGGGGTTTTTTGCTGAAAGGAGGAACTATATCCGGATCTGG
Figure 13-1 SEQ ID NO: 9

```
CGTAATAGCGAAGAGGCCCGCACCGATCGCCCTTCCCAACAGTTGCGCAGCCTGAATGGCGAATGGGACGCGCCC
TGTAGCGGCGCATTAAGCGCGGCGGGTGTGGTGGTTACGCGCAGCGTGACCGCTACACTTGCCAGCGCCCTAGCG
CCCGCTCCTTTCGCTTTCTTCCCTTCCTTTCTCGCCACGTTCGCCGGCTTTCCCCGTCAAGCTCTAAATCGGGGG
CTCCCTTTAGGGTTCCGATTTAGTGCTTTACGGCACCTCGACCCCAAAAAACTTGATTAGGGTGATGGTTCACGT
AGTGGGCCATCGCCCTGATAGACGGTTTTTCGCCCTTTGACGTTGGAGTCCACGTTCTTTAATAGTGGACTCTTG
TTCCAAACTGGAACAACACTCAACCCTATCTCGGTCTATTCTTTTGATTTATAAGGGATTTTGCCGATTTCGGCC
TATTGGTTAAAAAATGAGCTGATTTAACAAAAATTTAACGCGAATTTTAACAAAATATTAACGCTTACAATTTAG
GTGGCACTTTTCGGGGAAATGTGCGCGGAACCCCTATTTGTTTATTTTTCTAAATACATTCAAATATGTATCCGC
TCATGAGACAATAACCCTGATAAATGCTTCAATAATATTGAAAAAGGAAGAGTATGAGTATTCAACATTTCCGTG
TCGCCCTTATTCCCTTTTTTGCGGCATTTTGCCTTCCTGTTTTTGCTCACCCAGAAACGCTGGTGAAAGTAAAAG
ATGCTGAAGATCAGTTGGGTGCACGAGTGGGTTACATCGAACTGGATCTCAACAGCGGTAAGATCCTTGAGAGTT
TTCGCCCCGAAGAACGTTTTCCAATGATGAGCACTTTTAAAGTTCTGCTATGTGGCGCGGTATTATCCCGTATTG
ACGCCGGGCAAGAGCAACTCGGTCGCCGCATACACTATTCTCAGAATGACTTGGTTGAGTACTCACCAGTCACAG
AAAAGCATCTTACGGATGGCATGACAGTAAGAGAATTATGCAGTGCTGCCATAACCATGAGTGATAACACTGCGG
CCAACTTACTTCTGACAACGATCGGAGGACCGAAGGAGCTAACCGCTTTTTTGCACAACATGGGGGATCATGTAA
CTCGCCTTGATCGTTGGGAACCGGAGCTGAATGAAGCCATACCAAACGACGAGCGTGACACCACGATGCCTGTAG
CAATGGCAACAACGTTGCGCAAACTATTAACTGGCGAACTACTTACTCTAGCTTCCCGGCAACAATTAATAGACT
GGATGGAGGCGGATAAAGTTGCAGGACCACTTCTGCGCTCGGCCCTTCCGGCTGGCTGGTTTATTGCTGATAAAT
CTGGAGCCGGTGAGCGTGGGTCTCGCGGTATCATTGCAGCACTGGGGCCAGATGGTAAGCCCTCCCGTATCGTAG
TTATCTACACGACGGGGAGTCAGGCAACTATGGATGAACGAAATAGACAGATCGCTGAGATAGGTGCCTCACTGA
TTAAGCATTGGTAACTGTCAGACCAAGTTTACTCATATATACTTTAGATTGATTTAAAACTTCATTTTTAATTTA
AAAGGATCTAGGTGAAGATCCTTTTTGATAATCTCATGACCAAAATCCCTTAACGTGAGTTTTCGTTCCACTGAG
CGTCAGACCCCGTAGAAAAGATCAAAGGATCTTCTTGAGATCCTTTTTTTCTGCGCGTAATCTGCTGCTTGCAAA
CAAAAAAACCACCGCTACCAGCGGTGGTTTGTTTGCCGGATCAAGAGCTACCAACTCTTTTTCCGAAGGTAACTG
GCTTCAGCAGAGCGCAGATACCAAATACTGTTCTTCTAGTGTAGCCGTAGTTAGGCCACCACTTCAAGAACTCTG
TAGCACCGCCTACATACCTCGCTCTGCTAATCCTGTTACCAGTGGCTGCTGCCAGTGGCGATAAGTCGTGTCTTA
CCGGGTTGGACTCAAGACGATAGTTACCGGATAAGGCGCAGCGGTCGGGCTGAACGGGGGGTTCGTGCACACAGC
CCAGCTTGGAGCGAACGACCTACACCGAACTGAGATACCTACAGCGTGAGCTATGAGAAAGCGCCACGCTTCCCG
AAGGGAGAAAGGCGGACAGGTATCCGGTAAGCGGCAGGGTCGGAACAGGAGAGCGCACGAGGGAGCTTCCAGGGG
GAAACGCCTGGTATCTTTATAGTCCTGTCGGGTTTCGCCACCTCTGACTTGAGCGTCGATTTTTGTGATGCTCGT
CAGGGGGGCGGAGCCTATGGAAAAACGCCAGCAACGCGGCCTTTTTACGGTTCCTGGCCTTTTGCTGGCCTTTTG
CTCACATGTTCTTTCCTGCGTTATCCCCTGATTCTGTGGATAACCGTATTACCGCCTTTGAGTGAGCTGATACCG
CTCGCCGCAGCCGAACGACCGAGCGCAGCGAGTCAGTGAGCGAGGAAGCGGAAGAGCGCCCAATACGCAAACCGC
CTCTCCCCGCGCGTTGGCCGATTCATTAATGCAG
```

Figure 13-2 SEQ ID NO: 9.

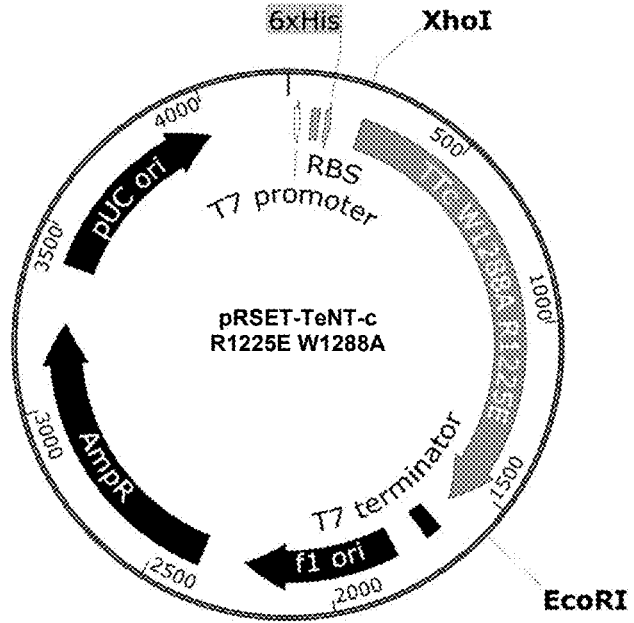

Figure 14.

```
PITINNFRYSDPVNNDTIIMMEPPYCKGLDIYYKAFKITDRIWIVPERYEFGTKPEDFNPPSSLIEGASEYYDPN
YLRTDSDKDRFLQTMVKLFNRIKNNVAGEALLDKIINAIPYLGNSYSLLDKFDTNSNSVSFNLLEQDPSGATTKS
AMLTNLIIFGPGPVLNKNEVRGIVLRVDNKNYFPCRDGFGSIMQMAFCPEYVPTFDNVIENITSLTIGKSKYFQD
PALLLMHELIHVLHGLYGMQVSSHEIIPSKQEIYMQHTYPISAEELFTFGGQDANLISIDIKNDLYEKTLNDYKA
IANKLSQVTSCNDPNIDIDSYKQIYQQKYQFDKDSNGQYIVNEDKFQILYNSIMYGFTEIELGKKFNIKTRLSYF
SMNHDPVKIPNLLDDTIYNDTEGFNIESKDLKSEYKGQNMRVNTNAFRNVDGSGLVSKLIGLCKKIIPPTNIREN
LYNRTASLTDLGGELCIKIKNEDLTFIAEKNSFSEEPFQDEIVSYNTKNKPLNFNYSLDKIIVDYNLQSKITLPN
DRTTPVTKGIPYAPEYKSNAASTIEIHNIDDNTIYQYLYAQKSPTTLQRITMTNSVDDALINSTKIYSYFPSVIS
KVNQGAQGILFLQWVRDIIDDFTNESSQKTTIDKISDVSTIVPYIGPALNIVKQGYEGNFIGALETTGVVLLLEY
IPEITLPVIAALSIAESSTQKEKIIKTIDNFLEKRYEKWIEVYKLVKAKWLGTVNTQFQKRSYQMYRSLEYQVDA
IKKIIDYEYKIYSGPDKEQIADEINNLKNKLEEKANKAMININIFMRESSRSFLVNQMINEAKKQLLEFDTQSKN
ILMQYIKANSKFIGITELKKLESKINKVFSTPIPFSYSKNLDCWVDNEEDIDVILKKSTILNLDINNDIISDISG
FNSSVITYPDAQLVPGINGKAIHLVNNESSEVIVHKAMDIEYNDMFNNFTVSFWLRVPKVSASHLEQYGTNEYSI
ISSMKKHSLSIGSGWSVSLKGNNLIWTLKDSAGEVRQITFRDLPDKFNAYLANKWVFITITNDRLSSANLYINGV
LMGSAEITGLGAIREDNNITLKLDRCNNNNQYVSIDKFRIFCKALNPKEIEKLYTSYLSITFLRDFWGNPLRYDT
EYYLIPVASSSKDVQLKNITDYMYLTNAPSYTNGKLNIYYRRLYNGLKFIIKRYTPNNEIDSFVKSGDFIKLYVS
YNNNEHIVGYPKDGNAFNNLDRILEVGYNAPGIPLYKKMEAVKLRDLKTYSVQLKLYDDKNASLGLVGTHNGQIG
NDPNRDILIASNAYFNHLKDKILGCDWYFVPTDEGWTND
```
Figure 15 SEQ ID NO: 10.

```
GATCTCGATCCCGCGAAATTAATACGACTCACTATAGGGAGACCACAACGGTTTCCCTCTAGAAATAATTTTGTT
TAACTTTAAGAAGGAGATATACATATGCGGGGTTCTCATCATCATCATCATCATGGTATGGCTAGCATGACTGGT
GGACAGCAAATGGGTCGGGATCTGTACGACGATGACGATAAGGATCGATGGGGATCCGAGCTCGAGCCGATCACC
ATCAACAACTTCCGTTACTCTGACCCGGTTAACAACGACACCATCATCATGATGGAACCGCCGTACTGCAAAGGT
CTGGACATCTACTACAAAGCGTTCAAAATCACCGACCGTATCTGGATCGTTCCGGAACGTTACGAATTCGGTACC
AAACCGGAAGACTTCAACCCGCCGTCTTCTCTGATCGAAGGTGCGTCTGAATACTACGACCCGAACTACCTGCGT
ACCGACTCTGACAAAGACCGTTTCCTGCAGACCATGGTTAAACTGTTCAACCGTATCAAAAACAACGTTGCGGGT
GAAGCGCTGCTGGACAAAATCATCAACGCGATCCCGTACCTGGGTAACTCTTACTCTCTGCTGGACAAATTCGAC
ACCAACTCTAACTCTGTTTCTTTCAACCTGCTGGAACAGGACCCGTCTGGTGCGACCACCAAATCTGCGATGCTG
ACCAACCTGATCATCTTCGGTCCGGGTCCGGTTCTGAACAAAAACGAAGTTCGTGGTATCGTTCTGCGTGTTGAC
AACAAAAACTACTTCCCGTGCCGTGACGGTTTCGGTTCTATCATGCAGATGGCGTTCTGCCCGGAATACGTTCCG
ACCTTCGACAACGTTATCGAAAACATCACCTCTCTGACCATCGGTAAATCTAAATACTTCCAGGACCCGGCGCTG
CTGCTGATGCACGAACTGATCCACGTTCTGCACGGTCTGTACGGTATGCAGGTTTCTTCTCACGAAATCATCCCG
TCTAAACAGGAAATCTACATGCAGCACACCTACCCGATCTCTGCGGAAGAACTGTTCACCTTCGGTGGTCAGGAC
GCGAACCTGATCTCTATCGACATCAAAAACGACCTGTACGAAAAAACCCTGAACGACTACAAAGCGATCGCGAAC
AAACTGTCTCAGGTTACCTCTTGCAACGACCCGAACATCGACATCGACTCTTACAAACAGATCTACCAGCAGAAA
TACCAGTTCGACAAAGACTCTAACGGTCAGTACATCGTTAACGAAGACAAATTCCAGATCCTGTACAACTCTATC
ATGTACGGTTTCACCGAAATCGAACTGGGTAAAAAATTCAACATCAAAACCCGTCTGTCTTACTTCTCTATGAAC
CACGACCCGGTTAAAATCCCGAACCTGCTGGACGACACCATCTACAACGACACCGAAGGTTTCAACATCGAATCT
AAAGACCTGAAATCTGAATACAAAGGTCAGAACATGCGTGTTAACACCAACGCGTTCCGTAACGTTGACGGTTCT
GGTCTGGTTTCTAAACTGATCGGTCTGTGCAAAAAAATCATCCCGCCGACCAACATCCGTGAAAACCTGTACAAC
CGTACCGCGTCTCTGACCGACCTGGGTGGTGAACTGTGCATCAAAATCAAAAACGAAGACCTGACCTTCATCGCG
GAAAAAAACTCTTTCTCTGAAGAACCGTTCCAGGACGAAATCGTTTCTTACAACACCAAAAACAAACCGCTGAAC
TTCAACTACTCTCTGGACAAAATCATCGTTGACTACAACCTGCAGTCTAAAATCACCCTGCCGAACGACCGTACC
ACCCCGGTTACCAAAGGTATCCCGTACGCGCCGGAATACAAATCTAACGCGGCGTCTACCATCGAAATCCACAAC
ATCGACGACAACACCATCTACCAGTACCTGTACGCGCAGAAATCTCCGACCACCCTGCAGCGTATCACCATGACC
AACTCTGTTGACGACGCGCTGATCAACTCTACCAAAATCTACTCTTACTTCCCGTCTGTTATCTCTAAAGTTAAC
CAGGGTGCGCAGGGTATCCTGTTCCTGCAGTGGGTTCGTGACATCATCGACGACTTCACCAACGAATCTTCTCAG
AAAACCACCATCGACAAAATCTCTGACGTTTCTACCATCGTTCCGTACATCGGTCCGGCGCTGAACATCGTTAAA
CAGGGTTACGAAGGTAACTTCATCGGTGCGCTGGAAACCACCGGTGTTGTTCTGCTGCTGGAATACATCCCGGAA
ATCACCCTGCCGGTTATCGCGGCGCTGTCTATCGCGGAATCTTCTACCCAGAAAGAAAAAATCATCAAAACCATC
GACAACTTCCTGGAAAAACGTTACGAAAAATGGATCGAAGTTTACAAACTGGTTAAAGCGAAATGGCTGGGTACC
GTTAACACCCAGTTCCAGAACGTTCTTACCAGATGTACCGTTCTCTGGAATACCAGGTTGACGCGATCAAAAAA
ATCATCGACTACGAATACAAATCTACTCTGGTCCGGACAAAGAACAGATCGCGGACGAAATCAACAACCTGAAA
AACAAACTGGAAGAAAAAGCGAACAAAGCGATGATCAACATCAACATCTTCATGCGTGAATCTTCTCGTTCTTTC
CTGGTTAACCAGATGATCAACGAAGCGAAAAAACAGCTGCTGGAATTCGACACCCAGTCTAAAAACATCCTGATG
CAGTACATCAAAGCGAACTCTAAATTCATCGGTATCACCGAACTGAAAAAACTGGAATCTAAAATCAACAAAGTT
TTCTCTACCCCGATCCCGTTCTCTTACTCTAAAAACCTGGACTGCTGGGTTGACAACGAAGAAGACATCGACGTT
```
Figure 16-1 SEQ ID NO: 11

```
ATCCTGAAAAAATCTACCATCCTGAACCTGGACATCAACAACGACATCATCTCTGACATCTCTGGTTTCAACTCT
TCTGTTATCACCTACCCGGACGCGCAGCTGGTTCCGGGTATCAACGGTAAAGCGATCCACCTGGTTAACAACGAA
TCTTCTGAAGTTATCGTTCACAAAGCGATGGACATCGAATACAACGACATGTTCAACAACTTCACCGTTTCTTTC
TGGCTGCGTGTTCCGAAAGTTTCTGCGTCTCACCTGGAACAGTACGGTACCAACGAATACTCTATCATCTCTTCT
ATGAAAAAACACTCTCTGTCTATCGGTTCTGGTTGGTCTGTTTCTCTGAAAGGTAACAACCTGATCTGGACCCTG
AAAGACTCTGCGGGTGAAGTTCGTCAGATCACCTTCCGTGACCTGCCGGACAAATTCAACGCGTACCTGGCGAAC
AAATGGGTTTTCATCACCATCACCAACGACCGTCTGTCTTCTGCGAACCTGTACATCAACGGTGTTCTGATGGGT
TCTGCGGAAATCACCGGTCTGGGTGCGATCCGTGAAGACAACAACATCACCCTGAAACTGGACCGTTGCAACAAC
AACAACCAGTACGTTTCTATCGACAAATTCCGTATCTTCTGCAAAGCGCTGAACCCGAAAGAAATCGAAAAACTG
TACACCTCTTACCTGTCTATCACCTTCCTGCGTGACTTCTGGGGTAACCCGCTGCGTTACGACACCGAATACTAC
CTGATCCCCGGTTGCGTCTTCTTCTAAAGACGTTCAGCTGAAAAACATCACCGACTACATGTACCTGACCAACGCG
CCGTCTTACACCAACGGTAAACTGAACATCTACTACCGTCGTCTGTACAACGGTCTGAAATTCATCATCAAACGT
TACACCCCGAACAACGAAATCGACTCTTTCGTTAAATCTGGTGACTTCATCAAACTGTACGTTTCTTACAACAAC
AACGAACACATCGTTGGTTACCCGAAAGACGGTAACGCGTTCAACAACCTGGACCGTATCCTGGAAGTTGGTTAC
AACGCGCCGGGTATCCCGCTGTACAAAAAAATGGAAGCGGTTAAACTGCGTGACCTGAAAACCTACTCTGTTCAG
CTGAAACTGTACGACGACAAAAACGCGTCTCTGGGTCTGGTTGGTACCCACAACGGTCAGATCGGTAACGACCCG
AACCGTGACATCCTGATCGCGTCTAACGCGTACTTCAACCACCTGAAAGACAAAATCCTGGGTTGCGACTGGTAC
TTCGTTCCGACCGACGAAGGTTGGACCAACGACTAAAAGCTTGATCCGGCTGCTAACAAAGCCCGAAAGGAAGCT
GAGTTGGCTGCTGCCACCGCTGAGCAATAACTAGCATAACCCCTTGGGGCCTCTAAACGGGTCTTGAGGGGTTTT
TTGCTGAAAGGAGGAACTATATCCGGATCTGGCGTAATAGCGAAGAGGCCCGCACCGATCGCCCTTCCCAACAGT
TGCGCAGCCTGAATGGCGAATGGGACGCGCCCTGTAGCGGCGCATTAAGCGCGGCGGGTGTGGTGGTTACGCGCA
GCGTGACCGCTACACTTGCCAGCGCCCTAGCGCCCGCTCCTTTCGCTTTCTTCCCTTCCTTTCTCGCCACGTTCG
CCGGCTTTCCCCGTCAAGCTCTAAATCGGGGGCTCCCTTTAGGGTTCCGATTTAGTGCTTTACGGCACCTCGACC
CCAAAAAACTTGATTAGGGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCTATCTCGGTCTATTCTT
TTGATTTATAAGGGATTTTGCCGATTTCGGCCTATTGGTTAAAAAATGAGCTGATTTAACAAAAATTTAACGCGA
ATTTTAACAAAATATTAACGCTTACAATTTAGGTGGCACTTTTCGGGGAAATGTGCGCGGAACCCCTATTTGTTT
ATTTTTCTAAATACATTCAAATATGTATCCGCTCATGAGACAATAACCCTGATAAATGCTTCAATAATATTGAAA
AAGGAAGAGTATGAGTATTCAACATTTCCGTGTCGCCCTTATTCCCTTTTTTGCGGCATTTTGCCTTCCTGTTTT
TGCTCACCCAGAAACGCTGGTGAAAGTAAAAGATGCTGAAGATCAGTTGGGTGCACGAGTGGGTTACATCGAACT
GGATCTCAACAGCGGTAAGATCCTTGAGAGTTTTCGCCCCGAAGAACGTTTTCCAATGATGAGCACTTTTAAAGT
TCTGCTATGTGGCGCGGTATTATCCCGTATTGACGCCGGGCAAGAGCAACTCGGTCGCCGCATACACTATTCTCA
GAATGACTTGGTTGAGTACTCACCAGTCACAGAAAAGCATCTTACGGATGGCATGACAGTAAGAGAATTATGCAG
TGCTGCCATAACCATGAGTGATAACACTGCGGCCAACTTACTTCTGACAACGATCGGAGGACCGAAGGAGCTAAC
CGCTTTTTTGCACAACATGGGGGATCATGTAACTCGCCTTGATCGTTGGGAACCGGAGCTGAATGAAGCCATACC
AAACGACGAGCGTGACACCACGATGCCTGTAGCAATGGCAACAACGTTGCGCAAACTATTAACTGGCGAACTACT
TACTCTAGCTTCCCGGCAACAATTAATAGACTGGATGGAGGCGGATAAAGTTGCAGGACCACTTCTGCGCTCGGC
CCTTCCGGCTGGCTGGTTTATTGCTGATAAATCTGGAGCCGGTGAGCGTGGGTCTCGCGGTATCATTGCAGCACT
GGGGCCAGATGGTAAGCCCTCCCGTATCGTAGTTATCTACACGACGGGGAGTCAGGCAACTATGGATGAACGAAA
TAGACAGATCGCTGAGATAGGTGCCTCACTGATTAAGCATTGGTAACTGTCAGACCAAGTTTACTCATATATACT
TTAGATTGATTTAAAACTTCATTTTTAATTTAAAAGGATCTAGGTGAAGATCCTTTTTGATAATCTCATGACCAA
AATCCCTTAACGTGAGTTTTCGTTCCACTGAGCGTCAGACCCCGTAGAAAAGATCAAAGGATCTTCTTGAGATCC
TTTTTTTCTGCGCGTAATCTGCTGCTTGCAAACAAAAAAACCACCGCTACCAGCGGTGGTTTGTTTGCCGGATCA
AGAGCTACCAACTCTTTTTCCGAAGGTAACTGGCTTCAGCAGAGCGCAGATACCAAATACTGTTCTTCTAGTGTA
GCCGTAGTTAGGCCACCACTTCAAGAACTCTGTAGCACCGCCTACATACCTCGCTCTGCTAATCCTGTTACCAGT
GGCTGCTGCCAGTGGCGATAAGTCGTGTCTTACCGGGTTGGACTCAAGACGATAGTTACCGGATAAGGCGCAGCG
GTCGGGCTGAACGGGGGGTTCGTGCACACAGCCCAGCTTGGAGCGAACGACCTACACCGAACTGAGATACCTACA
GCGTGAGCTATGAGAAAGCGCCACGCTTCCCGAAGGGAGAAAGGCGGACAGGTATCCGGTAAGCGGCAGGGTCGG
AACAGGAGAGCGCACGAGGGAGCTTCCAGGGGGAAACGCCTGGTATCTTTATAGTCCTGTCGGGTTTCGCCACCT
CTGACTTGAGCGTCGATTTTTGTGATGCTCGTCAGGGGGGCGGAGCCTATGGAAAAACGCCAGCAACGCGGCCTT
TTTACGGTTCCTGGCCTTTTGCTGGCCTTTTGCTCACATGTTCTTTCCTGCGTTATCCCCTGATTCTGTGGATAA
CCGTATTACCGCCTTTGAGTGAGCTGATACCGCTCGCCGCAGCCGAACGACCGAGCGCAGCGAGTCAGTGAGCGA
GGAAGCGGAAGAGCGCCCAATACGCAAACCGCCTCTCCCCGCGCGTTGGCCGATTCATTAATGCAG
```

Figure 16-2 SEQ ID NO: 11.

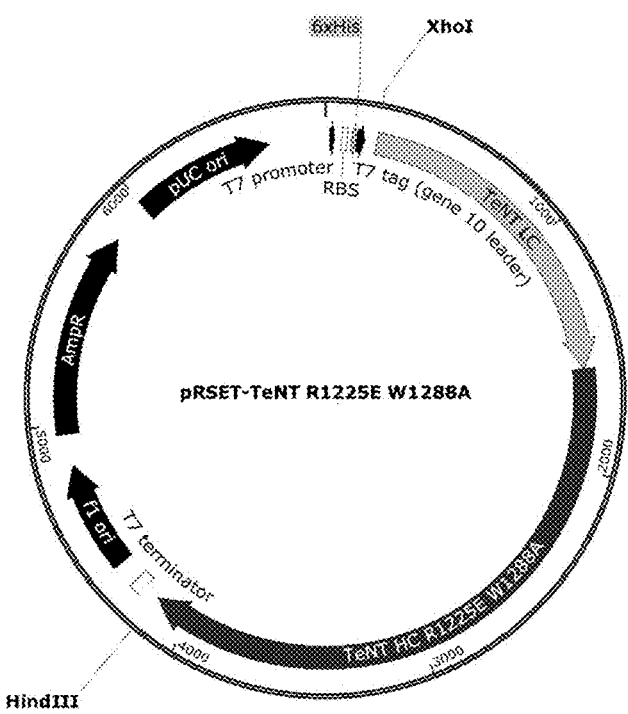

Figure 17.

PITINNFRYSDPVNNDTIIMMEPPYCKGLDIYYKAFKITDRIWIVPERYEFGTKPEDFNPPSSLIEGASEYYDPN
YLRTDCDKDRFLQTMVKLFNRIKNNVAGEALLDKIINAIPYLGNCYSLLDKFDTNSNSVSFNLLEQDPCGATTKS
AMLTNLIIFGPGPVLNKNEVRGIVLRVDNKNYFPCRDGFGSIMQMAFCPEYVPTFDNVIENITSLTIGKSKYFQD
PALLLMHELIHVLHGLYGMQVSCHEIIPSKQEIYMQHTYPISAEELFTFGGQDANLISIDIKNDLYEKTLNDYKA
IANKLSQVTSCNDPNIDIDSYKQIYQQKYQFDKDCNGQYIVNEDKFQILYNSIMYGFTEIELGKKFNIKTRLSYF
SMNHDPVKIPNLLDDTIYNDTEGFNIESKDLKSEYKGQNMRVNTNAFRNVDGCGLVSKLIGLCKKIIPPTNIREN
LYNRTASLTDLGGELCIKIKNEDLTFIAEKNSFSEEPFQDEIVSYNTKNKPLNFNYSLDKIIVDYNLQSKITLPN
DRTTPVTKGIPYAPEYKSNAASTIEIHNIDDNTIYQYLYAQKSPTTLQRITMTNSVDDALINSTKIYSYFPSVIC
KVNQGAQGILFLQWVRDIIDDFTNESSQKTTIDKISDVSTIVPYIGPALNIVKQGYEGNFIGALETTGVVLLLEY
IPEITLPVIAALSIAESSTQKEKIIKTIDNFLEKRYEKWIEVYKLVKAKWLGTVNTQFQKRSYQMYRSLEYQVDA
IKKIIDYEYKIYSGPDKEQIADEINNLKNKLEEKANKAMININIFMRESSRSFLVNQMINEAKKQLLEFDTQSKN
ILMQYIKANSKFIGITELKKLESKINKVFSTPIPFSYSKNLDCWVDNEEDIDVILKKSTILNLDINNDIISDISG
FNSSVITYPDAQLVPGINGKAIHLVNNESSEVIVHKAMDIEYNDMFNNFTVSFWLRVPKVSACHLEQYGTNEYSI
ISSMKKHSLSIGSGWSVSLKGNNLIWTLKDSAGEVRQITFRDLPDKFNAYLANKWVFITITNDRLCSANLYINGV
LMGSAEITGLGAIREDNNITLKLDRCNNNNQYVSIDKFRIFCKALNPKEIEKLYTSYLSITFLRDFWGNPLRYDT
EYYLIPVASSSKDVQLKNITDYMYLTNAPCYTNGKLNIYYRRLYNGLKFIIKRYTPNNEIDCFVKSGDFIKLYVS
YNNNEHIVGYPKDGNAFNNLDRILRVGYNAPGIPLYKKMEAVKLRDLKTYSVQLKLYDDKNASLGLVGTHNGQIG
NDPNRDILIASNWYFNHLKDKILGCDWYFVPTDEGWTND
Figure 18 SEQ ID NO: 12.

GATCTCGATCCCGCGAAATTAATACGACTCACTATAGGGAGACCACAACGGTTTCCCTCTAGAAATAATTTTGTT
TAACTTTAAGAAGGAGATATACATATGCGGGGTTCTCATCATCATCATCATCATGGTATGGCTAGCATGACTGGT
GGACAGCAAATGGGTCGGGATCTGTACGACGATGACGATAAGGATCGATGGGGATCCGAGCTCGAGCCGATCACC
ATCAACAACTTCCGTTACTCTGACCCGGTTAACAACGACACCATCATCATGATGGAACCGCCGTACTGCAAAGGT
CTGGACATCTACTACAAAGCGTTCAAAATCACCGACCGTATCTGGATCGTTCCGGAACGTTACGAATTCGGTACC
AAACCGGAAGACTTCAACCCGCCGTCTTCTCTGATCGAAGGTGCGTCTGAATACTACGACCCGAACTACCTGCGT
ACCGACTGCGACAAAGACCGTTTCCTGCAGACCATGGTTAAACTGTTCAACCGTATCAAAAACAACGTTGCGGGT
GAAGCGCTGCTGGACAAAATCATCAACGCGATCCCGTACCTGGGTAACTGCTACTCTCTGCTGGACAAATTCGAC
ACCAACTCTAACTCTGTTTCTTTCAACCTGCTGGAACAGGACCCGTGCGGTGCGACCACCAAATCTGCGATGCTG
Figure 19-1 SEQ ID NO: 13

```
ACCAACCTGATCATCTTCGGTCCGGGTCCGGTTCTGAACAAAAACGAAGTTCGTGGTATCGTTCTGCGTGTTGAC
AACAAAAACTACTTCCCGTGCCGTGACGGTTTCGGTTCTATCATGCAGATGGCGTTCTGCCCGGAATACGTTCCG
ACCTTCGACAACGTTATCGAAAACATCACCTCTCTGACCATCGGTAAATCTAAATACTTCCAGGACCCGGCGCTG
CTGCTGATGCACGAACTGATCCACGTTCTGCACGGTCTGTACGGTATGCAGGTTTCTTGCCACGAAATCATCCCG
TCTAAACAGGAAATCTACATGCAGCACACCTACCCGATCTCTGCGGAAGAACTGTTCACCTTCGGTGGTCAGGAC
GCGAACCTGATCTCTATCGACATCAAAAACGACCTGTACGAAAAAACCCTGAACGACTACAAAGCGATCGCGAAC
AAACTGTCTCAGGTTACCTCTTGCAACGACCCGAACATCGACATCGACTCTTACAAACAGATCTACCAGCAGAAA
TACCAGTTCGACAAAGACTGCAACGGTCAGTACATCGTTAACGAAGACAAATTCCAGATCCTGTACAACTCTATC
ATGTACGGTTTCACCGAAATCGAACTGGGTAAAAAATTCAACATCAAAACCCGTCTGTCTTACTTCTCTATGAAC
CACGACCCGGTTAAAATCCCGAACCTGCTGGACGACACCATCTACAACGACACCGAAGGTTTCAACATCGAATCT
AAAGACCTGAAATCTGAATACAAAGGTCAGAACATGCGTGTTAACACCAACGCGTTCCGTAACGTTGACGGTTGC
GGTCTGGTTTCTAAACTGATCGGTCTGTGCAAAAAAATCATCCCGCCGACCAACATCCGTGAAAACCTGTACAAC
CGTACCGCGTCTCTGACCGACCTGGGTGGTGAACTGTGCATCAAAATCAAAAACGAAGACCTGACCTTCATCGCG
GAAAAAAACTCTTTCTCTGAAGAACCGTTCCAGGACGAAATCGTTTCTTACAACACCAAAAACAAACCGCTGAAC
TTCAACTACTCTCTGGACAAAATCATCGTTGACTACAACCTGCAGTCTAAAATCACCCTGCCGAACGACCGTACC
ACCCCGGTTACCAAAGGTATCCCGTACGCGCCGGAATACAAATCTAACGCGGCGTCTACCATCGAAATCCACAAC
ATCGACGACAACACCATCTACCAGTACCTGTACGCGCAGAAATCTCCGACCACCCTGCAGCGTATCACCATGACC
AACTCTGTTGACGACGCGCTGATCAACTCTACCAAAATCTACTCTTACTTCCCGTCTGTTATCTGCAAAGTTAAC
CAGGGTGCGCAGGGTATCCTGTTCCTGCAGTGGGTTCGTGACATCATCGACGACTTCACCAACGAATCTTCTCAG
AAAACCACCATCGACAAAATCTCTGACGTTTCTACCATCGTTCCGTACATCGGTCCGGCGCTGAACATCGTTAAA
CAGGGTTACGAAGGTAACTTCATCGGTGCGCTGGAAACCACCGGTGTTGTTCTGCTGCTGGAATACATCCCGGAA
ATCACCCTGCCGGTTATCGCGGCGCTGTCTATCGCGGAATCTTCTACCCAGAAAGAAAAAATCATCAAAACCATC
GACAACTTCCTGGAAAAACGTTACGAAAAATGGATCGAAGTTTACAAACTGGTTAAAGCGAAATGGCTGGGTACC
GTTAACACCCAGTTCCAGAAACGTTCTTACCAGATGTACCGTTCTCTGGAATACCAGGTTGACGCGATCAAAAAA
ATCATCGACTACGAATACAAATCTACTCTGGTCCGGACAAAGAACAGATCGCGGACGAAATCAACAACCTGAAA
AACAAACTGGAAGAAAAAGCGAACAAAGCGATGATCAACATCAACATCTTCATGCGTGAATCTTCTCGTTCTTTC
CTGGTTAACCAGATGATCAACGAAGCGAAAAAACAGCTGCTGGAATTCGACACCCAGTCTAAAAACATCCTGATG
CAGTACATCAAAGCGAACTCTAAATTCATCGGTATCACCGAACTGAAAAAACTGGAATCTAAATCAACAAAGTT
TTCTCTACCCCGATCCCGTTCTCTTACTCTAAAAACCTGGACTGCTGGGTTGACAACGAAGAAGACATCGACGTT
ATCCTGAAAAAATCTACCATCCTGAACCTGGACATCAACAACGACATCATCTCTGACATCTCTGGTTTCAACTCT
TCTGTTATCACCTACCCGGACGCGCAGCTGGTTCCGGGTATCAACGGTAAAGCGATCCACCTGGTTAACAACGAA
TCTTCTGAAGTTATCGTTCACAAAGCGATGGACATCGAATACAACGACATGTTCAACAACTTCACCGTTTCTTTC
TGGCTGCGTGTTCCGAAAGTTTCTGCGTGCCACCTGGAACAGTACGGTACCAACGAATACTCTATCATCTCTTCT
ATGAAAAAACACTCTCTGTCTATCGGTTCTGGTTGGTCTGTTTCTCTGAAAGGTAACAACCTGATCTGGACCCTG
AAAGACTCTGCGGGTGAAGTTCGTCAGATCACCTTCCGTGACCTGCCGGACAAATTCAACGCGTACCTGGCGAAC
AAATGGGTTTTCATCACCATCACCAACGACCGTCTGTGCTCTGCGAACCTGTACATCAACGGTGTTCTGATGGGT
TCTGCGGAAATCACCGGTCTGGGTGCGATCCGTGAAGACAACAACATCACCCTGAAACTGGACCGTTGCAACAAC
AACAACCAGTACGTTTCTATCGACAAATTCCGTATCTTCTGCAAAGCGCTGAACCCGAAAGAAATCGAAAAACTG
TACACCTCTTACCTGTCTATCACCTTCCTGCGTGACTTCTGGGGTAACCCGCTGCGTTACGACACCGAATACTAC
CTGATCCCGGTTGCGTCTTCTTCTAAAGACGTTCAGCTGAAAAAACATCACCGACTACATGTACCTGACCAACGCG
CCGTGCTACACCAACGGTAAACTGAACATCTACTACCGTCGTCTGTACAACGGTCTGAAATTCATCATCAAACGT
TACACCCCGAACAACGAAATCGACTGCTTCGTTAAATCTGGTGACTTCATCAAACTGTACGTTTCTTACAACAAC
AACGAACACATCGTTGGTTACCCGAAAGACGGTAACGCGTTCAACAACCTGGACCGTATCCTGCGTGTTGGTTAC
AACGCGCCGGGTATCCCGCTGTACAAAAAAATGGAAGCGGTTAAACTGCGTGACCTGAAAACCTACTCTGTTCAG
CTGAAACTGTACGACGACAAAAACGCGTCTCTGGGTCTGGTTGGTACCCACAACGGTCAGATCGGTAACGACCCG
AACCGTGACATCCTGATCGCGTCTAACTGGTACTTCAACCACCTGAAAGACAAAATCCTGGGTTGCGACTGGTAC
TTCGTTCCGACCGACGAAGGTTGGACCAACGACTAAAAGCTTGATCCGGCTGCTAACAAAGCCCGAAAGGAAGCT
GAGTTGGCTGCTGCCACCGCTGAGCAATAACTAGCATAACCCCTTGGGGCCTCTAAACGGGTCTTGAGGGGTTTT
TTGCTGAAAGGAGGAACTATATCCGGATCTGGCGTAATAGCGAAGAGGCCCGCACCGATCGCCCTTCCCAACAGT
TGCGCAGCCTGAATGGCGAATGGGACGCGCCCTGTAGCGGCGCATTAAGCGCGGCGGGTGTGGTGGTTACGCGCA
GCGTGACCGCTACACTTGCCAGCGCCCTAGCGCCCGCTCCTTTCGCTTTCTTCCCTTCCTTTCTCGCCACGTTCG
CCGGCTTTCCCCGTCAAGCTCTAAATCGGGGGCTCCCTTTAGGGTTCCGATTTAGTGCTTTACGGCACCTCGACC
CCAAAAAACTTGATTAGGGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCTATCTCGGTCTATTCTT
TTGATTTATAAGGGATTTTGCCGATTTCGGCCTATTGGTTAAAAAATGAGCTGATTTAACAAAAATTTAACGCGA
ATTTTAACAAATATTAACGCTTACAATTTAGGTGGCACTTTTCGGGGAAATGTGCGCGGAACCCCTATTTGTTT
ATTTTTCTAAATACATTCAAATATGTATCCGCTCATGAGACAATAACCCTGATAAATGCTTCAATAATATTGAAA
AAGGAAGAGTATGAGTATTCAACATTTCCGTGTCGCCCTTATTCCCTTTTTTGCGGCATTTTGCCTTCCTGTTTT
TGCTCACCCAGAAACGCTGGTGAAAGTAAAAGATGCTGAAGATCAGTTGGGTGCACGAGTGGGTTACATCGAACT
```

Figure 19-2 SEQ ID NO: 13

```
GGATCTCAACAGCGGTAAGATCCTTGAGAGTTTTCGCCCCGAAGAACGTTTTCCAATGATGAGCACTTTTAAAGT
TCTGCTATGTGGCGCGGTATTATCCCGTATTGACGCCGGGCAAGAGCAACTCGGTCGCCGCATACACTATTCTCA
GAATGACTTGGTTGAGTACTCACCAGTCACAGAAAAGCATCTTACGGATGGCATGACAGTAAGAGAATTATGCAG
TGCTGCCATAACCATGAGTGATAACACTGCGGCCAACTTACTTCTGACAACGATCGGAGGACCGAAGGAGCTAAC
CGCTTTTTTGCACAACATGGGGGATCATGTAACTCGCCTTGATCGTTGGGAACCGGAGCTGAATGAAGCCATACC
AAACGACGAGCGTGACACCACGATGCCTGTAGCAATGGCAACAACGTTGCGCAAACTATTAACTGGCGAACTACT
TACTCTAGCTTCCCGGCAACAATTAATAGACTGGATGGAGGCGGATAAAGTTGCAGGACCACTTCTGCGCTCGGC
CCTTCCGGCTGGCTGGTTTATTGCTGATAAATCTGGAGCCGGTGAGCGTGGGTCTCGCGGTATCATTGCAGCACT
GGGGCCAGATGGTAAGCCCTCCCGTATCGTAGTTATCTACACGACGGGGAGTCAGGCAACTATGGATGAACGAAA
TAGACAGATCGCTGAGATAGGTGCCTCACTGATTAAGCATTGGTAACTGTCAGACCAAGTTTACTCATATATACT
TTAGATTGATTTAAAACTTCATTTTTAATTTAAAAGGATCTAGGTGAAGATCCTTTTTGATAATCTCATGACCAA
AATCCCTTAACGTGAGTTTTCGTTCCACTGAGCGTCAGACCCCGTAGAAAAGATCAAAGGATCTTCTTGAGATCC
TTTTTTTCTGCGCGTAATCTGCTGCTTGCAAACAAAAAAACCACCGCTACCAGCGGTGGTTTGTTTGCCGGATCA
AGAGCTACCAACTCTTTTTCCGAAGGTAACTGGCTTCAGCAGAGCGCAGATACCAAATACTGTTCTTCTAGTGTA
GCCGTAGTTAGGCCACCACTTCAAGAACTCTGTAGCACCGCCTACATACCTCGCTCTGCTAATCCTGTTACCAGT
GGCTGCTGCCAGTGGCGATAAGTCGTGTCTTACCGGGTTGGACTCAAGACGATAGTTACCGGATAAGGCGCAGCG
GTCGGGCTGAACGGGGGGTTCGTGCACACAGCCCAGCTTGGAGCGAACGACCTACACCGAACTGAGATACCTACA
GCGTGAGCTATGAGAAAGCGCCACGCTTCCCGAAGGGAGAAAGGCGGACAGGTATCCGGTAAGCGGCAGGGTCGG
AACAGGAGAGCGCACGAGGGAGCTTCCAGGGGGAAACGCCTGGTATCTTTATAGTCCTGTCGGGTTTCGCCACCT
CTGACTTGAGCGTCGATTTTTGTGATGCTCGTCAGGGGGGCGGAGCCTATGGAAAAACGCCAGCAACGCGGCCTT
TTTACGGTTCCTGGCCTTTTGCTGGCCTTTTGCTCACATGTTCTTTCCTGCGTTATCCCCTGATTCTGTGGATAA
CCGTATTACCGCCTTTGAGTGAGCTGATACCGCTCGCCGCAGCCGAACGACCGAGCGCAGCGAGTCAGTGAGCGA
GGAAGCGGAAGAGCGCCCAATACGCAAACCGCCTCTCCCCGCGCGTTGGCCGATTCATTAATGCAG
```
Figure 19-3 SEQ ID NO: 13.

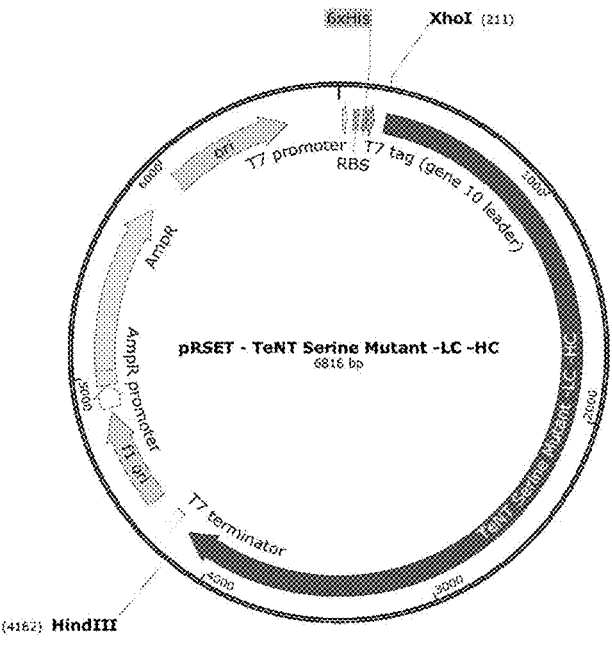

Figure 20.

```
PITINNFRYSDPVNNDTIIMMEPPYCKGLDIYYKAFKITDRIWIVPERYEFGTKPEDFNPPSSLIEGASEYYDPN
YLRTDCDKDRFLQTMVKLFNRIKNNVAGEALLDKIINAIPYLGNCYSLLDKFDTNSNSVSFNLLEQDPCGATTKS
AMLTNLIIFGPGPVLNKNEVRGIVLRVDNKNYFPCRDGFGSIMQMAFCPEYVPTFDNVIENITSLTIGKSKYFQD
PALLLMHELIHVLHGLYGMQVSCHEIIPSKQEIYMQHTYPISAEELFTFGGQDANLISIDIKNDLYEKTLNDYKA
IANKLSQVTSCNDPNIDIDSYKQIYQQKYQFDKDCNGQYIVNEDKFQILYNSIMYGFTEIELGKKFNIKTRLSYF
SMNHDPVKIPNLLDDTIYNDTEGFNIESKDLKSEYKGQNMRVNTNAFRNVDGCGLVSKLIGLCKKIIPPTNIREN
LYNRTASLTDLGGELCIKIKNEDLTFIAEKNSFSEEPFQDEIVSYNTKNKPLNFNYSLDKIIVDYNLQSKITLPN
```
Figure 21-1 SEQ ID NO: 14

```
DRTTPVTKGIPYAPEYKSNAASTIEIHNIDDNTIYQYLYAQKSPTTLQRITMTNSVDDALINSTKIYSYFPSVIS
KVNQGAQGILFLQWVRDIIDDFTNESSQKTTIDKISDVSTIVPYIGPALNIVKQGYEGNFIGALETTGVVLLLEY
IPEITLPVIAALSIAESSTQKEKIIKTIDNFLEKRYEKWIEVYKLVKAKWLGTVNTQFQKRSYQMYRSLEYQVDA
IKKIIDYEYKIYSGPDKEQIADEINNLKNKLEEKANKAMININIFMRESSRSFLVNQMINEAKKQLLEFDTQSKN
ILMQYIKANSKFIGITELKKLESKINKVFSTPIPFSYSKNLDCWVDNEEDIDVILKKSTILNLDINNDIISDISG
FNSSVITYPDAQLVPGINGKAIHLVNNESSEVIVHKAMDIEYNDMFNNFTVSFWLRVPKVSACHLEQYGTNEYSI
ISSMKKHSLSIGSGWSVSLKGNNLIWTLKDSAGEVRQITFRDLPDKFNAYLANKWVFITITNDRLCSANLYINGV
LMGSAEITGLGAIREDNNITLKLDRCNNNNQYVSIDKFRIFCKALNPKEIEKLYTSYLSITFLRDFWGNPLRYDT
EYYLIPVASSSKDVQLKNITDYMYLTNAPCYTNGKLNIYYRRLYNGLKFIIKRYTPNNEIDCFVKSGDFIKLYVS
YNNNEHIVGYPKDGNAFNNLDRILRVGYNAPGIPLYKKMEAVKLRDLKTYSVQLKLYDDKNASLGLVGTHNGQIG
NDPNRDILIASNWYFNHLKDKILGCDWYFVPTDEGWTND
```
Figure 21-2 SEQ ID NO: 14.

```
GATCTCGATCCCGCGAAATTAATACGACTCACTATAGGGAGACCACAACGGTTTCCCTCTAGAAATAATTTTGTT
TAACTTTAAGAAGGAGATATACATATGCGGGGTTCTCATCATCATCATCATGGTATGGCTAGCATGACTGGT
GGACAGCAAATGGGTCGGGATCTGTACGACGATGACGATAAGGATCGATGGGGATCCGAGCTCGAGCCGATCACC
ATCAACAACTTCCGTTACTCTGACCCGGTTAACAACGACACCATCATCATGATGGAACCGCCGTACTGCAAAGGT
CTGGACATCTACTACAAAGCGTTCAAAATCACCGACCGTATCTGGATCGTTCCGGAACGTTACGAATTCGGTACC
AAACCGGAAGACTTCAACCCGCCGTCTTCTCTGATCGAAGGTGCGTCTGAATACTACGACCCGAACTACCTGCGT
ACCGACTGCGACAAAGACCGTTTCCTGCAGACCATGGTTAAACTGTTCAACCGTATCAAAAACAACGTTGCGGGT
GAAGCGCTGCTGGACAAAATCATCAACGCGATCCCGTACCTGGGTAACTGCTACTCTCTGCTGGACAAATTCGAC
ACCAACTCTAACTCTGTTTCTTTCAACCTGCTGGAACAGGACCCGTGCGGTGCGACCACCAAATCTGCGATGCTG
ACCAACCTGATCATCTTCGGTCCGGGTCCGGTTCTGAACAAAAACGAAGTTCGTGGTATCGTTCTGCGTGTTGAC
AACAAAAACTACTTCCCGTGCCGTGACGGTTTCGGTTCTATCATGCAGATGGCGTTCTGCCCGGAATACGTTCCG
ACCTTCGACAACGTTATCGAAAACATCACCTCTCTGACCATCGGTAAATCTAAATACTTCCAGGACCCGGCGCTG
CTGCTGATGCACGAACTGATCCACGTTCTGCACGGTCTGTACGGTATGCAGGTTTCTTGCCACGAAATCATCCCG
TCTAAACAGGAAATCTACATGCAGCACACCTACCCGATCTCTGCGGAAGAACTGTTCACCTTCGGTGGTCAGGAC
GCGAACCTGATCTCTATCGACATCAAAAACGACCTGTACGAAAAAACCCTGAACGACTACAAAGCGATCGCGAAC
AAACTGTCTCAGGTTACCTCTTGCAACGACCCGAACATCGACATCGACTCTTACAAACAGATCTACCAGCAGAAA
TACCAGTTCGACAAAGACTGCAACGGTCAGTACATCGTTAACGAAGACAAATTCCAGATCCTGTACAACTCTATC
ATGTACGGTTTCACCGAAATCGAACTGGGTAAAAAATTCAACATCAAAACCCGTCTGTCTTACTTCTCTATGAAC
CACGACCCGGTTAAAATCCCGAACCTGCTGGACGACACCATCTACAACGACACCGAAGGTTTCAACATCGAATCT
AAAGACCTGAAATCTGAATACAAAGGTCAGAACATGCGTGTTAACACCAACGCGTTCCGTAACGTTGACGGTTGC
GGTCTGGGTTTCTAAACTGATCGGTCTGTGCAAAAAAATCATCCCGCCGACCAACATCCGTGAAAACCTGTACAAC
CGTACCGCGTCTCTGACCGACCTGGGTGGTGAACTGTGCATCAAAATCAAAAACGAAGACCTGACCTTCATCGCG
GAAAAAAACTCTTTCTCTGAAGAACCGTTCCAGGACGAAATCGTTTCTTACAACACCAAAAACAAACCGCTGAAC
TTCAACTACTCTCTGGACAAAATCATCGTTGACTACAACCTGCAGTCTAAAATCACCCTGCCGAACGACCGTACC
ACCCCGGTTACCAAAGGTATCCCGTACGCGCCGGAATACAAATCTAACGCGGCGTCTACCATCGAAATCCACAAC
ATCGACGACAACACCATCTACCAGTACCTGTACGCGCAGAAATCTCCGACCACCCTGCAGCGTATCACCATGACC
AACTCTGTTGACGACGCGCTGATCAACTCTACCAAAATCTACTCTTACTTCCCGTCTGTTATCTCTAAAGTTAAC
CAGGGTGCGCAGGGTATCCTGTTCCTGCAGTGGGTTCGTGACATCATCGACGACTTCACCAACGAATCTTCTCAG
AAAACCACCATCGACAAAATCTCTGACGTTTCTACCATCGTTCCGTACATCGGTCCGGCGCTGAACATCGTTAAA
CAGGGTTACGAAGGTAACTTCATCGGTGCGCTGGAAACCACCGGTGTTGTTCTGCTGCTGGAATACATCCCGGAA
ATCACCCTGCCGGTTATCGCGGCGCTGTCTATCGCGGAATCTTCTACCCAGAAAGAAAAAATCATCAAAACCATC
GACAACTTCCTGGAAAAACGTTACGAAAAATGGATCGAAGTTTACAAACTGGTTAAAGCGAAATGGCTGGGTACC
GTTAACACCCAGTTCCAGAAACGTTCTTACCAGATGTACCGTTCTCTGGAATACCAGGTTGACGCGATCAAAAAA
ATCATCGACTACGAATACAAAATCTACTCTGGTCCGGACAAAGAACAGATCGCGGACGAAATCAACAACCTGAAA
AACAAACTGGAAGAAAAAGCGAACAAAGCGATGATCAACATCAACATCTTCATGCGTGAATCTTCTCGTTCTTTC
CTGGTTAACCAGATGATCAACGAAGCGAAAAAACAGCTGCTGGAATTCGACACCCAGTCTAAAAACATCCTGATG
CAGTACATCAAAGCGAACTCTAAATTCATCGGTATCACCGAACTGAAAAAACTGGAATCTAAATCAACAAAGTT
TTCTCTACCCCGATCCCGTTCTCTTACTCTAAAAACCTGGACTGCTGGGTTGACAACGAAGAAGACATCGACGTT
ATCCTGAAAAAATCTACCATCCTGAACCTGGACATCAACAACGACATCATCTCTGACATCTCTGGTTTCAACTCT
TCTGTTATCACCTACCCGGACGCGCAGCTGGTTCCGGGTATCAACGGTAAAGCGATCCACCTGGTTAACAACGAA
TCTTCTGAAGTTATCGTTCACAAAGCGATGGACATCGAATACAACGACATGTTCAACAACTTCACCGTTTCTTTC
TGGCTGCGTGTTCCGAAAGTTTCTGCGTGCCACCTGGAACAGTACGGTACCAACGAATACTCTATCATCTCTTCT
ATGAAAAAACACTCTCTGTCTATCGGTTCTGGTTGGTCTGTTTCTCTGAAAGGTAACAACCTGATCTGGACCCTG
AAAGACTCTGCGGGTGAAGTTCGTCAGATCACCTTCCGTGACCTGCCGGACAAATTCAACGCGTACCTGGCGAAC
AAATGGGTTTTCATCACCATCACCAACGACCGTCTGTGCTCTGCGAACCTGTACATCAACGGTGTTCTGATGGGT
```
Figure 22-1 SEQ ID NO: 15

```
TCTGCGGAAATCACCGGTCTGGGTGCGATCCGTGAAGACAACAACATCACCCTGAAACTGGACCGTTGCAACAAC
AACAACCAGTACGTTTCTATCGACAAATTCCGTATCTTCTGCAAAGCGCTGAACCCGAAAGAAATCGAAAAACTG
TACACCTCTTACCTGTCTATCACCTTCCTGCGTGACTTCTGGGGTAACCCGCTGCGTTACGACACCGAATACTAC
CTGATCCCGGTTGCGTCTTCTTCTAAAGACGTTCAGCTGAAAAACATCACCGACTACATGTACCTGACCAACGCG
CCGTGCTACACCAACGGTAAACTGAACATCTACTACCGTCGTCTGTACAACGGTCTGAAATTCATCATCAAACGT
TACACCCCGAACAACGAAATCGACTGCTTCGTTAAATCTGGTGACTTCATCAAACTGTACGTTTCTTACAACAAC
AACGAACACATCGTTGGTTACCCGAAAGACGGTAACGCGTTCAACAACCTGGACCGTATCCTGCGTGTTGGTTAC
AACGCGCCGGGTATCCCGCTGTACAAAAAAATGGAAGCGGTTAAACTGCGTGACCTGAAAACCTACTCTGTTCAG
CTGAAACTGTACGACGACAAAAACGCGTCTCTGGGTCTGGTTGGTACCCACAACGGTCAGATCGGTAACGACCCG
AACCGTGACATCCTGATCGCGTCTAACTGGTACTTCAACCACCTGAAAGACAAAATCCTGGGTTGCGACTGGTAC
TTCGTTCCGACCGACGAAGGTTGGACCAACGACTAAAAGCTTGATCCGGCTGCTAACAAAGCCCGAAAGGAAGCT
GAGTTGGCTGCTGCCACCGCTGAGCAATAACTAGCATAACCCCTTGGGGCCTCTAAACGGGTCTTGAGGGGTTTT
TTGCTGAAAGGAGGAACTATATCCGGATCTGGCGTAATAGCGAAGAGGCCCGCACCGATCGCCCTTCCCAACAGT
TGCGCAGCCTGAATGGCGAATGGGACGCGCCCTGTAGCGGCGCATTAAGCGCGGCGGGTGTGGTGGTTACGCGCA
GCGTGACCGCTACACTTGCCAGCGCCCTAGCGCCCGCTCCTTTCGCTTTCTTCCCTTCCTTTCTCGCCACGTTCG
CCGGCTTTCCCCGTCAAGCTCTAAATCGGGGGCTCCCTTTAGGGTTCCGATTTAGTGCTTTACGGCACCTCGACC
CCAAAAAACTTGATTAGGGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCTATCTCGGTCTATTCTT
TTGATTTATAAGGGATTTTGCCGATTTCGGCCTATTGGTTAAAAAATGAGCTGATTTAACAAAAATTTAACGCGA
ATTTTAACAAAATATTAACGCTTACAATTTAGGTGGCACTTTTCGGGGAAATGTGCGCGGAACCCCTATTTGTTT
ATTTTTCTAAATACATTCAAATATGTATCCGCTCATGAGACAATAACCCTGATAAATGCTTCAATAATATTGAAA
AAGGAAGAGTATGAGTATTCAACATTTCCGTGTCGCCCTTATTCCCTTTTTTGCGGCATTTTGCCTTCCTGTTTT
TGCTCACCCAGAAACGCTGGTGAAAGTAAAAGATGCTGAAGATCAGTTGGGTGCACGAGTGGGTTACATCGAACT
GGATCTCAACAGCGGTAAGATCCTTGAGAGTTTTCGCCCCGAAGAACGTTTTCCAATGATGAGCACTTTTAAAGT
TCTGCTATGTGGCGCGGTATTATCCCGTATTGACGCCGGGCAAGAGCAACTCGGTCGCCGCATACACTATTCTCA
GAATGACTTGGTTGAGTACTCACCAGTCACAGAAAAGCATCTTACGGATGGCATGACAGTAAGAGAATTATGCAG
TGCTGCCATAACCATGAGTGATAACACTGCGGCCAACTTACTTCTGACAACGATCGGAGGACCGAAGGAGCTAAC
CGCTTTTTTGCACAACATGGGGGATCATGTAACTCGCCTTGATCGTTGGGAACCGGAGCTGAATGAAGCCATACC
AAACGACGAGCGTGACACCACGATGCCTGTAGCAATGGCAACAACGTTGCGCAAACTATTAACTGGCGAACTACT
TACTCTAGCTTCCCGGCAACAATTAATAGACTGGATGGAGGCGGATAAAGTTGCAGGACCACTTCTGCGCTCGGC
CCTTCCGGCTGGCTGGTTTATTGCTGATAAATCTGGAGCCGGTGAGCGTGGGTCTCGCGGTATCATTGCAGCACT
GGGGCCAGATGGTAAGCCCTCCCGTATCGTAGTTATCTACACGACGGGGAGTCAGGCAACTATGGATGAACGAAA
TAGACAGATCGCTGAGATAGGTGCCTCACTGATTAAGCATTGGTAACTGTCAGACCAAGTTTACTCATATATACT
TTAGATTGATTTAAAACTTCATTTTTAATTTAAAAGGATCTAGGTGAAGATCCTTTTTGATAATCTCATGACCAA
AATCCCTTAACGTGAGTTTTCGTTCCACTGAGCGTCAGACCCCGTAGAAAAGATCAAAGGATCTTCTTGAGATCC
TTTTTTTCTGCGCGTAATCTGCTGCTTGCAAACAAAAAAACCACCGCTACCAGCGGTGGTTTGTTTGCCGGATCA
AGAGCTACCAACTCTTTTTCCGAAGGTAACTGGCTTCAGCAGAGCGCAGATACCAAATACTGTTCTTCTAGTGTA
GCCGTAGTTAGGCCACCACTTCAAGAACTCTGTAGCACCGCCTACATACCTCGCTCTGCTAATCCTGTTACCAGT
GGCTGCTGCCAGTGGCGATAAGTCGTGTCTTACCGGGTTGGACTCAAGACGATAGTTACCGGATAAGGCGCAGCG
GTCGGGCTGAACGGGGGGTTCGTGCACACAGCCCAGCTTGGAGCGAACGACCTACACCGAACTGAGATACCTACA
GCGTGAGCTATGAGAAAGCGCCACGCTTCCCGAAGGGAGAAAGGCGGACAGGTATCCGGTAAGCGGCAGGGTCGG
AACAGGAGAGCGCACGAGGGAGCTTCCAGGGGGAAACGCCTGGTATCTTTATAGTCCTGTCGGGTTTCGCCACCT
CTGACTTGAGCGTCGATTTTTGTGATGCTCGTCAGGGGGGCGGAGCCTATGGAAAAACGCCAGCAACGCGGCCTT
TTTACGGTTCCTGGCCTTTTGCTGGCCTTTTGCTCACATGTTCTTTCCTGCGTTATCCCCTGATTCTGTGGATAA
CCGTATTACCGCCTTTGAGTGAGCTGATACCGCTCGCCGCAGCCGAACGACCGAGCGCAGCGAGTCAGTGAGCGA
GGAAGCGGAAGAGCGCCCAATACGCAAACCGCCTCTCCCCGCGCGTTGGCCGATTCATTAATGCAG
```

Figure 22-2 SEQ ID NO: 15.

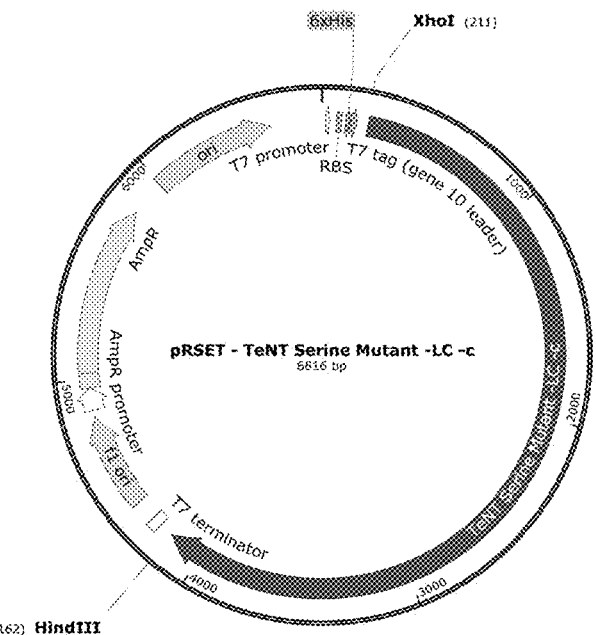

Figure 23.

PITINNFRYSDPVNNDTIIMMEPPYCKGLDIYYKAFKITDRIWIVPERYEFGTKPEDFNPPSSLIEGASEYYDPN
YLRTDSDKDRFLQTMVKLFNRIKNNVAGEALLDKIINAIPYLGNSYSLLDKFDTNSNSVSFNLLEQDPSGATTKS
AMLTNLIIFGPGPVLNKNEVRGIVLRVDNKNYFPCRDGFGSIMQMAFCPEYVPTFDNVIENITSLTIGKSKYFQD
PALLLMHELIHVLHGLYGMQVSSHEIIPSKQEIYMQHTYPISAEELFTFGGQDANLISIDIKNDLYEKTLNDYKA
IANKLSQVTSCNDPNIDIDSYKQIYQQKYQFDKDSNGQYIVNEDKFQILYNSIMYGFTEIELGKKFNIKTRLSYF
SMNHDPVKIPNLLDDTIYNDTEGFNIESKDLKSEYKGQNMRVNTNAFRNVDGSGLVSKLIGLCKKIIPPTNIREN
LYNRTASLTDLGGELCIKIKNEDLTFIAEKNSFSEEPFQDEIVSYNTKNKPLNFNYSLDKIIVDYNLQSKITLPN
DRTTPVTKGIPYAPEYKSNAASTIEIHNIDDNTIYQYLYAQKSPTTLQRITMTNSVDDALINSTKIYSYFPSVIC
KVNQGAQGILFLQWVRDIIDDFTNESSQKTTIDKISDVSTIVPYIGPALNIVKQGYEGNFIGALETTGVVLLLEY
IPEITLPVIAALSIAESSTQKEKIIKTIDNFLEKRYEKWIEVYKLVKAKWLGTVNTQFQKRSYQMYRSLEYQVDA
IKKIIDYEYKIYSGPDKEQIADEINNLKNKLEEKANKAMININIFMRESSRSFLVNQMINEAKKQLLEFDTQSKN
ILMQYIKANSKFIGITELKKLESKINKVFSTPIPFSYSKNLDCWVDNEEDIDVILKKSTILNLDINNDIISDISG
FNSSVITYPDAQLVPGINGKAIHLVNNESSEVIVHKAMDIEYNDMFNNFTVSFWLRVPKVSACHLEQYGTNEYSI
ISSMKKHSLSIGSGWSVSLKGNNLIWTLKDSAGEVRQITFRDLPDKFNAYLANKWVFITITNDRLCSANLYINGV
LMGSAEITGLGAIREDNNITLKLDRCNNNNQYVSIDKFRIFCKALNPKEIEKLYTSYLSITFLRDFWGNPLRYDT
EYYLIPVASSSKDVQLKNITDYMYLTNAPCYTNGKLNIYYRRLYNGLKFIIKRYTPNNEIDCFVKSGDFIKLYVS
YNNNEHIVGYPKDGNAFNNLDRILRVGYNAPGIPLYKKMEAVKLRDLKTYSVQLKLYDDKNASLGLVGTHNGQIG
NDPNRDILIASNWYFNHLKDKILGCDWYFVPTDEGWTND

Figure 24 SEQ ID NO: 16.

GATCTCGATCCCGCGAAATTAATACGACTCACTATAGGGAGACCACAACGGTTTCCCTCTAGAAATAATTTTGTT
TAACTTTAAGAAGGAGATATACATATGCGGGGTTCTCATCATCATCATCATCATGGTATGGCTAGCATGACTGGT
GGACAGCAAATGGGTCGGGATCTGTACGACGATGACGATAAGGATCGATGGGGATCCGAGCTCGAGCCGATCACC
ATCAACAACTTCCGTTACTCTGACCCGGTTAACAACGACACCATCATCATGATGGAACCGCCGTACTGCAAAGGT
CTGGACATCTACTACAAAGCGTTCAAAATCACCGACCGTATCTGGATCGTTCCGGAACGTTACGAATTCGGTACC
AAACCGGAAGACTTCAACCCGCCGTCTTCTCTGATCGAAGGTGCGTCTGAATACTACGACCCGAACTACCTGCGT
ACCGACTCTGACAAAGACCGTTTCCTGCAGACCATGGTTAAACTGTTCAACCGTATCAAAAACAACGTTGCGGGT
GAAGCGCTGCTGGACAAAATCATCAACGCGATCCCGTACCTGGGTAACTCTTACTCTCTGCTGGACAAATTCGAC
ACCAACTCTAACTCTGTTTCTTTCAACCTGCTGGAACAGGACCCGTCTGGTGCGACCACCAAATCTGCGATGCTG
ACCAACCTGATCATCTTCGGTCCGGGTCCGGTTCTGAACAAAAACGAAGTTCGTGGTATCGTTCTGCGTGTTGAC
AACAAAAACTACTTCCCGTGCCGTGACGGTTTCGGTTCTATCATGCAGATGGCGTTCTGCCCGGAATACGTTCCG
ACCTTCGACAACGTTATCGAAAACATCACCTCTCTGACCATCGGTAAATCTAAATACTTCCAGGACCCGGCGCTG

Figure 25-1 SEQ ID NO: 17

CTGCTGATGCACGAACTGATCCACGTTCTGCACGGTCTGTACGGTATGCAGGTTTCTTCTCACGAAATCATCCCG
TCTAAACAGGAAATCTACATGCAGCACACCTACCCGATCTCTGCGGAAGAACTGTTCACCTTCGGTGGTCAGGAC
GCGAACCTGATCTCTATCGACATCAAAAACGACCTGTACGAAAAAACCCTGAACGACTACAAAGCGATCGCGAAC
AAACTGTCTCAGGTTACCTCTTGCAACGACCCGAACATCGACATCGACTCTTACAAACAGATCTACCAGCAGAAA
TACCAGTTCGACAAAGACTCTAACGGTCAGTACATCGTTAACGAAGACAAATTCCAGATCCTGTACAACTCTATC
ATGTACGGTTTCACCGAAATCGAACTGGGTAAAAAATTCAACATCAAAACCCGTCTGTCTTACTTCTCTATGAAC
CACGACCCGGTTAAAATCCCGAACCTGCTGGACGACACCATCTACAACGACACCGAAGGTTTCAACATCGAATCT
AAAGACCTGAAATCTGAATACAAAGGTCAGAACATGCGTGTTAACACCAACGCGTTCCGTAACGTTGACGGTTCT
GGTCTGGTTTCTAAACTGATCGGTCTGTGCAAAAAAATCATCCCGCCGACCAACATCCGTGAAAACCTGTACAAC
CGTACCGCGTCTCTGACCGACCTGGGTGGTGAACTGTGCATCAAAATCAAAAACGAAGACCTGACCTTCATCGCG
GAAAAAAACTCTTTCTCTGAAGAACCGTTCCAGGACGAAATCGTTTCTTACAACACCAAAAACAAACCGCTGAAC
TTCAACTACTCTCTGGACAAAATCATCGTTGACTACAACCTGCAGTCTAAAATCACCCTGCCGAACGACCGTACC
ACCCCGGTTACCAAAGGTATCCCGTACGCGCCGGAATACAAATCTAACGCGGCGTCTACCATCGAAATCCACAAC
ATCGACGACAACACCATCTACCAGTACCTGTACGCGCAGAAATCTCCGACCACCCTGCAGCGTATCACCATGACC
AACTCTGTTGACGACGCGCTGATCAACTCTACCAAAATCTACTCTTACTTCCCGTCTGTTATCTGCAAAGTTAAC
CAGGGTGCGCAGGGTATCCTGTTCCTGCAGTGGGTTCGTGACATCATCGACGACTTCACCAACGAATCTTCTCAG
AAAACCACCATCGACAAAATCTCTGACGTTTCTACCATCGTTCCGTACATCGGTCCGGCGCTGAACATCGTTAAA
CAGGGTTACGAAGGTAACTTCATCGGTGCGCTGGAAACCACCGGTGTTGTTCTGCTGCTGGAATACATCCCGGAA
ATCACCCTGCCGGTTATCGCGGCGCTGTCTATCGCGGAATCTTCTACCCAGAAAGAAAAATCATCAAAACCATC
GACAACTTCCTGGAAAAACGTTACGAAAAATGGATCGAAGTTTACAAACTGGTTAAAGCGAAATGGCTGGGTACC
GTTAACACCCAGTTCCAGAAACGTTCTTACCAGATGTACCGTTCTCTGGAATACCAGGTTGACGCGATCAAAAAA
ATCATCGACTACGAATACAAATCTACTCTGGTCCGGACAAAGAACAGATCGCGGACGAAATCAACAACCTGAAA
AACAAACTGGAAGAAAAAGCGAACAAAGCGATGATCAACATCAACATCTTCATGCGTGAATCTTCTCGTTCTTTC
CTGGTTAACCAGATGATCAACGAAGCGAAAAAACAGCTGCTGGAATTCGACACCCAGTCTAAAAACATCCTGATG
CAGTACATCAAAGCGAACTCTAAATTCATCGGTATCACCGAACTGAAAAAACTGGAATCTAAATCAACAAAGTT
TTCTCTACCCCGATCCCGTTCTCTTACTCTAAAAACCTGGACTGCTGGGTTGACAACGAAGAAGACATCGACGTT
ATCCTGAAAAAATCTACCATCCTGAACCTGGACATCAACAACGACATCATCTCTGACATCTCTGGTTTCAACTCT
TCTGTTATCACCTACCCGGACGCGCAGCTGGTTCCGGGTATCAACGGTAAAGCGATCCACCTGGTTAACAACGAA
TCTTCTGAAGTTATCGTTCACAAAGCGATGGACATCGAATACAACGACATGTTCAACAACTTCACCGTTTCTTTC
TGGCTGCGTGTTCCGAAAGTTTCTGCGTGCCACCTGGAACAGTACGGTACCAACGAATACTCTATCATCTCTTCT
ATGAAAAAACACTCTCTGTCTATCGGTTCTGGTTGGTCTGTTTCTCTGAAAGGTAACAACCTGATCTGGACCCTG
AAAGACTCTGCGGGTGAAGTTCGTCAGATCACCTTCCGTGACCTGCCGGACAAATTCAACGCGTACCTGGCGAAC
AAATGGGTTTTCATCACCATCACCAACGACCGTCTGTGCTCTGCGAACCTGTACATCAACGGTGTTCTGATGGGT
TCTGCGGAAATCACCGGTCTGGGTGCGATCCGTGAAGACAACAACATCACCCTGAAACTGGACCGTTGCAACAAC
AACAACCAGTACGTTTCTATCGACAAATTCCGTATCTTCTGCAAAGCGCTGAACCCGAAAGAAATCGAAAAACTG
TACACCTCTTACCTGTCTATCACCTTCCTGCGTGACTTCTGGGGTAACCCGCTGCGTTACGACACCGAATACTAC
CTGATCCCGGTTGCGTCTTCTTCTAAAGACGTTCAGCTGAAAAAACATCACCGACTACATGTACCTGACCAACGCG
CCGTGCTACACCAACGGTAAACTGAACATCTACTACCGTCGTCTGTACAACGGTCTGAAATTCATCATCAAACGT
TACACCCCGAACAACGAAATCGACTGCTTCGTTAAATCTGGTGACTTCATCAAACTGTACGTTTCTTACAACAAC
AACGAACATCGTTGGTTACCCGAAAGACGGTAACGCGTTCAACAACCTGGACCGTATCCTGCGTGTTGGTTAC
AACGCGCCGGGTATCCCGCTGTACAAAAAAATGGAAGCGGTTAAACTGCGTGACCTGAAAACCTACTCTGTTCAG
CTGAAACTGTACGACGACAAAAACGCGTCTCTGGGTCTGGTTGGTACCCACAACGGTCAGATCGGTAACGACCCG
AACCGTGACATCCTGATCGCGTCTAACTGGTACTTCAACCACCTGAAAGACAAAATCCTGGGTTGCGACTGGTAC
TTCGTTCCGACCGACGAAGGTTGGACCAACGACTAAAAGCTTGATCCGGCTGCTAACAAAGCCCGAAAGGAAGCT
GAGTTGGCTGCTGCCACCGCTGAGCAATAACTAGCATAACCCCTTGGGGCCTCTAAACGGGTCTTGAGGGGTTTT
TTGCTGAAAGGAGGAACTATATCCGGATCTGGCGTAATAGCGAAGAGGCCCGCACCGATCGCCCTTCCCAACAGT
TGCGCAGCCTGAATGGCGAATGGGACGCGCCCTGTAGCGGCGCATTAAGCGCGGCGGGTGTGGTGGTTACGCGCA
GCGTGACCGCTACACTTGCCAGCGCCCTAGCGCCCGCTCCTTTCGCTTTCTTCCCTTCCTTTCTCGCCACGTTCG
CCGGCTTTCCCCGTCAAGCTCTAAATCGGGGGCTCCCTTTAGGGTTCCGATTTAGTGCTTTACGGCACCTCGACC
CCAAAAAACTTGATTAGGGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCTATCTCGGTCTATTCTT
TTGATTTATAAGGGATTTTGCCGATTTCGGCCTATTGGTTAAAAAATGAGCTGATTTAACAAAAATTTAACGCGA
ATTTTAACAAAATATTAACGCTTACAATTTAGGTGGCACTTTTCGGGGAAATGTGCGCGGAACCCCTATTTGTTT
ATTTTTCTAAATACATTCAAATATGTATCCGCTCATGAGACAATAACCCTGATAAATGCTTCAATAATATTGAAA
AAGGAAGAGTATGAGTATTCAACATTTCCGTGTCGCCCTTATTCCCTTTTTTGCGGCATTTTGCCTTCCTGTTTT
TGCTCACCCAGAAACGCTGGTGAAAGTAAAAGATGCTGAAGATCAGTTGGGTGCACGAGTGGGTTACATCGAACT
GGATCTCAACAGCGGTAAGATCCTTGAGAGTTTTCGCCCCGAAGAACGTTTTCCAATGATGAGCACTTTTAAAGT
TCTGCTATGTGGCGCGGTATTATCCCGTATTGACGCCGGGCAAGAGCAACTCGGTCGCCGCATACACTATTCTCA
GAATGACTTGGTTGAGTACTCACCAGTCACAGAAAAGCATCTTACGGATGGCATGACAGTAAGAGAATTATGCAG

Figure 25-2 SEQ ID NO: 17

```
TGCTGCCATAACCATGAGTGATAACACTGCGGCCAACTTACTTCTGACAACGATCGGAGGACCGAAGGAGCTAAC
CGCTTTTTTGCACAACATGGGGGATCATGTAACTCGCCTTGATCGTTGGGAACCGGAGCTGAATGAAGCCATACC
AAACGACGAGCGTGACACCACGATGCCTGTAGCAATGGCAACAACGTTGCGCAAACTATTAACTGGCGAACTACT
TACTCTAGCTTCCCGGCAACAATTAATAGACTGGATGGAGGCGGATAAAGTTGCAGGACCACTTCTGCGCTCGGC
CCTTCCGGCTGGCTGGTTTATTGCTGATAAATCTGGAGCCGGTGAGCGTGGGTCTCGCGGTATCATTGCAGCACT
GGGGCCAGATGGTAAGCCCTCCCGTATCGTAGTTATCTACACGACGGGGAGTCAGGCAACTATGGATGAACGAAA
TAGACAGATCGCTGAGATAGGTGCCTCACTGATTAAGCATTGGTAACTGTCAGACCAAGTTTACTCATATATACT
TTAGATTGATTTAAAACTTCATTTTTAATTTAAAAGGATCTAGGTGAAGATCCTTTTTGATAATCTCATGACCAA
AATCCCTTAACGTGAGTTTTCGTTCCACTGAGCGTCAGACCCCGTAGAAAAGATCAAAGGATCTTCTTGAGATCC
TTTTTTTCTGCGCGTAATCTGCTGCTTGCAAACAAAAAAACCACCGCTACCAGCGGTGGTTTGTTTGCCGGATCA
AGAGCTACCAACTCTTTTTCCGAAGGTAACTGGCTTCAGCAGAGCGCAGATACCAAATACTGTTCTTCTAGTGTA
GCCGTAGTTAGGCCACCACTTCAAGAACTCTGTAGCACCGCCTACATACCTCGCTCTGCTAATCCTGTTACCAGT
GGCTGCTGCCAGTGGCGATAAGTCGTGTCTTACCGGGTTGGACTCAAGACGATAGTTACCGGATAAGGCGCAGCG
GTCGGGCTGAACGGGGGGTTCGTGCACACAGCCCAGCTTGGAGCGAACGACCTACACCGAACTGAGATACCTACA
GCGTGAGCTATGAGAAAGCGCCACGCTTCCCGAAGGGAGAAAGGCGGACAGGTATCCGGTAAGCGGCAGGGTCGG
AACAGGAGAGCGCACGAGGGAGCTTCCAGGGGGAAACGCCTGGTATCTTTATAGTCCTGTCGGGTTTCGCCACCT
CTGACTTGAGCGTCGATTTTTGTGATGCTCGTCAGGGGGGCGGAGCCTATGGAAAAACGCCAGCAACGCGGCCTT
TTTACGGTTCCTGGCCTTTTGCTGGCCTTTTGCTCACATGTTCTTTCCTGCGTTATCCCCTGATTCTGTGGATAA
CCGTATTACCGCCTTTGAGTGAGCTGATACCGCTCGCCGCAGCCGAACGACCGAGCGCAGCGAGTCAGTGAGCGA
GGAAGCGGAAGAGCGCCCAATACGCAAACCGCCTCTCCCCGCGCGTTGGCCGATTCATTAATGCAG
```
Figure 25-3 SEQ ID NO: 17.

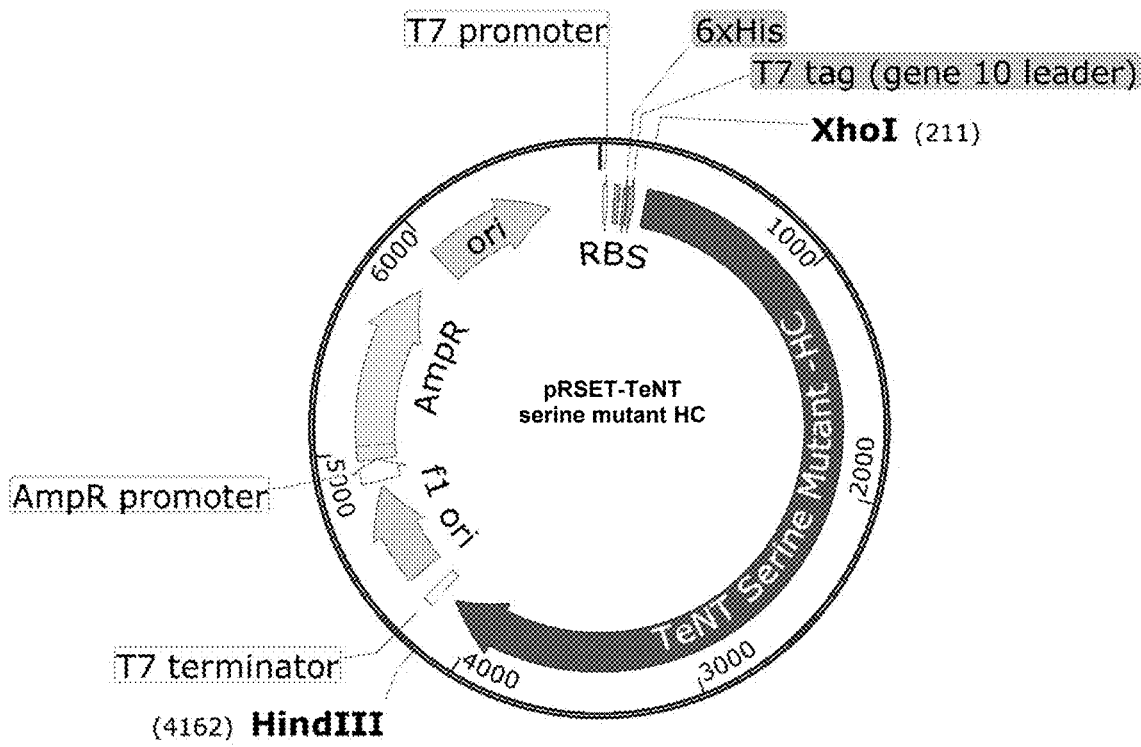

Figure 26.

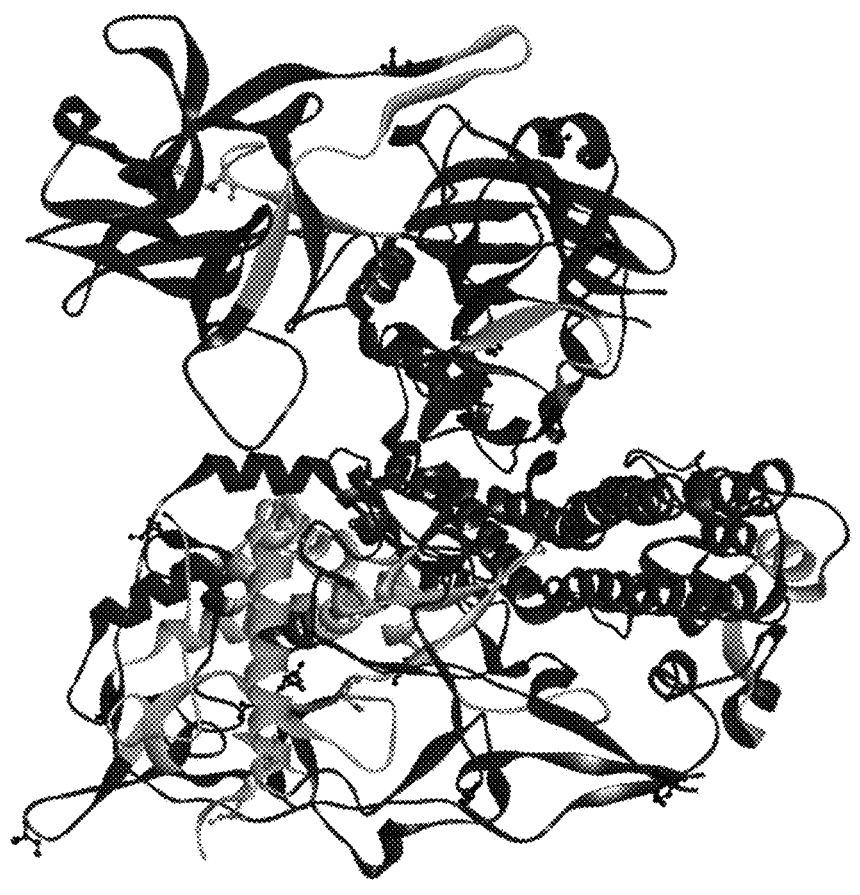
Figure 27.
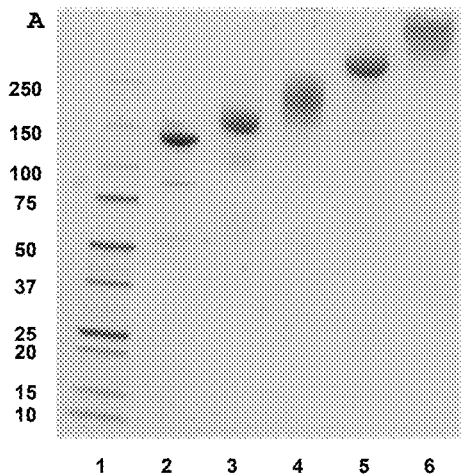
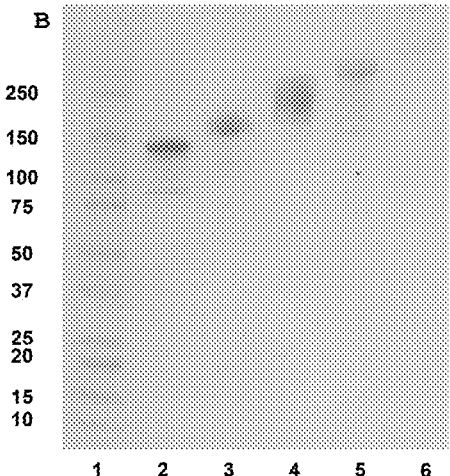
Figure 28.

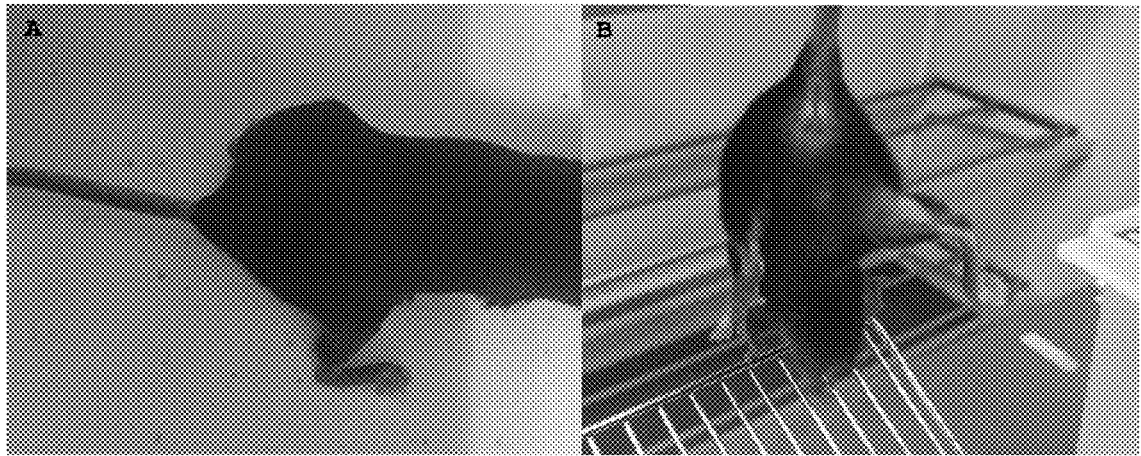
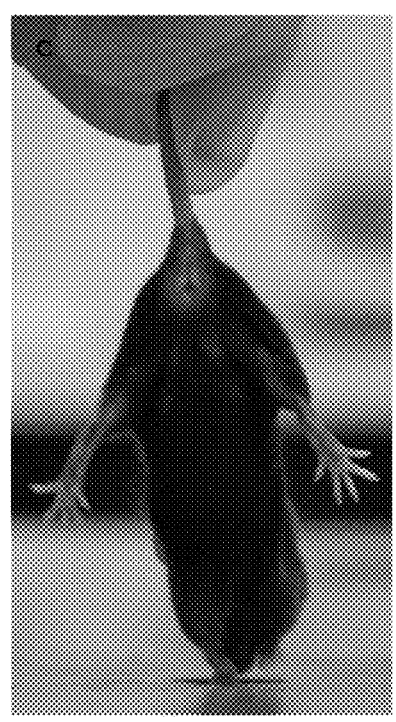
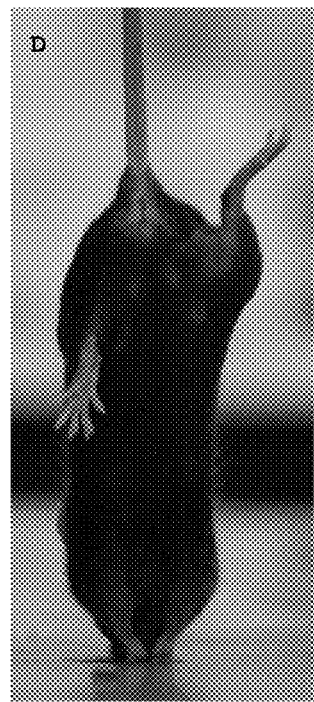
Figure 30.

A
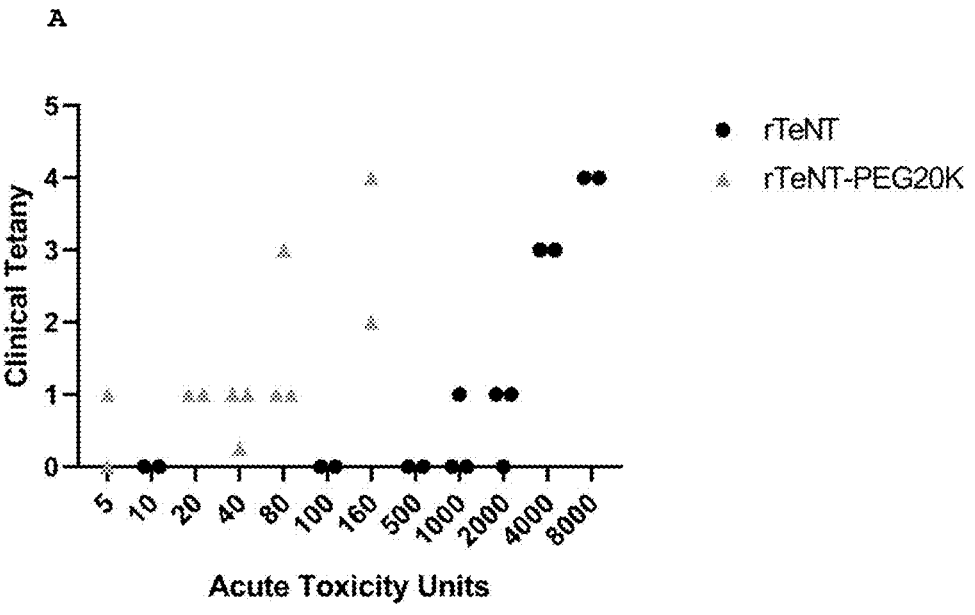
B
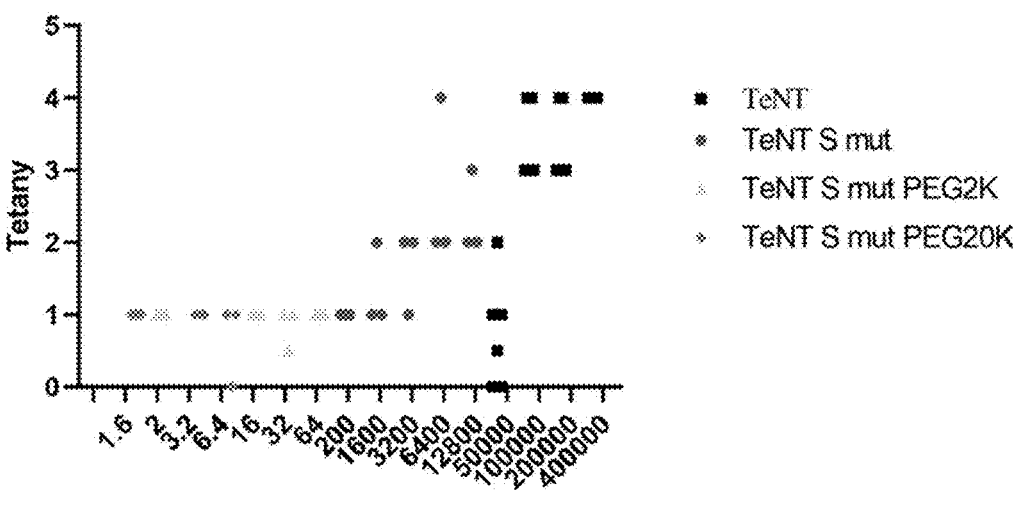
Figure 31.

SEQUENCE LISTING

<160> NUMBER OF SEQ ID NOS: 17

<210> SEQ ID NO 1
<211> LENGTH: 1314
<212> TYPE: PRT
<213> ORGANISM: Escherichia coli

<400> SEQUENCE: 1

```
Pro Ile Thr Ile Asn Asn Phe Arg Tyr Ser Asp Pro Val Asn Asn Asp
1               5                   10                  15

Thr Ile Ile Met Met Glu Pro Pro Tyr Cys Lys Gly Leu Asp Ile Tyr
```

-continued

```
                20              25              30

Tyr Lys Ala Phe Lys Ile Thr Asp Arg Ile Trp Ile Val Pro Glu Arg
        35              40              45

Tyr Glu Phe Gly Thr Lys Pro Glu Asp Phe Asn Pro Pro Ser Ser Leu
    50              55              60

Ile Glu Gly Ala Ser Glu Tyr Tyr Asp Pro Asn Tyr Leu Arg Thr Asp
65              70              75              80

Ser Asp Lys Asp Arg Phe Leu Gln Thr Met Val Lys Leu Phe Asn Arg
            85              90              95

Ile Lys Asn Asn Val Ala Gly Glu Ala Leu Leu Asp Lys Ile Ile Asn
            100             105             110

Ala Ile Pro Tyr Leu Gly Asn Ser Tyr Ser Leu Leu Asp Lys Phe Asp
        115             120             125

Thr Asn Ser Asn Ser Val Ser Phe Asn Leu Leu Glu Gln Asp Pro Ser
    130             135             140

Gly Ala Thr Thr Lys Ser Ala Met Leu Thr Asn Leu Ile Ile Phe Gly
145             150             155             160

Pro Gly Pro Val Leu Asn Lys Asn Glu Val Arg Gly Ile Val Leu Arg
            165             170             175

Val Asp Asn Lys Asn Tyr Phe Pro Cys Arg Asp Gly Phe Gly Ser Ile
            180             185             190

Met Gln Met Ala Phe Cys Pro Glu Tyr Val Pro Thr Phe Asp Asn Val
        195             200             205

Ile Glu Asn Ile Thr Ser Leu Thr Ile Gly Lys Ser Lys Tyr Phe Gln
    210             215             220

Asp Pro Ala Leu Leu Leu Met His Glu Leu Ile His Val Leu His Gly
225             230             235             240

Leu Tyr Gly Met Gln Val Ser Ser His Glu Ile Ile Pro Ser Lys Gln
            245             250             255

Glu Ile Tyr Met Gln His Thr Tyr Pro Ile Ser Ala Glu Glu Leu Phe
            260             265             270

Thr Phe Gly Gly Gln Asp Ala Asn Leu Ile Ser Ile Asp Ile Lys Asn
            275             280             285

Asp Leu Tyr Glu Lys Thr Leu Asn Asp Tyr Lys Ala Ile Ala Asn Lys
    290             295             300

Leu Ser Gln Val Thr Ser Cys Asn Asp Pro Asn Ile Asp Ile Asp Ser
305             310             315             320

Tyr Lys Gln Ile Tyr Gln Gln Lys Tyr Gln Phe Asp Lys Asp Ser Asn
            325             330             335

Gly Gln Tyr Ile Val Asn Glu Asp Lys Phe Gln Ile Leu Tyr Asn Ser
            340             345             350

Ile Met Tyr Gly Phe Thr Glu Ile Glu Leu Gly Lys Lys Phe Asn Ile
            355             360             365

Lys Thr Arg Leu Ser Tyr Phe Ser Met Asn His Asp Pro Val Lys Ile
    370             375             380

Pro Asn Leu Leu Asp Asp Thr Ile Tyr Asn Asp Thr Glu Gly Phe Asn
385             390             395             400

Ile Glu Ser Lys Asp Leu Lys Ser Glu Tyr Lys Gly Gln Asn Met Arg
            405             410             415

Val Asn Thr Asn Ala Phe Arg Asn Val Asp Gly Ser Gly Leu Val Ser
            420             425             430

Lys Leu Ile Gly Leu Cys Lys Lys Ile Ile Pro Pro Thr Asn Ile Arg
            435             440             445
```

-continued

```
Glu Asn Leu Tyr Asn Arg Thr Ala Ser Leu Thr Asp Leu Gly Gly Glu
    450                 455                 460

Leu Cys Ile Lys Ile Lys Asn Glu Asp Leu Thr Phe Ile Ala Glu Lys
465                 470                 475                 480

Asn Ser Phe Ser Glu Glu Pro Phe Gln Asp Glu Ile Val Ser Tyr Asn
                485                 490                 495

Thr Lys Asn Lys Pro Leu Asn Phe Asn Tyr Ser Leu Asp Lys Ile Ile
                500                 505                 510

Val Asp Tyr Asn Leu Gln Ser Lys Ile Thr Leu Pro Asn Asp Arg Thr
            515                 520                 525

Thr Pro Val Thr Lys Gly Ile Pro Tyr Ala Pro Glu Tyr Lys Ser Asn
    530                 535                 540

Ala Ala Ser Thr Ile Glu Ile His Asn Ile Asp Asp Asn Thr Ile Tyr
545                 550                 555                 560

Gln Tyr Leu Tyr Ala Gln Lys Ser Pro Thr Thr Leu Gln Arg Ile Thr
                565                 570                 575

Met Thr Asn Ser Val Asp Asp Ala Leu Ile Asn Ser Thr Lys Ile Tyr
                580                 585                 590

Ser Tyr Phe Pro Ser Val Ile Ser Lys Val Asn Gln Gly Ala Gln Gly
            595                 600                 605

Ile Leu Phe Leu Gln Trp Val Arg Asp Ile Ile Asp Asp Phe Thr Asn
    610                 615                 620

Glu Ser Ser Gln Lys Thr Thr Ile Asp Lys Ile Ser Asp Val Ser Thr
625                 630                 635                 640

Ile Val Pro Tyr Ile Gly Pro Ala Leu Asn Ile Val Lys Gln Gly Tyr
                645                 650                 655

Glu Gly Asn Phe Ile Gly Ala Leu Glu Thr Thr Gly Val Val Leu Leu
                660                 665                 670

Leu Glu Tyr Ile Pro Glu Ile Thr Leu Pro Val Ile Ala Ala Leu Ser
            675                 680                 685

Ile Ala Glu Ser Ser Thr Gln Lys Glu Lys Ile Ile Lys Thr Ile Asp
    690                 695                 700

Asn Phe Leu Glu Lys Arg Tyr Glu Lys Trp Ile Glu Val Tyr Lys Leu
705                 710                 715                 720

Val Lys Ala Lys Trp Leu Gly Thr Val Asn Thr Gln Phe Gln Lys Arg
                725                 730                 735

Ser Tyr Gln Met Tyr Arg Ser Leu Glu Tyr Gln Val Asp Ala Ile Lys
                740                 745                 750

Lys Ile Ile Asp Tyr Glu Tyr Lys Ile Tyr Ser Gly Pro Asp Lys Glu
            755                 760                 765

Gln Ile Ala Asp Glu Ile Asn Asn Leu Lys Asn Lys Leu Glu Glu Lys
    770                 775                 780

Ala Asn Lys Ala Met Ile Asn Ile Asn Ile Phe Met Arg Glu Ser Ser
785                 790                 795                 800

Arg Ser Phe Leu Val Asn Gln Met Ile Asn Glu Ala Lys Lys Gln Leu
                805                 810                 815

Leu Glu Phe Asp Thr Gln Ser Lys Asn Ile Leu Met Gln Tyr Ile Lys
                820                 825                 830

Ala Asn Ser Lys Phe Ile Gly Ile Thr Glu Leu Lys Lys Leu Glu Ser
            835                 840                 845

Lys Ile Asn Lys Val Phe Ser Thr Pro Ile Pro Phe Ser Tyr Ser Lys
    850                 855                 860
```

```
Asn Leu Asp Cys Trp Val Asp Asn Glu Glu Asp Ile Asp Val Ile Leu
865             870             875             880

Lys Lys Ser Thr Ile Leu Asn Leu Asp Ile Asn Asn Asp Ile Ile Ser
            885             890             895

Asp Ile Ser Gly Phe Asn Ser Ser Val Ile Thr Tyr Pro Asp Ala Gln
            900             905             910

Leu Val Pro Gly Ile Asn Gly Lys Ala Ile His Leu Val Asn Asn Glu
        915             920             925

Ser Ser Glu Val Ile Val His Lys Ala Met Asp Ile Glu Tyr Asn Asp
    930             935             940

Met Phe Asn Asn Phe Thr Val Ser Phe Trp Leu Arg Val Pro Lys Val
945             950             955             960

Ser Ala Ser His Leu Glu Gln Tyr Gly Thr Asn Glu Tyr Ser Ile Ile
            965             970             975

Ser Ser Met Lys Lys His Ser Leu Ser Ile Gly Ser Gly Trp Ser Val
            980             985             990

Ser Leu Lys Gly Asn Asn Leu Ile Trp Thr Leu Lys Asp Ser Ala Gly
        995             1000            1005

Glu Val Arg Gln Ile Thr Phe Arg Asp Leu Pro Asp Lys Phe Asn
    1010            1015            1020

Ala Tyr Leu Ala Asn Lys Trp Val Phe Ile Thr Ile Thr Asn Asp
    1025            1030            1035

Arg Leu Ser Ser Ala Asn Leu Tyr Ile Asn Gly Val Leu Met Gly
    1040            1045            1050

Ser Ala Glu Ile Thr Gly Leu Gly Ala Ile Arg Glu Asp Asn Asn
    1055            1060            1065

Ile Thr Leu Lys Leu Asp Arg Cys Asn Asn Asn Gln Tyr Val
    1070            1075            1080

Ser Ile Asp Lys Phe Arg Ile Phe Cys Lys Ala Leu Asn Pro Lys
    1085            1090            1095

Glu Ile Glu Lys Leu Tyr Thr Ser Tyr Leu Ser Ile Thr Phe Leu
    1100            1105            1110

Arg Asp Phe Trp Gly Asn Pro Leu Arg Tyr Asp Thr Glu Tyr Tyr
    1115            1120            1125

Leu Ile Pro Val Ala Ser Ser Ser Lys Asp Val Gln Leu Lys Asn
    1130            1135            1140

Ile Thr Asp Tyr Met Tyr Leu Thr Asn Ala Pro Ser Tyr Thr Asn
    1145            1150            1155

Gly Lys Leu Asn Ile Tyr Tyr Arg Arg Leu Tyr Asn Gly Leu Lys
    1160            1165            1170

Phe Ile Ile Lys Arg Tyr Thr Pro Asn Asn Glu Ile Asp Ser Phe
    1175            1180            1185

Val Lys Ser Gly Asp Phe Ile Lys Leu Tyr Val Ser Tyr Asn Asn
    1190            1195            1200

Asn Glu His Ile Val Gly Tyr Pro Lys Asp Gly Asn Ala Phe Asn
    1205            1210            1215

Asn Leu Asp Arg Ile Leu Arg Val Gly Tyr Asn Ala Pro Gly Ile
    1220            1225            1230

Pro Leu Tyr Lys Lys Met Glu Ala Val Lys Leu Arg Asp Leu Lys
    1235            1240            1245

Thr Tyr Ser Val Gln Leu Lys Leu Tyr Asp Asp Lys Asn Ala Ser
    1250            1255            1260

Leu Gly Leu Val Gly Thr His Asn Gly Gln Ile Gly Asn Asp Pro
```

-continued

<table>
<tr><td>1265</td><td>1270</td><td>1275</td></tr>
</table>

```
Asn Arg  Asp Ile Leu Ile Ala  Ser Asn Trp Tyr Phe  Asn His Leu
    1280              1285              1290

Lys Asp  Lys Ile Leu Gly Cys  Asp Trp Tyr Phe Val  Pro Thr Asp
    1295              1300              1305

Glu Gly  Trp Thr Asn Asp
    1310

<210> SEQ ID NO 2
<211> LENGTH: 6816
<212> TYPE: DNA
<213> ORGANISM: Escherichia coli

<400> SEQUENCE: 2
gatctcgatc ccgcgaaatt aatacgactc actataggga gaccacaacg gtttccctct    60
agaaataatt ttgtttaact ttaagaagga gatatacata tgcggggttc tcatcatcat   120
catcatcatg gtatggctag catgactggt ggacagcaaa tgggtcggga tctgtacgac   180
gatgacgata aggatcgatg gggatccgag ctcgagccga ttaccatcaa taattttcgt   240
tattcagatc cggtgaataa tgataccatc atcatgatgg aaccaccgta ctgtaaaggg   300
ctggatattt attataaagc gttcaaaatc accgaccgca tctggatcgt gccggaacgc   360
tacgaattcg gcaccaaacc ggaagatttt aatccgccga gtagtctgat cgaaggtgca   420
tcggaatact acgatccgaa ttatctgcgt actgactctg ataaagatcg ctttctgcaa   480
acgatggtaa aactgttcaa tcgtatcaaa aacaatgtag caggcgaagc cctgctggat   540
aaaatcatca acgccattcc gtatctggga aacagttatt ctctgctgga taaattcgat   600
acaaactcga actctgtgtc attcaacctg ctggaacagg acccgagcgg cgcgaccact   660
aagagtgcga tgctgactaa cctgattatt ttcggtccgg gaccggtact gaataaaaat   720
gaagttcgcg gcattgtact gcgtgtcgat aataaaaact atttcccatg tcgtgatggc   780
ttcggcagca tcatgcagat ggcctttttgt ccggaatatg tgccaacttt cgataatgtg   840
attgagaaca tcacctctct gacgattggt aaaagtaaat atttccagga tccggctctg   900
ctgctgatgc atgaactgat ccatgttctg catggcctgt atggcatgca ggtttcatcc   960
cacgaaatta tcccatccaa acaggaaatt tacatgcagc atacatatcc gattagtgcc  1020
gaagaactgt tcacttttgg cggccaggat gcgaacctga tttcgattga cattaaaaac  1080
gatctgtatg aaaaaactct gaacgattat aaagcgattg ccaacaaact gtctcaggta  1140
acctcctgta cgatccgaa tattgatatt gacagttata aacaaattta tcagcagaag  1200
tatcagttcg ataaagactc taatggccag tatattgtta cgaagataa attccagatt  1260 ctgtacaata gcattatgta tggctttact gagatcgaac tgggtaaaaa atttaacatc  1320
aagactcgtc tgagctattt tagcatgaat catgatccag tgaaaatccc gaatctgctg  1380
gatgatacga tttataatga taccgaagga tttaacatcg aaagcaagga tctgaaatcc  1440
gaatataaag ggcagaacat cgcgcgttaa accaatgcat ttcgcaatgt tgatggttca  1500
ggcctggtgt cgaaactgat tgggctgtgt aagaaaatca ttccaccgac aaatattcgc  1560
gaaaatctgt acaaccgtac ggcgagcctg accgatctgg ggggagaact gtgtattaaa  1620
atcaaaaatg aagatctgac cttcattgct gagaagaata gcttttccga gagccattc  1680 caggacgaaa tcgtgtctta taacaccaag aataaaaccgc tgaatttcaa ctactccctg  1740
gacaaaatca ttgtggatta caacctgcag agtaaaaatta ccctgccgaa tgatcgtacc  1800
```

-continued

```
accccggtga cgaaaggcat cccttacgca ccagaatata aatcaaatgc agcctcgact   1860
atcgagatcc ataatattga tgacaacact atttaccagt acctgtatgc tcagaaatct   1920
ccgacgacgc tgcagcgcat caccatgact aacagcgtgg acgatgccct gattaatagc   1980
accaaaatct actcttactt tccgtcggtg atctctaagg ttaatcaggg cgcgcaaggt   2040
atcctgtttc tgcaatgggt gcgtgatatt attgatgatt tcactaatga atctagccag   2100
aaaacgacaa ttgataaaat ttcggatgtt tccaccatcg tgccttacat cggcccagcg   2160
ctgaacatcg tgaagcaggg ttatgagggt aactttatcg gagcactgga aacgaccggc   2220
gtggttctgc tgctggaata tattccggag attactctgc cagttattgc ggctctgtcg   2280
attgcagaga gctcaacgca gaaagaaaaa attattaaga cgatcgacaa tttcctggaa   2340
aagcgctacg aaaaatggat cgaagtgtat aagctggtga aagcgaaatg gctggggacc   2400
gtgaacaccc agttccaaaa acgttcctat caaatgtatc gtagcctgga atatcaggtg   2460
gacgccatta aaaagatcat cgattacgaa tataagatct actccggtcc ggacaaagaa   2520
cagattgcgg acgaaattaa caatctgaaa aataaactgg aggaaaaagc caacaaagcg   2580
atgattaata tcaatatttt catgcgtgaa agcagccgta gcttcctggt caatcagatg   2640
attaatgaag cgaagaaaca actgctggaa tttgatacgc aatctaaaaa tattctgatg   2700
caatacatca aagccaattc taaatttatt gggatcacgg aactgaaaaa gctggaatcg   2760
aaaatcaata aagtctttag caccccgatt ccgttctcct actcgaaaaa tctggattgt   2820
tgggttgaca atgaagaaga tattgatgtt attctgaaaa agagcacgat cctgaacctg   2880
gatattaata cgatattat ctctgatatc agtggtttta attcatcagt tattacttac   2940
ccagacgctc aactggtgcc gggaatcaat gggaaagcca ttcatctggt gaataatgaa   3000
tcaagtgaag tgatcgtgca taaagcgatg gatatcgagt acaacgatat gtttaataat   3060
ttcacggtgt cgttctggct gcgtgttccg aaagtgagtg cctcccacct ggaacaatat   3120
ggaaccaacg aatactcaat cattagcagc atgaagaaac attcgctgag tattggttca   3180
ggttggagcg tttccctgaa agggaacaat ctgatctgga cactgaagga ctcagcgggc   3240
gaagtgcgtc agattacgtt tcgtgatctg ccggataaat ttaatgcata cctggctaac   3300
aaatgggtgt tcatcacaat caccaatgac cgtctgtcgt ctgcaaacct gtatattaat   3360
ggggtactga tgggctcggc agaaattaca gggctgggcg ccattcgtga agataacaat   3420
attacgctga aactggatcg ttgtaataac aataatcagt atgtgagcat tgataaattt   3480
cgtattttct gcaaagcgct gaacccgaaa gaaattgaaa aactgtatac ctcgtatctg   3540
tcaattacgt ttctgcgcga tttctgggga aacccgctgc gttacgatac ggaatactac   3600
ctgatcccgg tagccagttc tagtaaagac gttcaactga aaaatattac cgactacatg   3660
tatctgacaa acgctccatc atacacaaac ggcaaactga acatctatta ccgtcgcctg   3720
tacaatgggc tgaaattcat cattaaacgt tataccccga ataacgaaat tgattccttt   3780
gtgaagtccg gtgacttcat taagctgtat gtatcctata acaataatga acacatcgtt   3840
ggctatccga aggatggcaa tgcctttaac aacctggatc gtattctgcg tgtaggttac   3900
aacgccccgg gtattccgct gtataagaaa atggaagcag tgaaactgcg tgatctgaaa   3960
acatattccg tgcaactgaa gctgtatgat gacaaaaatg ctagcctggg tctggtaggc   4020
acgcataacg gtcagattgg aaacgatcct aatcgtgaca tcctgatcgc ctctaactgg   4080
tattttaacc acctgaaaga taaaattctg ggctgcgatt ggtatttttgt ccctaccgat   4140 gaaggctgga cgaacgatta aaagcttgat ccggctgcta acaaagcccg aaaggaagct   4200
```

```
gagttggctg ctgccaccgc tgagcaataa ctagcataac cccttggggc ctctaaacgg    4260
gtcttgaggg gttttttgct gaaaggagga actatatccg gatctggcgt aatagcgaag    4320
aggcccgcac cgatcgccct tcccaacagt tgcgcagcct gaatggcgaa tgggacgcgc    4380
cctgtagcgg cgcattaagc gcggcgggtg tggtggttac gcgcagcgtg accgctacac    4440
ttgccagcgc cctagcgccc gctcctttcg ctttcttccc ttcctttctc gccacgttcg    4500
ccggctttcc ccgtcaagct ctaaatcggg ggctcccttt agggttccga tttagtgctt    4560
tacggcacct cgaccccaaa aaacttgatt agggtgatgg ttcacgtagt gggccatcgc    4620
cctgatagac ggtttttcgc cctttgacgt tggagtccac gttctttaat agtggactct    4680
tgttccaaac tggaacaaca ctcaacccta tctcggtcta ttcttttgat ttataaggga    4740
ttttgccgat ttcggcctat tggttaaaaa atgagctgat ttaacaaaaa tttaacgcga    4800
attttaacaa aatattaacg cttacaattt aggtggcact tttcggggaa atgtgcgcgg    4860
aacccctatt tgtttatttt tctaaataca ttcaaatatg tatccgctca tgagacaata    4920
accctgataa atgcttcaat aatattgaaa aaggaagagt atgagtattc aacatttccg    4980
tgtcgccctt attccctttt ttgcggcatt ttgccttcct gtttttgctc acccagaaac    5040
gctggtgaaa gtaaaagatg ctgaagatca gttgggtgca cgagtgggtt acatcgaact    5100
ggatctcaac agcggtaaga tccttgagag ttttcgcccc gaagaacgtt ttccaatgat    5160
gagcactttt aaagttctgc tatgtggcgc ggtattatcc cgtattgacg ccgggcaaga    5220
gcaactcggt cgccgcatac actattctca gaatgacttg gttgagtact caccagtcac    5280
agaaaagcat cttacggatg gcatgacagt aagagaatta tgcagtgctg ccataaccat    5340
gagtgataac actgcggcca acttacttct gacaacgatc ggaggaccga aggagctaac    5400
cgcttttttg cacaacatgg gggatcatgt aactcgcctt gatcgttggg aaccggagct    5460
gaatgaagcc ataccaaacg acgagcgtga caccacgatg cctgtagcaa tggcaacaac    5520
gttgcgcaaa ctattaactg gcgaactact tactctagct tcccggcaac aattaataga    5580
ctggatggag gcggataaag ttgcaggacc acttctgcgc tcggcccttc cggctggctg    5640
gtttattgct gataaatctg gagccggtga gcgtgggtct cgcggtatca ttgcagcact    5700
ggggccagat ggtaagccct cccgtatcgt agttatctac acgacgggga gtcaggcaac    5760 tatgatgaa cgaaatagac agatcgctga gataggtgcc tcactgatta gcattggta    5820 actgtcagac caagtttact catatatact ttagattgat ttaaaacttc attttttaatt    5880 taaaaggatc taggtgaaga tccttttttga taatctcatg accaaaatcc cttaacgtga    5940
gttttcgttc cactgagcgt cagaccccgt agaaaagatc aaaggatctt cttgagatcc    6000 ttttttttctg cgcgtaatct gctgcttgca acaaaaaaaa ccaccgctac cagcggtggt    6060
ttgtttgccg gatcaagagc taccaactct ttttccgaag gtaactggct tcagcagagc    6120
gcagatacca aatactgttc ttctagtgta gccgtagtta ggccaccact tcaagaactc    6180
tgtagcaccg cctacatacc tcgctctgct aatcctgtta ccagtggctg ctgccagtgg    6240
cgataagtcg tgtcttaccg ggttggactc aagacgatag ttaccggata aggcgcagcg    6300
gtcgggctga acggggggtt cgtgcacaca gcccagcttg gagcgaacga cctacaccga    6360
actgagatac ctacagcgtg agctatgaga aagcgccacg cttcccgaag ggagaaaggc    6420
ggacaggtat ccggtaagcg gcagggtcgg aacaggagag cgcacgaggg agcttccagg    6480
gggaaacgcc tggtatcttt atagtcctgt cgggtttcgc cacctctgac ttgagcgtcg    6540
```

```
attttttgtga tgctcgtcag gggggcggag cctatggaaa aacgccagca acgcggcctt    6600
tttacggttc ctggcctttt gctggccttt tgctcacatg ttctttcctg cgttatcccc    6660
tgattctgtg dataaccgta ttaccgcctt tgagtgagct gataccgctc gccgcagccg    6720
aacgaccgag cgcagcgagt cagtgagcga ggaagcggaa gagcgcccaa tacgcaaacc    6780
gcctctcccc gcgcgttggc cgattcatta atgcag                              6816
```

```
<210> SEQ ID NO 3
<211> LENGTH: 858
<212> TYPE: PRT
<213> ORGANISM: Escherichia coli

<400> SEQUENCE: 3

Ser Leu Thr Asp Leu Gly Gly Glu Leu Cys Ile Lys Ile Lys Asn Glu
1               5                   10                  15

Asp Leu Thr Phe Ile Ala Glu Lys Asn Ser Phe Ser Glu Glu Pro Phe
            20                  25                  30

Gln Asp Glu Ile Val Ser Tyr Asn Thr Lys Asn Lys Pro Leu Asn Phe
        35                  40                  45

Asn Tyr Ser Leu Asp Lys Ile Ile Val Asp Tyr Asn Leu Gln Ser Lys
    50                  55                  60

Ile Thr Leu Pro Asn Asp Arg Thr Thr Pro Val Thr Lys Gly Ile Pro
65                  70                  75                  80

Tyr Ala Pro Glu Tyr Lys Ser Asn Ala Ala Ser Thr Ile Glu Ile His
            85                  90                  95

Asn Ile Asp Asp Asn Thr Ile Tyr Gln Tyr Leu Tyr Ala Gln Lys Ser
            100                 105                 110

Pro Thr Thr Leu Gln Arg Ile Thr Met Thr Asn Ser Val Asp Asp Ala
        115                 120                 125

Leu Ile Asn Ser Thr Lys Ile Tyr Ser Tyr Phe Pro Ser Val Ile Ser
    130                 135                 140

Lys Val Asn Gln Gly Ala Gln Gly Ile Leu Phe Leu Gln Trp Val Arg
145                 150                 155                 160

Asp Ile Ile Asp Asp Phe Thr Asn Glu Ser Ser Gln Lys Thr Thr Ile
                165                 170                 175

Asp Lys Ile Ser Asp Val Ser Thr Ile Val Pro Tyr Ile Gly Pro Ala
            180                 185                 190

Leu Asn Ile Val Lys Gln Gly Tyr Glu Gly Asn Phe Ile Gly Ala Leu
            195                 200                 205

Glu Thr Thr Gly Val Val Leu Leu Leu Glu Tyr Ile Pro Glu Ile Thr
        210                 215                 220

Leu Pro Val Ile Ala Ala Leu Ser Ile Ala Glu Ser Ser Thr Gln Lys
225                 230                 235                 240

Glu Lys Ile Ile Lys Thr Ile Asp Asn Phe Leu Glu Lys Arg Tyr Glu
                245                 250                 255

Lys Trp Ile Glu Val Tyr Lys Leu Val Lys Ala Lys Trp Leu Gly Thr
            260                 265                 270

Val Asn Thr Gln Phe Gln Lys Arg Ser Tyr Gln Met Tyr Arg Ser Leu
        275                 280                 285

Glu Tyr Gln Val Asp Ala Ile Lys Lys Ile Ile Asp Tyr Glu Tyr Lys
        290                 295                 300

Ile Tyr Ser Gly Pro Asp Lys Glu Gln Ile Ala Asp Glu Ile Asn Asn
305                 310                 315                 320

Leu Lys Asn Lys Leu Glu Glu Lys Ala Asn Lys Ala Met Ile Asn Ile
```

-continued

```
                325               330               335
Asn Ile Phe Met Arg Glu Ser Ser Arg Ser Phe Leu Val Asn Gln Met
            340               345               350
Ile Asn Glu Ala Lys Lys Gln Leu Leu Glu Phe Asp Thr Gln Ser Lys
            355               360               365
Asn Ile Leu Met Gln Tyr Ile Lys Ala Asn Ser Lys Phe Ile Gly Ile
            370               375               380
Thr Glu Leu Lys Lys Leu Glu Ser Lys Ile Asn Lys Val Phe Ser Thr
385               390               395               400
Pro Ile Pro Phe Ser Tyr Ser Lys Asn Leu Asp Cys Trp Val Asp Asn
            405               410               415
Glu Glu Asp Ile Asp Val Ile Leu Lys Lys Ser Thr Ile Leu Asn Leu
            420               425               430
Asp Ile Asn Asn Asp Ile Ile Ser Asp Ile Ser Gly Phe Asn Ser Ser
            435               440               445
Val Ile Thr Tyr Pro Asp Ala Gln Leu Val Pro Gly Ile Asn Gly Lys
            450               455               460
Ala Ile His Leu Val Asn Asn Glu Ser Ser Glu Val Ile Val His Lys
465               470               475               480
Ala Met Asp Ile Glu Tyr Asn Asp Met Phe Asn Asn Phe Thr Val Ser
            485               490               495
Phe Trp Leu Arg Val Pro Lys Val Ser Ala Ser His Leu Glu Gln Tyr
            500               505               510
Gly Thr Asn Glu Tyr Ser Ile Ile Ser Ser Met Lys Lys His Ser Leu
            515               520               525
Ser Ile Gly Ser Gly Trp Ser Val Ser Leu Lys Gly Asn Asn Leu Ile
            530               535               540
Trp Thr Leu Lys Asp Ser Ala Gly Glu Val Arg Gln Ile Thr Phe Arg
545               550               555               560
Asp Leu Pro Asp Lys Phe Asn Ala Tyr Leu Ala Asn Lys Trp Val Phe
            565               570               575
Ile Thr Ile Thr Asn Asp Arg Leu Ser Ser Ala Asn Leu Tyr Ile Asn
            580               585               590
Gly Val Leu Met Gly Ser Ala Glu Ile Thr Gly Leu Gly Ala Ile Arg
            595               600               605
Glu Asp Asn Asn Ile Thr Leu Lys Leu Asp Arg Cys Asn Asn Asn Asn
            610               615               620
Gln Tyr Val Ser Ile Asp Lys Phe Arg Ile Phe Cys Lys Ala Leu Asn
625               630               635               640
Pro Lys Glu Ile Glu Lys Leu Tyr Thr Ser Tyr Leu Ser Ile Thr Phe
            645               650               655
Leu Arg Asp Phe Trp Gly Asn Pro Leu Arg Tyr Asp Thr Glu Tyr Tyr
            660               665               670
Leu Ile Pro Val Ala Ser Ser Ser Lys Asp Val Gln Leu Lys Asn Ile
            675               680               685
Thr Asp Tyr Met Tyr Leu Thr Asn Ala Pro Ser Tyr Thr Asn Gly Lys
            690               695               700
Leu Asn Ile Tyr Tyr Arg Arg Leu Tyr Asn Gly Leu Lys Phe Ile Ile
705               710               715               720
Lys Arg Tyr Thr Pro Asn Asn Glu Ile Asp Ser Phe Val Lys Ser Gly
            725               730               735
Asp Phe Ile Lys Leu Tyr Val Ser Tyr Asn Asn Asn Glu His Ile Val
            740               745               750
```

-continued

```
Gly Tyr Pro Lys Asp Gly Asn Ala Phe Asn Asn Leu Asp Arg Ile Leu
        755             760             765

Arg Val Gly Tyr Asn Ala Pro Gly Ile Pro Leu Tyr Lys Lys Met Glu
    770             775             780

Ala Val Lys Leu Arg Asp Leu Lys Thr Tyr Ser Val Gln Leu Lys Leu
785             790             795             800

Tyr Asp Asp Lys Asn Ala Ser Leu Gly Leu Val Gly Thr His Asn Gly
                805             810             815

Gln Ile Gly Asn Asp Pro Asn Arg Asp Ile Leu Ile Ala Ser Asn Trp
            820             825             830

Tyr Phe Asn His Leu Lys Asp Lys Ile Leu Gly Cys Asp Trp Tyr Phe
            835             840             845

Val Pro Thr Asp Glu Gly Trp Thr Asn Asp
        850             855

<210> SEQ ID NO 4
<211> LENGTH: 451
<212> TYPE: PRT
<213> ORGANISM: Escherichia coli

<400> SEQUENCE: 4

Lys Asn Leu Asp Cys Trp Val Asp Asn Glu Glu Asp Ile Asp Val Ile
1               5               10              15

Leu Lys Lys Ser Thr Ile Leu Asn Leu Asp Ile Asn Asn Asp Ile Ile
            20              25              30

Ser Asp Ile Ser Gly Phe Asn Ser Ser Val Ile Thr Tyr Pro Asp Ala
        35              40              45

Gln Leu Val Pro Gly Ile Asn Gly Lys Ala Ile His Leu Val Asn Asn
    50              55              60

Glu Ser Ser Glu Val Ile Val His Lys Ala Met Asp Ile Glu Tyr Asn
65              70              75              80

Asp Met Phe Asn Asn Phe Thr Val Ser Phe Trp Leu Arg Val Pro Lys
                85              90              95

Val Ser Ala Ser His Leu Glu Gln Tyr Gly Thr Asn Glu Tyr Ser Ile
            100             105             110

Ile Ser Ser Met Lys Lys His Ser Leu Ser Ile Gly Ser Gly Trp Ser
        115             120             125

Val Ser Leu Lys Gly Asn Asn Leu Ile Trp Thr Leu Lys Asp Ser Ala
    130             135             140

Gly Glu Val Arg Gln Ile Thr Phe Arg Asp Leu Pro Asp Lys Phe Asn
145             150             155             160

Ala Tyr Leu Ala Asn Lys Trp Val Phe Ile Thr Ile Thr Asn Asp Arg
                165             170             175

Leu Ser Ser Ala Asn Leu Tyr Ile Asn Gly Val Leu Met Gly Ser Ala
            180             185             190

Glu Ile Thr Gly Leu Gly Ala Ile Arg Glu Asp Asn Asn Ile Thr Leu
            195             200             205

Lys Leu Asp Arg Cys Asn Asn Asn Asn Gln Tyr Val Ser Ile Asp Lys
    210             215             220

Phe Arg Ile Phe Cys Lys Ala Leu Asn Pro Lys Glu Ile Glu Lys Leu
225             230             235             240

Tyr Thr Ser Tyr Leu Ser Ile Thr Phe Leu Arg Asp Phe Trp Gly Asn
                245             250             255

Pro Leu Arg Tyr Asp Thr Glu Tyr Tyr Leu Ile Pro Val Ala Ser Ser
```

-continued

```
                260               265               270
Ser Lys Asp Val Gln Leu Lys Asn Ile Thr Asp Tyr Met Tyr Leu Thr
        275               280               285

Asn Ala Pro Ser Tyr Thr Asn Gly Lys Leu Asn Ile Tyr Tyr Arg Arg
        290               295               300

Leu Tyr Asn Gly Leu Lys Phe Ile Ile Lys Arg Tyr Thr Pro Asn Asn
305               310               315               320

Glu Ile Asp Ser Phe Val Lys Ser Gly Asp Phe Ile Lys Leu Tyr Val
                325               330               335

Ser Tyr Asn Asn Asn Glu His Ile Val Gly Tyr Pro Lys Asp Gly Asn
            340               345               350

Ala Phe Asn Asn Leu Asp Arg Ile Leu Arg Val Gly Tyr Asn Ala Pro
        355               360               365

Gly Ile Pro Leu Tyr Lys Lys Met Glu Ala Val Lys Leu Arg Asp Leu
    370               375               380

Lys Thr Tyr Ser Val Gln Leu Lys Leu Tyr Asp Asp Lys Asn Ala Ser
385               390               395               400

Leu Gly Leu Val Gly Thr His Asn Gly Gln Ile Gly Asn Asp Pro Asn
            405               410               415

Arg Asp Ile Leu Ile Ala Ser Asn Trp Tyr Phe Asn His Leu Lys Asp
        420               425               430

Lys Ile Leu Gly Cys Asp Trp Tyr Phe Val Pro Thr Asp Glu Gly Trp
        435               440               445

Thr Asn Asp
    450

<210> SEQ ID NO 5
<211> LENGTH: 4234
<212> TYPE: DNA
<213> ORGANISM: Escherichia coli

<400> SEQUENCE: 5
gatctcgatc ccgcgaaatt aatacgactc actataggga gaccacaacg gtttccctct      60
agaaataatt ttgtttaact ttaagaagga gatatacata tgcggggttc tcatcatcat     120
catcatcatg gtatggctag catgactggt ggacagcaaa tgggtcggga tctgtacgac     180
gatgacgata aggatcgatg gggatccgag ctcgagaaaa atctggattg ttgggttgac     240
aatgaagaag atattgatgt tattctgaaa aagagcacga tcctgaacct ggatattaat     300
aacgatatta tctctgatat cagtggtttt aattcatcag ttattactta cccagacgct     360
caactggtgc cgggaatcaa tgggaaagcc attcatctgg tgaataatga atcaagtgaa     420
gtgatcgtgc ataaagcgat ggatatcgag tacaacgata tgtttaataa tttcacggtg     480
tcgttctggc tgcgtgttcc gaaagtgagt gcctcccacc tggaacaata tggaaccaac     540
gaatactcaa tcattagcag catgaagaaa cattcgctga gtattggttc aggttggagc     600
gtttccctga aagggaacaa tctgatctgg acactgaagg actcagcggg cgaagtgcgt     660
cagattacgt ttcgtgatct gccggataaa tttaatgcat acctggctaa caaatgggtg     720
ttcatcacaa tcaccaatga ccgtctgtcg tctgcaaacc tgtatattaa tggggtactg     780
atgggctcgg cagaaattac agggctgggc gccattcgtg aagataacaa tattacgctg     840
aaactggatc gttgtaataa caataatcag tatgtgagca ttgataaatt tcgtattttc     900
tgcaaagcgc tgaacccgaa agaaattgaa aaactgtata cctcgtatct gtcaattacg     960
tttctgcgcg atttctgggg aaaacccgctg cgttacgata cggaatacta cctgatcccg    1020
```

```
gtagccagtt ctagtaaaga cgttcaactg aaaaatatta ccgactacat gtatctgaca      1080
aacgctccat catacacaaa cggcaaactg aacatctatt accgtcgcct gtacaatggg      1140
ctgaaattca tcattaaacg ttataccccg aataacgaaa ttgattcctt tgtgaagtcc      1200
ggtgacttca ttaagctgta tgtatcctat aacaataatg aacacatcgt tggctatccg      1260
aaggatggca atgcctttaa caacctggat cgtattctgc gtgtaggtta caacgccccg      1320
ggtattccgc tgtataagaa aatggaagca gtgaaactgc gtgatctgaa aacatattcc      1380
gtgcaactga agctgtatga tgacaaaaat gctagcctgg gtctggtagg cacgcataac      1440
ggtcagattg gaaacgatcc taatcgtgac atcctgatcg cctctaactg gtattttaac      1500
cacctgaaag ataaaattct gggctgcgat tggtattttg tccctaccga tgaaggctgg      1560
acgaacgatt aagaattcga agcttgatcc ggctgctaac aaagcccgaa aggaagctga      1620
gttggctgct gccaccgctg agcaataact agcataaccc cttggggcct ctaaacgggt      1680
cttgaggggt tttttgctga aaggaggaac tatatccgga tctggcgtaa tagcgaagag      1740
gcccgcaccg atcgcccttc ccaacagttg cgcagcctga atggcgaatg ggacgcgccc      1800
tgtagcggcg cattaagcgc ggcgggtgtg gtggttacgc gcagcgtgac cgctacactt      1860
gccagcgccc tagcgcccgc tcctttcgct ttcttccctt cctttctcgc cacgttcgcc      1920
ggctttcccc gtcaagctct aaatcggggg ctccctttag ggttccgatt tagtgcttta      1980
cggcacctcg accccaaaaa acttgattag ggtgatggtt cacgtagtgg gccatcgccc      2040
tgatagacgt tttttcgccc tttgacgttg gagtccacgt tctttaatag tggactcttg      2100
ttccaaactg gaacaacact caaccctatc tcggtctatt cttttgattt ataagggatt      2160
ttgccgattt cggcctattg gttaaaaaat gagctgattt aacaaaaatt taacgcgaat      2220
tttaacaaaa tattaacgct tacaatttag gtggcacttt tcggggaaat gtgcgcggaa      2280
cccctatttg tttatttttc taaatacatt caaatatgta tccgctcatg agacaataac      2340
cctgataaat gcttcaataa tattgaaaaa ggaagagtat gagtattcaa catttccgtg      2400
tcgcccttat tccctttttt gcggcatttt gccttcctgt ttttgctcac ccagaaacgc      2460
tggtgaaagt aaaagatgct gaagatcagt tgggtgcacg agtgggttac atcgaactgg      2520
atctcaacag cggtaagatc cttgagagtt ttcgccccga agaacgtttt ccaatgatga      2580
gcacttttaa agttctgcta tgtggcgcgg tattatcccg tattgacgcc gggcaagagc      2640
aactcggtcg ccgcatacac tattctcaga atgacttggt tgagtactca ccagtcacag      2700
aaaagcatct tacggatggc atgacagtaa gagaattatg cagtgctgcc ataaccatga      2760
gtgataacac tgcggccaac ttacttctga acgatcgg aggaccgaag gagctaaccg      2820
cttttttgca acatggggg gatcatgtaa ctcgccttga tcgttgggaa ccggagctga      2880
atgaagccat accaaacgac gagcgtgaca ccacgatgcc tgtagcaatg gcaacaacgt      2940
tgcgcaaact attaactggc gaactactta ctctagcttc ccggcaacaa ttaatagact      3000
ggatggaggc ggataaagtt gcaggaccac ttctgcgctc ggcccttccg gctggctggt      3060
ttattgctga taaatctgga gccggtgagc gtgggtctcg cggtatcatt gcagcactgg      3120
ggccagatgg taagccctcc cgtatcgtag ttatctacac gacggggagt caggcaacta      3180
tggatgaacg aaatagacag atcgctgaga taggtgcctc actgattaag cattggtaac      3240
tgtcagacca agtttactca tatatacttt agattgattt aaaacttcat ttttaattta      3300
aaaggatcta ggtgaagatc ctttttgata atctcatgac caaaatccct taacgtgagt      3360
```

-continued

```
tttcgttcca ctgagcgtca gaccccgtag aaaagatcaa aggatcttct tgagatcctt    3420
tttttctgcg cgtaatctgc tgcttgcaaa caaaaaaacc accgctacca gcggtggttt    3480
gtttgccgga tcaagagcta ccaactcttt ttccgaaggt aactggcttc agcagagcgc    3540
agataccaaa tactgttctt ctagtgtagc cgtagttagg ccaccacttc aagaactctg    3600
tagcaccgcc tacatacctc gctctgctaa tcctgttacc agtggctgct gccagtggcg    3660
ataagtcgtg tcttaccggg ttggactcaa gacgatagtt accggataag gcgcagcggt    3720
cgggctgaac ggggggttcg tgcacacagc ccagcttgga gcgaacgacc tacaccgaac    3780
tgagatacct acagcgtgag ctatgagaaa gcgccacgct tcccgaaggg agaaaggcgg    3840
acaggtatcc ggtaagcggc agggtcggaa caggagagcg cacgagggag cttccagggg    3900
gaaacgcctg gtatctttat agtcctgtcg ggtttcgcca cctctgactt gagcgtcgat    3960
ttttgtgatg ctcgtcaggg gggcggagcc tatggaaaaa cgccagcaac gcggcctttt    4020
tacggttcct ggccttttgc tggccttttg ctcacatgtt ctttcctgcg ttatcccctg    4080
attctgtgga taaccgtatt accgcctttg agtgagctga taccgctcgc cgcagccgaa    4140
cgaccgagcg cagcgagtca gtgagcgagg aagcggaaga gcgcccaata cgcaaaccgc    4200
ctctccccgc gcgttggccg attcattaat gcag                                4234
```

```
<210> SEQ ID NO 6
<211> LENGTH: 863
<212> TYPE: PRT
<213> ORGANISM: Escherichia coli

<400> SEQUENCE: 6

Pro Ile Thr Ile Asn Asn Phe Arg Tyr Ser Asp Pro Val Asn Asn Asp
1               5                   10                  15

Thr Ile Ile Met Met Glu Pro Pro Tyr Cys Lys Gly Leu Asp Ile Tyr
                20                  25                  30

Tyr Lys Ala Phe Lys Ile Thr Asp Arg Ile Trp Ile Val Pro Glu Arg
            35                  40                  45

Tyr Glu Phe Gly Thr Lys Pro Glu Asp Phe Asn Pro Pro Ser Ser Leu
        50                  55                  60

Ile Glu Gly Ala Ser Glu Tyr Tyr Asp Pro Asn Tyr Leu Arg Thr Asp
65                  70                  75                  80

Ser Asp Lys Asp Arg Phe Leu Gln Thr Met Val Lys Leu Phe Asn Arg
                85                  90                  95

Ile Lys Asn Asn Val Ala Gly Glu Ala Leu Leu Asp Lys Ile Ile Asn
            100                 105                 110

Ala Ile Pro Tyr Leu Gly Asn Ser Tyr Ser Leu Leu Asp Lys Phe Asp
        115                 120                 125

Thr Asn Ser Asn Ser Val Ser Phe Asn Leu Leu Glu Gln Asp Pro Ser
    130                 135                 140

Gly Ala Thr Thr Lys Ser Ala Met Leu Thr Asn Leu Ile Ile Phe Gly
145                 150                 155                 160

Pro Gly Pro Val Leu Asn Lys Asn Glu Val Arg Gly Ile Val Leu Arg
                165                 170                 175

Val Asp Asn Lys Asn Tyr Phe Pro Cys Arg Asp Gly Phe Gly Ser Ile
            180                 185                 190

Met Gln Met Ala Phe Cys Pro Glu Tyr Val Pro Thr Phe Asp Asn Val
        195                 200                 205

Ile Glu Asn Ile Thr Ser Leu Thr Ile Gly Lys Ser Lys Tyr Phe Gln
    210                 215                 220
```

```
Asp Pro Ala Leu Leu Leu Met His Glu Leu Ile His Val Leu His Gly
225                 230                 235                 240

Leu Tyr Gly Met Gln Val Ser Ser His Glu Ile Ile Pro Ser Lys Gln
                245                 250                 255

Glu Ile Tyr Met Gln His Thr Tyr Pro Ile Ser Ala Glu Glu Leu Phe
                260                 265                 270

Thr Phe Gly Gly Gln Asp Ala Asn Leu Ile Ser Ile Asp Ile Lys Asn
                275                 280                 285

Asp Leu Tyr Glu Lys Thr Leu Asn Asp Tyr Lys Ala Ile Ala Asn Lys
    290                 295                 300

Leu Ser Gln Val Thr Ser Cys Asn Asp Pro Asn Ile Asp Ile Asp Ser
305                 310                 315                 320

Tyr Lys Gln Ile Tyr Gln Gln Lys Tyr Gln Phe Asp Lys Asp Ser Asn
                325                 330                 335

Gly Gln Tyr Ile Val Asn Glu Asp Lys Phe Gln Ile Leu Tyr Asn Ser
                340                 345                 350

Ile Met Tyr Gly Phe Thr Glu Ile Glu Leu Gly Lys Lys Phe Asn Ile
                355                 360                 365

Lys Thr Arg Leu Ser Tyr Phe Ser Met Asn His Asp Pro Val Lys Ile
    370                 375                 380

Pro Asn Leu Leu Asp Asp Thr Ile Tyr Asn Asp Thr Glu Gly Phe Asn
385                 390                 395                 400

Ile Glu Ser Lys Asp Leu Lys Ser Glu Tyr Lys Gly Gln Asn Met Arg
                405                 410                 415

Val Asn Thr Asn Ala Phe Arg Asn Val Asp Gly Ser Gly Leu Val Ser
                420                 425                 430

Lys Leu Ile Gly Leu Cys Lys Lys Ile Ile Pro Pro Thr Asn Ile Arg
                435                 440                 445

Glu Asn Leu Tyr Asn Arg Thr Ala Ser Leu Thr Asp Leu Gly Gly Glu
    450                 455                 460

Leu Cys Ile Lys Ile Lys Asn Glu Asp Leu Thr Phe Ile Ala Glu Lys
465                 470                 475                 480

Asn Ser Phe Ser Glu Glu Pro Phe Gln Asp Glu Ile Val Ser Tyr Asn
                485                 490                 495

Thr Lys Asn Lys Pro Leu Asn Phe Asn Tyr Ser Leu Asp Lys Ile Ile
                500                 505                 510

Val Asp Tyr Asn Leu Gln Ser Lys Ile Thr Leu Pro Asn Asp Arg Thr
                515                 520                 525

Thr Pro Val Thr Lys Gly Ile Pro Tyr Ala Pro Glu Tyr Lys Ser Asn
    530                 535                 540

Ala Ala Ser Thr Ile Glu Ile His Asn Ile Asp Asp Asn Thr Ile Tyr
545                 550                 555                 560

Gln Tyr Leu Tyr Ala Gln Lys Ser Pro Thr Thr Leu Gln Arg Ile Thr
                565                 570                 575

Met Thr Asn Ser Val Asp Asp Ala Leu Ile Asn Ser Thr Lys Ile Tyr
                580                 585                 590

Ser Tyr Phe Pro Ser Val Ile Ser Lys Val Asn Gln Gly Ala Gln Gly
                595                 600                 605

Ile Leu Phe Leu Gln Trp Val Arg Asp Ile Ile Asp Asp Phe Thr Asn
    610                 615                 620

Glu Ser Ser Gln Lys Thr Thr Ile Asp Lys Ile Ser Asp Val Ser Thr
625                 630                 635                 640
```

-continued

```
Ile Val Pro Tyr Ile Gly Pro Ala Leu Asn Ile Val Lys Gln Gly Tyr
                645                 650                 655

Glu Gly Asn Phe Ile Gly Ala Leu Glu Thr Thr Gly Val Val Leu Leu
                660                 665                 670

Leu Glu Tyr Ile Pro Glu Ile Thr Leu Pro Val Ile Ala Ala Leu Ser
                675                 680                 685

Ile Ala Glu Ser Ser Thr Gln Lys Glu Lys Ile Ile Lys Thr Ile Asp
                690                 695                 700

Asn Phe Leu Glu Lys Arg Tyr Glu Lys Trp Ile Glu Val Tyr Lys Leu
705                 710                 715                 720

Val Lys Ala Lys Trp Leu Gly Thr Val Asn Thr Gln Phe Gln Lys Arg
                725                 730                 735

Ser Tyr Gln Met Tyr Arg Ser Leu Glu Tyr Gln Val Asp Ala Ile Lys
                740                 745                 750

Lys Ile Ile Asp Tyr Glu Tyr Lys Ile Tyr Ser Gly Pro Asp Lys Glu
                755                 760                 765

Gln Ile Ala Asp Glu Ile Asn Asn Leu Lys Asn Lys Leu Glu Glu Lys
                770                 775                 780

Ala Asn Lys Ala Met Ile Asn Ile Asn Ile Phe Met Arg Glu Ser Ser
785                 790                 795                 800

Arg Ser Phe Leu Val Asn Gln Met Ile Asn Glu Ala Lys Lys Gln Leu
                805                 810                 815

Leu Glu Phe Asp Thr Gln Ser Lys Asn Ile Leu Met Gln Tyr Ile Lys
                820                 825                 830

Ala Asn Ser Lys Phe Ile Gly Ile Thr Glu Leu Lys Lys Leu Glu Ser
                835                 840                 845

Lys Ile Asn Lys Val Phe Ser Thr Pro Ile Pro Phe Ser Tyr Ser
    850                 855                 860
```

<210> SEQ ID NO 7
<211> LENGTH: 5479
<212> TYPE: DNA
<213> ORGANISM: Escherichia coli

<400> SEQUENCE: 7

```
gatctcgatc ccgcgaaatt aatacgactc actatagggga gaccacaacg gtttccctct        60
agaaataatt ttgtttaact ttaagaagga gatatacata tgcggggttc tcatcatcat       120
catcatcatg gtatggctag catgactggt ggacagcaaa tgggtcggga tctgtacgac       180
gatgacgata aggatcgatg gggatccgag ctcgagccga ttaccatcaa taattttcgt       240
tattcagatc cggtgaataa tgataccatc atcatgatgg aaccaccgta ctgtaaaggg       300
ctggatattt attataaagc gttcaaaatc accgaccgca tctggatcgt gccggaacgc       360
tacgaattcg gcaccaaacc ggaagatttt aatccgccga gtagtctgat cgaaggtgca       420
tcggaatact acgatccgaa ttatctgcgt actgactctg ataaagatcg ctttctgcaa       480
acgatggtaa aactgttcaa tcgtatcaaa aacaatgtag caggcgaagc cctgctggat       540
aaaatcatca acgccattcc gtatctggga aacagttatt ctctgctgga taaattcgat       600
acaaactcga actctgtgtc attcaacctg ctggaacagg acccgagcgg cgcgaccact       660
aagagtgcga tgctgactaa cctgattatt ttcggtccgg accggtact gaataaaaat       720 gaagttcgcg gcattgtact gcgtgtcgat aataaaaact atttcccatg tcgtgatggc       780
ttcggcagca tcatgcagat ggccttttgt ccggaatatg tgccaacttt cgataatgtg       840
attgagaaca tcacctctct gacgattggt aaaagtaaat atttccagga tccggctctg       900
```

-continued

```
ctgctgatgc atgaactgat ccatgttctg catggcctgt atggcatgca ggtttcatcc      960
cacgaaatta tcccatccaa acaggaaatt tacatgcagc atacatatcc gattagtgcc     1020
gaagaactgt tcacttttgg cggccaggat gcgaacctga tttcgattga cattaaaaac     1080
gatctgtatg aaaaaactct gaacgattat aaagcgattg ccaacaaact gtctcaggta     1140
acctcctgta acgatccgaa tattgatatt gacagttata aacaaattta tcagcagaag     1200
tatcagttcg ataaagactc taatggccag tatattgtta acgaagataa attccagatt     1260
ctgtacaata gcattatgta tggctttact gagatcgaac tgggtaaaaa atttaacatc     1320
aagactcgtc tgagctattt tagcatgaat catgatccag tgaaaatccc gaatctgctg     1380
gatgatacga tttataatga taccgaagga tttaacatcg aaagcaagga tctgaaatcc     1440
gaatataaag ggcagaacat gcgcgttaat accaatgcat ttcgcaatgt tgatggttca     1500
ggcctggtgt cgaaactgat tgggctgtgt aagaaaatca ttccaccgac aaatattcgc     1560
gaaaatctgt acaaccgtac ggcgagcctg accgatctgg ggggagaact gtgtattaaa     1620
atcaaaaatg aagatctgac cttcattgct gagaagaata gcttttccga gagccattc      1680 caggacgaaa tcgtgtctta taacaccaag aataaaccgc tgaatttcaa ctactccctg     1740
gacaaaatca ttgtggatta caacctgcag agtaaaatta ccctgccgaa tgatcgtacc     1800
accccggtga cgaaaggcat cccttacgca ccagaatata aatcaaatgc agcctcgact     1860
atcgagatcc ataatattga tgacaacact atttaccagt acctgtatgc tcagaaatct     1920
ccgacgacgc tgcagcgcat caccatgact aacagcgtgg acgatgccct gattaatagc     1980
accaaaatct actcttactt tccgtcggtg atctctaagg ttaatcaggg cgcgcaaggt     2040
atcctgtttc tgcaatgggt gcgtgatatt attgatgatt tcactaatga atctagccag     2100
aaaacgacaa ttgataaaat ttcggatgtt tccaccatcg tgccttacat cggcccagcg     2160
ctgaacatcg tgaagcaggg ttatgagggt aactttatcg gagcactgga aacgaccggc     2220
gtggttctgc tgctggaata tattccggag attactctgc cagttattgc ggctctgtcg     2280
attgcagaga gctcaacgca gaaagaaaaa attattaaga cgatcgacaa tttcctggaa     2340
aagcgctacg aaaaatggat cgaagtgtat aagctggtga aagcgaaatg gctggggacc     2400
gtgaacaccc agttccaaaa acgttcctat caaatgtatc gtagcctgga atatcaggtg     2460
gacgccatta aaaagatcat cgattacgaa tataagatct actccggtcc ggacaaagaa     2520
cagattgcgg acgaaattaa caatctgaaa aataaactgg aggaaaaagc caacaaagcg     2580
atgattaata tcaatatttt catgcgtgaa agcagccgta gcttcctggt caatcagatg     2640
attaatgaag cgaagaaaca actgctggaa tttgatacgc aatctaaaaa tattctgatg     2700
caatacatca aagccaattc taaatttatt gggatcacgg aactgaaaaa gctggaatcg     2760
aaaatcaata agtctttag cacccccgatt ccgttctcct actcgtaagg taccatggaa     2820
ttcgaagctt gatccggctg ctaacaaagc ccgaaaggaa gctgagttgg ctgctgccac     2880
cgctgagcaa taactagcat aacccccttgg ggcctctaaa cgggtcttga ggggtttttt     2940
gctgaaagga ggaactatat ccggatctgg cgtaatagcg aagaggcccg caccgatcgc     3000
ccttcccaac agttgcgcag cctgaatggc gaatgggacg cgccctgtag cggcgcatta     3060
agcgcggcgg gtgtggtggt tacgcgcagc gtgaccgcta cacttgccag cgccctagcg     3120
cccgctcctt tcgctttctt cccttccttt ctcgccacgt tcgccggctt tccccgtcaa     3180
gctctaaatc gggggctccc tttagggttc cgatttagtg ctttacggca cctcgacccc     3240
```

-continued

```
aaaaaacttg attagggtga tggttcacgt agtgggccat cgccctgata gacggttttt      3300
cgcccttgaa cgttggagtc cacgttcttt aatagtggac tcttgttcca aactggaaca      3360
acactcaacc ctatctcggt ctattctttt gatttataag ggattttgcc gatttcggcc      3420
tattggttaa aaaatgagct gatttaacaa aaatttaacg cgaattttaa caaaatatta      3480
acgcttacaa tttaggtggc acttttcggg gaaatgtgcg cggaacccct atttgtttat      3540
ttttctaaat acattcaaat atgtatccgc tcatgagaca ataaccctga taaatgcttc      3600
aataatattg aaaaaggaag agtatgagta ttcaacattt ccgtgtcgcc cttattccct      3660 ttttttgcggc attttgcctt cctgtttttg ctcacccaga aacgctggtg aaagtaaaag      3720
atgctgaaga tcagttgggt gcacgagtgg gttacatcga actggatctc aacagcggta      3780
agatccttga gagttttcgc cccgaagaac gttttccaat gatgagcact tttaaagttc      3840
tgctatgtgg cgcggtatta tcccgtattg acgccgggca agagcaactc ggtcgccgca      3900
tacactattc tcagaatgac ttggttgagt actcaccagt cacagaaaag catcttacgg      3960
atggcatgac agtaagagaa ttatgcagtg ctgccataac catgagtgat aacactgcgg      4020
ccaacttact tctgacaacg atcggaggac cgaaggagct aaccgctttt ttgcacaaca      4080
tgggggatca tgtaactcgc cttgatcgtt gggaaccgga gctgaatgaa gccataccaa      4140
acgacgagcg tgacaccacg atgcctgtag caatggcaac aacgttgcgc aaactattaa      4200
ctggcgaact acttactcta gcttcccggc aacaattaat agactggatg gaggcggata      4260
aagttgcagg accacttctg cgctcggccc ttccggctgg ctggtttatt gctgataaat      4320
ctggagccgg tgagcgtggg tctcgcggta tcattgcagc actggggcca gatggtaagc      4380
cctcccgtat cgtagttatc tacacgacgg ggagtcaggc aactatggat gaacgaaata      4440
gacagatcgc tgagataggt gcctcactga ttaagcattg gtaactgtca gaccaagttt      4500
actcatatat actttagatt gatttaaaac ttcattttta atttaaaagg atctaggtga      4560
agatcctttt tgataatctc atgaccaaaa tcccttaacg tgagttttcg ttccactgag      4620
cgtcagaccc cgtagaaaag atcaaaggat cttcttgaga tccttttttt ctgcgcgtaa      4680
tctgctgctt gcaaacaaaa aaaccaccgc taccagcggt ggtttgtttg ccggatcaag      4740
agctaccaac tctttttccg aaggtaactg gcttcagcag agcgcagata ccaaatactg      4800
ttcttctagt gtagccgtag ttaggccacc acttcaagaa ctctgtagca ccgcctacat      4860
acctcgctct gctaatcctg ttaccagtgg ctgctgccag tggcgataag tcgtgtctta      4920
ccgggttgga ctcaagacga tagttaccgg ataaggcgca gcggtcgggc tgaacggggg      4980
gttcgtgcac acagcccagc ttggagcgaa cgacctacac cgaactgaga tacctacagc      5040
gtgagctatg agaaagcgcc acgcttcccg aagggagaaa ggcggacagg tatccggtaa      5100
gcggcagggt cggaacagga gagcgcacga gggagcttcc aggggaaac gcctggtatc      5160 tttatagtcc tgtcgggttt cgccacctct gacttgagcg tcgatttttg tgatgctcgt      5220
caggggggcg gagcctatgg aaaaacgcca gcaacgcggc cttttacgg ttcctggcct      5280 tttgctggcc ttttgctcac atgttctttc ctgcgttatc ccctgattct gtggataacc      5340
gtattaccgc ctttgagtga gctgataccg ctcgccgcag ccgaacgacc gagcgcagcg      5400
agtcagtgag cgaggaagcg gaagagcgcc caatacgcaa accgcctctc cccgcgcgtt      5460
ggccgattca ttaatgcag                                                 5479
```

<210> SEQ ID NO 8
<211> LENGTH: 451

```
<212> TYPE: PRT
<213> ORGANISM: Escherichia coli

<400> SEQUENCE: 8

Lys Asn Leu Asp Cys Trp Val Asp Asn Glu Glu Asp Ile Asp Val Ile
1               5                   10                  15

Leu Lys Lys Ser Thr Ile Leu Asn Leu Asp Ile Asn Asn Asp Ile Ile
            20                  25                  30

Ser Asp Ile Ser Gly Phe Asn Ser Ser Val Ile Thr Tyr Pro Asp Ala
        35                  40                  45

Gln Leu Val Pro Gly Ile Asn Gly Lys Ala Ile His Leu Val Asn Asn
    50                  55                  60

Glu Ser Ser Glu Val Ile Val His Lys Ala Met Asp Ile Glu Tyr Asn
65                  70                  75                  80

Asp Met Phe Asn Asn Phe Thr Val Ser Phe Trp Leu Arg Val Pro Lys
                85                  90                  95

Val Ser Ala Ser His Leu Glu Gln Tyr Gly Thr Asn Glu Tyr Ser Ile
            100                 105                 110

Ile Ser Ser Met Lys Lys His Ser Leu Ser Ile Gly Ser Gly Trp Ser
        115                 120                 125

Val Ser Leu Lys Gly Asn Asn Leu Ile Trp Thr Leu Lys Asp Ser Ala
    130                 135                 140

Gly Glu Val Arg Gln Ile Thr Phe Arg Asp Leu Pro Asp Lys Phe Asn
145                 150                 155                 160

Ala Tyr Leu Ala Asn Lys Trp Val Phe Ile Thr Ile Thr Asn Asp Arg
                165                 170                 175

Leu Ser Ser Ala Asn Leu Tyr Ile Asn Gly Val Leu Met Gly Ser Ala
            180                 185                 190

Glu Ile Thr Gly Leu Gly Ala Ile Arg Glu Asp Asn Asn Ile Thr Leu
        195                 200                 205

Lys Leu Asp Arg Cys Asn Asn Asn Asn Gln Tyr Val Ser Ile Asp Lys
    210                 215                 220

Phe Arg Ile Phe Cys Lys Ala Leu Asn Pro Lys Glu Ile Glu Lys Leu
225                 230                 235                 240

Tyr Thr Ser Tyr Leu Ser Ile Thr Phe Leu Arg Asp Phe Trp Gly Asn
                245                 250                 255

Pro Leu Arg Tyr Asp Thr Glu Tyr Tyr Leu Ile Pro Val Ala Ser Ser
            260                 265                 270

Ser Lys Asp Val Gln Leu Lys Asn Ile Thr Asp Tyr Met Tyr Leu Thr
        275                 280                 285

Asn Ala Pro Ser Tyr Thr Asn Gly Lys Leu Asn Ile Tyr Tyr Arg Arg
    290                 295                 300

Leu Tyr Asn Gly Leu Lys Phe Ile Ile Lys Arg Tyr Thr Pro Asn Asn
305                 310                 315                 320

Glu Ile Asp Ser Phe Val Lys Ser Gly Asp Phe Ile Lys Leu Tyr Val
                325                 330                 335

Ser Tyr Asn Asn Asn Glu His Ile Val Gly Tyr Pro Lys Asp Gly Asn
            340                 345                 350

Ala Phe Asn Asn Leu Asp Arg Ile Leu Glu Val Gly Tyr Asn Ala Pro
        355                 360                 365

Gly Ile Pro Leu Tyr Lys Lys Met Glu Ala Val Lys Leu Arg Asp Leu
    370                 375                 380

Lys Thr Tyr Ser Val Gln Leu Lys Leu Tyr Asp Asp Lys Asn Ala Ser
385                 390                 395                 400
```

Leu Gly Leu Val Gly Thr His Asn Gly Gln Ile Gly Asn Asp Pro Asn
            405                 410                 415

Arg Asp Ile Leu Ile Ala Ser Asn Ala Tyr Phe Asn His Leu Lys Asp
            420                 425                 430

Lys Ile Leu Gly Cys Asp Trp Tyr Phe Val Pro Thr Asp Glu Gly Trp
        435                 440                 445

Thr Asn Asp
    450

<210> SEQ ID NO 9
<211> LENGTH: 4234
<212> TYPE: DNA
<213> ORGANISM: Escherichia coli

<400> SEQUENCE: 9
gatctcgatc ccgcgaaatt aatacgactc actataggga gaccacaacg gtttccctct      60
agaaataatt ttgtttaact ttaagaagga gatatacata tgcggggttc tcatcatcat     120
catcatcatg gtatggctag catgactggt ggacagcaaa tgggtcggga tctgtacgac     180
gatgacgata aggatcgatg gggatccgag ctcgagaaaa atttggattg ctgggtcgac     240
aatgaggagg acattgatgt gatattaaag aaatccacta tcttaaatct tgatataaac     300
aatgacatca tctcggatat atctgggttc aattcttccg tcataactta ccctgatgct     360
caactggtac cgggaattaa tgggaaggcc atacacttag tcaacaacga atcttccgag     420
gtgattgtac ataaggcaat ggacatagag tacaatgaca tgtttaataa cttractgtc     480
tcgttctggt tacgcgtgcc caaagtatct gcctcacacc tggaacagta tggcacaaat     540
gaatattcta ttatcagtag tatgaagaaa cactcgcttt ctataggatc cggctggagt     600
gtttcgctga agggcaataa cttgatctgg acccttaaag attcagcggg agaagtaaga     660
caaataactt ccggggattt gcctgataag ttcaacgcat acctggccaa taagtgggtt     720
ttcataacta taacaaatga ccgcttgtct agcgccaact tatacatcaa tggagtattg     780
atgggttccg ctgagattac aggcttgggt gccataagag aggacaataa tatcaccctg     840
aaactggacc gctgcaataa taacaatcag tacgtgagca tagataaatt ccgtattttt     900
tgcaaagccc tgaacccgaa agaaatcgaa aaactgtata cttcatatct gagcataaca     960
tttctgcgtg atttttgggg taacccgctg cgttatgata ccgaatacta cctgattccg    1020
gttgccagca gcagcaaaga tgttcagctg aaaaatatta ccgactatat gtatctgaca    1080
aatgcgccgt cttataccaa tggcaaactg aatatttatt atcgccggtt gtacaacggg    1140
ctgaagttca ttattaaacg gtacaccccg aacaacgaaa tcgattcatt tgttaaatcc    1200
ggggatttca taaagttata cgtgagctat aataacaacg agcatattgt aggttatccg    1260
aaagacggta atgctttcaa caacttggat cggatactgg aagttggtta caacgcccca    1320
ggtattccac tgtataagaa aatggaagcc gtcaagttgc gtgatttaaa gacgtactca    1380
gtacagctta aattatacga cgataagaat gcaagccttg gattggttgg gacccacaat    1440
ggtcagattg gaaatgaccc caatcgggac attctgatag catccaacgc gtacttcaac    1500
catttgaaag ataaaatcct gggctgtgat tggtactttg taccgactga tgaaggatgg    1560
acgaatgact aagaattcga agcttgatcc ggctgctaac aaagcccgaa aggaagctga    1620
gttggctgct gccaccgctg agcaataact agcataaccc cttggggcct ctaaacgggt    1680
cttgaggggt tttttgctga aaggaggaac tatatccgga tctggcgtaa tagcgaagag    1740

-continued

```
gcccgcaccg atcgcccttc ccaacagttg cgcagcctga atggcgaatg ggacgcgccc   1800
tgtagcggcg cattaagcgc ggcgggtgtg gtggttacgc gcagcgtgac cgctacactt   1860
gccagcgccc tagcgcccgc tcctttcgct ttcttccctt cctttctcgc cacgttcgcc   1920
ggctttcccc gtcaagctct aaatcggggg ctccctttag ggttccgatt tagtgcttta   1980
cggcacctcg accccaaaaa acttgattag ggtgatggtt cacgtagtgg gccatcgccc   2040
tgatagacgt tttttcgccc tttgacgttg gagtccacgt tctttaatag tggactcttg   2100
ttccaaactg gaacaacact caaccctatc tcggtctatt cttttgattt ataagggatt   2160
ttgccgattt cggcctattg gttaaaaaat gagctgattt aacaaaaatt taacgcgaat   2220
tttaacaaaa tattaacgct tacaatttag gtggcacttt tcggggaaat gtgcgcggaa   2280
cccctatttg tttatttttc taaatacatt caaatatgta tccgctcatg agacaataac   2340
cctgataaat gcttcaataa tattgaaaaa ggaagagtat gagtattcaa catttccgtg   2400
tcgcccttat tccctttttt gcggcatttt gccttcctgt ttttgctcac ccagaaacgc   2460
tggtgaaagt aaaagatgct gaagatcagt tgggtgcacg agtgggttac atcgaactgg   2520
atctcaacag cggtaagatc cttgagagtt ttcgccccga agaacgtttt ccaatgatga   2580
gcacttttaa agttctgcta tgtggcgcgg tattatcccg tattgacgcc gggcaagagc   2640
aactcggtcg ccgcatacac tattctcaga atgacttggt tgagtactca ccagtcacag   2700
aaaagcatct tacggatggc atgacagtaa gagaattatg cagtgctgcc ataaccatga   2760
gtgataacac tgcggccaac ttacttctga caacgatcgg aggaccgaag gagctaaccg   2820
cttttttgca caacatgggg gatcatgtaa ctcgccttga tcgttgggaa ccggagctga   2880
atgaagccat accaaacgac gagcgtgaca ccacgatgcc tgtagcaatg gcaacaacgt   2940
tgcgcaaact attaactggc gaactactta ctctagcttc ccggcaacaa ttaatagact   3000
ggatggaggc ggataaagtt gcaggaccac ttctgcgctc ggcccttccg gctggctggt   3060
ttattgctga taaatctgga gccggtgagc gtgggtctcg cggtatcatt gcagcactgg   3120
ggccagatgg taagccctcc cgtatcgtag ttatctacac gacggggagt caggcaacta   3180
tggatgaacg aaatagacag atcgctgaga taggtgcctc actgattaag cattggtaac   3240
tgtcagacca gtttactca tatatacttt agattgattt aaaacttcat ttttaattta   3300
aaaggatcta ggtgaagatc ctttttgata atctcatgac caaaatccct taacgtgagt   3360
tttcgttcca ctgagcgtca gaccccgtag aaaagatcaa aggatcttct tgagatcctt   3420 ttttttctgcg cgtaatctgc tgcttgcaaa caaaaaaacc accgctacca gcggtggttt   3480
gtttgccgga tcaagagcta ccaactcttt ttccgaaggt aactggcttc agcagagcgc   3540
agataccaaa tactgttctt ctagtgtagc cgtagttagg ccaccacttc aagaactctg   3600
tagcaccgcc tacatacctc gctctgctaa tcctgttacc agtggctgct gccagtggcg   3660
ataagtcgtg tcttaccggg ttggactcaa gacgatagtt accggataag gcgcagcggt   3720
cgggctgaac ggggggttcg tgcacacagc ccagcttgga gcgaacgacc tacaccgaac   3780
tgagatacct acagcgtgag ctatgagaaa gcgccacgct tcccgaaggg agaaaggcgg   3840
acaggtatcc ggtaagcggc agggtcggaa caggagagcg cacgagggag cttccagggg   3900
gaaacgcctg gtatctttat agtcctgtcg ggtttcgcca cctctgactt gagcgtcgat   3960
ttttgtgatg ctcgtcaggg gggcggagcc tatggaaaaa cgccagcaac gcggcctttt   4020
tacggttcct ggccttttgc tggccttttg ctcacatgtt ctttcctgcg ttatcccctg   4080
attctgtgga taaccgtatt accgcctttg agtgagctga taccgctcgc cgcagccgaa   4140
```

-continued cgaccgagcg cagcgagtca gtgagcgagg aagcggaaga gcgcccaata cgcaaaccgc    4200
ctctccccgc gcgttggccg attcattaat gcag    4234

<210> SEQ ID NO 10
<211> LENGTH: 1314
<212> TYPE: PRT
<213> ORGANISM: Escherichia coli

<400> SEQUENCE: 10

Pro Ile Thr Ile Asn Asn Phe Arg Tyr Ser Asp Pro Val Asn Asn Asp
1               5                   10                  15

Thr Ile Ile Met Met Glu Pro Pro Tyr Cys Lys Gly Leu Asp Ile Tyr
            20                  25                  30

Tyr Lys Ala Phe Lys Ile Thr Asp Arg Ile Trp Ile Val Pro Glu Arg
        35                  40                  45

Tyr Glu Phe Gly Thr Lys Pro Glu Asp Phe Asn Pro Pro Ser Ser Leu
    50                  55                  60

Ile Glu Gly Ala Ser Glu Tyr Tyr Asp Pro Asn Tyr Leu Arg Thr Asp
65                  70                  75                  80

Ser Asp Lys Asp Arg Phe Leu Gln Thr Met Val Lys Leu Phe Asn Arg
                85                  90                  95

Ile Lys Asn Asn Val Ala Gly Glu Ala Leu Leu Asp Lys Ile Ile Asn
            100                 105                 110

Ala Ile Pro Tyr Leu Gly Asn Ser Tyr Ser Leu Leu Asp Lys Phe Asp
        115                 120                 125

Thr Asn Ser Asn Ser Val Ser Phe Asn Leu Leu Glu Gln Asp Pro Ser
    130                 135                 140

Gly Ala Thr Thr Lys Ser Ala Met Leu Thr Asn Leu Ile Ile Phe Gly
145                 150                 155                 160

Pro Gly Pro Val Leu Asn Lys Asn Glu Val Arg Gly Ile Val Leu Arg
                165                 170                 175

Val Asp Asn Lys Asn Tyr Phe Pro Cys Arg Asp Gly Phe Gly Ser Ile
            180                 185                 190

Met Gln Met Ala Phe Cys Pro Glu Tyr Val Pro Thr Phe Asp Asn Val
            195                 200                 205

Ile Glu Asn Ile Thr Ser Leu Thr Ile Gly Lys Ser Lys Tyr Phe Gln
    210                 215                 220

Asp Pro Ala Leu Leu Leu Met His Glu Leu Ile His Val Leu His Gly
225                 230                 235                 240

Leu Tyr Gly Met Gln Val Ser Ser His Glu Ile Ile Pro Ser Lys Gln
                245                 250                 255

Glu Ile Tyr Met Gln His Thr Tyr Pro Ile Ser Ala Glu Glu Leu Phe
            260                 265                 270

Thr Phe Gly Gly Gln Asp Ala Asn Leu Ile Ser Ile Asp Ile Lys Asn
        275                 280                 285

Asp Leu Tyr Glu Lys Thr Leu Asn Asp Tyr Lys Ala Ile Ala Asn Lys
    290                 295                 300

Leu Ser Gln Val Thr Ser Cys Asn Asp Pro Asn Ile Asp Ile Asp Ser
305                 310                 315                 320

Tyr Lys Gln Ile Tyr Gln Gln Lys Tyr Gln Phe Asp Lys Asp Ser Asn
                325                 330                 335

Gly Gln Tyr Ile Val Asn Glu Asp Lys Phe Gln Ile Leu Tyr Asn Ser
            340                 345                 350

-continued

```
Ile Met Tyr Gly Phe Thr Glu Ile Glu Leu Gly Lys Lys Phe Asn Ile
    355                 360                 365

Lys Thr Arg Leu Ser Tyr Phe Ser Met Asn His Asp Pro Val Lys Ile
    370                 375                 380

Pro Asn Leu Leu Asp Asp Thr Ile Tyr Asn Asp Thr Glu Gly Phe Asn
385                 390                 395                 400

Ile Glu Ser Lys Asp Leu Lys Ser Glu Tyr Lys Gly Gln Asn Met Arg
                405                 410                 415

Val Asn Thr Asn Ala Phe Arg Asn Val Asp Gly Ser Gly Leu Val Ser
                420                 425                 430

Lys Leu Ile Gly Leu Cys Lys Lys Ile Ile Pro Pro Thr Asn Ile Arg
                435                 440                 445

Glu Asn Leu Tyr Asn Arg Thr Ala Ser Leu Thr Asp Leu Gly Gly Glu
    450                 455                 460

Leu Cys Ile Lys Ile Lys Asn Glu Asp Leu Thr Phe Ile Ala Glu Lys
465                 470                 475                 480

Asn Ser Phe Ser Glu Glu Pro Phe Gln Asp Glu Ile Val Ser Tyr Asn
                485                 490                 495

Thr Lys Asn Lys Pro Leu Asn Phe Asn Tyr Ser Leu Asp Lys Ile Ile
                500                 505                 510

Val Asp Tyr Asn Leu Gln Ser Lys Ile Thr Leu Pro Asn Asp Arg Thr
                515                 520                 525

Thr Pro Val Thr Lys Gly Ile Pro Tyr Ala Pro Glu Tyr Lys Ser Asn
    530                 535                 540

Ala Ala Ser Thr Ile Glu Ile His Asn Ile Asp Asp Asn Thr Ile Tyr
545                 550                 555                 560

Gln Tyr Leu Tyr Ala Gln Lys Ser Pro Thr Thr Leu Gln Arg Ile Thr
                565                 570                 575

Met Thr Asn Ser Val Asp Asp Ala Leu Ile Asn Ser Thr Lys Ile Tyr
                580                 585                 590

Ser Tyr Phe Pro Ser Val Ile Ser Lys Val Asn Gln Gly Ala Gln Gly
                595                 600                 605

Ile Leu Phe Leu Gln Trp Val Arg Asp Ile Ile Asp Asp Phe Thr Asn
    610                 615                 620

Glu Ser Ser Gln Lys Thr Thr Ile Asp Lys Ile Ser Asp Val Ser Thr
625                 630                 635                 640

Ile Val Pro Tyr Ile Gly Pro Ala Leu Asn Ile Val Lys Gln Gly Tyr
                645                 650                 655

Glu Gly Asn Phe Ile Gly Ala Leu Glu Thr Thr Gly Val Val Leu Leu
                660                 665                 670

Leu Glu Tyr Ile Pro Glu Ile Thr Leu Pro Val Ile Ala Ala Leu Ser
                675                 680                 685

Ile Ala Glu Ser Ser Thr Gln Lys Glu Lys Ile Ile Lys Thr Ile Asp
    690                 695                 700

Asn Phe Leu Glu Lys Arg Tyr Glu Lys Trp Ile Glu Val Tyr Lys Leu
705                 710                 715                 720

Val Lys Ala Lys Trp Leu Gly Thr Val Asn Thr Gln Phe Gln Lys Arg
                725                 730                 735

Ser Tyr Gln Met Tyr Arg Ser Leu Glu Tyr Gln Val Asp Ala Ile Lys
                740                 745                 750

Lys Ile Ile Asp Tyr Glu Tyr Lys Ile Tyr Ser Gly Pro Asp Lys Glu
                755                 760                 765

Gln Ile Ala Asp Glu Ile Asn Asn Leu Lys Asn Lys Leu Glu Glu Lys
```

```
        770             775             780

Ala Asn Lys Ala Met Ile Asn Ile Asn Ile Phe Met Arg Glu Ser Ser
785             790             795             800

Arg Ser Phe Leu Val Asn Gln Met Ile Asn Glu Ala Lys Lys Gln Leu
                805             810             815

Leu Glu Phe Asp Thr Gln Ser Lys Asn Ile Leu Met Gln Tyr Ile Lys
                820             825             830

Ala Asn Ser Lys Phe Ile Gly Ile Thr Glu Leu Lys Lys Leu Glu Ser
            835             840             845

Lys Ile Asn Lys Val Phe Ser Thr Pro Ile Pro Phe Ser Tyr Ser Lys
    850             855             860

Asn Leu Asp Cys Trp Val Asp Asn Glu Glu Asp Ile Asp Val Ile Leu
865             870             875             880

Lys Lys Ser Thr Ile Leu Asn Leu Asp Ile Asn Asn Asp Ile Ile Ser
                885             890             895

Asp Ile Ser Gly Phe Asn Ser Ser Val Ile Thr Tyr Pro Asp Ala Gln
            900             905             910

Leu Val Pro Gly Ile Asn Gly Lys Ala Ile His Leu Val Asn Asn Glu
            915             920             925

Ser Ser Glu Val Ile Val His Lys Ala Met Asp Ile Glu Tyr Asn Asp
    930             935             940

Met Phe Asn Asn Phe Thr Val Ser Phe Trp Leu Arg Val Pro Lys Val
945             950             955             960

Ser Ala Ser His Leu Glu Gln Tyr Gly Thr Asn Glu Tyr Ser Ile Ile
                965             970             975

Ser Ser Met Lys Lys His Ser Leu Ser Ile Gly Ser Gly Trp Ser Val
            980             985             990

Ser Leu Lys Gly Asn Asn Leu Ile  Trp Thr Leu Lys Asp  Ser Ala Gly
            995             1000             1005

Glu Val  Arg Gln Ile Thr Phe  Arg Asp Leu Pro Asp  Lys Phe Asn
    1010             1015             1020

Ala Tyr  Leu Ala Asn Lys Trp  Val Phe Ile Thr Ile  Thr Asn Asp
    1025             1030             1035

Arg Leu  Ser Ser Ala Asn Leu  Tyr Ile Asn Gly Val  Leu Met Gly
    1040             1045             1050

Ser Ala  Glu Ile Thr Gly Leu  Gly Ala Ile Arg Glu  Asp Asn Asn
    1055             1060             1065

Ile Thr  Leu Lys Leu Asp Arg  Cys Asn Asn Asn  Gln Tyr Val
    1070             1075             1080

Ser Ile  Asp Lys Phe Arg Ile  Phe Cys Lys Ala Leu  Asn Pro Lys
    1085             1090             1095

Glu Ile  Glu Lys Leu Tyr Thr  Ser Tyr Leu Ser Ile  Thr Phe Leu
    1100             1105             1110

Arg Asp  Phe Trp Gly Asn Pro  Leu Arg Tyr Asp Thr  Glu Tyr Tyr
    1115             1120             1125

Leu Ile  Pro Val Ala Ser Ser  Ser Lys Asp Val Gln  Leu Lys Asn
    1130             1135             1140

Ile Thr  Asp Tyr Met Tyr Leu  Thr Asn Ala Pro Ser  Tyr Thr Asn
    1145             1150             1155

Gly Lys  Leu Asn Ile Tyr Tyr  Arg Arg Leu Tyr Asn  Gly Leu Lys
    1160             1165             1170

Phe Ile  Ile Lys Arg Tyr Thr  Pro Asn Asn Glu Ile  Asp Ser Phe
    1175             1180             1185
```

```
Val Lys  Ser Gly Asp Phe Ile  Lys Leu Tyr Val Ser  Tyr Asn Asn
    1190                1195                1200

Asn Glu  His Ile Val Gly Tyr  Pro Lys Asp Gly Asn  Ala Phe Asn
    1205                1210                1215

Asn Leu  Asp Arg Ile Leu Glu  Val Gly Tyr Asn Ala  Pro Gly Ile
    1220                1225                1230

Pro Leu  Tyr Lys Lys Met Glu  Ala Val Lys Leu Arg  Asp Leu Lys
    1235                1240                1245

Thr Tyr  Ser Val Gln Leu Lys  Leu Tyr Asp Asp Lys  Asn Ala Ser
    1250                1255                1260

Leu Gly  Leu Val Gly Thr His  Asn Gly Gln Ile Gly  Asn Asp Pro
    1265                1270                1275

Asn Arg  Asp Ile Leu Ile Ala  Ser Asn Ala Tyr Phe  Asn His Leu
    1280                1285                1290

Lys Asp  Lys Ile Leu Gly Cys  Asp Trp Tyr Phe Val  Pro Thr Asp
    1295                1300                1305

Glu Gly  Trp Thr Asn Asp
    1310

<210> SEQ ID NO 11
<211> LENGTH: 6816
<212> TYPE: DNA
<213> ORGANISM: Escherichia coli

<400> SEQUENCE: 11
gatctcgatc ccgcgaaatt aatacgactc actatatggga gaccacaacg gtttccctct      60
agaaataatt ttgtttaact ttaagaagga gatatacata tgcggggttc tcatcatcat     120
catcatcatg gtatggctag catgactggt ggacagcaaa tgggtcggga tctgtacgac     180
gatgacgata aggatcgatg gggatccgag ctcgagccga tcaccatcaa caacttccgt     240
tactctgacc cggttaacaa cgacaccatc atcatgatgg aaccgccgta ctgcaaaggt     300
ctggacatct actacaaagc gttcaaaatc accgaccgta tctggatcgt tccggaacgt     360
tacgaattcg gtaccaaacc ggaagacttc aacccgccgt cttctctgat cgaaggtgcg     420
tctgaatact acgacccgaa ctacctgcgt accgactctg acaaagaccg tttcctgcag     480
accatggtta aactgttcaa ccgtatcaaa aacaacgttg cgggtgaagc gctgctggac     540
aaaatcatca cgcgatcccg tacctgggt aactcttact ctctgctgga caaattcgac     600
accaactcta actctgtttc tttcaacctg ctggaacagg accctgtctgg tgcgaccacc     660 aaatctgcga tgctgaccaa cctgatcatc ttcggtccgg gtccggttct gaacaaaaac     720
gaagttcgtg gtatcgttct gcgtgttgac aacaaaaact acttcccgtg ccgtgacggt     780
ttcggttcta tcatgcagat ggcgttctgc ccggaatacg ttccgacctt cgacaacgtt     840
atcgaaaaca tcacctctct gaccatcggt aaatctaaat acttccagga cccggcgctg     900
ctgctgatgc acgaactgat ccacgttctg cacggtctgt acggtatgca ggtttcttct     960
cacgaaatca tcccgtctaa acaggaaatc tacatgcagc acacctaccc gatctctgcg    1020
gaagaactgt tcaccttcgg tggtcaggac gcgaacctga tctctatcga catcaaaaac    1080
gacctgtacg aaaaaaccct gaacgactac aaagcgatcg cgaacaaact gtctcaggtt    1140
acctcttgca cgacccgaa catcgacatc gactcttaca acagatcta ccagcagaaa    1200 taccagttcg acaagactc taacggtcag tacatcgtta cgaagacaa attccagatc    1260 ctgtacaact ctatcatgta cggtttcacc gaaatcgaac tgggtaaaaa attcaacatc    1320
```

-continued

```
aaaacccgtc tgtcttactt ctctatgaac cacgacccgg ttaaaatccc gaacctgctg    1380
gacgacacca tctacaacga caccgaaggt ttcaacatcg aatctaaaga cctgaaatct    1440
gaatacaaag gtcagaacat gcgtgttaac accaacgcgt tccgtaacgt tgacggttct    1500
ggtctggttt ctaaactgat cggtctgtgc aaaaaaatca tcccgccgac caacatccgt    1560
gaaaacctgt acaaccgtac cgcgtctctg accgacctgg gtggtgaact gtgcatcaaa    1620
atcaaaaacg aagacctgac cttcatcgcg gaaaaaaact ctttctctga agaaccgttc    1680
caggacgaaa tcgtttctta caacaccaaa aacaaaccgc tgaacttcaa ctactctctg    1740
gacaaaatca tcgttgacta caacctgcag tctaaaatca ccctgccgaa cgaccgtacc    1800
accccggtta ccaaaggtat cccgtacgcg ccggaataca atctaacgc ggcgtctacc    1860 atcgaaatcc acaacatcga cgacaacacc atctaccagt acctgtacgc gcagaaatct    1920
ccgaccaccc tgcagcgtat caccatgacc aactctgttg acgacgcgct gatcaactct    1980
accaaaatct actcttactt cccgtctgtt atctctaaag ttaaccaggg tgcgcagggt    2040
atcctgttcc tgcagtgggt tcgtgacatc atcgacgact tcaccaacga atcttctcag    2100
aaaaccacca tcgacaaaat ctctgacgtt tctaccatcg ttccgtacat cggtccggcg    2160
ctgaacatcg ttaaacaggg ttacgaaggt aacttcatcg gtgcgctgga aaccaccggt    2220
gttgttctgc tgctggaata catcccggaa atcaccctgc cggttatcgc ggcgctgtct    2280
atcgcggaat cttctaccca gaaagaaaaa atcatcaaaa ccatcgacaa cttcctggaa    2340
aaacgttacg aaaaatggat cgaagtttac aaactggtta agcgaaatg gctgggtacc    2400 gttaacaccc agttccagaa acgttcttac cagatgtacc gttctctgga ataccaggtt    2460
gacgcgatca aaaaaatcat cgactacgaa tacaaaatct actctggtcc ggacaaagaa    2520
cagatcgcgg acgaaatcaa caacctgaaa aacaaactgg aagaaaaagc gaacaaagcg    2580
atgatcaaca tcaacatctt catgcgtgaa tcttctcgtt ctttcctggt taaccagatg    2640
atcaacgaag cgaaaaaaca gctgctggaa ttcgacaccc agtctaaaaa catcctgatg    2700
cagtacatca aagcgaactc taaattcatc ggtatcaccg aactgaaaaa actggaatct    2760
aaaatcaaca aagtttttctc taccccgatc ccgttctctt actctaaaaa cctggactgc    2820
tgggttgaca cgaagaaga catcgacgtt atcctgaaaa aatctaccat cctgaacctg    2880
gacatcaaca acgacatcat ctctgacatc tctggtttca actcttctgt tatcacctac    2940
ccggacgcgc agctggttcc gggtatcaac ggtaaagcga tccacctggt taacaacgaa    3000
tcttctgaag ttatcgttca caaagcgatg gacatcgaat acaacgacat gttcaacaac    3060
ttcaccgttt ctttctggct gcgtgttccg aaagtttctg cgtctcacct ggaacagtac    3120
ggtaccaacg aatactctat catctcttct atgaaaaaac actctctgtc tatcggttct    3180
ggttggtctg tttctctgaa aggtaacaac ctgatctgga ccctgaaaga ctctgcgggt    3240
gaagttcgtc agatcaccti ccgtgacctg ccggacaaat caacgcgta cctggcgaac    3300 aaatgggttt tcatcaccat caccaacgac cgtctgtctt ctgcgaacct gtacatcaac    3360
ggtgttctga tgggttctgc ggaaatcacc ggtctgggtg cgatccgtga agacaacaac    3420
atcaccctga aactggaccg ttgcaacaac aacaaccagt acgtttctat cgacaaattc    3480
cgtatcttct gcaaagcgct gaacccgaaa gaaatcgaaa aactgtacac ctcttacctg    3540
tctatcacct cctgcgctga cttctggggt aacccgctgc gttacgacac cgaatactac    3600
ctgatcccgg ttgcgtcttc ttctaaagac gttcagctga aaaacatcac cgactacatg    3660
```

-continued

```
tacctgacca acgcgccgtc ttacaccaac ggtaaactga acatctacta ccgtcgtctg      3720
tacaacggtc tgaaattcat catcaaacgt tacaccccga acaacgaaat cgactctttc      3780
gttaaatctg gtgacttcat caaactgtac gtttcttaca acaacaacga acacatcgtt      3840
ggttacccga aagacggtaa cgcgttcaac aacctggacc gtatcctgga agttggttac      3900
aacgcgccgg gtatcccgct gtacaaaaaa atggaagcgg ttaaactgcg tgacctgaaa      3960
acctactctg ttcagctgaa actgtacgac gacaaaaacg cgtctctggg tctggttggt      4020
acccacaacg gtcagatcgg taacgacccg aaccgtgaca tcctgatcgc gtctaacgcg      4080
tacttcaacc acctgaaaga caaaatcctg ggttgcgact ggtacttcgt tccgaccgac      4140
gaaggttgga ccaacgacta aaagcttgat ccggctgcta caaagcccg aaaggaagct       4200 gagttggctg ctgccaccgc tgagcaataa ctagcataac cccttggggc tctaaacgg       4260 gtcttgaggg gttttttgct gaaaggagga actatatccg gatctggcgt aatagcgaag      4320
aggcccgcac cgatcgccct tcccaacagt tgcgcagcct gaatggcgaa tgggacgcgc      4380
cctgtagcgg cgcattaagc gcggcgggtg tggtggttac gcgcagcgtg accgctacac      4440
ttgccagcgc cctagcgccc gctcctttcg ctttcttccc ttcctttctc gccacgttcg      4500
ccggctttcc ccgtcaagct ctaaatcggg gctcccttt agggttccga tttagtgctt       4560
tacggcacct cgacccaaa aaacttgatt agggtgatgg ttcacgtagt gggccatcgc       4620
cctgatagac ggtttttcgc cctttgacgt tggagtccac gttctttaat agtggactct      4680
tgttccaaac tggaacaaca ctcaacccta tctcggtcta ttctttgat ttataaggga       4740 ttttgccgat ttcggcctat tggttaaaaa atgagctgat ttaacaaaaa tttaacgcga      4800
attttaacaa aatattaacg cttacaattt aggtggcact tttcggggaa atgtgcgcgg      4860
aacccctatt tgtttatttt tctaaataca ttcaaatatg tatccgctca tgagacaata      4920
accctgataa atgcttcaat aatattgaaa aaggaagagt atgagtattc aacatttccg      4980
tgtcgccctt attcccttt ttgcggcatt ttgccttcct gttttttgctc acccagaaac       5040 gctggtgaaa gtaaaagatg ctgaagatca gttgggtgca cgagtgggtt acatcgaact      5100
ggatctcaac agcggtaaga tccttgagag ttttcgcccc gaagaacgtt ttccaatgat      5160
gagcactttt aaagttctgc tatgtggcgc ggtattatcc cgtattgacg ccgggcaaga      5220
gcaactcggt cgccgcatac actattctca gaatgacttg gttgagtact caccagtcac      5280
agaaaagcat cttacggatg gcatgacagt aagagaatta tgcagtgctg ccataaccat      5340
gagtgataac actgcggcca acttacttct gacaacgatc ggaggaccga aggagctaac      5400
cgcttttttg cacaacatgg gggatcatgt aactcgcctt gatcgttggg aaccggagct      5460
gaatgaagcc ataccaaacg acgagcgtga caccacgatg cctgtagcaa tggcaacaac      5520
gttgcgcaaa ctattaactg gcgaactact tactctagct tcccggcaac aattaataga      5580
ctggatggag gcggataaag ttgcaggacc acttctgcgc tcggcccttc cggctggctg      5640
gtttattgct gataaatctg gagccggtga gcgtgggtct cgcggtatca ttgcagcact      5700
ggggccagat ggtaagccct cccgtatcgt agttatctac acgacgggga gtcaggcaac      5760 tatgatgaa cgaaatagac agatcgctga gataggtgcc tcactgatta agcattggta       5820
actgtcagac caagtttact catatatact ttagattgat ttaaaacttc attttttaatt     5880 taaaaggatc taggtgaaga tccttttttga taatctcatg accaaaatcc cttaacgtga     5940
gttttcgttc cactgagcgt cagacccgt agaaaagatc aaaggatctt cttgagatcc       6000
tttttttctg cgcgtaatct gctgcttgca acaaaaaaa ccaccgctac cagcggtggt       6060
```

```
ttgtttgccg gatcaagagc taccaactct ttttccgaag gtaactggct tcagcagagc   6120
gcagatacca aatactgttc ttctagtgta gccgtagtta ggccaccact tcaagaactc   6180
tgtagcaccg cctacatacc tcgctctgct aatcctgtta ccagtggctg ctgccagtgg   6240
cgataagtcg tgtcttaccg ggttggactc aagacgatag ttaccggata aggcgcagcg   6300
gtcgggctga acggggggtt cgtgcacaca gcccagcttg gagcgaacga cctacaccga   6360
actgagatac ctacagcgtg agctatgaga aagcgccacg cttcccgaag ggagaaaggc   6420
ggacaggtat ccggtaagcg gcagggtcgg aacaggagag cgcacgaggg agcttccagg   6480
gggaaacgcc tggtatcttt atagtcctgt cgggtttcgc cacctctgac ttgagcgtcg   6540 attttgtga tgctcgtcag ggggcggag cctatggaaa aacgccagca acgcggcctt   6600
tttacggttc ctggcctttt gctggccttt tgctcacatg ttctttcctg cgttatcccc   6660
tgattctgtg ataaccgta ttaccgcctt tgagtgagct gataccgctc gccgcagccg   6720
aacgaccgag cgcagcgagt cagtgagcga ggaagcggaa gagcgcccaa tacgcaaacc   6780
gcctctcccc gcgcgttggc cgattcatta atgcag                            6816
```

<210> SEQ ID NO 12
<211> LENGTH: 1314
<212> TYPE: PRT
<213> ORGANISM: Escherichia coli

<400> SEQUENCE: 12

```
Pro Ile Thr Ile Asn Asn Phe Arg Tyr Ser Asp Pro Val Asn Asn Asp
1               5                   10                  15

Thr Ile Ile Met Met Glu Pro Pro Tyr Cys Lys Gly Leu Asp Ile Tyr
            20                  25                  30

Tyr Lys Ala Phe Lys Ile Thr Asp Arg Ile Trp Ile Val Pro Glu Arg
        35                  40                  45

Tyr Glu Phe Gly Thr Lys Pro Glu Asp Phe Asn Pro Pro Ser Ser Leu
    50                  55                  60

Ile Glu Gly Ala Ser Glu Tyr Tyr Asp Pro Asn Tyr Leu Arg Thr Asp
65                  70                  75                  80

Cys Asp Lys Asp Arg Phe Leu Gln Thr Met Val Lys Leu Phe Asn Arg
                85                  90                  95

Ile Lys Asn Asn Val Ala Gly Glu Ala Leu Leu Asp Lys Ile Ile Asn
            100                 105                 110

Ala Ile Pro Tyr Leu Gly Asn Cys Tyr Ser Leu Leu Asp Lys Phe Asp
        115                 120                 125

Thr Asn Ser Asn Ser Val Ser Phe Asn Leu Leu Glu Gln Asp Pro Cys
    130                 135                 140

Gly Ala Thr Thr Lys Ser Ala Met Leu Thr Asn Leu Ile Ile Phe Gly
145                 150                 155                 160

Pro Gly Pro Val Leu Asn Lys Asn Glu Val Arg Gly Ile Val Leu Arg
                165                 170                 175

Val Asp Asn Lys Asn Tyr Phe Pro Cys Arg Asp Gly Phe Gly Ser Ile
            180                 185                 190

Met Gln Met Ala Phe Cys Pro Glu Tyr Val Pro Thr Phe Asp Asn Val
        195                 200                 205

Ile Glu Asn Ile Thr Ser Leu Thr Ile Gly Lys Ser Lys Tyr Phe Gln
    210                 215                 220

Asp Pro Ala Leu Leu Leu Met His Glu Leu Ile His Val Leu His Gly
225                 230                 235                 240
```

-continued

```
Leu Tyr Gly Met Gln Val Ser Cys His Glu Ile Ile Pro Ser Lys Gln
            245             250             255

Glu Ile Tyr Met Gln His Thr Tyr Pro Ile Ser Ala Glu Glu Leu Phe
            260             265             270

Thr Phe Gly Gly Gln Asp Ala Asn Leu Ile Ser Ile Asp Ile Lys Asn
            275             280             285

Asp Leu Tyr Glu Lys Thr Leu Asn Asp Tyr Lys Ala Ile Ala Asn Lys
            290             295             300

Leu Ser Gln Val Thr Ser Cys Asn Asp Pro Asn Ile Asp Ile Asp Ser
305             310             315             320

Tyr Lys Gln Ile Tyr Gln Gln Lys Tyr Gln Phe Asp Lys Asp Cys Asn
            325             330             335

Gly Gln Tyr Ile Val Asn Glu Asp Lys Phe Gln Ile Leu Tyr Asn Ser
            340             345             350

Ile Met Tyr Gly Phe Thr Glu Ile Glu Leu Gly Lys Lys Phe Asn Ile
            355             360             365

Lys Thr Arg Leu Ser Tyr Phe Ser Met Asn His Asp Pro Val Lys Ile
            370             375             380

Pro Asn Leu Leu Asp Asp Thr Ile Tyr Asn Asp Thr Glu Gly Phe Asn
385             390             395             400

Ile Glu Ser Lys Asp Leu Lys Ser Glu Tyr Lys Gly Gln Asn Met Arg
            405             410             415

Val Asn Thr Asn Ala Phe Arg Asn Val Asp Gly Cys Gly Leu Val Ser
            420             425             430

Lys Leu Ile Gly Leu Cys Lys Lys Ile Ile Pro Pro Thr Asn Ile Arg
            435             440             445

Glu Asn Leu Tyr Asn Arg Thr Ala Ser Leu Thr Asp Leu Gly Gly Glu
            450             455             460

Leu Cys Ile Lys Ile Lys Asn Glu Asp Leu Thr Phe Ile Ala Glu Lys
465             470             475             480

Asn Ser Phe Ser Glu Glu Pro Phe Gln Asp Glu Ile Val Ser Tyr Asn
            485             490             495

Thr Lys Asn Lys Pro Leu Asn Phe Asn Tyr Ser Leu Asp Lys Ile Ile
            500             505             510

Val Asp Tyr Asn Leu Gln Ser Lys Ile Thr Leu Pro Asn Asp Arg Thr
            515             520             525

Thr Pro Val Thr Lys Gly Ile Pro Tyr Ala Pro Glu Tyr Lys Ser Asn
            530             535             540

Ala Ala Ser Thr Ile Glu Ile His Asn Ile Asp Asp Asn Thr Ile Tyr
545             550             555             560

Gln Tyr Leu Tyr Ala Gln Lys Ser Pro Thr Thr Leu Gln Arg Ile Thr
            565             570             575

Met Thr Asn Ser Val Asp Asp Ala Leu Ile Asn Ser Thr Lys Ile Tyr
            580             585             590

Ser Tyr Phe Pro Ser Val Ile Cys Lys Val Asn Gln Gly Ala Gln Gly
            595             600             605

Ile Leu Phe Leu Gln Trp Val Arg Asp Ile Ile Asp Asp Phe Thr Asn
            610             615             620

Glu Ser Ser Gln Lys Thr Thr Ile Asp Lys Ile Ser Asp Val Ser Thr
625             630             635             640

Ile Val Pro Tyr Ile Gly Pro Ala Leu Asn Ile Val Lys Gln Gly Tyr
            645             650             655
```

```
Glu Gly Asn Phe Ile Gly Ala Leu Glu Thr Thr Gly Val Val Leu Leu
            660             665             670

Leu Glu Tyr Ile Pro Glu Ile Thr Leu Pro Val Ile Ala Ala Leu Ser
    675             680             685

Ile Ala Glu Ser Ser Thr Gln Lys Glu Lys Ile Ile Lys Thr Ile Asp
    690             695             700

Asn Phe Leu Glu Lys Arg Tyr Glu Lys Trp Ile Glu Val Tyr Lys Leu
705             710             715             720

Val Lys Ala Lys Trp Leu Gly Thr Val Asn Thr Gln Phe Gln Lys Arg
                725             730             735

Ser Tyr Gln Met Tyr Arg Ser Leu Glu Tyr Gln Val Asp Ala Ile Lys
            740             745             750

Lys Ile Ile Asp Tyr Glu Tyr Lys Ile Tyr Ser Gly Pro Asp Lys Glu
            755             760             765

Gln Ile Ala Asp Glu Ile Asn Asn Leu Lys Asn Lys Leu Glu Glu Lys
    770             775             780

Ala Asn Lys Ala Met Ile Asn Ile Asn Ile Phe Met Arg Glu Ser Ser
785             790             795             800

Arg Ser Phe Leu Val Asn Gln Met Ile Asn Glu Ala Lys Lys Gln Leu
            805             810             815

Leu Glu Phe Asp Thr Gln Ser Lys Asn Ile Leu Met Gln Tyr Ile Lys
            820             825             830

Ala Asn Ser Lys Phe Ile Gly Ile Thr Glu Leu Lys Lys Leu Glu Ser
            835             840             845

Lys Ile Asn Lys Val Phe Ser Thr Pro Ile Pro Phe Ser Tyr Ser Lys
    850             855             860

Asn Leu Asp Cys Trp Val Asp Asn Glu Glu Asp Ile Asp Val Ile Leu
865             870             875             880

Lys Lys Ser Thr Ile Leu Asn Leu Asp Ile Asn Asn Asp Ile Ile Ser
            885             890             895

Asp Ile Ser Gly Phe Asn Ser Ser Val Ile Thr Tyr Pro Asp Ala Gln
            900             905             910

Leu Val Pro Gly Ile Asn Gly Lys Ala Ile His Leu Val Asn Asn Glu
            915             920             925

Ser Ser Glu Val Ile Val His Lys Ala Met Asp Ile Glu Tyr Asn Asp
    930             935             940

Met Phe Asn Asn Phe Thr Val Ser Phe Trp Leu Arg Val Pro Lys Val
945             950             955             960

Ser Ala Cys His Leu Glu Gln Tyr Gly Thr Asn Glu Tyr Ser Ile Ile
            965             970             975

Ser Ser Met Lys Lys His Ser Leu Ser Ile Gly Ser Gly Trp Ser Val
            980             985             990

Ser Leu Lys Gly Asn Asn Leu Ile  Trp Thr Leu Lys Asp  Ser Ala Gly
        995             1000            1005

Glu Val  Arg Gln Ile Thr Phe  Arg Asp Leu Pro Asp  Lys Phe Asn
    1010            1015            1020

Ala Tyr  Leu Ala Asn Lys Trp  Val Phe Ile Thr Ile  Thr Asn Asp
    1025            1030            1035

Arg Leu  Cys Ser Ala Asn Leu  Tyr Ile Asn Gly Val  Leu Met Gly
    1040            1045            1050

Ser Ala  Glu Ile Thr Gly Leu  Gly Ala Ile Arg Glu  Asp Asn Asn
    1055            1060            1065

Ile Thr  Leu Lys Leu Asp Arg  Cys Asn Asn Asn Asn  Gln Tyr Val
```

```
         1070              1075              1080

Ser Ile  Asp Lys Phe Arg  Ile  Phe Cys Lys  Ala Leu  Asn Pro Lys
    1085              1090              1095

Glu Ile  Glu Lys Leu Tyr  Thr  Ser Tyr Leu  Ser Ile  Thr Phe Leu
    1100              1105              1110

Arg Asp  Phe Trp Gly Asn  Pro  Leu Arg Tyr  Asp Thr  Glu Tyr Tyr
    1115              1120              1125

Leu Ile  Pro Val Ala Ser  Ser  Ser Lys Asp  Val Gln  Leu Lys Asn
    1130              1135              1140

Ile Thr  Asp Tyr Met Tyr  Leu  Thr Asn Ala  Pro Cys  Tyr Thr Asn
    1145              1150              1155

Gly Lys  Leu Asn Ile Tyr  Tyr  Arg Arg Leu  Tyr Asn  Gly Leu Lys
    1160              1165              1170

Phe Ile  Ile Lys Arg Tyr  Thr  Pro Asn Asn  Glu Ile  Asp Cys Phe
    1175              1180              1185

Val Lys  Ser Gly Asp Phe  Ile  Lys Leu Tyr  Val Ser  Tyr Asn Asn
    1190              1195              1200

Asn Glu  His Ile Val Gly  Tyr  Pro Lys Asp  Gly Asn  Ala Phe Asn
    1205              1210              1215

Asn Leu  Asp Arg Ile Leu  Arg  Val Gly Tyr  Asn Ala  Pro Gly Ile
    1220              1225              1230

Pro Leu  Tyr Lys Lys Met  Glu  Ala Val Lys  Leu Arg  Asp Leu Lys
    1235              1240              1245

Thr Tyr  Ser Val Gln Leu  Lys  Leu Tyr Asp  Asp Lys  Asn Ala Ser
    1250              1255              1260

Leu Gly  Leu Val Gly Thr  His  Asn Gly Gln  Ile Gly  Asn Asp Pro
    1265              1270              1275

Asn Arg  Asp Ile Leu Ile  Ala  Ser Asn Trp  Tyr Phe  Asn His Leu
    1280              1285              1290

Lys Asp  Lys Ile Leu Gly  Cys  Asp Trp Tyr  Phe Val  Pro Thr Asp
    1295              1300              1305

Glu Gly  Trp Thr Asn Asp
    1310

<210> SEQ ID NO 13
<211> LENGTH: 6816
<212> TYPE: DNA
<213> ORGANISM: Escherichia coli

<400> SEQUENCE: 13
gatctcgatc ccgcgaaatt aatacgactc actataggga gaccacaacg gtttccctct      60
agaaataatt ttgtttaact ttaagaagga gatatacata tgcggggttc tcatcatcat     120
catcatcatg gtatggctag catgactggt ggacagcaaa tgggtcggga tctgtacgac     180
gatgacgata aggatcgatg gggatccgag ctcgagccga tcaccatcaa caacttccgt     240
tactctgacc cggttaacaa cgacaccatc atcatgatgg aaccgccgta ctgcaaaggt     300
ctggacatct actacaaagc gttcaaaatc accgaccgta tctggatcgt tccggaacgt     360
tacgaattcg gtaccaaacc ggaagacttc aacccgccgt cttctctgat cgaaggtgcg     420
tctgaatact acgacccgaa ctacctgcgt accgactgcg acaaagaccg tttcctgcag     480
accatggtta aactgttcaa ccgtatcaaa aacaacgttg cgggtgaagc gctgctggac     540
aaaatcatca cgcgatccc gtacctgggt aactgctact ctctgctgga caaattcgac     600
accaactcta actctgtttc tttcaacctg ctggaacagg acccgtgcgg tgcgaccacc     660
```

```
aaatctgcga tgctgaccaa cctgatcatc ttcggtccgg gtccggttct gaacaaaaac      720
gaagttcgtg gtatcgttct gcgtgttgac aacaaaaact acttcccgtg ccgtgacggt      780
ttcggttcta tcatgcagat ggcgttctgc ccggaatacg ttccgacctt cgacaacgtt      840
atcgaaaaca tcacctctct gaccatcggt aaatctaaat acttccagga cccggcgctg      900
ctgctgatgc acgaactgat ccacgttctg cacggtctgt acggtatgca ggtttcttgc      960
cacgaaatca tcccgtctaa acaggaaatc tacatgcagc acacctaccc gatctctgcg     1020
gaagaactgt tcaccttcgg tggtcaggac gcgaacctga tctctatcga catcaaaaac     1080
gacctgtacg aaaaaaccct gaacgactac aaagcgatcg cgaacaaact gtctcaggtt     1140
acctcttgca acgacccgaa catcgacatc gactcttaca aacagatcta ccagcagaaa     1200
taccagttcg acaaagactg caacggtcag tacatcgtta acgaagacaa attccagatc     1260
ctgtacaact ctatcatgta cggtttcacc gaaatcgaac tgggtaaaaa attcaacatc     1320
aaaacccgtc tgtcttactt ctctatgaac cacgacccgg ttaaaatccc gaacctgctg     1380
gacgacacca tctacaacga caccgaaggt ttcaacatcg aatctaaaga cctgaaatct     1440
gaatacaaag gtcagaacat gcgtgttaac accaacgcgt tccgtaacgt tgacggttgc     1500
ggtctggttt ctaaactgat cggtctgtgc aaaaaaatca tcccgccgac caacatccgt     1560
gaaaacctgt acaaccgtac cgcgtctctg accgacctgg gtggtgaact gtgcatcaaa     1620
atcaaaaacg aagacctgac cttcatcgcg gaaaaaaact ctttctctga agaaccgttc     1680
caggacgaaa tcgtttctta caacaccaaa aacaaaccgc tgaacttcaa ctactctctg     1740
gacaaaatca tcgttgacta caacctgcag tctaaaatca ccctgccgaa cgaccgtacc     1800
accccggtta ccaaaggtat cccgtacgcg ccggaataca atctaacgc ggcgtctacc      1860 atcgaaatcc acaacatcga cgacaacacc atctaccagt acctgtacgc gcagaaatct     1920
ccgaccaccc tgcagcgtat caccatgacc aactctgttg acgacgcgct gatcaactct     1980
accaaaatct actcttactt cccgtctgtt atctgcaaag ttaaccaggg tgcgcagggt     2040
atcctgttcc tgcagtgggt tcgtgacatc atcgacgact tcaccaacga atcttctcag     2100
aaaaccacca tcgacaaaat ctctgacgtt tctaccatcg ttccgtacat cggtccggcg     2160
ctgaacatcg ttaaacaggg ttacgaaggt aacttcatcg gtgcgctgga aaccaccggt     2220
gttgttctgc tgctggaata catcccggaa atcaccctgc cggttatcgc ggcgctgtct     2280
atcgcggaat cttctaccca gaaagaaaaa atcatcaaaa ccatcgacaa cttcctggaa     2340
aaacgttacg aaaaatggat cgaagtttac aaactggtta agcgaaatg gctgggtacc      2400 gttaacaccc agttccagaa acgttcttac cagatgtacc gttctctgga ataccaggtt     2460
gacgcgatca aaaaaatcat cgactacgaa tacaaaatct actctggtcc ggacaaagaa     2520
cagatcgcgg acgaaatcaa caacctgaaa aacaaactgg aagaaaaagc gaacaaagcg     2580
atgatcaaca tcaacatctt catgcgtgaa tcttctcgtt ctttcctggt taaccagatg     2640
atcaacgaag cgaaaaaaca gctgctggaa ttcgacaccc agtctaaaaa catcctgatg     2700
cagtacatca aagcgaactc taaattcatc ggtatcaccg aactgaaaaa actggaatct     2760
aaaatcaaca agttttctc taccccgatc ccgttctctt actctaaaaa cctggactgc      2820
tgggttgaca cgaagaaga catcgacgtt atcctgaaaa aatctaccat cctgaacctg      2880
gacatcaaca acgacatcat ctctgacatc tctggtttca actcttctgt tatcacctac     2940
ccggacgcgc agctggttcc gggtatcaac ggtaaagcga tccacctggt taacaacgaa     3000
```

-continued

```
tcttctgaag ttatcgttca caaagcgatg gacatcgaat acaacgacat gttcaacaac    3060
ttcaccgttt ctttctggct gcgtgttccg aaagtttctg cgtgccacct ggaacagtac    3120
ggtaccaacg aatactctat catctcttct atgaaaaaac actctctgtc tatcggttct    3180
ggttggtctg tttctctgaa aggtaacaac ctgatctgga ccctgaaaga ctctgcgggt    3240
gaagttcgtc agatcacctt ccgtgacctg ccggacaaat tcaacgcgta cctggcgaac    3300
aaatgggttt tcatcaccat caccaacgac cgtctgtgct ctgcgaacct gtacatcaac    3360
ggtgttctga tgggttctgc ggaaatcacc ggtctgggtg cgatccgtga agacaacaac    3420
atcaccctga aactggaccg ttgcaacaac aacaaccagt acgtttctat cgacaaattc    3480
cgtatcttct gcaaagcgct gaacccgaaa gaaatcgaaa aactgtacac ctcttacctg    3540
tctatcacct tcctgcgtga cttctggggt aacccgctgc gttacgacac cgaatactac    3600
ctgatcccgg ttgcgtcttc ttctaaagac gttcagctga aaaacatcac cgactacatg    3660
tacctgacca acgcgccgtg ctacaccaac ggtaaactga acatctacta ccgtcgtctg    3720
tacaacggtc tgaaattcat catcaaacgt tacaccccga acaacgaaat cgactgcttc    3780
gttaaatctg gtgacttcat caaactgtac gtttcttaca acaacaacga acacatcgtt    3840
ggttacccga aagacggtaa cgcgttcaac aacctggacc gtatcctgcg tgttggttac    3900
aacgcgccgg gtatcccgct gtacaaaaaa atggaagcgg ttaaactgcg tgacctgaaa    3960
acctactctg ttcagctgaa actgtacgac gacaaaaacg cgtctctggg tctggttggt    4020
acccacaacg gtcagatcgg taacgacccg aaccgtgaca tcctgatcgc gtctaactgg    4080
tacttcaacc acctgaaaga caaaatcctg ggttgcgact ggtacttcgt tccgaccgac    4140
gaaggttgga ccaacgacta aaagcttgat ccggctgcta acaaagcccg aaaggaagct    4200
gagttggctg ctgccaccgc tgagcaataa ctagcataac cccttggggc ctctaaacgg    4260
gtcttgaggg gttttttgct gaaaggagga actatatccg gatctggcgt aatagcgaag    4320
aggcccgcac cgatcgccct tcccaacagt tgcgcagcct gaatggcgaa tgggacgcgc    4380
cctgtagcgg cgcattaagc gcggcgggtg tggtggttac gcgcagcgtg accgctacac    4440
ttgccagcgc cctagcgccc gctcctttcg ctttcttccc ttcctttctc gccacgttcg    4500
ccggctttcc ccgtcaagct ctaaatcggg gctccctttt agggttccga tttagtgctt    4560
tacggcacct cgaccccaaa aaacttgatt agggtgatgg ttcacgtagt gggccatcgc    4620
cctgatagac ggtttttcgc cctttgacgt tggagtccac gttctttaat agtggactct    4680
tgttccaaac tggaacaaca ctcaacccta tctcggtcta ttcttttgat ttataaggga    4740
ttttgccgat ttcggcctat tggttaaaaa atgagctgat ttaacaaaaa tttaacgcga    4800
attttaacaa aatattaacg cttacaattt aggtggcact tttcggggaa atgtgcgcgg    4860
aacccctatt tgtttatttt tctaaataca ttcaaatatg tatccgctca tgagacaata    4920
accctgataa atgcttcaat aatattgaaa aaggaagagt atgagtattc aacatttccg    4980
tgtcgccctt attccctttt ttgcggcatt ttgccttcct gttttttgctc acccagaaac    5040 gctggtgaaa gtaaaagatg ctgaagatca gttgggtgca cgagtgggtt acatcgaact    5100
ggatctcaac agcggtaaga tccttgagag ttttcgcccc gaagaacgtt ttccaatgat    5160
gagcactttt aaagttctgc tatgtggcgc ggtattatcc cgtattgacg ccgggcaaga    5220
gcaactcggt cgccgcatac actattctca gaatgacttg gttgagtact caccagtcac    5280
agaaaagcat cttacggatg gcatgacagt aagagaatta tgcagtgctg ccataaccat    5340
gagtgataac actgcggcca acttacttct gacaacgatc ggaggaccga aggagctaac    5400
```

```
cgctttttttg cacaacatgg gggatcatgt aactcgcctt gatcgttggg aaccggagct    5460
gaatgaagcc ataccaaacg acgagcgtga caccacgatg cctgtagcaa tggcaacaac    5520
gttgcgcaaa ctattaactg gcgaactact tactctagct tcccggcaac aattaataga    5580
ctggatggag gcggataaag ttgcaggacc acttctgcgc tcggcccttc cggctggctg    5640
gtttattgct gataaatctg gagccggtga gcgtgggtct cgcggtatca ttgcagcact    5700
ggggccagat ggtaagccct cccgtatcgt agttatctac acgacgggga gtcaggcaac    5760
tatggatgaa cgaaatagac agatcgctga gataggtgcc tcactgatta agcattggta    5820
actgtcagac caagtttact catatatact ttagattgat ttaaaacttc atttttaatt    5880
taaaaggatc taggtgaaga tcctttttga taatctcatg accaaaatcc cttaacgtga    5940
gttttcgttc cactgagcgt cagaccccgt agaaaagatc aaaggatctt cttgagatcc    6000 ttttttttctg cgcgtaatct gctgcttgca aacaaaaaaa ccaccgctac cagcggtggt    6060
ttgtttgccg gatcaagagc taccaactct ttttccgaag gtaactggct tcagcagagc    6120
gcagatacca aatactgttc ttctagtgta gccgtagtta ggccaccact tcaagaactc    6180
tgtagcaccg cctacatacc tcgctctgct aatcctgtta ccagtggctg ctgccagtgg    6240
cgataagtcg tgtcttaccg ggttggactc aagacgatag ttaccggata aggcgcagcg    6300
gtcgggctga acggggggtt cgtgcacaca gcccagcttg gagcgaacga cctacaccga    6360
actgagatac ctacagcgtg agctatgaga aagcgccacg cttcccgaag ggagaaaggc    6420
ggacaggtat ccggtaagcg gcagggtcgg aacaggagag cgcacgaggg agcttccagg    6480
gggaaacgcc tggtatcttt atagtcctgt cgggtttcgc cacctctgac ttgagcgtcg    6540
atttttgtga tgctcgtcag gggggcggag cctatggaaa aacgccagca acgcggcctt    6600
tttacggttc ctggcctttt gctggccttt tgctcacatg ttctttcctg cgttatcccc    6660
tgattctgtg ataaccgta ttaccgcctt tgagtgagct gataccgctc gccgcagccg    6720
aacgaccgag cgcagcgagt cagtgagcga ggaagcggaa gagcgcccaa tacgcaaacc    6780
gcctctcccc gcgcgttggc cgattcatta atgcag                              6816
```

```
<210> SEQ ID NO 14
<211> LENGTH: 1314
<212> TYPE: PRT
<213> ORGANISM: Escherichia coli

<400> SEQUENCE: 14

Pro Ile Thr Ile Asn Asn Phe Arg Tyr Ser Asp Pro Val Asn Asn Asp
1               5                   10                  15

Thr Ile Ile Met Met Glu Pro Pro Tyr Cys Lys Gly Leu Asp Ile Tyr
            20                  25                  30

Tyr Lys Ala Phe Lys Ile Thr Asp Arg Ile Trp Ile Val Pro Glu Arg
        35                  40                  45

Tyr Glu Phe Gly Thr Lys Pro Glu Asp Phe Asn Pro Pro Ser Ser Leu
    50                  55                  60

Ile Glu Gly Ala Ser Glu Tyr Tyr Asp Pro Asn Tyr Leu Arg Thr Asp
65                  70                  75                  80

Cys Asp Lys Asp Arg Phe Leu Gln Thr Met Val Lys Leu Phe Asn Arg
                85                  90                  95

Ile Lys Asn Asn Val Ala Gly Glu Ala Leu Leu Asp Lys Ile Ile Asn
            100                 105                 110

Ala Ile Pro Tyr Leu Gly Asn Cys Tyr Ser Leu Leu Asp Lys Phe Asp
```

-continued

```
              115                 120                 125

Thr Asn Ser Asn Ser Val Ser Phe Asn Leu Leu Glu Gln Asp Pro Cys
    130                 135                 140

Gly Ala Thr Thr Lys Ser Ala Met Leu Thr Asn Leu Ile Ile Phe Gly
145                 150                 155                 160

Pro Gly Pro Val Leu Asn Lys Asn Glu Val Arg Gly Ile Val Leu Arg
                165                 170                 175

Val Asp Asn Lys Asn Tyr Phe Pro Cys Arg Asp Gly Phe Gly Ser Ile
                180                 185                 190

Met Gln Met Ala Phe Cys Pro Glu Tyr Val Pro Thr Phe Asp Asn Val
                195                 200                 205

Ile Glu Asn Ile Thr Ser Leu Thr Ile Gly Lys Ser Lys Tyr Phe Gln
    210                 215                 220

Asp Pro Ala Leu Leu Leu Met His Glu Leu Ile His Val Leu His Gly
225                 230                 235                 240

Leu Tyr Gly Met Gln Val Ser Cys His Glu Ile Ile Pro Ser Lys Gln
                245                 250                 255

Glu Ile Tyr Met Gln His Thr Tyr Pro Ile Ser Ala Glu Glu Leu Phe
                260                 265                 270

Thr Phe Gly Gly Gln Asp Ala Asn Leu Ile Ser Ile Asp Ile Lys Asn
                275                 280                 285

Asp Leu Tyr Glu Lys Thr Leu Asn Asp Tyr Lys Ala Ile Ala Asn Lys
    290                 295                 300

Leu Ser Gln Val Thr Ser Cys Asn Asp Pro Asn Ile Asp Ile Asp Ser
305                 310                 315                 320

Tyr Lys Gln Ile Tyr Gln Gln Lys Tyr Gln Phe Asp Lys Asp Cys Asn
                325                 330                 335

Gly Gln Tyr Ile Val Asn Glu Asp Lys Phe Gln Ile Leu Tyr Asn Ser
                340                 345                 350

Ile Met Tyr Gly Phe Thr Glu Ile Glu Leu Gly Lys Lys Phe Asn Ile
                355                 360                 365

Lys Thr Arg Leu Ser Tyr Phe Ser Met Asn His Asp Pro Val Lys Ile
    370                 375                 380

Pro Asn Leu Leu Asp Asp Thr Ile Tyr Asn Asp Thr Glu Gly Phe Asn
385                 390                 395                 400

Ile Glu Ser Lys Asp Leu Lys Ser Glu Tyr Lys Gly Gln Asn Met Arg
                405                 410                 415

Val Asn Thr Asn Ala Phe Arg Asn Val Asp Gly Cys Gly Leu Val Ser
                420                 425                 430

Lys Leu Ile Gly Leu Cys Lys Lys Ile Ile Pro Pro Thr Asn Ile Arg
                435                 440                 445

Glu Asn Leu Tyr Asn Arg Thr Ala Ser Leu Thr Asp Leu Gly Gly Glu
    450                 455                 460

Leu Cys Ile Lys Ile Lys Asn Glu Asp Leu Thr Phe Ile Ala Glu Lys
465                 470                 475                 480

Asn Ser Phe Ser Glu Glu Pro Phe Gln Asp Glu Ile Val Ser Tyr Asn
                485                 490                 495

Thr Lys Asn Lys Pro Leu Asn Phe Asn Tyr Ser Leu Asp Lys Ile Ile
                500                 505                 510

Val Asp Tyr Asn Leu Gln Ser Lys Ile Thr Leu Pro Asn Asp Arg Thr
                515                 520                 525

Thr Pro Val Thr Lys Gly Ile Pro Tyr Ala Pro Glu Tyr Lys Ser Asn
    530                 535                 540
```

-continued

```
Ala Ala Ser Thr Ile Glu Ile His Asn Ile Asp Asp Asn Thr Ile Tyr
545                 550                 555                 560

Gln Tyr Leu Tyr Ala Gln Lys Ser Pro Thr Thr Leu Gln Arg Ile Thr
                565                 570                 575

Met Thr Asn Ser Val Asp Asp Ala Leu Ile Asn Ser Thr Lys Ile Tyr
                580                 585                 590

Ser Tyr Phe Pro Ser Val Ile Ser Lys Val Asn Gln Gly Ala Gln Gly
            595                 600                 605

Ile Leu Phe Leu Gln Trp Val Arg Asp Ile Ile Asp Asp Phe Thr Asn
    610                 615                 620

Glu Ser Ser Gln Lys Thr Thr Ile Asp Lys Ile Ser Asp Val Ser Thr
625                 630                 635                 640

Ile Val Pro Tyr Ile Gly Pro Ala Leu Asn Ile Val Lys Gln Gly Tyr
                645                 650                 655

Glu Gly Asn Phe Ile Gly Ala Leu Glu Thr Thr Gly Val Val Leu Leu
                660                 665                 670

Leu Glu Tyr Ile Pro Glu Ile Thr Leu Pro Val Ile Ala Ala Leu Ser
            675                 680                 685

Ile Ala Glu Ser Ser Thr Gln Lys Glu Lys Ile Ile Lys Thr Ile Asp
    690                 695                 700

Asn Phe Leu Glu Lys Arg Tyr Glu Lys Trp Ile Glu Val Tyr Lys Leu
705                 710                 715                 720

Val Lys Ala Lys Trp Leu Gly Thr Val Asn Thr Gln Phe Gln Lys Arg
                725                 730                 735

Ser Tyr Gln Met Tyr Arg Ser Leu Glu Tyr Gln Val Asp Ala Ile Lys
                740                 745                 750

Lys Ile Ile Asp Tyr Glu Tyr Lys Ile Tyr Ser Gly Pro Asp Lys Glu
            755                 760                 765

Gln Ile Ala Asp Glu Ile Asn Asn Leu Lys Asn Lys Leu Glu Glu Lys
    770                 775                 780

Ala Asn Lys Ala Met Ile Asn Ile Asn Ile Phe Met Arg Glu Ser Ser
785                 790                 795                 800

Arg Ser Phe Leu Val Asn Gln Met Ile Asn Glu Ala Lys Lys Gln Leu
                805                 810                 815

Leu Glu Phe Asp Thr Gln Ser Lys Asn Ile Leu Met Gln Tyr Ile Lys
                820                 825                 830

Ala Asn Ser Lys Phe Ile Gly Ile Thr Glu Leu Lys Lys Leu Glu Ser
            835                 840                 845

Lys Ile Asn Lys Val Phe Ser Thr Pro Ile Pro Phe Ser Tyr Ser Lys
    850                 855                 860

Asn Leu Asp Cys Trp Val Asp Asn Glu Glu Asp Ile Asp Val Ile Leu
865                 870                 875                 880

Lys Lys Ser Thr Ile Leu Asn Leu Asp Ile Asn Asn Asp Ile Ile Ser
                885                 890                 895

Asp Ile Ser Gly Phe Asn Ser Ser Val Ile Thr Tyr Pro Asp Ala Gln
            900                 905                 910

Leu Val Pro Gly Ile Asn Gly Lys Ala Ile His Leu Val Asn Asn Glu
            915                 920                 925

Ser Ser Glu Val Ile Val His Lys Ala Met Asp Ile Glu Tyr Asn Asp
    930                 935                 940

Met Phe Asn Asn Phe Thr Val Ser Phe Trp Leu Arg Val Pro Lys Val
945                 950                 955                 960
```

-continued

```
Ser Ala Cys His Leu Glu Gln Tyr Gly Thr Asn Glu Tyr Ser Ile Ile
            965                 970                 975

Ser Ser Met Lys Lys His Ser Leu Ser Ile Gly Ser Gly Trp Ser Val
            980                 985                 990

Ser Leu Lys Gly Asn Asn Leu Ile  Trp Thr Leu Lys Asp  Ser Ala Gly
        995                 1000                1005

Glu Val  Arg Gln Ile Thr Phe  Arg Asp Leu Pro Asp  Lys Phe Asn
    1010             1015                1020

Ala Tyr  Leu Ala Asn Lys Trp  Val Phe Ile Thr Ile  Thr Asn Asp
    1025             1030                1035

Arg Leu  Cys Ser Ala Asn Leu  Tyr Ile Asn Gly Val  Leu Met Gly
    1040             1045                1050

Ser Ala  Glu Ile Thr Gly Leu  Gly Ala Ile Arg Glu  Asp Asn Asn
    1055             1060                1065

Ile Thr  Leu Lys Leu Asp Arg  Cys Asn Asn Asn Asn  Gln Tyr Val
    1070             1075                1080

Ser Ile  Asp Lys Phe Arg Ile  Phe Cys Lys Ala Leu  Asn Pro Lys
    1085             1090                1095

Glu Ile  Glu Lys Leu Tyr Thr  Ser Tyr Leu Ser Ile  Thr Phe Leu
    1100             1105                1110

Arg Asp  Phe Trp Gly Asn Pro  Leu Arg Tyr Asp Thr  Glu Tyr Tyr
    1115             1120                1125

Leu Ile  Pro Val Ala Ser Ser  Ser Lys Asp Val Gln  Leu Lys Asn
    1130             1135                1140

Ile Thr  Asp Tyr Met Tyr Leu  Thr Asn Ala Pro Cys  Tyr Thr Asn
    1145             1150                1155

Gly Lys  Leu Asn Ile Tyr Tyr  Arg Arg Leu Tyr Asn  Gly Leu Lys
    1160             1165                1170

Phe Ile  Ile Lys Arg Tyr Thr  Pro Asn Asn Glu Ile  Asp Cys Phe
    1175             1180                1185

Val Lys  Ser Gly Asp Phe Ile  Lys Leu Tyr Val Ser  Tyr Asn Asn
    1190             1195                1200

Asn Glu  His Ile Val Gly Tyr  Pro Lys Asp Gly Asn  Ala Phe Asn
    1205             1210                1215

Asn Leu  Asp Arg Ile Leu Arg  Val Gly Tyr Asn Ala  Pro Gly Ile
    1220             1225                1230

Pro Leu  Tyr Lys Lys Met Glu  Ala Val Lys Leu Arg  Asp Leu Lys
    1235             1240                1245

Thr Tyr  Ser Val Gln Leu Lys  Leu Tyr Asp Asp Lys  Asn Ala Ser
    1250             1255                1260

Leu Gly  Leu Val Gly Thr His  Asn Gly Gln Ile Gly  Asn Asp Pro
    1265             1270                1275

Asn Arg  Asp Ile Leu Ile Ala  Ser Asn Trp Tyr Phe  Asn His Leu
    1280             1285                1290

Lys Asp  Lys Ile Leu Gly Cys  Asp Trp Tyr Phe Val  Pro Thr Asp
    1295             1300                1305

Glu Gly  Trp Thr Asn Asp
    1310
```

<210> SEQ ID NO 15
<211> LENGTH: 6816
<212> TYPE: DNA
<213> ORGANISM: Escherichia coli

<400> SEQUENCE: 15

```
gatctcgatc ccgcgaaatt aatacgactc actataggga gaccacaacg gtttccctct      60
agaaataatt ttgtttaact ttaagaagga gatatacata tgcggggttc tcatcatcat     120
catcatcatg gtatggctag catgactggt ggacagcaaa tgggtcggga tctgtacgac     180
gatgacgata aggatcgatg gggatccgag ctcgagccga tcaccatcaa caacttccgt     240
tactctgacc cggttaacaa cgacaccatc atcatgatgg aaccgccgta ctgcaaaggt     300
ctggacatct actacaaagc gttcaaaatc accgaccgta tctggatcgt tccggaacgt     360
tacgaattcg gtaccaaacc ggaagacttc aacccgccgt cttctctgat cgaaggtgcg     420
tctgaatact acgacccgaa ctacctgcgt accgactgcg acaaagaccg tttcctgcag     480
accatggtta aactgttcaa ccgtatcaaa aacaacgttg cgggtgaagc gctgctggac     540
aaaatcatca acgcgatccc gtacctgggt aactgctact ctctgctgga caaattcgac     600
accaactcta actctgtttc tttcaacctg ctggaacagg acccgtgcgg tgcgaccacc     660
aaatctgcga tgctgaccaa cctgatcatc ttcggtccgg tccggttct gaacaaaaac      720 gaagttcgtg gtatcgttct gcgtgttgac aacaaaaact acttcccgtg ccgtgacggt     780
ttcggttcta tcatgcagat ggcgttctgc ccggaatacg ttccgacctt cgacaacgtt     840
atcgaaaaca tcacctctct gaccatcggt aaatctaaat acttccagga cccggcgctg     900
ctgctgatgc acgaactgat ccacgttctg cacggtctgt acggtatgca ggtttcttgc     960
cacgaaatca tcccgtctaa acaggaaatc tacatgcagc acacctaccc gatctctgcg    1020
gaagaactgt tcaccttcgg tggtcaggac gcgaacctga tctctatcga catcaaaaac    1080
gacctgtacg aaaaaaccct gaacgactac aaagcgatcg cgaacaaact gtctcaggtt    1140
acctcttgca cgacccgaa catcgacatc gactcttaca aacagatcta ccagcagaaa     1200
taccagttcg acaaagactg caacggtcag tacatcgtta acgaagacaa attccagatc    1260
ctgtacaact ctatcatgta cggtttcacc gaaatcgaac tgggtaaaaa attcaacatc    1320
aaaacccgtc tgtcttactt ctctatgaac cacgacccgg ttaaaatccc gaacctgctg    1380
gacgacacca tctacaacga caccgaaggt ttcaacatcg aatctaaaga cctgaaatct    1440
gaatacaaag gtcagaacat gcgtgttaac accaacgcgt tccgtaacgt tgacggttgc    1500
ggtctggttt ctaaactgat cggtctgtgc aaaaaaatca tcccgccgac caacatccgt    1560
gaaaacctgt acaaccgtac cgcgtctctg accgacctgg gtggtgaact gtgcatcaaa    1620
atcaaaaacg aagacctgac cttcatcgcg gaaaaaaact ctttctctga agaaccgttc    1680
caggacgaaa tcgtttctta caacaccaaa aacaaaccgc tgaacttcaa ctactctctg    1740
gacaaaatca tcgttgacta caacctgcag tctaaaatca ccctgccgaa cgaccgtacc    1800
accccggtta ccaaaggtat cccgtacgcg ccggaataca aatctaacgc ggcgtctacc    1860
atcgaaatcc acaacatcga cgacaacacc atctaccagt acctgtacgc gcagaaatct    1920
ccgaccaccc tgcagcgtat caccatgacc aactctgttg acgacgcgct gatcaactct    1980
accaaaatct actcttactt cccgtctgtt atctctaaag ttaaccaggg tgcgcagggt    2040
atcctgttcc tgcagtgggt tcgtgacatc atcgacgact tcaccaacga atcttctcag    2100
aaaaccacca tcgacaaaat ctctgacgtt tctaccatcg ttccgtacat cggtccggcg    2160
ctgaacatcg ttaaacaggg ttacgaaggt aacttcatcg gtgcgctgga aaccaccggt    2220
gttgttctgc tgctggaata catcccggaa atcaccctgc cggttatcgc ggcgctgtct    2280
atcgcggaat cttctaccca gaaagaaaaa atcatcaaaa ccatcgacaa cttcctggaa    2340
```

-continued

```
aaacgttacg aaaaatggat cgaagtttac aaactggtta aagcgaaatg gctgggtacc      2400
gttaacaccc agttccagaa acgttcttac cagatgtacc gttctctgga ataccaggtt      2460
gacgcgatca aaaaaatcat cgactacgaa tacaaaatct actctggtcc ggacaaagaa      2520
cagatcgcgg acgaaatcaa caacctgaaa aacaaactgg aagaaaaagc gaacaaagcg      2580
atgatcaaca tcaacatctt catgcgtgaa tcttctcgtt ctttcctggt taaccagatg      2640
atcaacgaag cgaaaaaaca gctgctggaa ttcgacaccc agtctaaaaa catcctgatg      2700
cagtacatca aagcgaactc taaattcatc ggtatcaccg aactgaaaaa actggaatct      2760
aaaatcaaca aagttttctc taccccgatc ccgttctctt actctaaaaa cctggactgc      2820
tgggttgaca acgaagaaga catcgacgtt atcctgaaaa aatctaccat cctgaacctg      2880
gacatcaaca acgacatcat ctctgacatc tctggtttca actcttctgt tatcaccctac      2940 ccggacgcgc agctggttcc gggtatcaac ggtaaagcga tccacctggt taacaacgaa      3000
tcttctgaag ttatcgttca caaagcgatg gacatcgaat acaacgacat gttcaacaac      3060
ttcaccgttt ctttctggct gcgtgttccg aaagtttctg cgtgccacct ggaacagtac      3120
ggtaccaacg aatactctat catctcttct atgaaaaaac actctctgtc tatcggttct      3180
ggttggtctg tttctctgaa aggtaacaac ctgatctgga ccctgaaaga ctctgcgggt      3240
gaagttcgtc agatcacctt ccgtgacctg ccggacaaat tcaacgcgta cctggcgaac      3300
aaatgggttt tcatcaccat caccaacgac cgtctgtgct ctgcgaacct gtacatcaac      3360
ggtgttctga tgggttctgc ggaaatcacc ggtctgggtg cgatccgtga agacaacaac      3420
atcaccctga aactggaccg ttgcaacaac aacaaccagt acgtttctat cgacaaattc      3480
cgtatcttct gcaaagcgct gaacccgaaa gaaatcgaaa aactgtacac ctcttacctg      3540
tctatcacct cctgcgtgga cttctggggt aacccgctgc gttacgacac cgaatactac      3600
ctgatcccgg ttgcgtcttc ttctaaagac gttcagctga aaaacatcac cgactacatg      3660
tacctgacca acgcgccgtg ctacaccaac ggtaaactga acatctacta ccgtcgtctg      3720
tacaacggtc tgaaattcat catcaaacgt tacacccecga acaacgaaat cgactgcttc      3780
gttaaatctg gtgacttcat caaactgtac gtttcttaca acaacaacga acacatcgtt      3840
ggttacccga aagacggtaa cgcgttcaac aacctggacc gtatcctgcg tgttggttac      3900
aacgcgccgg gtatcccgct gtacaaaaaa atggaagcgg ttaaactgcg tgacctgaaa      3960
acctactctg ttcagctgaa actgtacgac gacaaaaacg cgtctctggg tctggttggt      4020
acccacaacg gtcagatcgg taacgacccg aaccgtgaca tcctgatcgc gtctaactgg      4080
tacttcaacc acctgaaaga caaaatcctg ggttgcgact ggtacttcgt tccgaccgac      4140
gaaggttgga ccaacgacta aaagcttgat ccggctgcta acaaagcccg aaaggaagct      4200
gagttggctg ctgccaccgc tgagcaataa ctagcataac cccttggggc ctctaaacgg      4260
gtcttgaggg gttttttgct gaaaggagga actatatccg gatctggcgt aatagcgaag      4320
aggcccgcac cgatcgccct tcccaacagt tgcgcagcct gaatggcgaa tgggacgcgc      4380
cctgtagcgg cgcattaagc gcggcgggtg tggtggttac gcgcagcgtg accgctacac      4440
ttgccagcgc cctagcgccc gctcctttcg ctttcttccc ttcctttctc gccacgttcg      4500
ccggctttcc ccgtcaagct ctaaatcggg ggctcccttt agggttccga tttagtgctt      4560
tacggcacct cgaccccaaa aaacttgatt agggtgatgg ttcacgtagt gggccatcgc      4620
cctgatagac ggtttttcgc cctttgacgt tggagtccac gttctttaat agtggactct      4680
tgttccaaac tggaacaaca ctcaacccta tctcggtcta ttcttttgat ttataaggga      4740
```

-continued

```
ttttgccgat ttcggcctat tggttaaaaa atgagctgat ttaacaaaaa tttaacgcga      4800
attttaacaa aatattaacg cttacaattt aggtggcact tttcggggaa atgtgcgcgg      4860
aacccctatt tgtttatttt tctaaataca ttcaaatatg tatccgctca tgagacaata     4920
accctgataa atgcttcaat aatattgaaa aaggaagagt atgagtattc aacatttccg     4980
tgtcgccctt attccctttt ttgcggcatt ttgccttcct gttttttgctc acccagaaac    5040 gctggtgaaa gtaaaagatg ctgaagatca gttgggtgca cgagtgggtt acatcgaact    5100
ggatctcaac agcggtaaga tccttgagag ttttcgcccc gaagaacgtt ttccaatgat    5160
gagcactttt aaagttctgc tatgtggcgc ggtattatcc cgtattgacg ccgggcaaga    5220
gcaactcggt cgccgcatac actattctca gaatgacttg gttgagtact caccagtcac    5280
agaaaagcat cttacggatg gcatgacagt aagagaatta tgcagtgctg ccataaccat    5340
gagtgataac actgcggcca acttacttct gacaacgatc ggaggaccga aggagctaac    5400
cgcttttttg cacaacatgg gggatcatgt aactcgcctt gatcgttggg aaccggagct    5460
gaatgaagcc ataccaaacg acgagcgtga caccacgatg cctgtagcaa tggcaacaac    5520
gttgcgcaaa ctattaactg gcgaactact tactctagct tcccggcaac aattaataga    5580
ctggatggag gcggataaag ttgcaggacc acttctgcgc tcggcccttc cggctggctg    5640
gtttattgct gataaatctg gagccggtga gcgtgggtct cgcggtatca ttgcagcact    5700
ggggccagat ggtaagccct cccgtatcgt agttatctac acgacgggga gtcaggcaac    5760 tatgatgaa cgaaatagac agatcgctga gataggtgcc tcactgatta agcattggta      5820
actgtcagac caagtttact catatatact ttagattgat ttaaaacttc atttttaatt    5880
taaaaggatc taggtgaaga tcctttttga taatctcatg accaaaatcc cttaacgtga    5940
gttttcgttc cactgagcgt cagacccccgt agaaaagatc aaaggatctt cttgagatcc    6000 ttttttttctg cgcgtaatct gctgcttgca acaaaaaaa ccaccgctac cagcggtggt      6060
ttgtttgccg gatcaagagc taccaactct ttttccgaag gtaactggct tcagcagagc    6120
gcagatacca aatactgttc ttctagtgta gccgtagtta ggccaccact tcaagaactc    6180
tgtagcaccg cctacatacc tcgctctgct aatcctgtta ccagtggctg ctgccagtgg    6240
cgataagtcg tgtcttaccg ggttggactc aagacgatag ttaccggata aggcgcagcg    6300
gtcgggctga acggggggtt cgtgcacaca gcccagcttg gagcgaacga cctacaccga    6360
actgagatac ctacagcgtg agctatgaga aagcgccacg cttcccgaag ggagaaaggc    6420
ggacaggtat ccggtaagcg gcagggtcgg aacaggagag cgcacgaggg agcttccagg    6480
gggaaacgcc tggtatcttt atagtcctgt cgggtttcgc cacctctgac ttgagcgtcg    6540
attttgtgta tgctcgtcag ggggggcggag cctatggaaa aacgccagca acgcggcctt    6600
tttacggttc ctggcctttt gctggccttt tgctcacatg ttctttcctg cgttatcccc    6660
tgattctgtg gataaccgta ttaccgcctt tgagtgagct gataccgctc gccgcagccg    6720
aacgaccgag cgcagcgagt cagtgagcga ggaagcggaa gagcgcccaa tacgcaaacc    6780
gcctctcccc gcgcgttggc cgattcatta atgcag                              6816
```

<210> SEQ ID NO 16
<211> LENGTH: 1314
<212> TYPE: PRT
<213> ORGANISM: Escherichia coli

<400> SEQUENCE: 16

-continued

```
Pro Ile Thr Ile Asn Asn Phe Arg Tyr Ser Asp Pro Val Asn Asn Asp
1               5                   10                  15

Thr Ile Ile Met Met Glu Pro Pro Tyr Cys Lys Gly Leu Asp Ile Tyr
            20                  25                  30

Tyr Lys Ala Phe Lys Ile Thr Asp Arg Ile Trp Ile Val Pro Glu Arg
        35                  40                  45

Tyr Glu Phe Gly Thr Lys Pro Glu Asp Phe Asn Pro Pro Ser Ser Leu
    50                  55                  60

Ile Glu Gly Ala Ser Glu Tyr Tyr Asp Pro Asn Tyr Leu Arg Thr Asp
65                  70                  75                  80

Ser Asp Lys Asp Arg Phe Leu Gln Thr Met Val Lys Leu Phe Asn Arg
                85                  90                  95

Ile Lys Asn Asn Val Ala Gly Glu Ala Leu Leu Asp Lys Ile Ile Asn
            100                 105                 110

Ala Ile Pro Tyr Leu Gly Asn Ser Tyr Ser Leu Leu Asp Lys Phe Asp
        115                 120                 125

Thr Asn Ser Asn Ser Val Ser Phe Asn Leu Leu Glu Gln Asp Pro Ser
    130                 135                 140

Gly Ala Thr Thr Lys Ser Ala Met Leu Thr Asn Leu Ile Ile Phe Gly
145                 150                 155                 160

Pro Gly Pro Val Leu Asn Lys Asn Glu Val Arg Gly Ile Val Leu Arg
                165                 170                 175

Val Asp Asn Lys Asn Tyr Phe Pro Cys Arg Asp Gly Phe Gly Ser Ile
            180                 185                 190

Met Gln Met Ala Phe Cys Pro Glu Tyr Val Pro Thr Phe Asp Asn Val
        195                 200                 205

Ile Glu Asn Ile Thr Ser Leu Thr Ile Gly Lys Ser Lys Tyr Phe Gln
    210                 215                 220

Asp Pro Ala Leu Leu Leu Met His Glu Leu Ile His Val Leu His Gly
225                 230                 235                 240

Leu Tyr Gly Met Gln Val Ser Ser His Glu Ile Ile Pro Ser Lys Gln
                245                 250                 255

Glu Ile Tyr Met Gln His Thr Tyr Pro Ile Ser Ala Glu Glu Leu Phe
            260                 265                 270

Thr Phe Gly Gly Gln Asp Ala Asn Leu Ile Ser Ile Asp Ile Lys Asn
        275                 280                 285

Asp Leu Tyr Glu Lys Thr Leu Asn Asp Tyr Lys Ala Ile Ala Asn Lys
    290                 295                 300

Leu Ser Gln Val Thr Ser Cys Asn Asp Pro Asn Ile Asp Ile Asp Ser
305                 310                 315                 320

Tyr Lys Gln Ile Tyr Gln Gln Lys Tyr Gln Phe Asp Lys Asp Ser Asn
                325                 330                 335

Gly Gln Tyr Ile Val Asn Glu Asp Lys Phe Gln Ile Leu Tyr Asn Ser
            340                 345                 350

Ile Met Tyr Gly Phe Thr Glu Ile Glu Leu Gly Lys Lys Phe Asn Ile
        355                 360                 365

Lys Thr Arg Leu Ser Tyr Phe Ser Met Asn His Asp Pro Val Lys Ile
    370                 375                 380

Pro Asn Leu Leu Asp Asp Thr Ile Tyr Asn Asp Thr Glu Gly Phe Asn
385                 390                 395                 400

Ile Glu Ser Lys Asp Leu Lys Ser Glu Tyr Lys Gly Gln Asn Met Arg
                405                 410                 415

Val Asn Thr Asn Ala Phe Arg Asn Val Asp Gly Ser Gly Leu Val Ser
```

```
                    420             425             430

Lys Leu Ile Gly Leu Cys Lys Lys Ile Ile Pro Pro Thr Asn Ile Arg
            435             440             445

Glu Asn Leu Tyr Asn Arg Thr Ala Ser Leu Thr Asp Leu Gly Gly Glu
            450             455             460

Leu Cys Ile Lys Ile Lys Asn Glu Asp Leu Thr Phe Ile Ala Glu Lys
465             470             475             480

Asn Ser Phe Ser Glu Glu Pro Phe Gln Asp Glu Ile Val Ser Tyr Asn
            485             490             495

Thr Lys Asn Lys Pro Leu Asn Phe Asn Tyr Ser Leu Asp Lys Ile Ile
            500             505             510

Val Asp Tyr Asn Leu Gln Ser Lys Ile Thr Leu Pro Asn Asp Arg Thr
            515             520             525

Thr Pro Val Thr Lys Gly Ile Pro Tyr Ala Pro Glu Tyr Lys Ser Asn
            530             535             540

Ala Ala Ser Thr Ile Glu Ile His Asn Ile Asp Asp Asn Thr Ile Tyr
545             550             555             560

Gln Tyr Leu Tyr Ala Gln Lys Ser Pro Thr Thr Leu Gln Arg Ile Thr
            565             570             575

Met Thr Asn Ser Val Asp Asp Ala Leu Ile Asn Ser Thr Lys Ile Tyr
            580             585             590

Ser Tyr Phe Pro Ser Val Ile Cys Lys Val Asn Gln Gly Ala Gln Gly
            595             600             605

Ile Leu Phe Leu Gln Trp Val Arg Asp Ile Ile Asp Asp Phe Thr Asn
            610             615             620

Glu Ser Ser Gln Lys Thr Thr Ile Asp Lys Ile Ser Asp Val Ser Thr
625             630             635             640

Ile Val Pro Tyr Ile Gly Pro Ala Leu Asn Ile Val Lys Gln Gly Tyr
            645             650             655

Glu Gly Asn Phe Ile Gly Ala Leu Glu Thr Thr Gly Val Val Leu Leu
            660             665             670

Leu Glu Tyr Ile Pro Glu Ile Thr Leu Pro Val Ile Ala Ala Leu Ser
            675             680             685

Ile Ala Glu Ser Ser Thr Gln Lys Glu Lys Ile Ile Lys Thr Ile Asp
            690             695             700

Asn Phe Leu Glu Lys Arg Tyr Glu Lys Trp Ile Glu Val Tyr Lys Leu
705             710             715             720

Val Lys Ala Lys Trp Leu Gly Thr Val Asn Thr Gln Phe Gln Lys Arg
            725             730             735

Ser Tyr Gln Met Tyr Arg Ser Leu Glu Tyr Gln Val Asp Ala Ile Lys
            740             745             750

Lys Ile Ile Asp Tyr Glu Tyr Lys Ile Tyr Ser Gly Pro Asp Lys Glu
            755             760             765

Gln Ile Ala Asp Glu Ile Asn Asn Leu Lys Asn Lys Leu Glu Glu Lys
            770             775             780

Ala Asn Lys Ala Met Ile Asn Ile Asn Ile Phe Met Arg Glu Ser Ser
785             790             795             800

Arg Ser Phe Leu Val Asn Gln Met Ile Asn Glu Ala Lys Lys Gln Leu
            805             810             815

Leu Glu Phe Asp Thr Gln Ser Lys Asn Ile Leu Met Gln Tyr Ile Lys
            820             825             830

Ala Asn Ser Lys Phe Ile Gly Ile Thr Glu Leu Lys Lys Leu Glu Ser
            835             840             845
```

-continued

```
Lys Ile Asn Lys Val Phe Ser Thr Pro Ile Pro Phe Ser Tyr Ser Lys
    850                 855                 860

Asn Leu Asp Cys Trp Val Asp Asn Glu Glu Asp Ile Asp Val Ile Leu
865                 870                 875                 880

Lys Lys Ser Thr Ile Leu Asn Leu Asp Ile Asn Asn Asp Ile Ile Ser
                885                 890                 895

Asp Ile Ser Gly Phe Asn Ser Ser Val Ile Thr Tyr Pro Asp Ala Gln
                900                 905                 910

Leu Val Pro Gly Ile Asn Gly Lys Ala Ile His Leu Val Asn Asn Glu
            915                 920                 925

Ser Ser Glu Val Ile Val His Lys Ala Met Asp Ile Glu Tyr Asn Asp
    930                 935                 940

Met Phe Asn Asn Phe Thr Val Ser Phe Trp Leu Arg Val Pro Lys Val
945                 950                 955                 960

Ser Ala Cys His Leu Glu Gln Tyr Gly Thr Asn Glu Tyr Ser Ile Ile
                965                 970                 975

Ser Ser Met Lys Lys His Ser Leu Ser Ile Gly Ser Gly Trp Ser Val
                980                 985                 990

Ser Leu Lys Gly Asn Asn Leu Ile Trp Thr Leu Lys Asp Ser Ala Gly
            995                1000                1005

Glu Val Arg Gln Ile Thr Phe Arg Asp Leu Pro Asp Lys Phe Asn
    1010                1015                1020

Ala Tyr Leu Ala Asn Lys Trp Val Phe Ile Thr Ile Thr Asn Asp
    1025                1030                1035

Arg Leu Cys Ser Ala Asn Leu Tyr Ile Asn Gly Val Leu Met Gly
    1040                1045                1050

Ser Ala Glu Ile Thr Gly Leu Gly Ala Ile Arg Glu Asp Asn Asn
    1055                1060                1065

Ile Thr Leu Lys Leu Asp Arg Cys Asn Asn Asn Asn Gln Tyr Val
    1070                1075                1080

Ser Ile Asp Lys Phe Arg Ile Phe Cys Lys Ala Leu Asn Pro Lys
    1085                1090                1095

Glu Ile Glu Lys Leu Tyr Thr Ser Tyr Leu Ser Ile Thr Phe Leu
    1100                1105                1110

Arg Asp Phe Trp Gly Asn Pro Leu Arg Tyr Asp Thr Glu Tyr Tyr
    1115                1120                1125

Leu Ile Pro Val Ala Ser Ser Ser Lys Asp Val Gln Leu Lys Asn
    1130                1135                1140

Ile Thr Asp Tyr Met Tyr Leu Thr Asn Ala Pro Cys Tyr Thr Asn
    1145                1150                1155

Gly Lys Leu Asn Ile Tyr Tyr Arg Arg Leu Tyr Asn Gly Leu Lys
    1160                1165                1170

Phe Ile Ile Lys Arg Tyr Thr Pro Asn Asn Glu Ile Asp Cys Phe
    1175                1180                1185

Val Lys Ser Gly Asp Phe Ile Lys Leu Tyr Val Ser Tyr Asn Asn
    1190                1195                1200

Asn Glu His Ile Val Gly Tyr Pro Lys Asp Gly Asn Ala Phe Asn
    1205                1210                1215

Asn Leu Asp Arg Ile Leu Arg Val Gly Tyr Asn Ala Pro Gly Ile
    1220                1225                1230

Pro Leu Tyr Lys Lys Met Glu Ala Val Lys Leu Arg Asp Leu Lys
    1235                1240                1245
```

```
Thr Tyr  Ser Val Gln Leu Lys  Leu Tyr Asp Asp Lys  Asn Ala Ser
    1250             1255              1260

Leu Gly  Leu Val Gly Thr His  Asn Gly Gln Ile Gly  Asn Asp Pro
    1265             1270              1275

Asn Arg  Asp Ile Leu Ile Ala  Ser Asn Trp Tyr Phe  Asn His Leu
    1280             1285              1290

Lys Asp  Lys Ile Leu Gly Cys  Asp Trp Tyr Phe Val  Pro Thr Asp
    1295             1300              1305

Glu Gly  Trp Thr Asn Asp
    1310
```

```
<210> SEQ ID NO 17
<211> LENGTH: 6816
<212> TYPE: DNA
<213> ORGANISM: Escherichia coli

<400> SEQUENCE: 17
gatctcgatc ccgcgaaatt aatacgactc actatagggga gaccacaacg gtttccctct     60
agaaataatt ttgtttaact ttaagaagga gatatacata tgcggggttc tcatcatcat    120
catcatcatg gtatggctag catgactggt ggacagcaaa tgggtcggga tctgtacgac    180
gatgacgata aggatcgatg gggatccgag ctcgagccga tcaccatcaa caacttccgt    240
tactctgacc cggttaacaa cgacaccatc atcatgatgg aaccgccgta ctgcaaaggt    300
ctggacatct actacaaagc gttcaaaatc accgaccgta tctggatcgt tccggaacgt    360
tacgaattcg gtaccaaacc ggaagacttc aacccgccgt cttctctgat cgaaggtgcg    420
tctgaatact acgacccgaa ctacctgcgt accgactctg acaaagaccg tttcctgcag    480
accatggtta aactgttcaa ccgtatcaaa aacaacgttg cgggtgaagc gctgctggac    540
aaaatcatca cgcgatccc gtacctgggt aactcttact ctctgctgga caaattcgac    600
accaactcta actctgtttc tttcaacctg ctggaacagg acccgtctgg tgcgaccacc    660
aaatctgcga tgctgaccaa cctgatcatc ttcggtccgg gtccggttct gaacaaaaac    720
gaagttcgtg gtatcgttct gcgtgttgac aacaaaaact acttcccgtg ccgtgacggt    780
ttcggttcta tcatgcagat ggcgttctgc ccggaatacg ttccgacctt cgacaacgtt    840
atcgaaaaca tcacctctct gaccatcggt aaatctaaat acttccagga cccggcgctg    900
ctgctgatgc acgaactgat ccacgttctg cacggtctgt acggtatgca ggtttcttct    960
cacgaaatca tcccgtctaa acaggaaatc tacatgcagc acacctaccc gatctctgcg   1020
gaagaactgt tcaccttcgg tggtcaggac gcgaacctga tctctatcga catcaaaaac   1080
gacctgtacg aaaaaaccct gaacgactac aaagcgatcg cgaacaaact gtctcaggtt   1140
acctcttgca cgacccgaa catcgacatc gactcttaca acagatcta ccagcagaaa   1200 taccagttcg acaaagactc taacggtcag tacatcgtta acgaagacaa attccagatc   1260
ctgtacaact ctatcatgta cggtttcacc gaaatcgaac tgggtaaaaa attcaacatc   1320
aaaacccgtc tgtcttactt ctctatgaac cacgacccgg ttaaaatccc gaacctgctg   1380
gacgacacca tctacaacga caccgaaggt ttcaacatcg aatctaaaga cctgaaatct   1440
gaatacaaag tcagaacat gcgtgttaac accaacgcgt tccgtaacgt tgacggttct   1500
ggtctggttt ctaaactgat cggtctgtgc aaaaaaatca tcccgccgac caacatccgt   1560
gaaaacctgt acaaccgtac cgcgtctctg accgacctgg gtggtgaact gtgcatcaaa   1620
atcaaaaacg aagacctgac cttcatcgcg gaaaaaaact ctttctctga gaaccgttc   1680
```

```
caggacgaaa tcgtttctta caacaccaaa aacaaaccgc tgaacttcaa ctactctctg    1740
gacaaaatca tcgttgacta caacctgcag tctaaaatca ccctgccgaa cgaccgtacc    1800
accccggtta ccaaaggtat cccgtacgcg ccggaataca aatctaacgc ggcgtctacc    1860
atcgaaatcc acaacatcga cgacaacacc atctaccagt acctgtacgc gcagaaatct    1920
ccgaccaccc tgcagcgtat caccatgacc aactctgttg acgacgcgct gatcaactct    1980
accaaaatct actcttactt cccgtctgtt atctgcaaag ttaaccaggg tgcgcagggt    2040
atcctgttcc tgcagtgggt tcgtgacatc atcgacgact tcaccaacga atcttctcag    2100
aaaaccacca tcgacaaaat ctctgacgtt tctaccatcg ttccgtacat cggtccggcg    2160
ctgaacatcg ttaaacaggg ttacgaaggt aacttcatcg gtgcgctgga aaccaccggt    2220
gttgttctgc tgctggaata catcccggaa atcaccctgc cggttatcgc ggcgctgtct    2280
atcgcggaat cttctaccca gaaagaaaaa atcatcaaaa ccatcgacaa cttcctggaa    2340
aaacgttacg aaaaatggat cgaagtttac aaactggtta agcgaaatg gctgggtacc    2400 gttaacacccc agttccagaa acgttcttac cagatgtacc gttctctgga ataccaggtt    2460
gacgcgatca aaaaaatcat cgactacgaa tacaaaatct actctggtcc ggacaaagaa    2520
cagatcgcgg acgaaatcaa caacctgaaa aacaaactgg aagaaaaagc gaacaaagcg    2580
atgatcaaca tcaacatctt catgcgtgaa tcttctcgtt ctttcctggt taaccagatg    2640
atcaacgaag cgaaaaaaca gctgctggaa ttcgacaccc agtctaaaaa catcctgatg    2700
cagtacatca agcgaactc taaattcatc ggtatcaccg aactgaaaaa actggaatct    2760
aaaatcaaca agttttctc tacccccgatc ccgttctctt actctaaaaa cctggactgc    2820
tgggttgaca acgaagaaga catcgacgtt atcctgaaaa aatctaccat cctgaacctg    2880
gacatcaaca acgacatcat ctctgacatc tctggtttca actcttctgt tatcaccta    2940 ccggacgcgc agctggttcc gggtatcaac ggtaaagcga tccacctggt taacaacgaa    3000
tcttctgaag ttatcgttca caaagcgatg gacatcgaat acaacgacat gttcaacaac    3060
ttcaccgttt ctttctggct gcgtgttccg aaagtttctg cgtgccacct ggaacagtac    3120
ggtaccaacg aatactctat catctcttct atgaaaaaac actctctgtc tatcggttct    3180
ggttggtctg tttctctgaa aggtaacaac ctgatctgga ccctgaaaga ctctgcgggt    3240
gaagttcgtc agatcaccttt ccgtgacctg ccggacaaat tcaacgcgta cctggcgaac    3300
aaatgggttt tcatcaccat caccaacgac cgtctgtgct ctgcgaacct gtacatcaac    3360
ggtgttctga tgggttctgc ggaaatcacc ggtctgggtg cgatccgtga agacaacaac    3420 atcacccctga aactggaccg ttgcaacaac aacaaccagt acgtttctat cgacaaattc    3480
cgtatcttct gcaaagcgct gaacccgaaa gaaatcgaaa aactgtacac ctcttacctg    3540
tctatcacct tcctgcgtga cttctgggggt aacccgctgc gttacgacac cgaatactac    3600
ctgatcccgg ttgcgtcttc ttctaaagac gttcagctga aaaacatcac cgactacatg    3660
tacctgacca acgcgccgtg ctacaccaac ggtaaactga acatctacta ccgtcgtctg    3720
tacaacggtc tgaaattcat catcaaacgt tacacccccga caacgaaat cgactgcttc    3780 gttaaatctg gtgacttcat caaactgtac gtttcttaca acaacaacga acacatcgtt    3840
ggttacccga aagacggtaa cgcgttcaac aacctggacc gtatcctgcg tgttggttac    3900
aacgcgccgg gtatcccgct gtacaaaaaa atggaagcgg ttaaactgcg tgacctgaaa    3960
acctactctg ttcagctgaa actgtacgac gacaaaaacg cgtctctggg tctggttggt    4020
acccacaacg gtcagatcgg taacgacccg aaccgtgaca tcctgatcgc gtctaactgg    4080
```

```
tacttcaacc acctgaaaga caaaatcctg ggttgcgact ggtacttcgt tccgaccgac   4140
gaaggttgga ccaacgacta aaagcttgat ccggctgcta acaaagcccg aaaggaagct   4200
gagttggctg ctgccaccgc tgagcaataa ctagcataac cccttggggc ctctaaacgg   4260
gtcttgaggg gttttttgct gaaaggagga actatatccg gatctggcgt aatagcgaag   4320
aggcccgcac cgatcgccct tcccaacagt tgcgcagcct gaatggcgaa tgggacgcgc   4380
cctgtagcgg cgcattaagc gcggcgggtg tggtggttac gcgcagcgtg accgctacac   4440
ttgccagcgc cctagcgccc gctcctttcg ctttcttccc ttcctttctc gccacgttcg   4500
ccggctttcc ccgtcaagct ctaaatcggg ggctcccttt agggttccga tttagtgctt   4560
tacggcacct cgaccccaaa aaacttgatt agggtgatgg ttcacgtagt gggccatcgc   4620
cctgatagac ggtttttcgc cctttgacgt tggagtccac gttctttaat agtggactct   4680
tgttccaaac tggaacaaca ctcaacccta tctcggtcta ttcttttgat ttataaggga   4740
ttttgccgat ttcggcctat tggttaaaaa atgagctgat ttaacaaaaa tttaacgcga   4800
attttaacaa aatattaacg cttacaattt aggtggcact tttcggggaa atgtgcgcgg   4860
aacccctatt tgtttatttt tctaaataca ttcaaatatg tatccgctca tgagacaata   4920
accctgataa atgcttcaat aatattgaaa aaggaagagt atgagtattc aacatttccg   4980
tgtcgccctt attccctttt ttgcggcatt ttgccttcct gtttttgctc acccagaaac   5040
gctggtgaaa gtaaaagatg ctgaagatca gttgggtgca cgagtgggtt acatcgaact   5100
ggatctcaac agcggtaaga tccttgagag ttttcgcccc gaagaacgtt ttccaatgat   5160
gagcactttt aaagttctgc tatgtggcgc ggtattatcc cgtattgacg ccgggcaaga   5220
gcaactcggt cgccgcatac actattctca gaatgacttg gttgagtact caccagtcac   5280
agaaaagcat cttacggatg gcatgacagt aagagaatta tgcagtgctg ccataaccat   5340
gagtgataac actgcggcca acttacttct gacaacgatc ggaggaccga aggagctaac   5400
cgcttttttg cacaacatgg gggatcatgt aactcgcctt gatcgttggg aaccggagct   5460
gaatgaagcc ataccaaacg acgagcgtga caccacgatg cctgtagcaa tggcaacaac   5520
gttgcgcaaa ctattaactg gcgaactact tactctagct tcccggcaac aattaataga   5580
ctggatggag gcggataaag ttgcaggacc acttctgcgc tcggcccttc cggctggctg   5640
gtttattgct gataaatctg gagccggtga gcgtgggtct cgcggtatca ttgcagcact   5700
ggggccagat ggtaagccct cccgtatcgt agttatctac acgacgggga gtcaggcaac   5760 tatgatgaa cgaaatagac agatcgctga gataggtgcc tcactgatta agcattggta   5820
actgtcagac caagtttact catatatact ttagattgat ttaaaacttc attttttaatt  5880 taaaaggatc taggtgaaga tcctttttga taatctcatg accaaaatcc cttaacgtga   5940
gttttcgttc cactgagcgt cagaccccgt agaaaagatc aaaggatctt cttgagatcc   6000 ttttttttctg cgcgtaatct gctgcttgca acaaaaaaaa ccaccgctac cagcggtggt   6060
ttgtttgccg gatcaagagc taccaactct ttttccgaag gtaactggct tcagcagagc   6120
gcagatacca atactgttc ttctagtgta gccgtagtta ggccaccact tcaagaactc    6180
tgtagcaccg cctacatacc tcgctctgct aatcctgtta ccagtggctg ctgccagtgg   6240
cgataagtcg tgtcttaccg ggttggactc aagacgatag ttaccggata aggcgcagcg   6300
gtcgggctga acggggggtt cgtgcacaca gcccagcttg gagcgaacga cctacaccga   6360
actgagatac ctacagcgtg agctatgaga aagcgccacg cttcccgaag ggagaaaggc   6420
```

-continued

```
ggacaggtat ccggtaagcg gcagggtcgg aacaggagag cgcacgaggg agcttccagg    6480
gggaaacgcc tggtatcttt atagtcctgt cgggtttcgc cacctctgac ttgagcgtcg    6540
atttttgtga tgctcgtcag gggggcggag cctatggaaa aacgccagca acgcggcctt    6600
tttacggttc ctggcctttt gctggccttt tgctcacatg ttctttcctg cgttatcccc    6660
tgattctgtg gataaccgta ttaccgcctt tgagtgagct gataccgctc gccgcagccg    6720
aacgaccgag cgcagcgagt cagtgagcga ggaagcggaa gagcgcccaa tacgcaaacc    6780
gcctctcccc gcgcgttggc cgattcatta atgcag                               6816
```

PEGYLATED TETANUS NEUROTOXINS AND TREATMENT OF HYPOTONIA

FIELD

The invention relates to a composition comprising a first PEGylated tetanus neurotoxin (PEG-TeNT) comprising tetanus neurotoxin (TeNT) conjugated to polyethylene glycol (PEG) and a second TeNT. The invention also relates to a method of treating hypotonia using the composition.

BACKGROUND

Tetanus neurotoxin (TeNT) is produced by *Clostridium tetani*. TeNT acts at the spinal cord and blocks release at the spinal inhibitory interneurons of γ-aminobutyric acid (GABA) and glycine, which are inhibitory neurotransmitters. As such, TeNT causes spastic paralysis. TeNT does not occur in multiple serotypes.

Exploitation of biological properties of TeNT, or at least fragments of TeNT, for therapy has been proposed. However, long-term treatment with protein therapeutic agents tends to lead to a targeted immune response. As there is only one serotype of TeNT known, serotype switching to circumvent immunity is not an option for TeNT-based therapy. Moreover, many populations are vaccinated against TeNT, thereby precluding TeNT-based therapy.

US 2002/0197278 A1 discloses use of PEGylated botulinum toxins for treating disorders of inappropriate muscle contraction. US 2002/0197278 A1 also suggests use of PEGylated TeNT for treating disorders of inappropriate muscle contraction, e.g. migration headache or strabismus. However, as noted above, TeNT causes muscle contraction, thereby precluding its use, PEGylated or not, for treating disorders of inappropriate muscle contraction.

Wan et al. *Process Biochemistry* (2017) 52: 183-191 discloses the effect of PEGylation on the anti-PEG immune response resulting from administration of PEGylated proteins, but does not exploit its findings for any therapy.

WO 2016/001762 A1 discloses use of a PEGylated TeNT fragment c (c) for increasing muscle mass. Fragment c (50 kDa) is generated when TeNT is enzymatically cleaved by papain and corresponds to the 451 amino acids at the C-terminus of the TeNT heavy chain. Fragment c retains the binding, internalization and trans-synaptic transport capabilities of undigested TeNT, but does not disrupt any neuronal processes, and is therefore nontoxic.

A need exists for a TeNT-based therapy that avoids the pre-existing anti-TeNT immune response in tetanus toxoid immunised subjects.

It is to be understood that if any prior art publication is referred to herein, such reference does not constitute an admission that the publication forms a part of the common general knowledge in the art in Australia or any other country.

SUMMARY

The inventors have appreciated that exploitation of TeNT has not been fully realised because of the adaptive immune system, which upon administration of a protein therapeutic agent, produces an antibody response, thereby decreasing efficacy of the protein therapeutic agent. The adaptive immune response may be intentional, as a result of vaccination, as demonstrated by many populations that have been immunised against TeNT. Alternatively, the adaptive immune response may be unintentional, resulting from repeated exposure to the protein therapeutic agent.

The inventors have produced a family of modified TeNTs and a treatment regimen that address these problems. Specifically, the invention provides a family of PEGylated TeNTs (PEG-TeNTs) that each evade the immune system, and a tiered treatment regimen in which a different, replacement PEG-TeNT is used for treatment when efficacy of a previously administered PEG-TeNT decreases or when a patient's immunological profile precludes the use of another PEG-TeNT.

A first aspect provide, a tetanus neurotoxin (TeNT) or fragment thereof, comprising one or more surface serine to cysteine amino acid substitutions relative to SEQ ID NO: 1.

In one embodiment of the first aspect, the substituted cysteine is conjugated to polyethylene glycol (PEG).

A second aspect provides a TeNT or fragment thereof comprising, relative to SEQ ID NO: 1: R1225K; R1225E; W1288A; W1288Y; W1288F; W1288L; R1225K and W1288A; R1225E and W1288A; R1225K and W1288Y; R1225E and W1288Y; R1225K and W1288F; R1225E and W1288F; R1225K and W1288L; R1225E and W1288L; R1225del; W1288del; or R1225del and W1288del; E270A; Y374A; E270A and Y374A; G270del; Y374del; or a combination thereof, wherein the TeNT or fragment is inactive.

A third aspect provides a composition comprising: (i) a first PEGylated tetanus neurotoxin (PEG-TeNT) comprising tetanus neurotoxin (TeNT) conjugated to polyethylene glycol (PEG); and (ii) a second TeNT, wherein the first PEG-TeNT is not conjugated to the second TeNT.

A fourth aspect provides a method for treating hypotonia, the method comprising administering to a subject: (i) a first PEGylated tetanus neurotoxin (PEG-TeNT) comprising tetanus neurotoxin (TeNT) conjugated to polyethylene glycol (PEG); and (ii) a second TeNT.

The fourth aspect also provides use of a first PEGylated tetanus neurotoxin (PEG-TeNT) comprising a tetanus neurotoxin (TeNT) conjugated to polyethylene glycol (PEG) in the manufacture of a medicament for treating hypotonia in a subject administered a second TeNT.

The fourth aspect also provides use of a second tetanus neurotoxin (TeNT) in the manufacture of a medicament for treating hypotonia in a subject administered a first PEGylated tetanus neurotoxin (PEG-TeNT) comprising a tetanus neurotoxin (TeNT) conjugated to polyethylene glycol (PEG).

The fourth aspect also provides use of: (i) a first PEGylated tetanus neurotoxin (PEG-TeNT) comprising a tetanus neurotoxin (TeNT) conjugated to polyethylene glycol (PEG); and (ii) a second TeNT in the manufacture of a medicament for treating hypotonia.

The fourth aspect also provides a first PEGylated tetanus neurotoxin (PEG-TeNT) comprising a tetanus neurotoxin (TeNT) conjugated to polyethylene glycol (PEG) for use in a method for treating hypotonia in a subject administered a second TeNT.

The fourth aspect also provides a second tetanus neurotoxin (TeNT) for use in a method for treating hypotonia in a subject administered a first PEGylated tetanus neurotoxin (PEG-TeNT) comprising a tetanus neurotoxin (TeNT) conjugated to polyethylene glycol (PEG).

The fourth aspect also provides: (i) a first PEGylated tetanus neurotoxin (PEG-TeNT) comprising a tetanus neurotoxin (TeNT) conjugated to polyethylene glycol (PEG); and (ii) a second TeNT for use in a method for treating hypotonia.

In embodiments of the fourth aspect, a composition may comprise the first PEG-TeNT and the second TeNT.

The fourth aspect also provides a composition comprising: (i) a first PEGylated tetanus neurotoxin (PEG-TeNT) comprising tetanus neurotoxin (TeNT) conjugated to polyethylene glycol (PEG); and (ii) a second TeNT for use in a method for treating hypotonia.

In one embodiment, the first PEG-TeNT or the second TeNT comprises a PEGylated TeNT light chain (LC), a PEGylated TeNT heavy chain (HC), a PEGylated TeNT heavy chain (HC) and PEGylated TeNT light chain (LC), or a PEGylated TeNT fragment c (c). In one embodiment, the first PEG-TeNT or the second TeNT comprises PEG-TeNT-LC-HC.

In another embodiment, the first PEG-TeNT or the second TeNT is PEG-TeNT-HC comprising a PEGylated HC. In this embodiment, LC is not PEGylated. In another embodiment, the first PEG-TeNT or the second TeNT is PEG-TeNT-LC-c comprising a PEGylated LC and a PEGylated c. In this embodiment, HN is not PEGylated.

In a further embodiment, the first PEG-TeNT is PEG-TeNT-HC, and the second TeNT is PEG-TeNT-LC-c.

In one embodiment, the second TeNT comprises an inactivated TeNT. Relative to SEQ ID NO: 1, the inactivated TeNT may comprise: R1225K; R1225E; W1288A; W1288Y; W1288F; W1288L; R1225K and W1288A; R1225E and W1288A; R1225K and W1288Y; R1225E and W1288Y; R1225K and W1288F; R1225E and W1288F; R1225K and W1288L; R1225E and W1288L; R1225del; W1288del; R1225del or W1288del; E270A; Y347A; E270A and Y374A; E270del; Y374del; or a combination thereof. In one embodiment, the second TeNT comprises an inactivated TeNT comprising R1225E and W1288A.

In one embodiment, the subject is administered: a PEG-TeNT comprising PEGylated c (PEG-TeNT-c) until efficacy decreases; then a composition comprising PEG-TeNT-HC and PEG-TeNT-LC-c until efficacy decreases; then a PEG-TeNT comprising a PEGylated LC and a PEGylated HC (PEG-TeNT-LC-HC).

In one embodiment, treating comprises administering to the subject: a PEG-TeNT comprising PEGylated c (PEG-TeNT-c); then a composition comprising PEG-TeNT-HC and PEG-TeNT-LC-c; then a PEG-TeNT comprising a PEGylated LC and a PEGylated HC (PEG-TeNT-LC-HC), to determine the immunological profile of anti-TeNT antibodies of the subject and determine the effective composition of PEG-TeNTs based on that profile.

In one embodiment, the hypotonia is obstructive sleep apnoea.

In another embodiment, the composition is a therapeutic composition. In another embodiment, the composition is a cosmetic composition.

Also disclosed is a method for preparing a protein consisting of TeNT LC and TeNT HN (LC-HN), the method comprising expressing in a host cell a nucleic acid molecule encoding an amino acid comprising SEQ ID NO: 6.

A fifth aspect provides a PEGylated tetanus neurotoxin (PEG-TeNT), comprising tetanus neurotoxin (TeNT) conjugated to polyethylene glycol (PEG).

In one embodiment, the TeNT light chain (LC) is PEGylated, the TeNT heavy chain (HC) is PEGylated, or the TeNT fragment c (c) is PEGylated. In one embodiment, LC is PEGylated and HC is PEGylated (PEG-TeNT-LC-HC), or LC is PEGylated and c is PEGylated (PEG-TeNT-LC-c).

In another embodiment, PEG is conjugated to a lysine residue of TeNT. In another embodiment, PEG is conjugated to a cysteine residue of TeNT. In one embodiment, PEG is conjugated to a cysteine residue of TeNT, wherein the cysteine residue is either native or a substitution for a serine residue relative to SEQ ID NO: 1.

In one embodiment, the PEG has a molecular weight of about 2 kDa, about 5 kDa, about 10 kDa, or about 20 kDa, or about 30 kDa.

A sixth aspect provides a method for treating hypotonia, the method comprising administering to a subject the PEG-TeNT of the fifth aspect, wherein the PEG-TeNT is not conjugated to a second TeNT.

The sixth aspect also provides use of the PEG-TeNT of the fifth aspect in the manufacture of a medicament for treating hypotonia, wherein the PEG-TeNT is not conjugated to a second TeNT.

Alternatively, the sixth aspect provides the PEG-TeNT of the fifth aspect for use in a method for treating hypotonia, the method comprising administering to a subject the PEG-TeNT, wherein the PEG-TeNT is not conjugated to a second TeNT.

In one embodiment, the subject is administered a first PEG-TeNT comprising a PEGylated HC (PEG-TeNT-HC) and a second PEG-TeNT comprising a PEGylated LC and a PEGylated c (PEG-TeNT-LC-c).

In another embodiment, the subject is administered: a PEG-TeNT comprising a PEGylated c (PEG-TeNT-c); and/or a first PEG-TeNT comprising a PEGylated HC (PEG-TeNT-HC) and a second PEG-TeNT comprising a PEGylated LC-c (PEG-TeNT-LC-c); and/or a PEG-TeNT comprising a PEGylated HC and a PEGylated LC (PEG-TeNT-LC-HC).

In one embodiment, treating comprises administering to the subject: a PEG-TeNT comprising PEGylated c (PEG-TeNT-c) until efficacy decreases. Thereafter, treating may comprise administering to the subject: a PEG-TeNT-HC and a PEG-TeNT-LC-c until efficacy decreases. Thereafter, treating may comprise administering to the subject: a PEG-TeNT comprising a PEGylated LC and a PEGylated HC (PEG-TeNT-LC-HC).

In one embodiment, treating comprises administering to the subject: a PEG-TeNT comprising PEGylated c (PEG-TeNT-c) until efficacy decreases; then a PEG-TeNT-HC and a PEG-TeNT-LC-c until efficacy decreases; then a PEG-TeNT comprising a PEGylated LC and a PEGylated HC (PEG-TeNT-LC-HC).

In one embodiment, treating comprises administering to the subject: a PEG-TeNT comprising PEGylated c (PEG-TeNT-c) comprising PEG having a molecular weight of about 5 kDa until efficacy decreases; then a PEG-TeNT comprising PEGylated c (PEG-TeNT-c) comprising PEG having a molecular weight of about 10 kDa until efficacy decreases; then a PEG-TeNT comprising PEGylated c (PEG-TeNT-c) comprising PEG having a molecular weight of about 20 kDa until efficacy decreases. Thereafter, treating may comprise administering to the subject: a PEG-TeNT-HC and a PEG-TeNT-LC-c, either or both of which comprise PEG having a molecular weight of 5 kDa, until efficacy decreases; then a PEG-TeNT-HC and a PEG-TeNT-LC-c, either or both of which comprise PEG having a molecular weight of 10 kDa, until efficacy decreases; then a PEG-TeNT-NC and a PEG-TeNT-LC-c, either or both of which comprise PEG having a molecular weight of 20 kDa, until efficacy decreases. Thereafter, treating may comprise administering to the subject: a PEG-TeNT comprising a PEGylated LC and a PEGylated HC (PEG-TeNT-LC-HC), either or both of which comprise PEG having a molecular weight of 5 kDa, until efficacy decreases; then a PEG-TeNT comprising a PEGylated LC and a PEGylated HC (PEG-TeNT-LC- HC), either or both of which comprise PEG having a molecular weight of 10 kDa, until efficacy decreases; then a PEG-TeNT comprising a PEGylated LC and a PEGylated HC (PEG-TeNT-LC-HC), either or both of which comprise PEG having a molecular weight of 20 kDa.

In one embodiment, treating comprises administering to the subject: a PEG-TeNT comprising PEGylated c (PEG-TeNT-c); then a composition comprising PEG-TeNT-HC and PEG-TeNT-LC-c; then a PEG-TeNT comprising a PEGylated LC and a PEGylated HC (PEG-TeNT-LC-HC), to determine the immunological profile of anti-TeNT antibodies of the subject and determine the effective composition of PEG-TeNTs based on that profile.

In another embodiment, treating with a TeNT further comprises administering an inactivated TeNT. Relative to SEQ ID NO: 1, the inactivated TeNT may comprise: R1225K; R1225E; W1228A; W1288Y; W1288F; W1288L; R1225K and W1288A; R1225E and W1288A; R1225K and W1288Y; R1225E and W1288Y; R1225K and W1288F; R1225E and W1288F; R1225K and W1288L; R1225E and W1288L; R1225del; W1288del; R1225del or W1288del. In one embodiment, the second TeNT comprises an inactivated TeNT comprising R1225E and W1288A; E270A; Y374A; E270A and Y374A; E270del; Y374del; or a combination thereof.

In one embodiment, the hypotonia is obstructive sleep apnoea.

A seventh aspect provides a kit comprising the TeNT of the first aspect, the composition of the second aspect or the PEG-TeNT of the fifth aspect.

In one embodiment, the composition or PEG-TeNT is used according to the method of the third or sixth aspect, respectively.

BRIEF DESCRIPTION OF THE FIGURES

FIGS. 1A to 1D are schematic representations of examples of PEG-TeNTs of the invention: A PEG-TeNT-c; B PEG-TeNT-HC, C PEG-TeNT-LC-c, D PEG-TeNT-LC-HC, where the TeNT is entire and active, i.e. the TeNT comprises both chains, and PEGylation is present on specific regions, i.e. c, HC, LC-c, or LC-HC, respectively.

FIG. 2 is the amino acid sequence (SEQ ID NO: 1) of mature TeNT comprising 1314 amino acids.

FIGS. 3-1 and 3-2 represent a nucleic acid sequence (SEQ ID NO: 2) of the vector pRSET-TeNT encoding TeNT.

FIG. 4 is a map of the vector pRSET-TeNT encoding TeNT. TeNT is expressed with an N-terminal His$_6$-tag. The nucleic acid was inserted within the MCS of the pRSET-A vector and expressed under the control of a T7 promoter.

FIG. 5 is the amino acid sequence (SEQ ID NO: 3) of HC comprising amino acids 457 to 1314 of SEQ ID NO: 1.

FIG. 6 is the amino acid sequence (SEQ ID NO: 4) of c comprising amino acids 864 to 1314 of SEQ ID NO: 1.

FIG. 7 is a nucleic acid sequence (SEQ ID NO: 5) of the vector pRSET-TeNT-c encoding c.

FIG. 8 is a map of the vector pRSET-TeNT-c encoding c. c is expressed with an N-terminal His$_6$-tag. The nucleic acid was inserted within the MCS of the pRSET-A vector and expressed under the control of a T7 promoter.

FIG. 9 is the amino acid sequence (SEQ ID NO: 6) of LC-HN comprising amino acids 1 to 863 of SEQ ID NO: 1.

FIGS. 10-1 and 10-2 represent a nucleic acid sequence (SEQ ID NO: 7) of the vector pRSET-TeNT-LC-HN encoding LC-HN.

FIG. 11 is a map of the vector pRSET-TeNT-LC-HN encoding LC-HN. LC-HN is expressed with an N-terminal His$_6$-tag. The nucleic acid was inserted within the MCS of the pRSET-A vector and expressed under the control of a T7 promoter.

FIG. 12 is an amino acid sequence (SEQ ID NO: 8) of a non-functional c comprising amino acid substitutions W1288A and R1225E relative to SEQ ID NO: 1.

FIGS. 13-1 and 13-2 represent a nucleic acid sequence (SEQ ID NO: 9) of the vector pRSET-TeNT-c encoding the non-functional c of FIG. 12 (SEQ ID NO: 8) comprising amino acid substitutions W1288A and R1225E relative to SEQ ID NO: 1.

FIG. 14 is a map of the vector pRSET-TeNT-c encoding the non-functional c of FIG. 12 (SEQ ID NO: 8) comprising amino acid substitutions W1288A and R1225E relative to SEQ ID NO: 1. c, comprising amino acid substitutions W1288A and R1225E relative to SEQ ID NO: 1, is expressed with an N-terminal His$_6$-tag. The nucleic acid was inserted within the MCS of the pRSET-A vector and expressed under the control of a T7 promoter.

FIG. 15 is an amino acid sequence (SEQ ID NO: 10) of a non-functional TeNT comprising amino acid substitutions W1288A and R1225E relative to SEQ ID NO: 1.

FIGS. 16-1 and 16-2 represent a nucleic acid sequence (SEQ ID NO: 11) of the vector pRSET-TeNT encoding the non-functional TeNT of FIG. 15 (SEQ ID NO: 10) comprising amino acid substitutions W1288A and R1225E relative to SEQ ID NO: 1.

FIG. 17 is a map of the vector pRSET-TeNT encoding the non-functional TeNT of FIG. 15 (SEQ ID NO: 10) comprising amino acid substitutions W1288A and R1225E relative to SEQ ID NO: 1. TeNT, comprising amino acid substitutions W1288A and R1225E relative to SEQ ID NO: 1, is expressed with an N-terminal His$_6$-tag. The nucleic acid was inserted within the MCS of the pRSET-A vector and expressed under the control of a T7 promoter.

FIG. 18 is the amino acid sequence (SEQ ID NO: 12) of a mature 1314 amino acid TeNT comprising surface serine to cysteine amino acid substitutions S81C, S120C, S144C, S248C, S335C, S428C, S600C, S963C, S1041C, S1155C, and S1187C relative to SEQ ID NO: 1.

FIGS. 19-1, 19-2, and 19-3 represent a nucleic acid sequence (SEQ ID NO: 13) of the vector pRSET-TeNT encoding the surface serine to cysteine substituted mature TeNT of FIG. 18 (SEQ ID NO: 12).

FIG. 20 is a map of the vector pRSET-TeNT of FIGS. 19-1, 19-2, and 19-3 (SEQ ID NO: 13) encoding the surface serine to cysteine substituted mature TeNT of FIG. 18 (SEQ ID NO: 12). The surface serine to cysteine substituted TeNT is expressed with an N-terminal His6-tag. The nucleic acid was inserted within the MCS of the pRSET-A vector and expressed under the control of a T7 promoter.

FIGS. 21-1 and 21-2 represent the amino acid sequence (SEQ ID NO: 14) of a mature 1314 amino acid TeNT comprising surface serine to cysteine amino acid substitutions S81C, S120C, S144C, S248C, S335C, S428C, S963C, S1041C, S1155C, and S1187C, relative to SEQ ID NO: 1, in the LC and c regions.

FIGS. 22-1 and 22-2 represent a nucleic acid sequence (SEQ ID NO: 15) of the vector pRSET-TeNT encoding the surface serine to cysteine substituted mature TeNT of FIGS. 21-1 and 21-2 (SEQ ID NO: 14).

FIG. 23 is a map of the vector pRSET-TeNT of FIGS. 22-1 and 22-2 (SEQ ID NO: 15) encoding the surface serine to cysteine substituted mature TeNT of FIGS. 21-1 and 21-2 (SEQ ID NO: 14). The surface serine to cysteine substituted TeNT is expressed with an N-terminal His6-tag. The nucleic acid was inserted within the MCS of the pRSET-A vector and expressed under the control of a T7 promoter.

FIG. 24 is the amino acid sequence (SEQ ID NO: 16) of a TeNT comprising HC surface serine to cysteine amino acid substitutions S600C, S963C, S1041C, S1155C, and S1187C relative to SEQ ID NO: 1.

FIGS. 25-1, 25-2, and 25-3 represent a nucleic acid sequence (SEQ ID NO: 17) of the vector pRSET-TeNT encoding the surface serine to cysteine substituted mature TeNT of FIG. 24 (SEQ ID NO: 16).

FIG. 26 is a map of the vector pRSET-TeNT of FIGS. 25-1, 25-2, and 25-3 (SEQ ID NO: 17) encoding the surface serine to cysteine substituted TeNT of FIG. 24 (SEQ ID NO: 16). The surface serine to cysteine substituted TeNT is expressed with an N-terminal His6-tag. The nucleic acid was inserted within the MCS of the pRSET-A vector and expressed under the control of a T7 promoter.

FIG. 27 is a 3-dimensional protein structure model of TeNT derived from crystallography data deposited in the protein data bank (accession ID PDB: 5N0B) mapping epitopes recognised by major human antibody clonotypes, as identified by da Silva Antunes et al (2017) and Palermo et al (2017), onto the model using Discovery Studio. Surface serine residues in or around the identified epitopes were selected for mutation to cysteine for subsequent PEGylation.

FIGS. 28A and 29B comprise two photographs of SDS-PAGE analyses of PEG-TeNTs comprising PEGs of increasing molecular weight and detected (A) using COOMASSIE BLUE™ and (B) by Western blot using polyclonal anti-TeNT antibodies. (B) shows that immunogenicity is proportional to PEG molecular weight. Molecular weight marker lane 1 with kDa on left edge, TeNT lane 2, 2 kDa PEG-TeNT-HC-LC lane 3, 5 kDa PEG-TeNT-LC-HC lane 4, 10 kDa PEG-TeNT-LC-HC lane 5, 20 kDa PEG-TeNT-LC-HC lane 6.

FIGS. 29A to 29D comprise four line graphs representing competitive ELISA assays. Four PEG-TeNTs and four PEG-TeNT-LC-c Serine mutants, each comprising a different molecular weight PEG (2 kDa, 5 kDa, 10 kDa and 20 kDa), were assayed against TeNT using a polyclonal anti-TeNT antibody. (A) TeNT was adsorbed to an ELISA plate and then probed with a polyclonal anti-TeNT antibody pre-incubated with each of four concentrations (10 μg/mL, 1 μg/mL, 0.1 μg/mL and 0.01 μg/mL) of four PEG-TeNT antigens (2 kDa, 5 kDa, 10 kDa and 20 kDa). (B) Each PEG-TeNT (2 kDa, 5 kDa, 10 kDa and 20 kDa) was adsorbed to a separate ELISA plate and then probed with a polyclonal anti-TeNT antibody pre-incubated with each of four concentrations (10 μg/mL, 1 μg/mL, 0.1 μg/mL and 0.01 μg/mL) of TeNT antigen. (C) TeNT-LC-c Serine mutant was adsorbed to an ELISA plate and then probed with a polyclonal anti-TeNT antibody pre-incubated with each of four concentrations (10 μg/mL, 1 μg/mL, 0.1 μg/mL and 0.01 μg/mL) of four PEG-TeNT-LC-c Serine mutant antigens (2 kDa, 5 kDa, 10 kDa and 20 kDa). (D) Each PEG-TeNT-LC-c Serine mutant (2 kDa, 5 kDa, 10 kDa and 20 kDa) was adsorbed to a separate ELISA plate and then probed with a polyclonal anti-TeNT antibody pre-incubated with each of four concentrations (10 μg/mL, 1 μg/mL, 0.1 μg/mL and 0.01 μg/mL) of TeNT-LC-c Serine mutant antigen.

FIGS. 30A to 30D comprise four photographs showing localised limb tetany in the hind limb of a female C57BL/6 mouse injected with PEG-TeNT-LC-HC. FIGS. 30A and 30B show localised limb tetany in a naïve mouse. FIG. 30C shows a lack of limb tetany after injection of 100 units of TeNT in a mouse vaccinated with tetanus toxoid, whereas FIG. 30D shows sustained limb tetany after injection of 80 units of PEG-TeNT LC-HC 20 kDa in a mouse vaccinated with tetanus toxoid.

FIGS. 31A and 31B comprise two dot plots showing the clinical tetanus level exhibited in the hind leg of female C57BL/6 mice after injection with a defined number of units of TeNT, PEG-TeNT-LC-HC 20 kDa, TeNT-LC-c Serine mutant, PEG-TeNT-LC-c Serine mutant 2 kDa, or PEG-TeNT-LC-c Serine mutant 20 kDa. A) Mice were injected with TeNT or PEG-TeNT-LC-HC 20 kDa. B) Mice were injected with TeNT, TeNT-LC-c Serine mutant, PEG-TeNT-LC-c Serine mutant 2 kDa or PEG-TeNT-LC-c Serine mutant 20 kDa. One unit is the minimum amount of toxin required to produce stage four tetany within 24 hours in a naïve mouse.

FIG. 32A shows the progression of tetany after injection with 4000 units of TeNT with or without deactivated TeNT decoy. FIG. 32B shows the progression of tetany after injection with 40 units of TeNT-PEG 20 kDa with or without deactivated TeNT decoy. In both cases the progression is clearly enhanced by the presence of decoy.

DETAILED DESCRIPTION

Figure 29:
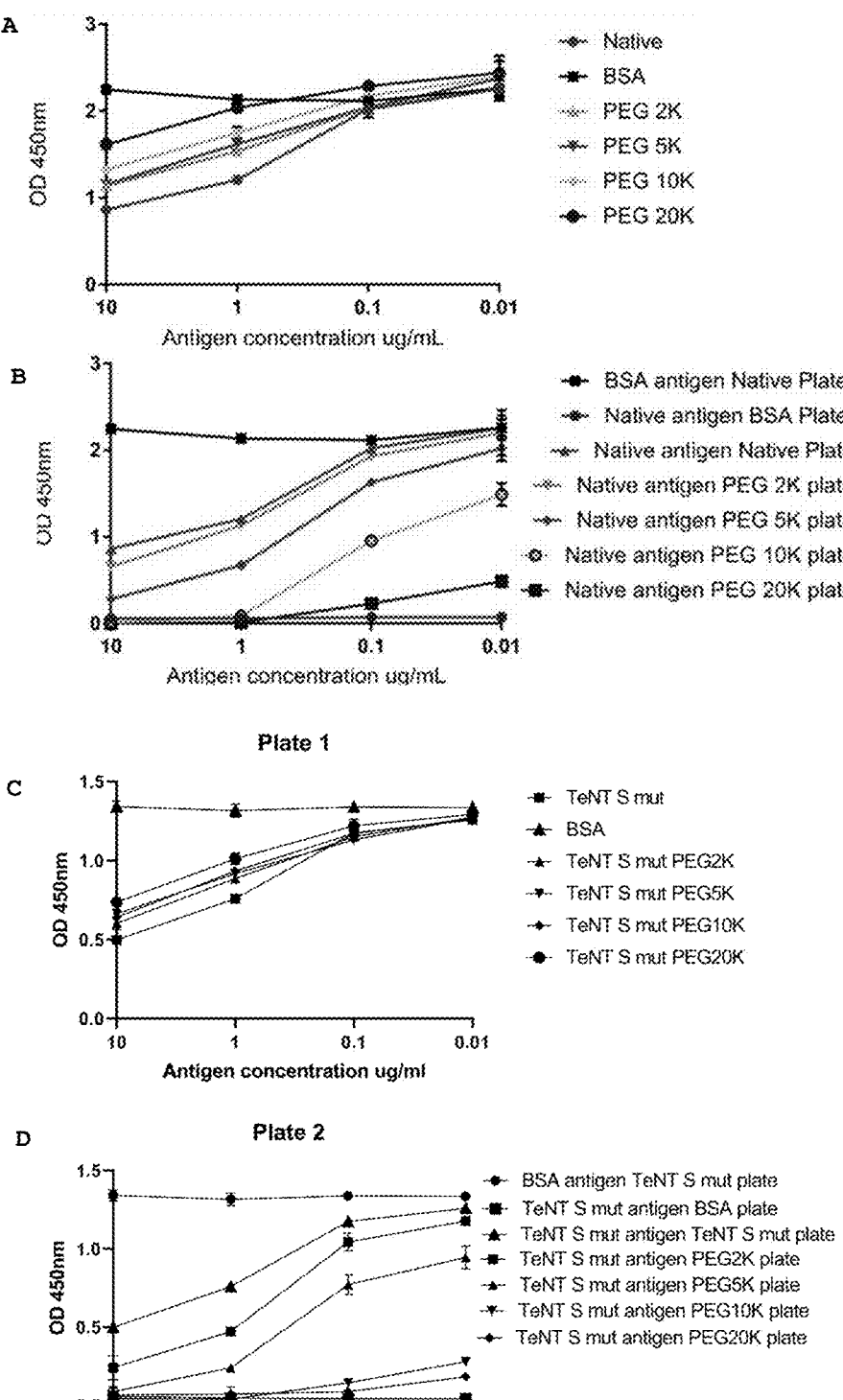

The present invention relates to immune-evading TeNT and PEG-TeNT molecules (FIGS. 1A to 1D), compositions thereof, and their therapeutic and cosmetic use. In one embodiment, the invention relates to treating hypotonia, optionally obstructive sleep apnoea.

Described herein is use of a specifically modified TeNT and composition of TeNT and decoy (inactive TeNT) to treat hypotonia in subjects with a protective immune response against tetanus toxoid. To achieve that end, an active TeNT is modified by adding PEG, introducing specific mutations, or a combination thereof, for delivering a biologically active compound capable of increasing muscle tone in a tetanus-immune patient.

The activity can be demonstrated by the administration of a unit defined dose of modified toxin, or formulation, where at the same unit dose TeNT would exhibit no activity in a vaccinated subject. The introduction of specific surface mutations for the directed attachment of PEG molecules, based on the analysis of the three-dimensional structure of TeNT, allowed the masking of specific TeNT epitopes known to be targeted by the protective antibody response in vaccinated subjects. The combinations of PEGylation, site-directed mutation and decoy molecule formulations, greatly increased the effect of the molecule on increasing muscle tone in vaccinated mammalian models, relative to the equivalent units administered of TeNT.

US 2002/0197278 disclosed a series of PEGylated botulinum toxins for treating disorders of inappropriate muscle contraction and suggested that TeNT could be used as an alternative to botulium toxin. However, TeNT cannot be used to treat muscle contraction. Further, the alleged invention of US 2002/0197278 appears not to be enabled, because the methods disclosed do not include site directed masking of epitopes, and, to the best of the present inventors' knowledge, the three-dimensional structure and identification of epitopes required for deliberate masking of TeNT epitopes was not available at the priority date of US 2002/0197278.

Wan et al. is directed to the effect of PEGylation on the anti-PEG immune response resulting from administration of PEGylated proteins, but does not exploit its findings for any therapy. Although Wan et al. disclose that a PEGylated tetanus toxoid demonstrated reduced immunogenicity relative to non-PEGylated tetanus toxoid, Wan et al. do not present a therapeutically relevant molecule or formulation. Moreover, PEGylation of tetanus toxoid is not relevant to modification of active TeNT, because tetanus toxoid is a biologically inactive TeNT used for vaccination, which may be produced by formaldehyde cross-linking of TeNT. That is, tetanus toxoid, PEGylated or not, does not possess the combination of enzymatic, binding and translocational activity of active TeNT.

WO 2016/001762 A1 relates to a TeNT c-fragment alone, which is a molecule with no specific activity beyond binding neurotransmitters and entering the neuron.

Therefore, a need exists for a TeNT-based therapy that avoids the pre-existing anti-TeNT immunity in tetanus toxoid immunised subjects. Disclosed herein is a solution to this problem, in part provided by a masked, active and therapeutically relevant PEGylated TeNT.

Tetanus Neurotoxin (TeNT)

TeNT is approximately 150 kDa and is expressed from the tetX gene. A codon optimised nucleic acid sequence corresponding to the coding region of tetX, but lacking the initiator methionine codon, is provided in the vector sequence of FIGS. 3-1 and 3-2 (SEQ ID NO: 2). TeNT is expressed as one protein that is post-translationally cleaved—first to remove the initiator methionine and then into two parts: a 50 kDa light chain (LC or A-chain) derived from the N-terminus of the uncleaved protein and a 100 kDa heavy chain (HC or B-chain) derived from the C-terminus of the uncleaved protein. The two chains are connected by an interchain disulfide bond, which is essential for neurotoxicity. The 1314 amino acid sequence of mature TeNT is provided in FIG. 2 (SEQ ID NO: 1).

LC has zinc endopeptidase activity and attacks the vesicle-associated membrane protein (VAMP) that is necessary for vesicle fusion to membranes, thereby preventing neurotransmitter release.

Upon digestion with papain, HC can be cleaved into two domains, each of 50 kDa: an N-terminus translocation domain named HN; and a C-terminus ganglioside (membrane) binding domain named fragment c (c). TeNT lacking c is referred to herein as LC-HN.

c harbours two polysialoganglioside binding sites and binds to polysialogangliosides (GD2 GD1b, and GT1b) on the neuronal membrane. Thus, c mediates binding of TeNT to the presynaptic membrane of peripheral motor axons and aids movement of TeNT across that membrane into the neuron.

An amino acid sequence for:

TeNT lacking the initiator methionine is provided in FIG. 2 (SEQ ID NO: 1);

HC is provided in FIG. 5 (SEQ ID NO: 3);

c is provided in FIG. 6 (SEQ ID NO: 4); and

LC-HN is provided in FIG. 9 (SEQ ID NO: 6).

A codon-optimised nucleic acid sequence of a vector encoding and a vector map for:

c are provided in FIG. 7 (SEQ ID NO: 5) and FIG. 8; and

LC-HN are provided in FIGS. 10-1 and 10-2 (SEQ ID NO: 7) and FIG. 11.

As used herein, "TeNT" is used in reference to a full TeNT molecule, consisting of the heavy chain and light chain. Subdomains and fragments are referred to herein by their abbreviations: light chain "LC"; heavy chain "HC"; heavy chain N-terminus domain "HN"; heavy chain fragment c "c"; light chain plus heavy chain N-terminus domain "LC-HN" (i.e. TeNT molecule lacking c). Where any subdomain or fragment is PEGylated, the prefix PEG is used: PEG-LC; PEG-HC; PEG-HN; PEG-c; PEG-LC-HN. In a full TeNT molecule comprising a PEGylated fragment or subdomain, the prefix PEG is used and the PEGylated subdomain or fragment is indicated: PEG-TeNT-LC; PEG-TeNT-HC; PEG-TeNT-LC-HC; PEG-TeNT-HN; PEG-TeNT-c; PEG-TeNT-LC-c; PEG-TeNT-LC-HN, and so on.

It will be appreciated that because of their specific functions, subdomains and fragents are not interchangeable for full TeNT.

TeNTs disclosed herein may be active or inactive. An active TeNT possesses the same biological activities of native TeNT. An inactive TeNT lacks one or more activities of native TeNT. In one embodiment, an inactive TeNT does not block release of inhibitory neurotransmitters. An inactive TeNT of the disclosure may also be referred to as a "decoy". In inactive TeNT includes tetanus toxoid. In one embodiment, an inactive TeNT is an inactive TeNT as disclosed herein.

In one embodiment, two or more TeNTs may be conjugated.

In another embodiment, TeNTs are not conjugated. In one embodiment of the compositions, methods and uses disclosed herein, a first PEG-TeNT is not conjugated to a second TeNT.

Immune-evading PEG-TeNTs disclosed herein and depicted in FIGS. 1A-1D include:

TeNT with PEGylated fragment c (PEG-TeNT-c) (FIG. 1A);

TeNT with PEGylated heavy chain (PEG-TeNT-HC) (FIG. 1B);

TeNT with PEGylated light chain and PEGylated fragment c (PEG-TeNT-LC-c) (FIG. 1C); and TeNT fully PEGylated (PEG-TeNT-LC-HC) (FIG. 1D).

PEG-TeNT-c advantageously evades the pre-existing immune response of the adaptive immune system in vaccinated subjects. In one embodiment, PEG-TeNT-c provides first tier treatment to be used until efficacy decreases.

PEG-TeNT-HC and PEG-TeNT-LC-c advantageously evade the pre-existing immune response of the adaptive immune system in vaccinated subjects and also evade the immune response of the adaptive immune system elicited by repeated exposure to PEG-TeNT-c.

In one embodiment, PEG-TeNT-HC and PEG-TeNT-LC-c together provide second tier treatment to be used until their efficacy decreases.

PEG-TeNT-LC-HC advantageously evades the pre-existing immune response of the adaptive immune system in vaccinated subjects and also evades the immune response of the adaptive immune system elicited by repeated exposure to PEG-TeNT-c and to PEG-TeNT-HC plus PEG-TeNT-LC-c.

In one embodiment, PEG-TeNT-LC-HC provides third tier treatment to be used until its efficacy decreases.

Also disclosed is TeNT with PEGylated light chain (PEG-TeNT-LC), TeNT with PEGylated LC and HN (PEG-TeNT-LC-HN), and TeNT with PEGylated HN (PEG-TeNT-HN).

The person skilled in the art will appreciate that the specific combinations of PEG-TeNTs and the order of treatment with those PEG-TeNT combinations may be altered.

Polyethylene Glycol (PEG)

PEG may be conjugated, for example, to lysine (e.g. amino-PEGylation), cysteine (e.g. thiol-PEGylation and bridging PEGylation), histidine, arginine, aspartic acid, asparagine (e.g. N-glyco-PEGylation), glutamic acid, glutamine (e.g. transglutaminase-mediated PEGylation), serine (e.g. O-glyco-PEGylation), threonine (e.g. O-glyco-PEGylation), or tyrosine residues in TeNT. Examples of PEGylation also include N-terminus PEGylation and C-terminus PEGylation.

PEGylation may be achieved by reacting PEG with a functional group that is hydroxyl-reactive, for example anhydrides, acid chlorides, chloroformates and carbonates. Alternatively, PEGylation may be achieved with functional groups such as aldehyde, ester, and amide.

PEG may be linear or branched.

PEG may be a modified PEG, for example, poly[oligo (ethylene glycol) methyl ether methacrylate] (POEGMA).

PEGylation may be site-specific PEGylation.

In one embodiment, surface serine residues of TeNT or a TeNT fragment are mutated to surface cysteine residues to facilitate directed PEG conjugation at immunogenic epitopes. In this context, a mutation is synonymous with substitution, for instance, a serine to cysteine substitution. Such mutations, or substitutions, include one or more, in any combination, of: S81C; S120C; S144C; S248C; S335C; S428C; S600C; S963C; S1041C; S1155C; and S1187C.

Functional groups for heterobifunctional PEGs include maleimide, vinyl sulfone, pyridyl disulfide, amine, carboxylic acid, and NHS ester.

In one embodiment, PEG is conjugated to a TeNT using carboxyl-to-amine crosslinking using the carbodiimide-EDC and sulfo-NHS.

The invention also contemplates a PEG-TeNT comprising different molecular weight PEGs conjugated to different subdomains or fragments of TeNT.

PEG may be conjugated or attached to TeNTs of the disclosure between 4° C. and 25° C. for between 2 and 6 hours, for example. In one embodiment, PEG was conjugated to TeNT at room temperature for 6 hours.

Indications

As used herein, "hypotonia" refers to any disorder comprising involuntary muscle weakness that may be treated by inhibiting inhibitory neurotransmitters, for instance GABA or glycine. As such, "hypotonia" includes reduced muscle tone secondary to reduced neurological drive or other causes and conditions of reduced or inadequate muscle tone, strength or neurological drive. Thus, in one embodiment, hypotonia may be neurological hypotonia.

Hypotonia disorders that may be treated with a PEG-TeNT, a composition or method according to the disclosure include obstructive sleep apnoea, apnoea, snoring, scoliosis, strabismus caused by muscle relaxation, ptosis, Horner's syndrome, muscle atrophy, neurologically impaired muscles, amyotrophic lateral sclerosis (ALS), motor neuron disease, any myopathy, multiple sclerosis, Parkinson's disease, myasthenia gravis, decrease in facial muscle tone, optionally ectropion, flaccid paralysis or weakness of any cause of any skeletal or smooth muscle, respiratory muscle weakness of any cause, including post-ventilator weakness, trauma-induced muscle weakness or poor posture caused by muscular flaccidity, pelvic floor muscle flaccidity or weakness, or nasal or upper respiratory flaccidity.

Other disorders that may be treated with a PEG-TeNT, a composition or method according to the disclosure include muscular atrophy, muscular dystrophy, decrease in muscle mass, nasal congestion, impotence, hair loss, hypotension, temporal mandibular joint syndrome, torticollis, neck pain, nerve regeneration within a muscle, migraine, headache, achalasia, obesity, spastic colon, anal fissures, tissues or organs affected by gastric acid, prostate hypertrophy, rhinorrhea, salivation, irritation of pulmonary mucosa, psoriasis, immune tolerance, immune reaction.

In the event that a disorder to be treated according to the disclosure is not a hypotonia disorder per se, increasing muscle tone by treating with a TeNT of the disclosure may alleviate a symptom of the disorder.

Cosmetic applications of PEG-TeNT may include tightening of the abdominal muscles, tightening of the pectoral muscles, tightening of the gluteus maximus, tightening of skeletal muscles, or treatment of facial droop caused by muscle flaccidity.

Smooth muscles, skeletal muscles, tissues or organs that may be treated with a PEG-TeNT, a composition or method according to the disclosure include upper oesophagus, oesophageal wall, oesophageal sphincter, lower oesophageal sphincter, anal sphincter, bladder, bladder sphincter, vaginal sphincter, pyloric sphincter, sphincter of Oddi, ileocaecal sphincter, pelvic floor muscles, vaginal wall muscles, prostate gland, submandibular gland, parotid gland, sublingual gland, minor salivary glands of the oral mucosa, vocal folds, facial muscles, mastication muscles, scalp muscles, chest muscles, back muscles, upper limb muscles, forearm muscles, lower limb muscles, hand muscles, foot muscles, stomach wall muscles, colon wall muscles, neck muscles, throat dilator muscles, masseter muscle, medial ptygeroid, lateral ptygeroid, geniohyoid, genioglossus, tensor veli palatine, levator veli palatini, stylopharyngeus, styloglossus, mylohyoid, stylohyoid, hyoglossus, diagastricus, sternocleidomastoid muscle, trapezius muscle, temporalis muscles, cricopharyngeus muscle, uterine muscle and cervix, gastric nerve supply, intranasal mucosa, pulmonary mucosa, skin, thymus, bone, coronary artery, pulmonary smooth muscle, and cardiac muscle.

Compositions and Administration

The composition of the disclosure may be a therapeutic composition or a cosmetic composition. That is, the composition may be used for therapy or cosmetic purposes.

As used herein, the term "therapeutic composition" or "cosmetic composition" refers to a composition comprising a TeNT that inhibits or treats hypotonia in the subject as described herein. The composition has been formulated for administration to a subject. In one embodiment, the composition is sterile. In one embodiment, the composition is pyrogen-free. The composition may comprise a pharmaceutically acceptable carrier. Preferably, the composition is manufactured according to Good Laboratory Practice (GLP) or Good Manufacturing Practice (GMP).

A TeNT of the disclosure may be administered at up to 10 mg/kg or more. A TeNT of the disclosure may be administered at about 1 fg/kg, about 5 fg/kg, about 10 fg/kg, about 50 fg/kg, about 100 fg/kg, about 500 fg/kg, about 1 pg/kg, about 5 pg/kg, about 10 pg/kg, about 50 pg/kg, about 100 pg/kg, about 500 pg/kg, about 1 ng/kg, about 2 ng/kg, about 3 ng/kg, about 4 ng/kg, about 5 ng/kg, about 6 ng/kg, about 7 ng/kg, about 8 ng/kg, about 9 ng/kg, about 10 ng/kg, about 11 ng/kg, about 12 ng/kg, about 13 ng/kg, about 14 ng/kg, about 15 ng/kg, about 16 ng/kg, about 17 ng/kg, about 18 ng/kg, about 19 ng/kg, about 20 ng/kg, about 30 ng/kg, about 40 ng/kg, about 50 ng/kg, about 60 ng/kg, about 70 ng/kg, about 80 ng/kg, about 90 ng/kg, about 100 ng/kg, about 200 ng/kg, about 300 ng/kg, about 400 ng/kg, about 500 ng/kg, about 600 ng/kg, about 700 ng/kg, about 800 ng/kg, about 900 ng/kg, about 1 µg/kg, about 5 µg/kg, about 10 µg/kg, about 50 µg/kg, about 100 µg/kg, about 500 µg/kg, about 1 mg/kg, or about 10 mg/kg. A TeNT of the disclosure may be administered within any range of any of the doses listed above.

A TeNT of the disclosure may be administered at up to 1000 IU/kg or more. A TeNT of the disclosure may be administered at about 0.1 IU/kg, about 0.2 IU/kg, about 0.3 IU/kg, about 0.4 IU/kg, about 0.5 IU/kg, about 0.6 IU/kg, about 0.7 IU/kg, about 0.8 IU/kg, about 0.9 IU/kg, about 1 IU/kg, about 2 IU/kg, about 3 IU/kg, about 4 IU/kg, about 5 IU/kg, about 6 IU/kg, about 7 IU/kg, about 8 IU/kg, about 9 IU/kg, about 10 IU/kg, about 11 IU/kg, about 12 IU/kg, about 13 IU/kg, about 14 IU/kg, about 15 IU/kg, about 16 IU/kg, about 17 IU/kg, about 18 IU/kg, about 19 IU/kg, about 20 IU/kg, about 30 IU/kg, about 40 IU/kg, about 50 IU/kg, about 60 IU/kg, about 70 IU/kg, about 80 IU/kg, about 90 IU/kg, about 100 IU/kg, about 200 IU/kg, about 300 IU/kg, about 400 IU/kg, about 500 IU/kg, about 600 IU/kg, about 700 IU/kg, about 800 IU/kg, about 900 IU/kg, about 1 000 IU/kg. A TeNT of the disclosure may be administered within any range of any of the doses listed above.

In a composition comprising two PEG-TeNTs, for example a composition comprising a first PEG-TeNT, wherein TeNT-HC is PEGylated (PEG-TeNT-HC), and a second PEG-TeNT wherein TeNT-LC is PEGylated and TeNT-c is PEGylated (PEG-TeNT-LC-c), the ratio of the first PEG-TeNT to the second PEG-TeNT may be varied. For example, the ratio of first PEG-TeNT to second PEG-TeNT may be about 1000:1, about 500:1, about 100:1, about 50:1, about 10:1, about 5:1, about 4:1, about 3:1, about 2:1, about 1:1; about 1:2, about 1:3, about 1:4, about 1:5, about 1:10, about 1:50, about 1:100, about 1:500, or about 1:1000.

A composition may comprise any combination of TeNTs and is not to be limited to a combination of PEG-TeNT-HC and PEG-TeNT-LC-c. A composition may comprise: PEG-TeNT-c and PEG-TeNT-HC; PEG-TeNT-c and PEG-TeNT-LC-c; PEG-TeNT-c and PEG-TeNT-LC-HC; PEG-TeNT-HC and PEG-TeNT-LC-HC; and PEG-TeNT-LC-c and PEG-TeNT-LC-HC. Also disclosed is a composition comprising: PEG-TeNT-c, PEG-TeNT-HC and PEG-TeNT-LC-c; PEG-TeNT-c, PEG-TeNT-HC and PEG-TeNT-LC-HC; PEG-TeNT-c, PEG-TeNT-LC-c and PEG-TeNT-LC-HC; PEG-TeNT-HC, PEG-TeNT-LC-c and PEG-TeNT-LC-HC; and PEG-TeNT-c, PEG-TeNT-HC, PEG-TeNT-LC-c and PEG-TeNT-LC-HC. In a composition, any TeNT may be substituted for, and any composition may further comprise, PEG-TeNT-LC, PEG-TeNT-LC-HN, and/or PEG-TeNT-HN.

In one embodiment, the composition further comprises an inactivated TeNT that acts as a decoy for anti-TeNT antibodies produced by prior exposure to TeNT, for example by vaccination. The inactivated TeNT may, relative to SEQ ID NO: 1, comprise: R1225K; R1225E; W1228A; W1288Y; W1288F; W1288L; R1225K and W1288A; R1225K and W1288Y; R1225E and W1288Y; R1225K and W1288F; R1225E and W1288F; R1225K and W1288L; R1225E and W1288L; R1225del; W1288del; or R1225del and W1288del; E270A; Y374A; E270A and Y374A; E270del; Y374del, or a combination thereof. In one embodiment, the second TeNT comprises an inactivated TeNT comprising R1225E, W1288A, E270A and Y374A.

In a composition comprising at least one PEG-TeNT and a decoy TeNT, the decoy TeNT will be in molar excess relative to the PEG-TeNT. For example, the ratio of decoy TeNT to the PEG-TeNT may be about $10^6:1$; $10^5:1$, $10^4:1$, 1000:1, about 500:1, about 400:1, about 300:1, about 200:1, about 100:1, about 90:1, about 80:1, about 70:1, about 60:1, about 50:1, about 40:1, about 30:1, about 20:1, about 10:1, about 9:1, about 8:1, about 7:1, about 6:1, about 5:1, about 4:1, about 3:1, about 2:1, or about 1:1.

A PEG-TeNT of the disclosure may be administered once, twice or three times per week, once, twice or three times per month, once, twice or three times per quarter, once, twice or three times per 6 months, or once, twice or three times per year.

The PEG-TeNT may be administered in a single dose, a split dose, or in multiple doses. Where a muscle exists as a pair, the PEG-TeNT may be administered unilaterally to one muscle of the pair or bilaterally to both muscles of the pair.

As an alternative to a combination comprising two or more PEG-TeNTs of the disclosure, such two or more PEG-TeNTs may be administered in combination sequentially or simultaneously.

The PEG-TeNT may be administered to a subject locally by any suitable method, for example by injection, surgical implantation, topical application, or intranasal administration. In one embodiment, the TeNT is administered intramuscularly by injection to the affected muscle.

The PEG-TeNT will be formulated, dosed, and administered in a fashion consistent with good medical practice. Factors for consideration in this context include the particular type of hypotonia being treated, the particular subject being treated, the clinical condition of the subject, the site of administration, the method of administration, the scheduling of administration, and other factors known to medical, including dental, practitioners. The therapeutically effective amount of the PEG-TeNT to be administered will be governed by such considerations.

Pharmaceutically acceptable carriers include water, buffered water, saline solutions such as, for example, normal saline or balanced saline solutions such as Hank's or Earle's balanced solutions, glycine, and hyaluronic acid.

The composition may be formulated for intramuscular administration. Compositions for intramuscular administration may comprise pharmaceutically acceptable sterile aqueous or non-aqueous solutions, dispersions, suspensions or emulsions as well as sterile powders for reconstitution into sterile injectable solutions or dispersions. Examples of suitable aqueous and non-aqueous carriers, solvents, diluents or vehicles include water, ethanol, polyols (such as glycerol, propylene glycol, polyethylene glycol), carboxymethylcellulose and mixtures thereof, vegetable oils (such as olive oil), injectable organic esters (e.g. ethyl oleate).

The composition may comprise penetration enhancers to enhance their delivery of TeNT. Penetration enhancers may include fatty acids such as oleic acid, lauric acid, capric acid, myristic acid, palmitic acid, stearic acid, linoleic acid, linolenic acid, dicaprate, reclineate, monoolein, dilaurin, caprylic acid, arachidonic acid, glyceryl 1-monocaprate, mono and di-glycerides and physiologically acceptable salts thereof.

The composition may further include chelating agents such as, for example, ethylenediaminetetraacetic acid (EDTA), citric acid, salicylates (e.g. sodium salycilate, 5-methoxysalicylate, homovanilate).

Also provided is an article of manufacture and/or a kit, comprising a container comprising the PEG-TeNT or composition comprising the PEG-TeNT. The container may be a bottle, vial or syringe comprising the PEG-TeNT or composition, optionally in unit dosage form. For example, the PEG-TeNT or composition may be in the form of an injectable solution in a disposable container, optionally a syringe. The article of manufacture and/or kit may further comprise printed instructions and/or a label or the like, indicating treatment of a subject according to the method disclosed herein.

The term "therapeutically effective amount" refers to an amount of PEG-TeNT effective to treat hypotonia in a subject.

The terms "treat", "treating" or "treatment" refer to both therapeutic treatment and prophylactic or preventative measures, wherein the aim is to prevent, reduce, or ameliorate hypotonia in a subject or slow down (lessen) progression of hypotonia in a subject. Subjects in need of treatment include those already with hypotonia as well as those in which hypotonia is to be prevented or ameliorated.

The terms "preventing", "prevention", "preventative" or "prophylactic" refers to keeping from occurring, or to hinder, defend from, or protect from the occurrence of hypotonia. A subject in need of prevention may be prone to develop hypotonia.

The term "ameliorate" or "amelioration" refers to a decrease, reduction or elimination of hypotonia.

Hypotonia may be quantified. Hypotonia may be quantified on a semi-quantitative scale, for example 0 to 5, where 0 represents absence, 1 to 4 represent identifiable increases in severity, and 5 represents maximum severity. Alternatively, hypotonia may be quantified as a binary event, i.e. presence or absence, 0 or 1. Other semi-quantitative scales will be readily apparent to the person skilled in the art. In another embodiment, hypotonia may be quantified on a quantitative scale, for instance using a force gauge.

Any quantification of hypotonia may be compared to a control, for example a healthy control subject not receiving a PEG-TeNT, an affected control subject receiving treatment for hypotonia, but not treated with a PEG-TeNT, or a population.

Treating hypotonia by administering a PEG-TeNT may be about 1% decrease, about a 2% decrease, about a 3% decrease, about a 4% decrease, about a 5% decrease, about a 6% decrease, about a 7% decrease, about an 8% decrease, about a 9% decrease, about, a 10% decrease, about a 20% decrease, about a 30% decrease, about a 40% decrease, about a 50% decrease, about a 60% decrease, about a 70% decrease, about an 80% decrease, about a 90% decrease, or about a 100% decrease in the hypotonia.

As used herein, the term "subject" may refer to a mammal. The mammal may be a primate, particularly a human, or may be a domestic, zoo, or companion animal. Although it is particularly contemplated that the PEG-TeNTs, compositions and method disclosed herein are suitable for medical treatment of humans, it is also applicable to veterinary treatment, including treatment of domestic animals such as horses, cattle and sheep, companion animals such as dogs and cats, or zoo animals such as felids, canids, bovids and ungulates.

Unless defined otherwise in this specification, technical and scientific terms used herein have the same meaning as commonly understood by the person skilled in the art to which this invention belongs and by reference to published texts.

It is to be noted that the term "a" or "an" refers to one or more, for example, "a TeNT" is understood to represent one or more TeNTs. As such, the terms "a" or "an", "one or more," and "at least one" may be used interchangeably herein.

In the claims which follow and in the description of the invention, except where the context requires otherwise due to express language or necessary implication, the word "comprise" or variations such as "comprises" or "comprising" is used in an inclusive sense, i.e. to specify the presence of the stated features, but not to preclude the presence or addition of further features in various embodiments of the invention.

The term "about" as used herein contemplates a range of values for a given number of ±25% the magnitude of that number. In other embodiments, the term "about" contemplates a range of values for a given number of ±20%, ±15%, ±10%, ±5%, ±4%, ±3%, ±2%, or ±1% the magnitude of that number. For example, in one embodiment, "about 3 grams" indicates a value of 2.7 grams to 3.3 grams (i.e. 3 grams±10%), and the like.

Similarly, the timing or duration of events may be varied by at least 25%. For example, while a particular event may be disclosed in one embodiment as lasting one day, the event may last for more or less than one day. For example, "one day" may include a period of about 18 hours to about 30 hours. In other embodiments, periods of time may vary by ±20%, ±15%, ±10%, ±5%, ±4%, ±3%, ±2%, or ±1% of that period of time.

EXAMPLES

Example 1—Preparation of PEG-TeNT-c (FIG. 1A)

In this example, surface serine residues of TeNT-c will be mutated to surface cysteine residues to facilitate directed PEG conjugation at immunogenic epitopes to produce the molecule of FIG. 1A. The mutations will be: S963C, S1041C, S1155C, and S1187C.

The gene for TeNT with surface serine to cysteine substitutions S963C, S1041C, S1155C, and S1187C will be synthesised by a commercial provider, for example Integrated DNA Technologies. The gene will be sub-cloned into the pRSET-A expression vector by restriction digestion so that 6× Histidine tag from the vector is added to the N-terminus of the mutant protein.

TeNT comprising S963C, S1041C, S1155C, and S1187C will be expressed, PEGylated and purified according to Example 5 to produce PEG-TeNT-c.

Example 2—Preparation of PEG-TeNT-HC (FIG. 1B)

In this example, surface serine residues of TeNT-HC will be mutated to surface cysteine residues to facilitate directed PEG conjugation at immunogenic epitopes to produce the molecule of FIG. 1B. The mutations will be: S600C, S963C, S1041C, S1155C, and S1187C (FIG. 24 SEQ ID NO: 16).

The gene for TeNT with surface serine to cysteine substitutions S600C, S963C, S1041C, S1155C, and S1187C will be synthesised by a commercial provider, for example Integrated DNA Technologies. The gene will be sub-cloned into the pRSET-A expression vector (FIGS. 25-1, 25-2, and 25-3 SEQ ID NO: 17, FIG. 26) by restriction digestion so that 6× Histidine tag from the vector is added to the N-terminus of the mutant protein.

TeNT comprising S600C, S963C, S1041C, S1155C, and S1187C will be expressed, PEGylated and purified according to Example 5 to produce PEG-TeNT-HC.

Example 3—Preparation of PEG-TeNT-LC-c (FIG. 1C)

In this example, surface serine residues of LC and c were mutated to surface cysteine residues to facilitate directed PEG conjugation at immunogenic epitopes to produce the molecule of FIG. 1C. The mutations were: S81C, S120C, S144C, S248C, S335C, S428C, S963C, S1041C, S1155C, and S1187C (FIG. 21 SEQ ID NO: 14).

The gene for TeNT with surface serine to cysteine substitutions S81C, S120C, S144C, S248C, S335C, S428C, S963C, S1041C, S1155C, and S1187C in LC and c was synthesised by a commercial provider, Integrated DNA Technologies. The gene was sub-cloned into the pRSET-A expression vector (FIGS. 22-1 and 22-2 SEQ ID NO: 15, FIG. 23) by restriction digestion so that 6× Histidine tag from the vector was added to the N-terminus of the mutant protein.

TeNT comprising S81C, S120C, S144C, S248C, S335C, S428C, S963C, S1041C, S1155C, and S1187C was expressed, PEGylated and purified according to Example 5 to produce PEG-TeNT-LC-c.

Endotoxin Removal

Endotoxin was removed from the TeNT-LC-c Serine mutant according to Example 4.

PEG Attachment to Cysteine Residues.

1. A molar excess of PEG-maleimide, with PEG of about 2 kDa, about 5 kDa, about 10 kDa or about 20 kDa, was combined with serine mutant TeNT-LC-c (0.5-2 mg/mL) in PBS at pH 6.5-7.5.
2. Attachment was performed at room temperature for 6 hours.
3. Excess PEG was removed by size exclusion chromatography.

Trypsin Digest Activation of Protein

Trypsin digestion for activation of the TeNT-LC-c Serine mutant was performed according to Example 4.

Example 4—Preparation of PEG-TeNT-LC-HC (FIG. 1D) (Method 1)

Preparation of TeNT

1. *E. coli* BL21 DE3 pLysS strain was electrotransformed with pRSET-TeNT vector (FIGS. 3 and 4) and grown overnight on LB agar with selection antibiotic (ampicillin and chloramphenicol) at 37° C.
2. 200 mL of pre-induction broth was inoculated with 1 colony from the selection plate. The pre-induction broth pH 7.2-7.4 comprised: 1.2% Tryptone; 2.4% Yeast extract; 2% Glucose; 0.4% Glycerol; 17 mM KH$_2$PO$_4$; 72 mM K$_2$HPO$_4$; and selection antibiotics (ampicillin and chloramphenicol).
3. The culture was incubated overnight at 30° C. with fast shaking.
4. The overnight culture was harvested by centrifugation at 4000 g for 10 minutes.
5. The pellet was resuspended in 200 mL expression broth pH 7.2-7.4, comprising: 1.2% Tryptone; 2.4% Yeast extract; 0.4% glycerol; 1 mM IPTG; 17 mM KH$_2$PO$_4$; 72 mM K$_2$HPO$_4$; 100 µg/mL ampicillin; and 10 µM ZnCl$_2$.
6. The protein was expressed for 6 hours at 30° C. with fast shaking.

7. The cells were harvested by centrifugation at 4500 g for 15 min and the pellet resuspended in 30 mL of TBS with 20 mM imidazole at pH 8.
8. The cells were lysed by sonication.
9. The cell lysate was cleared by centrifugation at 4500 g for 20 min and filtered through a 0.45 µm filter.
10. The protein was purified by His-tag affinity chromatography using the ÄKTA PURE™ 25 FPLC system (GE).
11. The purified protein underwent buffer exchange to PBS using size exclusion chromatography followed by a second stage purification by gel filtration using ÄKTA PURE™ 25 FPLC with SUPERDEX™ 200 increase 10/300 GL column.

Endotoxin Removal

1. A 0.5 mL endotoxin removal spin column was equilibrated to room temperature.
2. The column bottom plug was removed, column cap loosened, column placed in a 15 mL tube then centrifuged at 500 g for 1 minute to remove solution from column. The solution was discarded.
3. The column bottom plug was replaced, column cap removed, 0.2N NaOH in 95% ethanol added to resin, column cap replaced, column inverted several times to resuspend resin, then incubated at room temperature for 1-2 h.
4. The column bottom plug was removed, column cap loosened, column place in a 15 mL tube then centrifuged at 500 g for 1 minute to remove solution from column. The solution was discarded.
5. The column bottom plug was replaced, column cap removed, endotoxin-free 2M NaCl added to resin, column cap replaced, and column inverted several times to resuspend resin.
6. The column bottom plug was removed, column cap loosened, column placed in a 15 mL tube then centrifuged at 500 g for 1 minute to remove solution from column. The solution was discarded.
7. The column bottom plug was replaced, column cap removed, endotoxin-free ultrapure water added to resin, column cap replaced, and column inverted several times to resuspend resin.
8. The column bottom plug was removed, column cap loosened, column placed in a 15 mL tube, and centrifuged at 500 g for 1 minute to remove solution from column. The solution was discarded.
9. The column bottom plug was replaced, column cap removed, endotoxin-free phosphate buffer added to resin, column cap replaced, and column inverted several times to resuspend resin.
10. The column bottom plug was removed, column cap loosened, column place in a 15 mL tube, and centrifuged at 500 g for 1 minute to remove solution from column. The solution was discarded.
11. The column was rinsed twice more with phosphate buffer and the eluate discarded.
12. The column bottom plug was replaced, column cap removed, sample applied to the resin, column cap replaced, and column inverted several times to resuspend resin.
13. The column was incubated with end-over-end mixing at 4° C. for at least 1 h.
14. The column bottom plug was removed, column cap loosened, column placed in an endotoxin-free 15 mL tube, and centrifuged at 500 g for 1 minute to remove solution from column. The sample was retained.

15. The endotoxin removal procedure was repeated with a regenerated spin column until the endotoxin levels in the sample were at an equivalent or lower level so that all dosages would contain less than 5 EU units of endotoxin per kilogram of the subject.

Preparation of PEG-TeNT-LC-HC.

1. In a total volume of 500 µL PBS pH 7.4, 3 µmol purified TeNT and 0.5 mmol mpeg-NHS (SC) (Nanocs) were combined with one of 2 kDa, 5 kDa, 10 kDa, 20 kDa, or 30 kDa PEG.

2. The sample was mixed at room temperature for 3 hours.

3. Excess PEG was removed by size exclusion chromatography.

Trypsin Digestion of Protein Into Active Form 1. 1 mg of the protein was dissolved in 0.5 mL digestion buffer, comprising 0.1 M NH₄HCO₃ buffer, pH 8.0 or 0.1 M Tris buffer pH 8.5.

2. 0.10 mL to 0.25 mL of Immobilized TPCK Trypsin was washed with 3×500 µL of digestion buffer. The gel was separated from the buffer after each wash by centrifugation.

3. The gel was resuspended in about 0.2 mL of the digestion buffer.

4. The Immobilized TPCK Trypsin was added to the protein sample.

5. The reaction mixture was incubated for 2 hours to 18 hours at 37° C. in a rapidly shaking incubator.

6. The Immobilized TPCK Trypsin was separated by centrifugation.

Example 5—Preparation of PEG-TeNT-LC-HC (FIG. 1D) (Method 2)

In this example, surface serine residues of TeNT-LC-HC were mutated to surface cysteine residues (S to C mutant) to facilitate directed PEG conjugation at immunogenic epitopes. The TeNT mutations were: S81C; S120C; S144C; S248C; S335C; S428C; S600C; S963C; S1041C; S1155C; and S1187C, relative to SEQ ID NO: 1.

Preparation of Serine Mutant TeNT-LC-HC

*E. coli* BL21 (DE3) pLysS strain was electrotransformed with vector pRSET-TeNT (FIGS. 19 and 20) encoding the amino acid sequence of FIG. 18 (SEQ ID NO: 12) comprising the S to C mutations. TeNT-LC-HC comprising the S to C mutations was expressed and purified according to Example 4 with the addition of treatment by 0.5 mM DTT for 15 minutes between step 10 and 11.

Endotoxin Removal

Endotoxin was removed from the TeNT-LC-HC Serine mutant according to Example 4. PEG attachment to cysteine residues.

1. A molar excess of PEG-maleimide, with PEG of about 2 kDa, about 5 kDa, about 10 kDa or about 20 kDa, was combined with serine mutant TeNT-LC-HC (0.5-2 mg/mL) in PBS at pH 6.5-7.5.

2. Attachment was performed at room temperature for 6 hours.

3. Excess PEG was removed by size exclusion chromatography.

Trypsin Digest Activation of Protein

Trypsin digestion for activation of the TeNT-LC-HC Serine mutant was performed according to Example 4.

Example 6—Inactive Decoy TeNTs

In this example, a non-PEGylated, recombinant c with inactivating R1225E and W1288A amino acid substitutions, relative to SEQ ID NO: 1, in the ganglioside binding region was produced. The inactivated c was combined with an equimolar amount of non-PEGylated LC-HN to produce the inactive decoy TeNT. The resulting inactive TeNT will be used as a decoy for the antibody-based neutralising response in subjects vaccinated against tetanus toxoid.

Preparation of c Comprising R1225E W1288A

The gene for c with R1225E and W1288A was synthesised by a commercial provider, Integrated DNA Technologies. The gene was sub-cloned into the pRSET-A expression vector by restriction digestion so that 6× Histidine tag from the vector is added to the N-terminus of the mutant protein.

*E. coli* BL21 (DE3) pLysS strain was electrotransformed with pRSET-TeNT-c vector (FIGS. 13-1 and 13-2 (SEQ ID NO: 9) and FIG. 14) encoding c comprising R1225E W1288A (FIG. 12, SEQ ID NO: 8) and grown overnight on LB agar with selection antibiotics (ampicillin, chloramphenicol) at 37° C. c comprising R1225E W1288A was expressed and purified according to Example 4.

Endotoxin Removal

Endotoxin was removed from the purified protein according to Example 4.

Preparation of LC-HN

*E. coli* BL21 (DE3) pLysS strain was electrotransformed with pRSET-TeNT-LC-HN vector (FIGS. 10 and 11) and grown overnight on LB agar with selection antibiotics (ampicillin, chloramphenicol) at 37° C. LC-HN was expressed and purified according to Example 4.

Endotoxin Removal

Endotoxin was removed from the purified protein according to Example 4.

Preparation of LC-HN Comprising E270A Y374A

*E. coli* BL21 (DE3) pLysS strain was electrotransformed with pRSET-TeNT-LC-HN vector encoding LC-HN comprising E270A Y374A and grown overnight on LB agar with selection antibiotics (ampicillin, chloramphenicol) at 37° C. LC-HN comprising E270A Y374A was expressed and purified according to Example 4.

Endotoxin Removal

Endotoxin was removed from the purified protein according to Example 4.

Example 7 Inactive Decoy TeNTs

The gene for TeNT comprising R1225E and W1288A was synthesized by a commercial provider, Integrated DNA Technologies. The gene was sub-cloned into the pRSET-A expression vector by restriction digestion so that 6× Histidine tag from the vector was added to the N-terminus of the mutant protein (FIG. 15 SEQ ID NO: 10, FIG. 16 SEQ ID NO: 11, and FIG. 17).

The inactivated TeNT comprising R1225E and W1288A was expressed and purified according to Example 4.

Endotoxin Removal

Endotoxin was removed from the purified protein according to Example 4.

Example 8—PEG-TeNT Analysis

TeNT was prepared and PEGylated according to Example 4, then analysed by SDS-PAGE (FIGS. 28A-B) and detected (A) using COOMASSIE BLUE™ and (B) by Western blot using polyclonal anti-TeNT antibodies. (B) shows that immunogenicity is proportional to PEG molecular weight.

Example 9—Reduced Immunogenicity of PEG-TeNT Versus TeNT

Four PEG-TeNTs each comprising a different molecular weight PEG (2 kDa, 5 kDa, 10 kDa and 20 kDa) were prepared and PEGylated according to Example 4. The PEG-TeNTs were then assayed by competitive ELISA against TeNT.

In the first assay (FIG. 29A), TeNT was adsorbed to an ELISA plate. Adsorbed TeNT was then probed with a polyclonal anti-TeNT antibody pre-incubated with each of four concentrations (10 µg/mL, 1 µg/mL, 0.1 µg/mL and 0.01 µg/mL) of four PEG-TeNT antigens (2 kDa, 5 kDa, 10 kDa and 20 kDa). In this assay, higher responses (OD 450 nm) indicated greater affinity for TeNT and therefore reduced immunogenicity for the PEG-TeNT.

In the second assay (FIG. 29B), each PEG-TeNT was adsorbed to a separate ELISA plate. Each adsorbed PEG-TeNT (2 kDa, 5 kDa, 10 kDa and 20 kDa) was then probed with a polyclonal anti-TeNT antibody pre-incubated with each of four concentrations (10 µg/mL, 1 µg/mL, 0.1 µg/mL and 0.01 µg/mL) of TeNT antigen. In this assay, lower responses (OD 450 nm) indicated greater affinity for TeNT and therefore reduced immunogenicity for the PEG-TeNT.

This example showed that anti-TeNT antibodies bound preferentially to TeNT and that PEGylated TeNTs have reduced immunogenicity relative to TeNT (i.e. non-PEGylated).

Example 10—Reduced Immunogenicity of PEG-TeNT-LC-c Serine Mutant Versus TeNT-LC-c Serine Mutant TeNT-LC-c Serine mutant was prepared according to Example 5. Four samples of the TeNT-LC-c Serine mutant were PEGylated according to Example 5, each sample comprising a different molecular weight PEG (2 kDa, 5 kDa, 10 kDa and 20 kDa). The PEG-TeNT-LC-c Serine mutants were then assayed by competitive ELISA against TeNT-LC-c Serine mutant.

In the first assay (FIG. 29C), TeNT-LC-c Serine mutant was adsorbed to an ELISA plate. Adsorbed TeNT Serine mutant was then probed with a polyclonal anti-TeNT antibody pre-incubated with each of four concentrations (10 µg/mL, 1 µg/mL, 0.1 µg/mL and 0.01 µg/mL) of four PEG-TeNT Serine mutant antigens (2 kDa, 5 kDa, 10 kDa and 20 kDa). In this assay, higher responses (OD 450 nm) indicated greater affinity for TeNT Serine mutant and therefore reduced immunogenicity for the PEG-TeNT Serine mutant.

In the second assay (FIG. 29D), each PEG-TeNT-LC-c Serine mutant was adsorbed to a separate ELISA plate. Each adsorbed PEG-TeNT Serine mutant (2 kDa, 5 kDa, 10 kDa and 20 kDa) was then probed with a polyclonal anti-TeNT antibody pre-incubated with each of four concentrations (10 µg/mL, 1 µg/mL, 0.1 µg/mL and 0.01 µg/mL) of TeNT Serine mutant antigen. In this assay, lower responses (OD 450 run) indicated greater affinity for TeNT Serine mutant and therefore reduced immunogenicity for the PEG-TeNT Serine mutant.

This example showed that anti-TeNT antibodies bound preferentially to TeNT-LC-c Serine mutant and that PEGylated TeNT-LC-c Serine mutants have reduced immunogenicity relative to TeNT-LC-c Serine mutant (i.e. non-PEGylated).

Example 11—Reduced Immunogenicity of PEG-TeNT Versus TeNT

A competitive ELISA assay will be conducted in accordance with Example 9, except that the polyclonal antibody will be replaced by human serum collected from one or more subjects who have received a booster tetanus toxoid vaccination within the previous 12 months. Antibodies in the serum will show greater affinity for TeNT (i.e. non-PEGylated TeNT) versus PEG-TeNTs.

Example 12—In Vivo Model

PEG-TeNT-LC-HC were prepared by attaching PEG (about 5 kDa, about 10 kDa or about 20 kDa) to the surface exposed lysine residues of recombinant TeNT according to Example 4.

One or more units of PEG-TeNT-LC-HC in 15 µL of PBS was injected into the hind limb of female C57BL/6 mice. Each animal exhibited localised limb tetany within 48 hours of injection (FIGS. 30A and 30B).

Example 13—In Vivo Model

PEG-TeNT-LC-HC, with 5 kDa PEG attached to surface lysine residues of TeNT according to Example 4, was combined with c decoy, i.e. c inactivated by R1225E W1288A, at a molar ratio of 1:10. Fifteen microlitres of the composition in PBS, containing 5 ng of the PEG-TeNT, was injected into the muscle of the hind limb of female C57BL/6 mice. Each animal exhibited localised limb tetany within 48 hours, symptom development was indistinguishable from animals treated with the PEG-TeNT-LC-HC without the decoy present.

Example 14

PEG-TeNT-LC-HC comprising 5 kDa, 10 kDa or 20 kDa PEG was administered at 50-500000 ng/kg intramuscularly to the hind leg muscle of mice previously immunized with tetanus toxoid. Increased muscle contraction was observed in the injected muscle for up to 3 days, and was greater than the effect observed in mice administered the same units of TeNT. FIG. 31A reports results for PEG-TeNT-LC-HC 20 kDa.

Example 15

Figure 32:
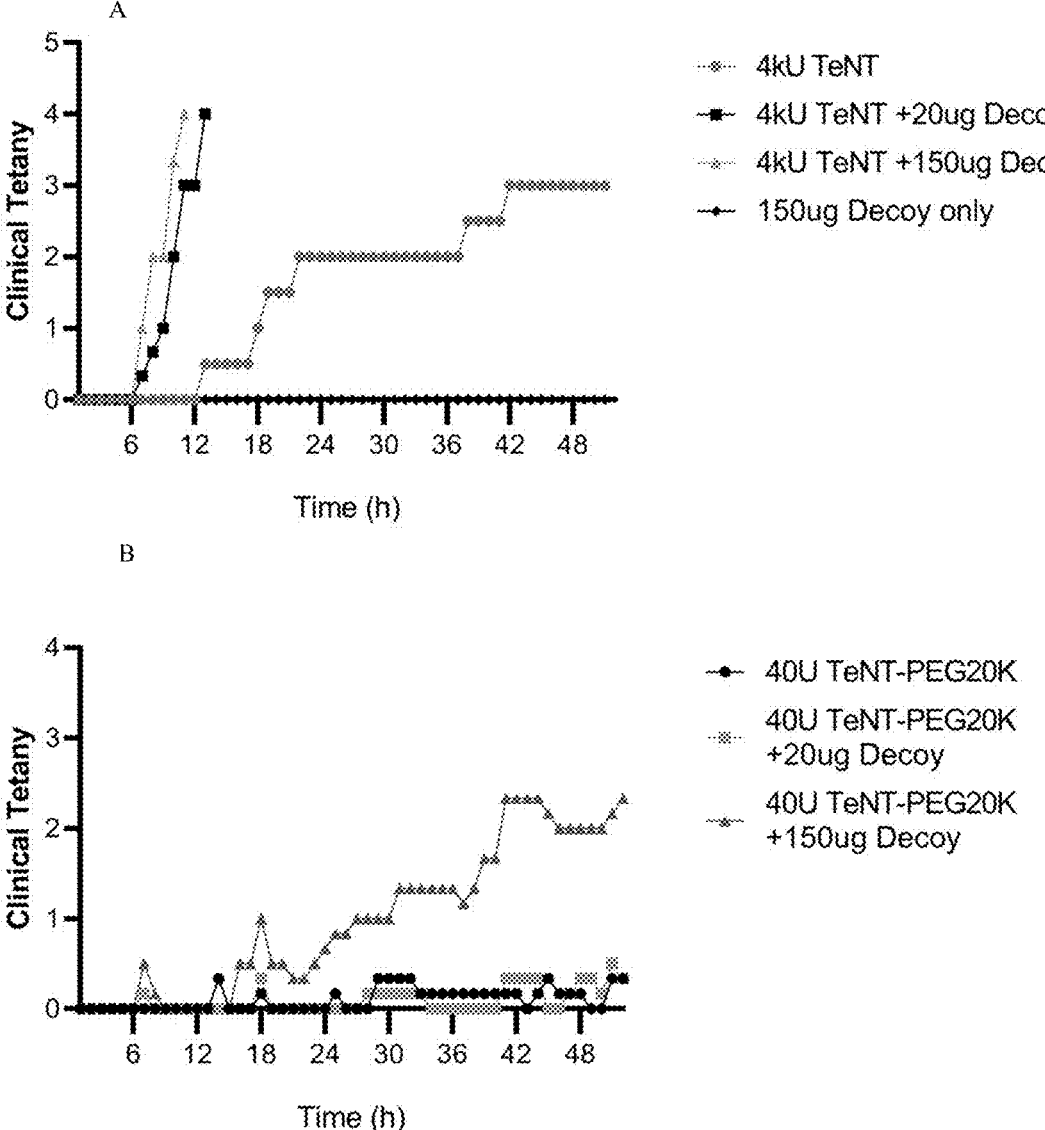
FIGS. 32A and 32B comprise two line graphs showing the progression of clinical tetany in mice vaccinated with tetanus toxoid.
Figure 33:
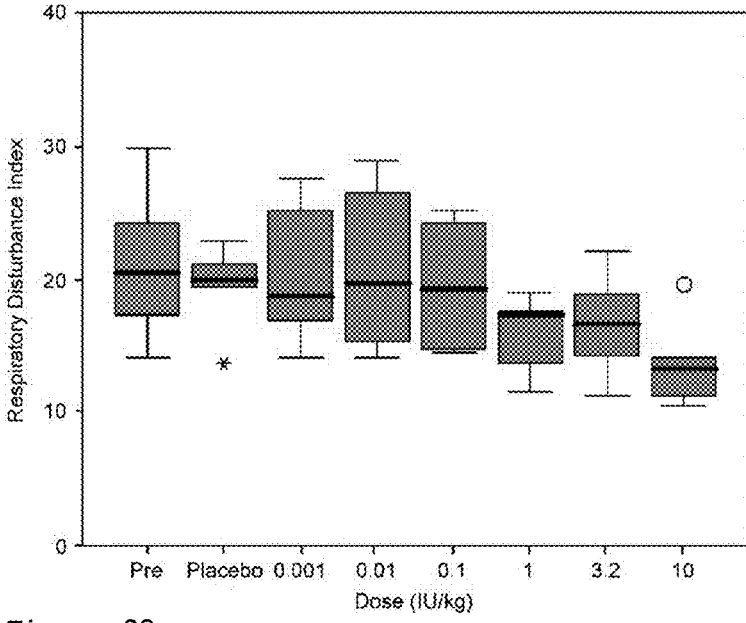
FIG. 33 is a box plot showing the effect of increasing doses of tetanus toxin on the Respiratory Disturbance Index (RDI) of British Bulldogs treated according to example 23. The black bars represent the median RDI of the six studies at each dose of tetanus toxin. The shaded boxes represent the interquartile range and the brackets represent the minimum and maximum RDI sample at each dose. Increasing tetanus toxin was associated with a reduced RDI following the administration of 10 IU/kg compared with the RDI following administration of the placebo (P=0.043; Wilcoxon Signed Ranks test). Placebo and 10 IU/kg medians are additionally represented by o and *, respectively.

A composition comprising TeNT-LC-HC and a 10:1 or 100:1 molar excess of a decoy TeNT produced according to Example 6 was administered at 50-500 000 ng/kg intramuscularly to the hind leg muscle of mice previously immunized with tetanus toxoid. Increased muscle contraction was observed in the injected muscle for up to three days, and was greater than the effect observed in mice administered TeNT (FIG. 32A).

Example 16

A composition comprising PEG-TeNT-LC-HC comprising 5 kDa, 10 kDa or 20 kDa PEG and a 10:1 or 100:1 molar excess of a decoy TeNT produced according to Example 6 was administered at 50-500 000 ng/kg intramuscularly to the hind leg muscle of mice previously immunized with tetanus toxoid. Increased muscle contraction was observed in the injected muscle for up to three days, and was greater than the effect observed in mice administered TeNT, and greater than the effect observed in mice administered PEG-TeNT only (FIG. 32B).

Example 17

PEG-TeNT-LC-HC comprising 20 kDa PEG will be administered at 0.01-50 000 ng/kg intramuscularly to the left geniohyoid of a human subject previously vaccinated with tetanus toxoid. Increased muscle contraction will be observed in the injected muscle for up to 2 weeks, and will be greater than the effect observed in the right geniohyoid administered vehicle only of the same subject.

Example 18

A composition comprising PEG-TeNT-LC-HC comprising 20 kDa PEG and a 10:1-1000:1 molar excess of a decoy TeNT produced according to Example 6 will be administered at 50 ng/kg intramuscularly to the left geniohyoid of a human subject previously vaccinated with tetanus toxoid. PEG-TeNT-LC-HC comprising 20 kDa PEG will be administered at 50 ng/kg intramuscularly to the right geniohyoid of the same human subject.

Increased muscle contraction will be observed in both the left and right geniohyoids for up to 2 weeks, but will be greater in the left geniohyoid treated with the composition comprising PEG-TeNT-LC-HC and the decoy TeNT compared to the PEG-TeNT-LC-HC alone.

Example 19

Bulldogs of approximately 30 kg will be administered 25-50 000 ng/kg PEG-TeNT-c comprising 20 kDa PEG intramuscularly with the dose divided bilaterally to the left and right geniohypid. Upon administration, obstructive sleep apnoea (OSA) will decrease in PEG-TeNT treated animals compared with animals treated with vehicle alone. The bulldogs will be observed weekly for OSA and the PEG-TeNT-c dose will be repeated as needed until efficacy decreases, as determined by a return of OSA comparable to animals treated with vehicle alone.

Thereafter, the bulldogs will be administered 25-50 000 ng/kg of PEG-TeNT-HC or 25-50 000 ng/kg PEG-TeNT-LC-c, each comprising 20 kDa PEG, divided bilaterally to the left and right geniohyoid. Upon administration, OSA will decrease in PEG-TeNT treated animals compared with animals treated with vehicle alone. The bulldogs will be observed weekly for OSA and the PEG-TeNT-HC and PEG-TeNT-LC-c dose will be repeated as needed until efficacy decreases, as determined by a return of OSA comparable to animals treated with vehicle alone.

Thereafter, the bulldogs will be administered 25-50 000 ng/kg PEG-TeNT-LC-HC, comprising 20 kDa PEG, divided bilaterally to the left and right geniohyoid. Upon administration, OSA will decrease in PEG-TeNT treated animals compared with animals treated with vehicle alone. The bulldogs will be observed weekly for OSA and the PEG-TeNT-LC-HC dose will be repeated as needed until efficacy decreases, as determined by a return of OSA comparable to animals treated with vehicle alone.

Example 20

Discovery Studio was used to map TeNT epitopes recognised by major human antibody clonotypes, as identified by da Silva Antunes et al (2017) *PloS One,* 12(1), e0169086 and Palermo et al (2017) *Biotechnology Journal,* 12(10), 1700197, onto a 3-dimensional model of TeNT derived from crystallography data deposited in the protein data bank (accession ID PDB: 5N0B). Surface serine residues in or around the identified epitopes were identified for mutation to cysteine for subsequent PEGylation as set out in Examples 1 to 3 and 5.

Example 21

One nanogram to 64 micrograms of a mixture of PEG-TeNT (5 kDa, 10 kDa, or 20 kDa branched or linear PEG attached to surface lysine or cysteine residues) and a 10-1000 molar excess of decoy TeNT will be injected intramuscularly into the hind leg muscle of mice vaccinated against tetanus toxoid. Localised tetany will be observed for a period of hours to months, greater than the effect observed in mice injected with native TeNT.

Example 22

One nanogram to 64 micrograms of a mixture of PEG-TeNT (5 kDa, 10 kDa, or 20 kDa branched or linear PEG attached to surface lysine or cysteine residues) and a 10-1000 molar excess of decoy TeNT will be injected intramuscularly into the geniohyoid of a human vaccinated against tetanus toxoid. Localised *tetani* is observed for a period of weeks to months, greater than the effect observed in a human injected with native TeNT.

Example 23

A British Bulldog with sleep disordered breathing was administered 0.001-10 IU/Kg of TeNT intramuscularly, with the dose divided bilaterally to the left and right geniohyoid. Upon administration, obstructive sleep apnoea (OSA) was observed to decrease significantly at the highest dose. The baseline respiratory disturbance index (RDI) score was 19.9 (interquartile range 5.45) decreasing to 13.2 (interquartile range 4.45) after treatment with 10 IU/Kg TeNT, determined to be significant compared to administration of a placebo by Wilcoxon signed rank test; by P=0.043. The bulldog was observed four months post trials with the reduction in RDI maintained; median RDI=13.4, P=0.043; Wilcoxon Signed Ranks test.

---

The invention claimed is:

1. A method of treating hypotonia in a mammalian subject having pre-existing anti-tetanus neurotoxin (TeNT) antibodies due to prior exposure to TeNT or due to pre-immunization with tetanus toxoid, the method comprising administering to said subject a therapeutically effective amount of:

a first TeNT that is active and PEGylated (PEG-TeNT) comprising one or more surface serine-to-cysteine amino acid substitutions within the amino acid sequence of SEQ ID NO: 1, wherein the one or more substituted cysteines are conjugated to polyethylene glycol (PEG); and a second TeNT that is an inactive TeNT consisting of SEQ ID NO: 1 carrying the R1225E and W1288A inactivating mutations, wherein the second inactive TeNT is not PEGylated.

2. The method of claim 1, wherein the PEG in the PEG-TeNT is of 2 kDa, 5 kDa, 10 kDa, or 20 kDa.

3. The method of claim 1, wherein the first PEG-TeNT comprises a PEGylated TeNT light chain (LC), a PEGylated TeNT heavy chain (HC), or a PEGylated TeNT fragment c (c).

4. The method of claim 1, wherein the first PEG-TeNT is PEG-TeNT-HC comprising a PEGylated heavy chain (HC), or is PEG-TeNT-LC-c comprising a PEGylated light chain (LC) and a PEGylated fragment c.

5. The method of claim 1, wherein the subject is administered: the first PEG-TeNT comprising PEGylated fragment c (PEG-TeNT-c) and the second TeNT until efficacy of the first PEG-TeNT decreases; then the first PEG-TeNT-HC comprising a PEGylated heavy chain (HC) and PEG-TeNT-LC-c comprising a PEGylated light chain (LC) and a PEGylated fragment c and the second TeNT until efficacy of the first PEG-TeNT decreases; and then the first PEG-TeNT comprising a PEGylated LC and a PEGylated HC (PEG-TeNT-LC-HC) and the second TeNT.

6. The method of claim 1, wherein the first PEG-TeNT's light chain (LC) is PEGylated and the first PEG-TeNT's heavy chain (HC) is PEGylated (PEG-TeNT-LC-HC), or the first PEG-TeNT's LC is PEGylated and the first PEG-TeNT's fragment c (c) is PEGylated (PEG-TeNT-LC-c).

7. The method of claim 1, wherein the second TeNT does not block release of inhibitory neurotransmitters.

8. The method of claim 1, wherein the second TeNT acts as a decoy for the anti-TeNT antibodies.

* * * * *